(12) United States Patent
Tanaka et al.

(10) Patent No.: US 9,441,161 B2
(45) Date of Patent: *Sep. 13, 2016

(54) LIQUID CRYSTAL COMPOUND, LIQUID CRYSTAL COMPOSITION AND LIQUID CRYSTAL DISPLAY DEVICE

(71) Applicant: JNC PETROCHEMICAL CORPORATION, Tokyo (JP)

(72) Inventors: Hiroyuki Tanaka, Ichihara (JP); Yasuyuki Sasada, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/814,202

(22) Filed: Jul. 30, 2015

(65) Prior Publication Data

US 2016/0032187 A1    Feb. 4, 2016

(30) Foreign Application Priority Data

Jul. 31, 2014    (JP) .................. 2014-156446

(51) Int. Cl.
*G02F 1/1333* (2006.01)
*C09K 19/34* (2006.01)
(Continued)

(52) U.S. Cl.
CPC ......... *C09K 19/3458* (2013.01); *C07D 239/26* (2013.01); *C07D 309/04* (2013.01);
(Continued)

(58) Field of Classification Search
CPC .......... C09K 19/3458; C09K 19/3068; C09K 19/3066; C09K 19/3001; C09K 19/3402; C09K 19/14; C09K 19/20; C09K 19/3028; C09K 19/322; C09K 2019/308; C09K 2019/3077; C09K 2019/3083; C09K 2019/3422; C09K 2019/3427; C09K 2019/0466; C09K 2019/325; C09K 2019/326; C09K 2019/3425; C07D 309/04; C07D 319/06; C07D 493/08; C07D 239/26
USPC .............. 252/299.01, 299.6, 299.62, 299.63; 428/1.1
See application file for complete search history.

(56) References Cited

U.S. PATENT DOCUMENTS 5,045,229 A    9/1991 Bartmann et al.
5,728,319 A    3/1998 Matsui et al.
(Continued)

FOREIGN PATENT DOCUMENTS

DE       4006921 A1    9/1990
JP    H10204016 A    8/1998
(Continued)

*Primary Examiner* — Geraldina Visconti
(74) *Attorney, Agent, or Firm* — Hogan Lovells US LLP

(57) ABSTRACT

To provide a liquid crystal compound satisfying at least one of physical properties such as high stability to light, a high clearing point, low minimum temperature of a liquid crystal phase, small viscosity, suitable optical anisotropy, large dielectric anisotropy, a suitable elastic constant, excellent compatibility with other liquid crystal compounds and a large dielectric constant in a minor axis direction.
The compound is represented by formula (1).

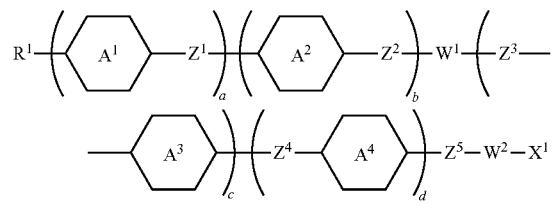

(1)

For example, $R^1$ is alkyl having 1 to 15 carbons; rings $A^1$ to $A^4$ are 1,4-cyclohexylene or 1,4-phenylene; $W^1$ is a group represented by formula (1a) or (1b);

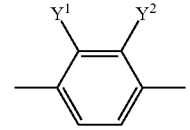

(1a)

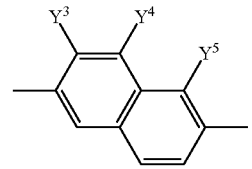

(1b)

$W^2$ is a group represented by formula (1c) or (1d);

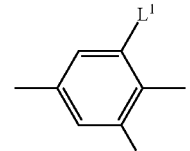

(1c)

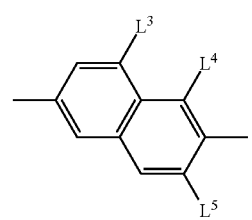

(1d)

$Y^1$ to $Y^5$ and $L^1$ to $L^5$ are fluorine; $Z^1$ to $Z^5$ are —(CH$_2$)$_2$— or —OCH$_2$—; $X^1$ is fluorine, —CF$_3$ or —OCF$_3$; and a to d are 0 or 1, and a sum of a to d is 3 or less.

14 Claims, No Drawings

(51) Int. Cl.
    *C09K 19/30*     (2006.01)
    *C07D 309/04*     (2006.01)
    *C07D 319/06*     (2006.01)
    *C07D 493/08*     (2006.01)
    *C07D 239/26*     (2006.01)
    *C09K 19/04*     (2006.01)
    *C09K 19/14*     (2006.01)
    *C09K 19/20*     (2006.01)
    *C09K 19/32*     (2006.01)

(52) U.S. Cl.
    CPC ........... *C07D319/06* (2013.01); *C07D 493/08* (2013.01); *C09K 19/0403* (2013.01); *C09K 19/14* (2013.01); *C09K 19/20* (2013.01); *C09K 19/3001* (2013.01); *C09K 19/3028* (2013.01); *C09K 19/3066* (2013.01); *C09K 19/3068* (2013.01); *C09K 19/322* (2013.01); *C09K 19/3402* (2013.01); *C09K 2019/0466* (2013.01); *C09K 2019/308* (2013.01); *C09K 2019/3077* (2013.01); *C09K 2019/3083* (2013.01); *C09K 2019/325* (2013.01); *C09K 2019/326* (2013.01); *C09K 2019/3422* (2013.01); *C09K 2019/3425* (2013.01); *C09K 2019/3427* (2013.01)

(56) References Cited

U.S. PATENT DOCUMENTS

| | | |
|---|---|---|
| 6,007,740 A | 12/1999 | Andou et al. |
| 2002/0028306 A1 | 3/2002 | Kirsch et al. |
| 2015/0368272 A1* | 12/2015 | Gotoh .................. C07D 519/00 252/299.61 |
| 2016/0046864 A1* | 2/2016 | Goto .................... C09K 19/322 252/299.61 |

FOREIGN PATENT DOCUMENTS

| | | |
|---|---|---|
| JP | 2002080452 A | 3/2002 |
| WO | 96-11897 A1 | 4/1996 |

\* cited by examiner

LIQUID CRYSTAL COMPOUND, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a compound having both a large dielectric anisotropy and a large dielectric constant in a minor axis direction, a liquid crystal composition containing the compound and having a nematic phase, and a liquid crystal display device including the composition.

BACKGROUND ART

A liquid crystal display device has been widely utilized for a display of a personal computer, a television or the like. The device utilizes optical anisotropy, dielectric anisotropy and so forth of a liquid crystal compound. As an operating mode of the liquid crystal display device, such a mode is known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (WS) mode and a polymer sustained alignment (PSA) mode.

In such a liquid crystal display device, a liquid crystal composition having suitable physical properties is used. In order to further improve characteristics of the liquid crystal display device, the liquid crystal compound contained in the composition preferably has physical properties described in (1) to (9) below.

(1) High stability to heat, light and so forth,
(2) a high clearing point,
(3) low minimum temperature of a liquid crystal phase,
(4) small viscosity ($\eta$),
(5) suitable optical anisotropy ($\Delta n$),
(6) large dielectric anisotropy ($\Delta \in$),
(7) a suitable elastic constant (K),
(8) excellent compatibility with other liquid crystal compounds, and
(9) a large dielectric constant in a minor axis direction ($\in \perp$).

An effect of the physical properties of the liquid crystal compound on the characteristics of the device is as described below. A compound having the high stability to heat, light and so forth as described in (1) increases a voltage holding ratio of the device. Therefore, a service life of the device becomes long. A compound having the high clearing point as described in (2) extends a temperature range in which the device can be used. A compound having the low minimum temperature of the liquid crystal phase such as the nematic phase and a smectic phase, as described in (3), in particular, a compound having the low minimum temperature of the nematic phase, also extends the temperature range in which the device can be used. A compound having the small viscosity as described in (4) shortens a response time of the device.

A compound having the suitable optical anisotropy as described in (5) improves contrast of the device. According to a design of the device, a compound having a large optical anisotropy or a small optical anisotropy, more specifically, a compound having the suitable optical anisotropy, is required. When the response time is shortened by decreasing a cell gap of the device, a compound having the large optical anisotropy is suitable. A compound having the large dielectric anisotropy as described in (6) decreases a threshold voltage of the device. Thus, an electric power consumption of the device is decreased. On the other hand, a compound having a small dielectric anisotropy shortens the response time of the device by decreasing viscosity of the composition.

With regard to (7), a compound having a large elastic constant decreases the response time of the device. A compound having a small elastic constant decreases the threshold voltage of the device. Therefore, a suitable elastic constant is required according to characteristics to be desirably improved. A compound having the excellent compatibility with other liquid crystal compounds as described in (8) is preferred. The reason is that the physical properties of the composition are adjusted by mixing liquid crystal compounds having different physical properties.

Further, an improvement of a transmittance in the liquid crystal composition has been strongly required in connection with a demand for achieving a low power consumption and a high definition in the liquid crystal display device in recent years. Above all, the transmittance in the liquid crystal composition used for an FFS mode liquid crystal display device is known to be correlated with the dielectric constant in the minor axis direction ($\in \perp$) of the liquid crystal composition, and therefore a liquid crystal compound having the large dielectric constant in the minor axis direction as described in (9) is preferred.

A variety of liquid crystal compounds each having a $CF_2O$ bonding group have so far been prepared as the liquid crystal compound having the large dielectric anisotropy, and some of the compounds have been practically used. However, in the above compounds, the dielectric constant in the minor axis direction is far from sufficiently large. Under such circumstances, desire has been expressed for development of a compound having excellent physical properties and a suitable balance regarding the physical properties (1) to (9) above, above all, a compound having both the large dielectric anisotropy ($\Delta \in$) and the large dielectric constant in the minor axis direction.

CITATION LIST

Patent Literature

Patent literature No. 1: WO 96/011897 A.
Patent literature No. 2: JP H10-204016 A.
Patent literature No. 3: DE 4006921 A.
Patent literature No. 4: JP 2002-80452 A.

SUMMARY OF INVENTION

Technical Problem

A first object of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds. In particular, the object is to provide a compound having both the large dielectric anisotropy and the large dielectric constant in a minor axis direction.

A second object is to provide a liquid crystal composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. The object is to provide a liquid crystal composition having a suitable balance regarding at least two of the physical properties. A third object is to provide a liquid crystal display device including the composition and having a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition:

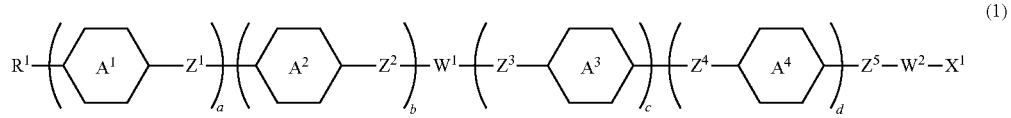
(1)

wherein, in formula (1),
R$^1$ is alkyl having 1 to 15 carbons, and in the alkyl, at least one of —CH$_2$— may be replaced by —O— or —S—, at least one of —(CH$_2$)$_2$— may be replaced by —CH=CH—, and in the groups, at least one of hydrogen may be replaced by halogen;

ring A$^1$, ring A$^2$, ring A$^3$ and ring A$^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and at least one of hydrogen directly bonded to the rings thereof may be replaced by halogen;

W$^1$ is a group represented by formula (1a) or formula (1b);

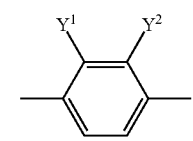
(1a)

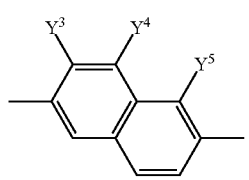
(1b)

wherein, in formula (1a),
Y$^1$ and Y$^2$ are independently fluorine or chlorine;
in formula (1b),
Y$^3$, Y$^4$ and Y$^5$ are independently hydrogen, fluorine or chlorine, and at least two of Y$^3$, Y$^4$ and Y$^5$ is fluorine or chlorine; and
in formula (1),
W$^2$ is a group represented by formula (1c) or formula (1d);

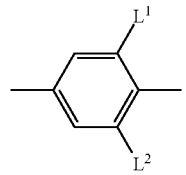
(1c)

-continued

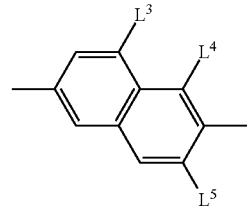
(1d)

wherein, in formula (1c) and (1d),
L$^1$, L$^2$, L$^3$, L$^4$ and L$^5$ are independently hydrogen, fluorine or chlorine; and
in formula (1),
X$^1$ is fluorine, —C≡N, —N=C=S, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;
a, b, c and d are independently 0 or 1, and a sum of a, b, c and d is 0, 1, 2 or 3;
Z$^1$, Z$^2$, Z$^3$, Z$^4$ and Z$^5$ are independently a single bond, —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—;
at least one of Z$^1$ when a is 1, Z$^2$ when b is 1, Z$^3$ when c is 1, Z$^4$ when d is 1, and Z$^5$ is —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—;
when Z$^5$ is —COO—, ring W$^1$ is a group represented by formula (1a) and ring W$^2$ is a group represented by formula (1c), $X^1$ is fluorine, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;

when $Z^5$ is —COO—, ring $W^1$ is a group represented by formula (1a), ring $W^2$ is a group represented by formula (1c), a sum of a and b is 1, a sum of c and d is 0, ring $A^1$ when a is 1 or ring $A^2$ when b is 1 is 1,4-phenylene, $Z^1$ when a is 1 or $Z^2$ when b is 1 is a single bond, both $Y^1$ and $Y^2$ are fluorine and $X^1$ is fluorine, both $L^1$ and $L^2$ are hydrogen or fluorine; and when $Z^5$ is —COO—, ring $W^1$ is a group represented by formula (1a), ring $W^2$ is a group represented by formula (1c), a sum of a, b, c and d is 0, both $Y^1$ and $Y^2$ are fluorine and $X^1$ is —$CF_3$, at least one of $L^1$ and $L^2$ is fluorine.

Advantageous Effects of Invention

A first advantage of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a suitable elastic constant, an excellent compatibility with other liquid crystal compounds and a large dielectric constant in a minor axis direction. The advantage is to provide a compound having both a particularly large dielectric anisotropy and a particularly large dielectric constant in the minor axis direction. A second advantage is to provide a liquid crystal composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in the minor axis direction and a suitable elastic constant. A third advantage is to provide a liquid crystal display device including the composition and having a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase and a smectic phase, and also a compound having no liquid crystal phase but being added for adjusting physical properties such as a maximum temperature, a minimum temperature, viscosity and dielectric anisotropy. The compounds have a six-membered ring such as 1,4-cyclohexylene and 1,4-phenylene, and rod like molecular structure. A liquid crystal composition is prepared by mixing such liquid crystal compounds. A ratio (content) of the liquid crystal compound is expressed in terms of weight percent (% by weight) based on the weight of the liquid crystal composition. An additive such as a polymerizable compound, a polymerization initiator, an optically active compound, an antioxidant, an ultraviolet light absorber, a light stabilizer, a heat stabilizer, an antifoaming agent and a dye is added to the composition, when necessary. A ratio (amount of addition) of the additive is expressed in terms of weight percent (% by weight) based on the weight of the liquid crystal composition in a manner similar to the ratio of the liquid crystal compounds. Weight parts per million (ppm) may be occasionally used. A liquid crystal display device is a generic term for a liquid crystal display panel and a liquid crystal display module. The liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. A lower limit of the temperature range of the liquid crystal phase is a transition temperature between a solid and the liquid crystal phase (the smectic phase, the nematic phase or the like) in the liquid crystal compound. A higher limit of the temperature range of the nematic phase is a transition temperature between the nematic phase and the isotropic phase in the liquid crystal composition, and may be occasionally abbreviated as "maximum temperature." A lower limit of the temperature range of the nematic phase may be occasionally abbreviated as "minimum temperature."

A compound represented by formula (1) may be occasionally abbreviated as "compound (1)." The abbreviation may also apply occasionally to a compound represented by formula (2) or the like. In formulas (1) to (15), a symbol such as $A^1$, $B^1$, $C^1$ or the like surrounded by a hexagonal shape corresponds to ring $A^1$, ring $B^1$, ring $C^1$ or the like, respectively. A symbol of terminal group $R^{11}$ is used for a plurality of compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule further applies to a symbol of any other terminal group, ring or the like. In formula (5), when i is 2, two of ring $C^1$ exists. In the compound, two groups represented by two of ring $C^1$ may be identical or different. A same rule also applies to arbitrary two when i is larger than 2. A same rule further applies to a symbol of any other ring, a bonding group or the like.

An expression "at least one of "A" may be replaced by "B"" means that a position of "A" when the number of "A" is 1 is arbitrary, and that the positions can be selected without limitation when the number of "A" is 2 or more. An expression "at least one of A may be replaced by B, C or D" means inclusion of a case where arbitrary A is replaced by B, a case where arbitrary A is replaced by C, and a case where arbitrary A is replaced by D, and also a case where a plurality of A are replaced by at least two of B, C or D. For example, alkyl in which at least one of —$CH_2$— may be replaced by —O— or —CH=CH— includes alkyl, alkenyl, alkoxy, alkoxyalkyl, alkoxyalkenyl and alkenyloxyalkyl. In addition, a case where replacement of two successive —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Then, 2-fluoro-1,4-phenylene means two divalent groups described below. In a chemical formula thereof, fluorine may be leftward (L) or rightward (R). A same rule also applies to an asymmetrical divalent ring, such as tetrahydropyran-2,5-diyl.

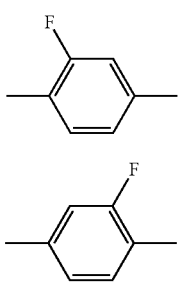

The invention includes the content described in items 1 to 14 below.

Item 1. A compound represented by formula (1):

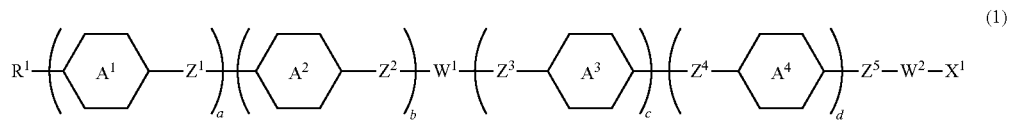

wherein, in formula (1),

R$^1$ is alkyl having 1 to 15 carbons, and in the alkyl, at least one of —CH$_2$— may be replaced by —O— or —S—, at least one of —(CH$_2$)$_2$— may be replaced by —CH=CH—, and in the groups, at least one of hydrogen may be replaced by halogen;

ring A$^1$, ring A$^2$, ring A$^3$ and ring A$^4$ independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and at least one of hydrogen directly bonded to the rings thereof may be replaced by halogen;

W$^1$ is a group represented by formula (1a) or formula (1b);

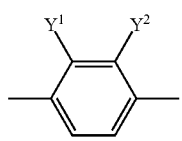

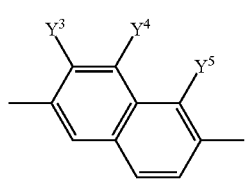

wherein, in formula (1a),

Y$^1$ and Y$^2$ are independently fluorine or chlorine;

in formula (1b),

Y$^3$, Y$^4$ and Y$^5$ are independently hydrogen, fluorine or chlorine, and at least two of Y$^3$, Y$^4$ and Y$^5$ are fluorine or chlorine; and in formula (1), W$^2$ is a group represented by formula (1c) or formula (1d);

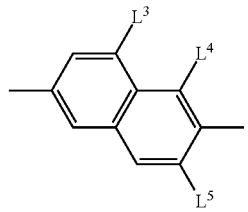

-continued

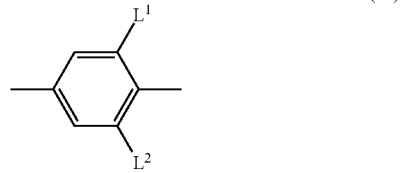

wherein, in formulas (1c) and (1d),

L$^1$, L$^2$, L$^3$, L$^4$ and L$^5$ are independently hydrogen, fluorine or chlorine; and in formula (1), X$^1$ is fluorine, —C≡N, —N=C=S, alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;

a, b, c and d are independently 0 or 1, and a sum of a, b, c and d is 0, 1, 2 or 3;

Z$^1$, Z$^2$, Z$^3$, Z$^4$ and Z$^5$ are independently a single bond, —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—;

at least one of Z$^1$ when a is 1, Z$^2$ when b is 1, Z$^3$ when c is 1, Z$^4$ when d is 1 and Z$^5$ is —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—;

when Z$^5$ is —COO—, ring W$^1$ is a group represented by formula (1a) and ring W$^2$ is a group represented by formula (1c), X$^1$ is fluorine, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;

when $Z^5$ is —COO—, ring $W^1$ is a group represented by formula (1a), ring $W^2$ is a group represented by formula (1c), a sum of a and b is 1, a sum of c and d is 0, ring $A^1$ when a is 1 or ring $A^2$ when b is 1 is 1,4-phenylene, $Z^1$ when a is 1 or $Z^2$ when b is 1 is a single bond, both $Y^1$ and $Y^2$ are fluorine and $X^1$ is fluorine, both $L^1$ and $L^2$ are hydrogen or fluorine; and when $Z^5$ is —COO—, ring $W^1$ is a group represented by formula (1a), ring $W^2$ is a group represented by formula (1c), a sum of a, b, c and d is 0, both $Y^1$ and $Y^2$ are fluorine and $X^1$ is —$CF_3$, at least one of $L^1$ and $L^2$ is fluorine.

Item 2. The compound according to item 1, wherein, in formula (1), $R^1$ is alkyl having 1 to 15 carbons, alkenyl having 2 to 15 carbons, alkoxy having 1 to 14 carbons or alkenyloxy having 2 to 14 carbons, and in the groups, at least one of hydrogen may be replaced by fluorine; and $X^1$ is fluorine, —C≡N, —N=C=S, —$CH_2F$, —$CHF_2$, —$CF_3$, —$(CH_2)_2$—F, —$CH_2CF_3$, —$CF_2CF_3$, —$(CH_2)_3$—F, —$(CH_2)_2$—$CF_3$, —$(CF_2)_3$—F, —$(CH_2)_4$—F, —$(CH_2)_3$—$CF_3$, —$(CF_2)_4$—F, —$(CF_2)_5$—F, —$(CF_2)_6$—F, —$(CF_2)_7$—F, —$OCH_2F$, —$OCHF_2$, —$OCF_3$, —O—$(CH_2)_2$—F, —$OCH_2CF_3$, —$OCF_2CF_3$, —O—$(CH_2)_3$—F, —O—$(CH_2)_2$—$CF_3$, —O—$(CF_2)_3$—F, —O$(CH_2)_4$—F, —O—$(CH_2)_3$—$CF_3$, —O—$(CF_2)_4$—F, —O—$(CF_2)_5$—F, —O—$(CF_2)_6$—F, —CH=CHF, —CH=$CF_2$, —CF=CHF, —CF=$CF_2$, —CH=$CHCH_2F$, —CH=$CHCF_3$, —CF=$CHCF_3$, —CF=$CFCF_3$, —$(CH_2)_2$—CH=$CF_2$, —$(CH_2)_2$—CF=$CF_2$, —$(CH_2)_2$—CH=$CHCF_3$, —$(CH_2)_2$—CF=$CHCF_3$ or —$(CH_2)_2$—CF=$CFCF_3$.

Item 3. The compound according to item 1, wherein, in formula (1), $R^1$ is alkyl having 1 to 10 carbons, alkenyl having 2 to 10 carbons, alkoxy having 1 to 9 carbons, or alkenyloxy having 2 to 9 carbons, and in the groups, at least one of hydrogen may be replaced by fluorine; and $X^1$ is fluorine, —C≡N, —$CF_3$, —$CHF_2$, —$OCF_3$, —$OCHF_2$, —CH=$CHCF_3$, —CF=$CHCF_3$ or —CF=$CFCF_3$.

Item 4. The compound according to item 1, represented by any one of formulas (1-1) to (1-8):

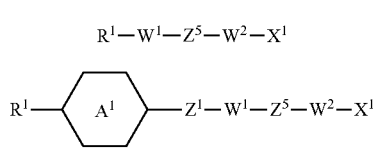
(1-1)

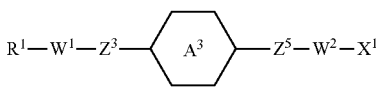
(1-2)

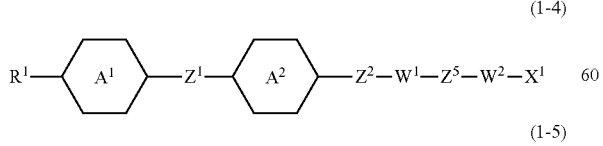
(1-3)

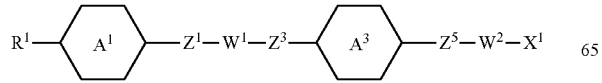
(1-4)

(1-5)

(1-6)
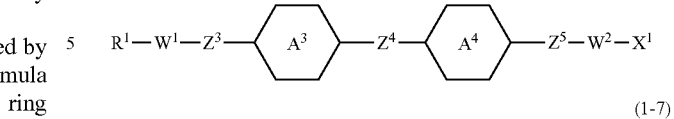

(1-7)
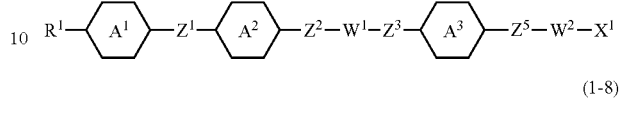

(1-8)
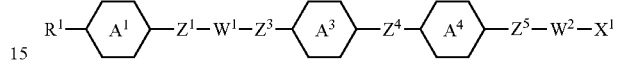

wherein, in formulas (1-1) to (1-8), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$W^1$ is a group represented by formula (1a) or formula (1b);

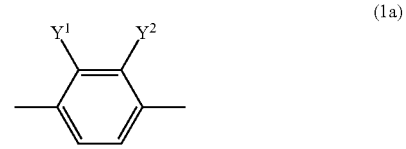
(1a)

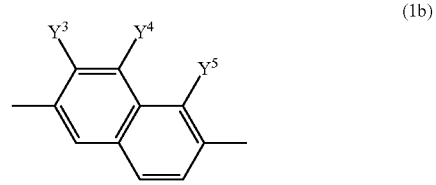
(1b)

wherein, in formula (1a), $Y^1$ and $Y^2$ are fluorine;

in formula (1b), $Y^3$, $Y^4$ and $Y^5$ are independently hydrogen or fluorine, and at least two of $Y^3$, $Y^4$ and $Y^5$ are fluorine; and in formulas (1-1) to (1-8), $W^2$ is a group represented by formula (1c) or formula (1d);

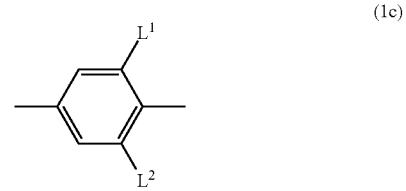
(1c)

-continued (1d)

[Structure 1d: naphthalene with L³, L⁴, L⁵ and two methyl groups]

wherein, in formulas (1c) and (1d),
L¹, L², L³, L⁴ and L⁵ are independently hydrogen or fluorine; and
in formulas (1-1) to (1-8),
Z¹, Z², Z³, Z⁴ and Z⁵ are independently a single bond, —(CH$_2$)$_2$—, —CH$_2$O—, —OCH$_2$—, —(CH$_2$)$_4$—, —(CH$_2$)$_2$CF$_2$O— or —OCH$_2$CF$_2$O—, and at least one of Z¹, Z², Z³, Z⁴ and Z⁵ is —(CH$_2$)$_2$—, —CH$_2$O—, —OCH$_2$—, —(CH$_2$)$_4$—, —(CH$_2$)$_2$CF$_2$O— or —OCH$_2$CF$_2$O—; and
X¹ is fluorine, —CF$_3$, —CHF$_2$, —OCF$_3$ or —OCHF$_2$.

Item 5. The compound according to item 1, represented by any one of formulas (1-9) to (1-22):

(1-9) through (1-20): [chemical structure diagrams]

(1-21)
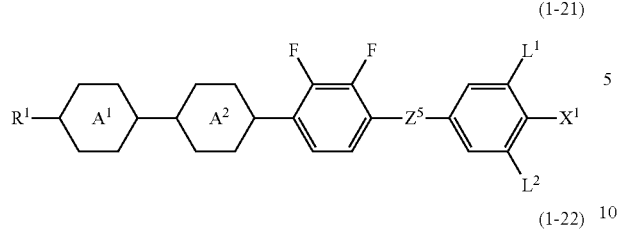

(1-22)
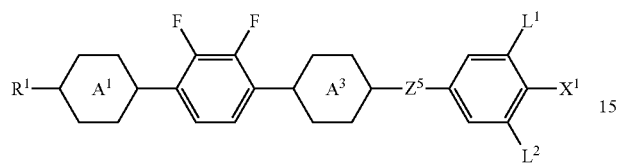

wherein, in formulas (1-9) to (1-22), $R^1$ is alkyl having 1 to 10 carbons or alkenyl having 2 to 10 carbons; ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;

$Z^5$ is —(CH$_2$)$_2$—, —CH$_2$O—, —OCH$_2$—, —(CH$_2$)$_4$—, —(CH$_2$)$_2$CF$_2$O— or —OCH$_2$CF$_2$O—, $X^1$ is fluorine, —CF$_3$ or —OCF$_3$; and $L^1$, $L^2$, $L^3$, $L^4$, $L^5$, $Y^3$ and $Y^5$ are independently hydrogen or fluorine.

Item 6. The compound according to item 1, represented by any one of formulas (1-23) to (1-36):

(1-23)
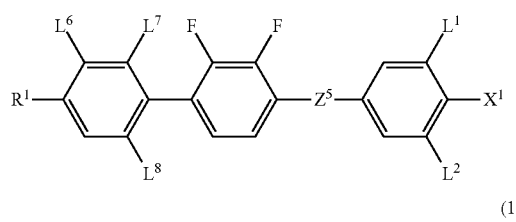

(1-24)

(1-25)
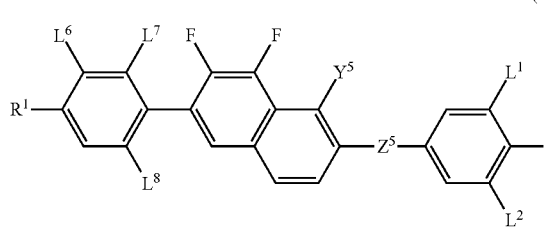

(1-26)
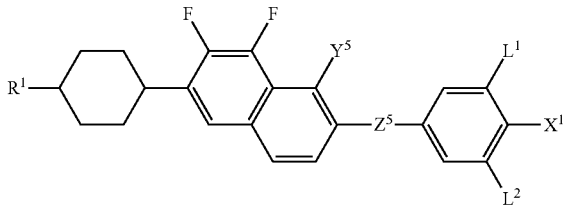

(1-27)
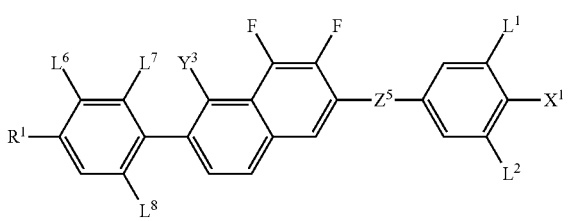

(1-28)
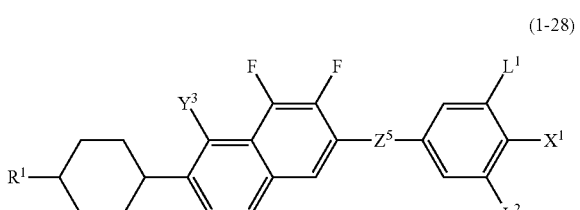

(1-29)
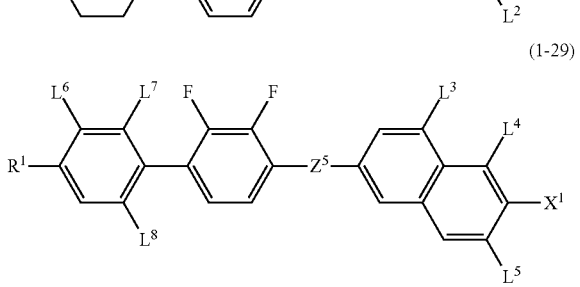

(1-30)
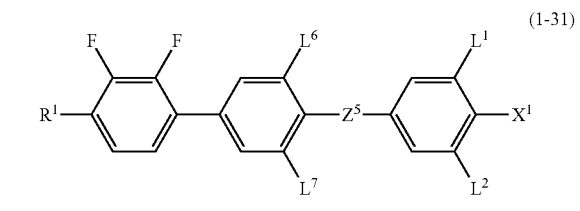

(1-31)

(1-32)

(1-33)
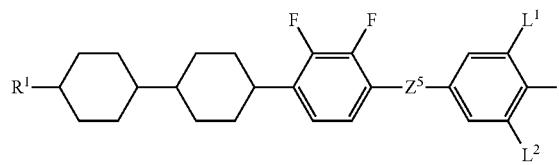
(1-34)
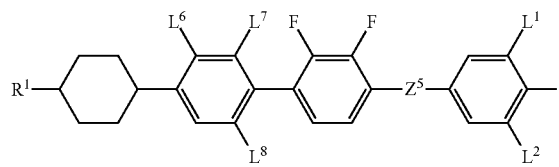
(1-35)
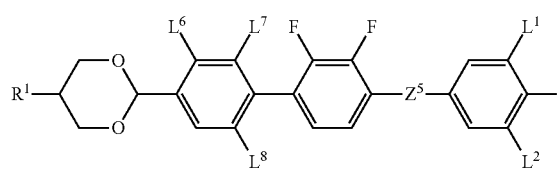
(1-36)
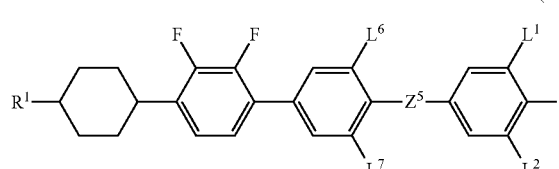
wherein, in formulas (1-23) to (1-36), $R^1$ is alkyl having 1 to 10 carbons or alkenyl having 2 to 10 carbons; $Z^5$ is —(CH$_2$)$_2$—, —OCH$_2$—, —(CH$_2$)$_2$CF$_2$O— or —OCH$_2$CF$_2$O—; $X^1$ is fluorine, —CF$_3$ or —OCF$_3$; and $L^1$, $L^2$, $L^3$, $L^4$, $L^5$, $L^6$, $L^7$, $L^8$, $Y^3$ and $Y^5$ are independently hydrogen or fluorine.
Item 7. The compound according to item 1, represented by any one of formulas (1-37) to (1-48):
(1-37)
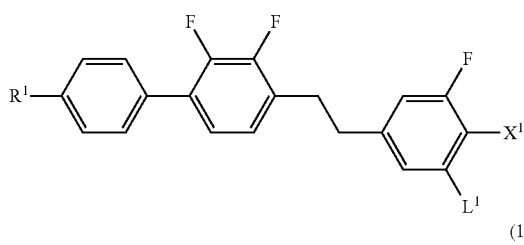
(1-38)
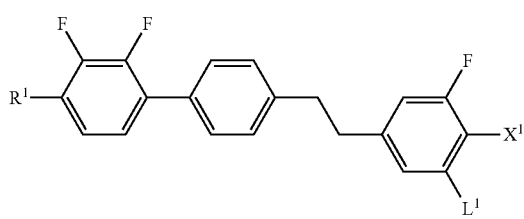
(1-39)
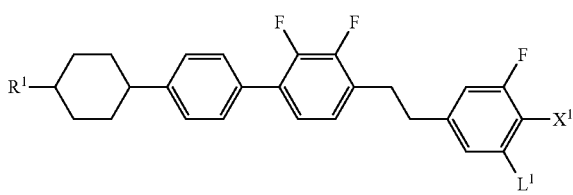
(1-40)
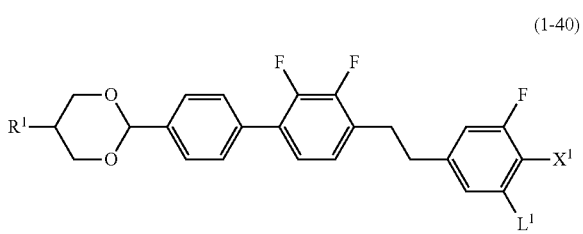
(1-41)
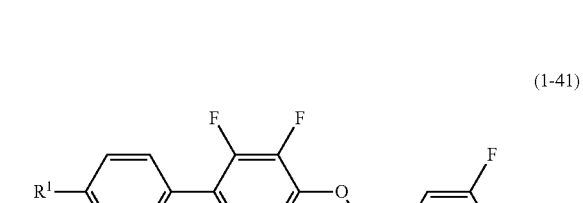
(1-42)
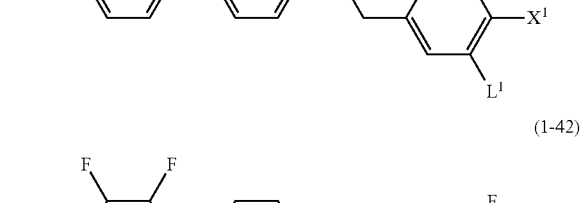
(1-43)
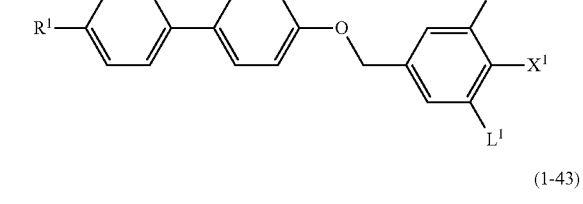
(1-44)
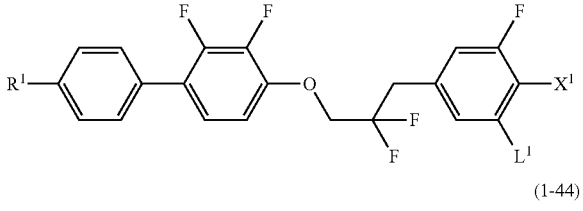
(1-45)
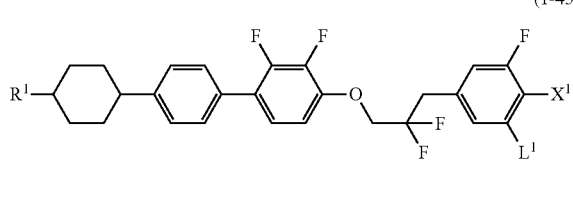

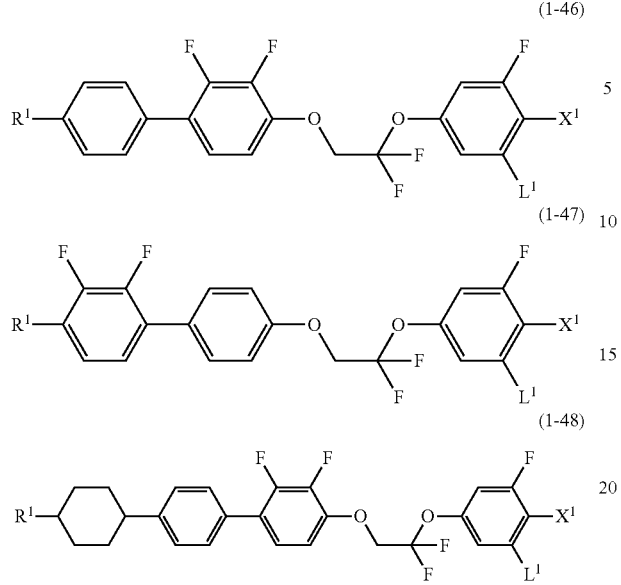

wherein, in formulas (1-37) to (1-48), $R^1$ is alkyl having 1 to 10 carbons or alkenyl having 2 to 10 carbons; $X^1$ is fluorine, —$CF_3$ or —$OCF_3$; and $L^1$ is hydrogen or fluorine.

Item 8. A liquid crystal composition, containing at least one compound according to any one of items 1 to 7.

Item 9. The liquid crystal composition according to item 8, further containing at least one compound selected from the group of compounds represented by formulas (2) to (4):

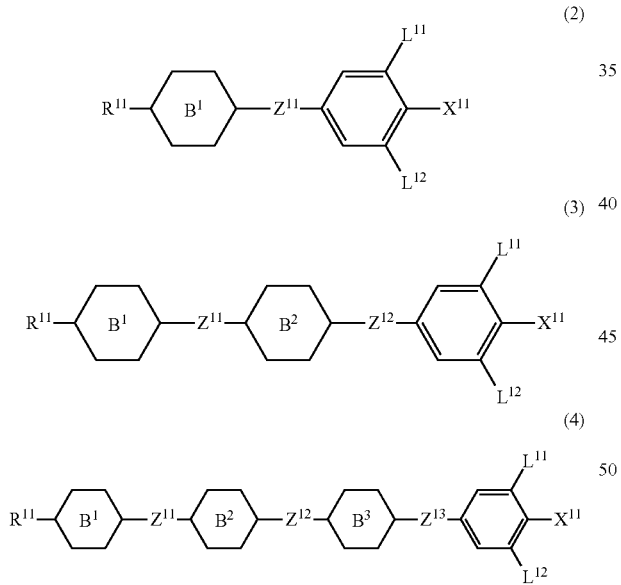

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 10. The liquid crystal composition according to item 8 or 9, further containing at least one compound selected from the group of compounds represented by formula (5):

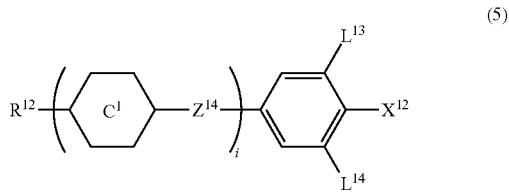

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{12}$ is —C≡N or —C≡C—C≡N;

ring $C^1$ is 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^{14}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 11. The liquid crystal composition according to any one of items 8 to 10, further containing at least one compound selected from the group of compounds represented by formulas (6) to (12):

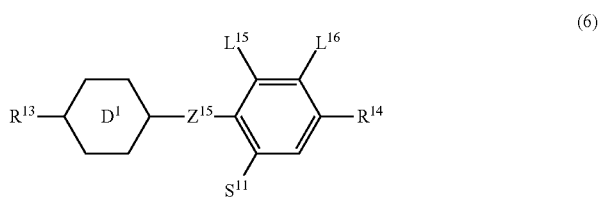
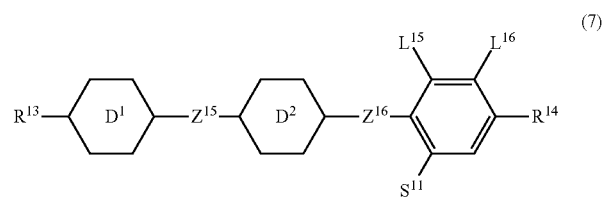

-continued (8)
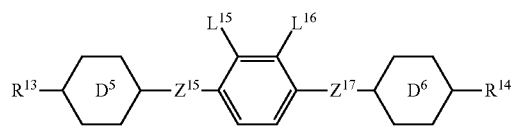

(9)
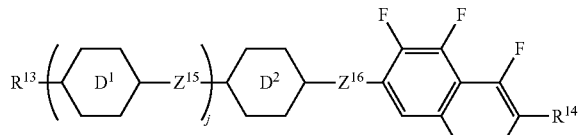

(10)
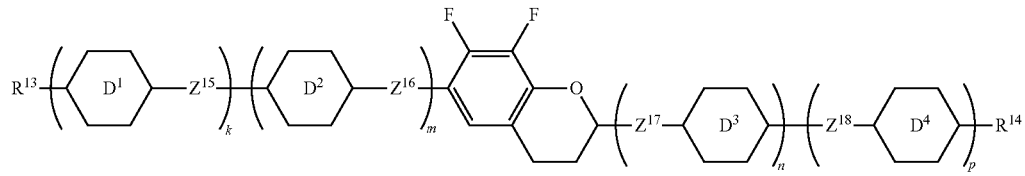

(11)
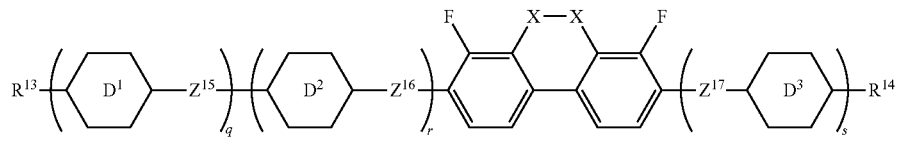

(12)
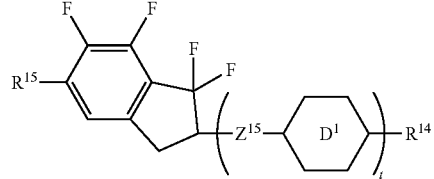

wherein, in formulas (6) to (12),

R$^{13}$ and R$^{14}$ are independently alkyl having 1 to 10 carbons or alkenyl having 2 to 10 carbons, and in the alkyl and the alkenyl, at least one of —CH$_2$— may be replaced by —O—;

R$^{15}$ is hydrogen, fluorine, alkyl having 1 to 10 carbons or alkenyl having 2 to 10 carbons, and in the alkyl and the alkenyl, at least one of —CH$_2$— may be replaced by —O—, at least one of hydrogen may be replaced by fluorine;

S$^{11}$ is hydrogen or methyl;

X is —CF$_2$—, —O— or —CHF—;

ring D$^1$, ring D$^2$, ring D$^3$ and ring D$^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring D$^5$ and ring D$^6$ are independently 1,4-cyclohexylene, 1,4-cyclohexenylene, 1,4-phenylene, tetrahydropyran-2,5-diyl or decahydronaphthalene-2,6-diyl;

Z$^{15}$, Z$^{16}$, Z$^{17}$ and Z$^{18}$ are independently a single bond, —CH$_2$CH$_2$—, —COO—, —CH$_2$O—, —OCF$_2$— or —OCF$_2$CH$_2$CH$_2$—;

L$^{15}$ and L$^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 12. The liquid crystal composition according to any one of items 8 to 11, further containing at least one compound selected from the group of compounds represented by formulas (13) to (15):

(13)
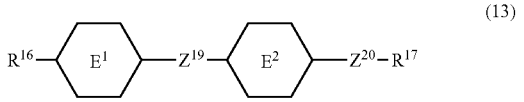

(14)
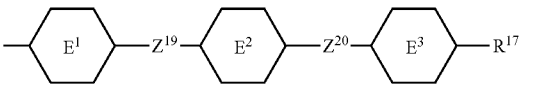

(15)
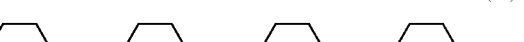

wherein, in formulas (13) to (15),

R$^{16}$ and R$^{17}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;

ring E$^1$, ring E$^2$, ring E$^3$ and ring E$^4$ are independently 1,4-cyclohexylene, 1,4-phenylene, 2-fluoro-1,4-phenylene, 2,5-difluoro-1,4-phenylene or pyrimidine-2,5-diyl; and Z$^{19}$, Z$^{20}$ and Z$^{21}$ are independently a single bond, —CH$_2$CH$_2$—, —CH=CH—, —C≡C— or —COO—.

Item 13. The liquid crystal composition according to any one of items 8 to 12, further containing at least one of a polymerizable compound, an optically active compound, an antioxidant, an ultraviolet light absorber, a light stabilizer, a heat stabilizer and an antifoaming agent.

Item 14. A liquid crystal display device, including the liquid crystal composition according to any one of items 8 to 13.

The compound, the liquid crystal composition and the liquid crystal display device of the invention are described in the order.

1-1. Compound (1)

Compound (1) of the invention has an electron-withdrawing large polar group as a terminal group, and as a ring, 1,4-phenylene in which hydrogen in 2-position and 3-position thereof are replaced by halogen, or naphthalene-2,6-diyl in which at least two of hydrogen in 3-position, 4-position and 5-position thereof are replaced by halogen, and therefore has a feature of having both a large dielectric anisotropy and a large dielectric constant in a minor axis direction. Preferred examples of compound (1) according to the invention are described. Preferred examples of a terminal group, a ring structure, a bonding group and a substituent in compound (1) are also applied to the subordinate formula of formula (1) for compound (1).

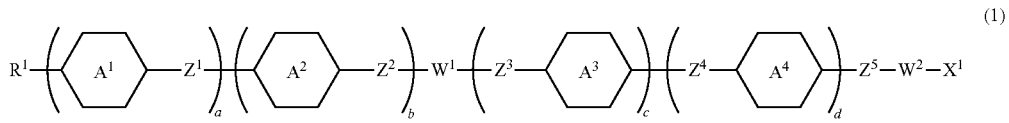

(1)

In formula (1), $R^1$ is alkyl having 1 to 15 carbons, and in the alkyl, at least one of —$CH_2$— may be replaced by —O— or —S—, at least one of —$(CH_2)_2$— may be replaced by —CH=CH—, and in the groups, at least one of hydrogen may be replaced by halogen.

Examples of such a terminal group $R^1$ include alkyl, alkoxy, alkoxyalkyl, alkoxyalkoxy, alkylthio, alkylthioalkoxy, alkenyl, alkenyloxy, alkenyloxyalkyl, alkoxyalkenyl or alkenylthio. In the groups, at least one of hydrogen may be replaced by halogen. Preferred halogen is fluorine or chlorine. Further preferred halogen is fluorine. The groups have a straight chain or a branched chain, and contain no cyclic group such as cyclohexyl. In the groups, the straight chain is preferred to the branched chain.

A preferred configuration of —CH=CH— in the alkenyl depends on a position of a double bond. In alkenyl having the double bond in an odd-numbered position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$, a trans configuration is preferred. In alkenyl having the double bond in an even-numbered position, such as —$CH_2$CH=$CHCH_3$, —$CH_2$CH=$CHC_2H_5$ and —$CH_2$CH=$CHC_3H_7$, a cis configuration is preferred. An alkenyl compound having the preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

Examples of alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$ or —$C_{15}H_{31}$.

Examples of alkoxy include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$, —$OC_{11}H_{23}$, —$OC_{12}H_{25}$, —$OC_{13}H_{27}$ or —$OC_{14}H_{29}$.

Examples of alkoxyalkyl include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ or —$(CH_2)_5$—$OCH_3$.

Examples of alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ or —$(CH_2)_3$—CH=$CH_2$.

Examples of alkenyloxy include —$OCH_2$CH=$CH_2$, —$OCH_2$CH=$CHCH_3$ or —$OCH_2$CH=$CHC_2H_5$.

Examples of alkyl in which at least one of hydrogen is replaced by halogen include —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F, —$(CF_2)_5$—F, —$CH_2Cl$, —$CHCl_2$, —$CCl_3$, —$(CH_2)_2$—Cl, —$CCl_2CH_2Cl$, —$CCl_2CHCl_2$, —$CH_2CCl_3$, —$CCl_2CCl_3$, —$(CH_2)_3$—Cl, —$(CCl_2)_3$—Cl, —$CCl_2CHClCCl_3$, —$CHClCCl_2CCl_3$, —$(CH_2)_4$—Cl, —$(CCl_2)_4$—Cl, —$(CH_2)_5$—Cl or —$(CCl_2)_5$—Cl.

Examples of alkoxy in which at least one of hydrogen is replaced by halogen include —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O$(CH_2)_4$—F, —O—$(CF_2)_4$—F, —O—$(CH_2)_5$—F, —O—$(CF_2)_5$—F, —$OCH_2Cl$, —$OCHCl_2$, —$OCCl_3$, —O—$(CH_2)_2$—Cl, —$OCCl_2CH_2Cl$, —$OCCl_2CHCl_2$, —$OCH_2CCl_3$, —O—$(CH_2)_3$—Cl, —O—$(CCl_2)_3$—Cl, —$OCCl_2CHClCCl_3$, —$OCHClCCl_2CCl_3$, —O$(CH_2)_4$—Cl, —O—$(CCl_2)_4$—Cl, —O—$(CH_2)_5$—Cl or —O—$(CCl_2)_5$—Cl.

Examples of alkenyl in which at least one of hydrogen is replaced by halogen include —CH=CHF, —CH=$CF_2$, —CF=CHF, —CH=$CHCH_2F$, —CH=$CHCF_3$, —$(CH_2)_2$—CH=$CF_2$, —$CH_2$CH=$CHCF_3$, —CH=$CHCF_2CF_3$, —CH=CHCl, —CH=$CCl_2$, —CCl=CHCl, —CH=$CHCH_2Cl$, —CH=$CHCCl_3$, —$(CH_2)_2$—CH=$CCl_2$, —$CH_2$CH=$CHCCl_3$ or —CH=$CHCCl_2CCl_3$.

Preferred examples of $R^1$ include alkyl having 1 to 15 carbons, alkenyl having 2 to 15 carbons or alkoxy having 2 to 15 carbons. Further preferred examples of $R^1$ include alkyl having 1 to 10 carbons or alkenyl having 2 to 10 carbons. Most preferred examples of $R^1$ include —$CH_3$, —$C_2H_5$, —$C_3H_7$, —$C_4H_9$, —$C_6H_{13}$, —$C_7H_{15}$, —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ or —$(CH_2)_3$—CH=$CH_2$.

In formula (1), ring $A^1$, ring $A^2$, ring $A^3$ and ring $A^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and at least one of hydrogen directly bonded to the rings thereof may be replaced by halogen.

Preferred examples of ring $A^1$, ring $A^2$, ring $A^3$ or ring $A^4$ include 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl or naphthalene-2,6-diyl in which at least one of hydrogen is replaced by fluorine. Cis and trans configurations exist in 1,4-cyclohexylene. From a viewpoint of a high maximum temperature, a trans configuration is preferred. Preferred examples of 1,4-phenylene in which at least one of hydrogen is replaced by halogen include rings (A-1) to (A-17).

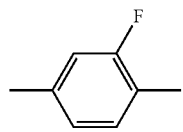
(A-1)

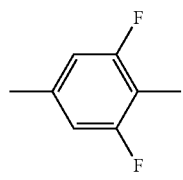
(A-2)

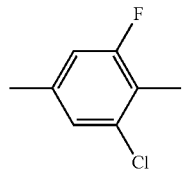
(A-3)

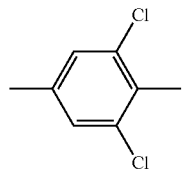
(A-4)

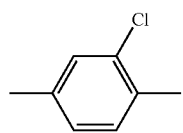
(A-5)

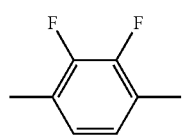
(A-6)

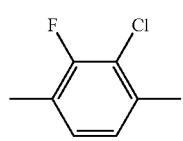
(A-7)

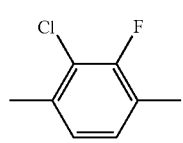
(A-8)

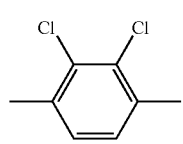
(A-9)

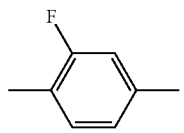
(A-10)

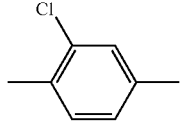
(A-11)

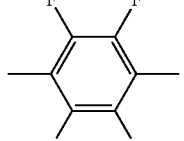
(A-12)

(A-13)

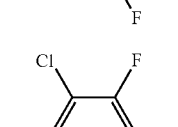
(A-14)

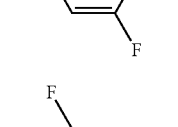
(A-15)

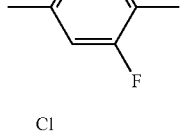
(A-16)

(A-17)

Then, 2-fluoro-1,4-phenylene (A-1) is left-right asymmetrical. In a chemical formula thereof, a case where fluorine is located on a side of a left-terminal group (leftward), and a case where fluorine is located on a side of a right-terminal group side (rightward) exist. Preferred 2-fluoro-1,4-phenylene is rightward (A-1) in order to increase the dielectric anisotropy. A same rule applies to 2,6-difluoro-1,4-phenylene or the like. Rings (A-1) to (A-9) are further preferred.

Further preferred examples of 1,4-phenylene in which at least one of hydrogen is replaced by halogen include 2-fluoro-1,4-phenylene (A-1), 2,6-difluoro-1,4-phenylene (A-2), 2-chloro-6-fluoro-1,4-phenylene (A-3), 2,3-difluoro-1,4-phenylene (A-6) or 2-chloro-3-fluoro-1,4-phenylene (A-7 and A-8). Most preferred examples of 1,4-phenylene in which at least one of hydrogen is replaced by halogen include 2-fluoro-1,4-phenylene (A-1), 2,6-difluoro-1,4-phenylene (A-2) or 2,3-difluoro-1,4-phenylene (A-6).

Then, 1,3-dioxane-2,5-diyl is left-right asymmetrical. A case where —O— is located on a side of a left-terminal group (leftward; A-18) and a case where —O— is located on a side of a right-terminal group (rightward; A-19) exist. Preferred 1,3-dioxane-2,5-diyl is rightward (A-19) in order to increase the dielectric anisotropy. In 2,6,7-trioxabicyclo[2.2.2]octane-1,4-diyl (A-20 and A-21), pyrimidine-2,5-diyl (A-22 and A-23) or pyridine-2,5-diyl (A-24 and A-25), —O— is also preferably rightward (A-21, A-23 and A-25). In tetrahydropyran-2,5-diyl (A-26 and A-27), from a viewpoint of the large dielectric anisotropy, —O— is preferably rightward (A-27), and from a viewpoint of the large dielectric constant in the minor axis direction, —O— is preferably leftward (A-26).

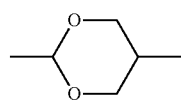 (A-18)

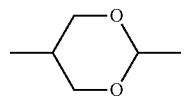 (A-19)

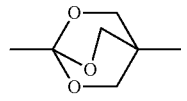 (A-20)

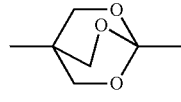 (A-21)

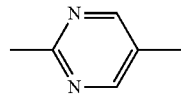 (A-22)

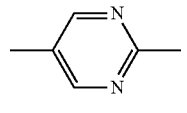 (A-23)

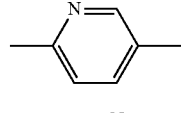 (A-24)

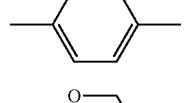 (A-25)

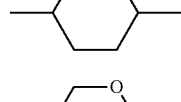 (A-26)

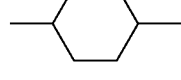 (A-27)

Further preferred examples of ring $A^1$, ring $A^2$, ring $A^3$ or ring $A^4$ include 1,4-cyclohexylene, 1,4-phenylene, 2-fluoro-1,4-phenylene, 2,6-difluoro-1,4-phenylene, tetrahydropyran-2,5-diyl or 1,3-dioxane-2,5-diyl.

In formula (1), $W^1$ is a group represented by formula (1a) or formula (1b).

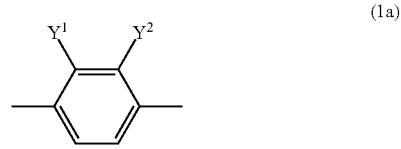 (1a)

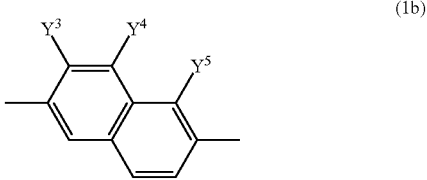 (1b)

In formula (1a), $Y^1$ and $Y^2$ are independently fluorine or chlorine, and in formula (1b), $Y^3$, $Y^4$ and $Y^5$ are independently hydrogen, fluorine or chlorine, and at least two of $Y^3$, $Y^4$ and $Y^5$ is fluorine or chlorine. In formula (1a), preferred examples of $Y^1$ and $Y^2$ include a combination in which both $Y^1$ and $Y^2$ are fluorine or a combination in which one is fluorine and the other is chlorine. Further preferred examples of $Y^1$ and $Y^2$ include a combination in which both $Y^1$ and $Y^2$ are fluorine. In formula (1b), preferred examples of $Y^3$, $Y^4$ and $Y^5$ include a combination in which all of $Y^3$, $Y^4$ and $Y^5$ are fluorine, a combination in which $Y^3$ and $Y^4$ are fluorine and $Y^5$ is hydrogen, a combination in which $Y^4$ and $Y^5$ are fluorine and $Y^3$ is hydrogen, a combination in which $Y^3$ and $Y^4$ are fluorine and $Y^5$ is chlorine or a combination in which $Y^4$ and $Y^5$ are fluorine and $Y^3$ is chlorine. Further preferred examples of $Y^3$, $Y^4$ and $Y^5$ include a combination in which all of $Y^3$, $Y^4$ and $Y^5$ are fluorine or a combination in which $Y^3$ and $Y^4$ are fluorine and $Y^5$ is hydrogen.

In formula (1), $W^2$ is a group represented by formula (1c) or formula (1d).

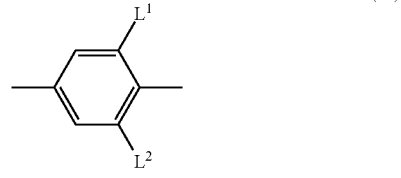 (1c)

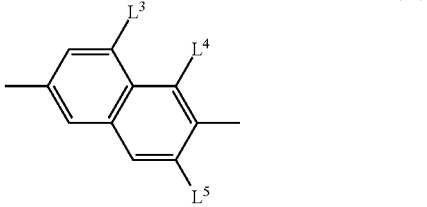 (1d)

In the formula, $L^1$, $L^2$, $L^3$, $L^4$ and $L^5$ are independently hydrogen, fluorine or chlorine. In formula (1c), preferred examples of $L^1$ and $L^2$ include a combination in which both $L^1$ and $L^2$ are fluorine, a combination in which one is fluorine and the other is hydrogen or a combination in which both $L^1$ and $L^2$ are hydrogen. Further preferred examples of $L^1$ and $L^2$ include a combination in which both $L^1$ and $L^2$ are fluorine or a combination in which one is fluorine and the other is hydrogen. In formula (1d), preferred examples of $L^3$, $L^4$ and $L^5$ include a combination in which all of $L^3$, $L^4$ and $L^5$ are fluorine, a combination in which $L^4$ and $L^5$ are fluorine and $L^3$ is hydrogen, a combination in which $L^3$ and $L^4$ are fluorine and $L^5$ is hydrogen, a combination in which $L^4$ is fluorine and both $L^3$ and $L^5$ are hydrogen and a combination in which all of $L^3$, $L^4$ and $L^5$ are hydrogen. Further preferred examples of $L^3$, $L^4$ and $L^5$ include a combination in which all of $L^3$, $L^4$ and $L^5$ are fluorine, a combination in which $L^3$ and $L^4$ are fluorine and $L^5$ is hydrogen or a combination in which $L^4$ is fluorine and both $L^3$ and $L^5$ are hydrogen.

In formula (1), bonding groups $Z^1$, $Z^2$, $Z^3$, $Z^4$ and $Z^5$ are independently a single bond, —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—, and at least one of $Z^1$ when a is 1, $Z^2$ when b is 1, $Z^3$ when c is 1, $Z^4$ when d is 1 and $Z^5$ is —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—. Preferred examples of $Z^1$, $Z^2$, $Z^3$, $Z^4$ or $Z^5$ include a single bond, —(CH$_2$)$_2$—, —CH$_2$O—, —OCH$_2$—, —COO—, —(CH$_2$)$_2$CF$_2$O— or —OCH$_2$CF$_2$O—. Further preferred examples of $Z^1$, $Z^2$, $Z^3$, $Z^4$ and $Z^5$ include a single bond, —(CH$_2$)$_2$—, —(CH$_2$)$_2$CF$_2$O— or —OCH$_2$CF$_2$O—.

In formula (1), terminal group $X^1$ is fluorine, —C≡N, —N=C=S, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine. When $Z^5$ is —COO—, ring $W^1$ is a group represented by formula (1a) and also ring $W^2$ is a group represented by formula (1c), $X^1$ is fluorine, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine.

Examples of alkyl in which at least one of hydrogen is replaced by fluorine include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_2$—CF$_3$, —CF$_2$CHFCF$_3$, —CHFCF$_2$CF$_3$, —(CH$_2$)$_4$—F, —(CF$_2$)$_3$—CF$_3$, —(CH$_2$)$_5$—F or —(CF$_2$)$_4$—CF$_3$.

Examples of alkoxy in which at least one of hydrogen is replaced by fluorine include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_2$—CF$_3$, —OCF$_2$CHFCF$_3$, —OCHFCF$_2$CF$_3$, —O—(CH$_2$)$_4$—F, —O—(CF$_2$)$_3$—CF$_3$, —O—(CH$_2$)$_5$—F or —O—(CF$_2$)$_4$—CF$_3$.

Examples of alkenyl in which at least one of hydrogen is replaced by fluorine include —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$.

Preferred examples of $X^1$ include fluorine, —C≡N, —N=C=S, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F; —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$.

Further preferred examples of $X^1$ include fluorine, —C≡N, —CHF$_2$, —CF$_3$, —OCHF$_2$, —OCF$_3$, —CH=CHCF$_3$, —CF=CHCF$_3$ or —CF=CFCF$_3$. Most preferred examples of $X^1$ include fluorine, —CF$_3$ or —OCF$_3$.

In formula (1), a, b, c and d are independently 0 or 1, and a sum of a, b, c and d is 0, 1, 2 or 3. Preferred combinations of a, b, c and d include combinations: (a=b=c=d=0), (a=1, b=c=d=0), (c=1, a=b=d=0), (a=b=1, c=d=0), (a=c=1, b=d=0) or (c=d=1, a=b=0). Further preferred combinations of a, b, c and d include combinations: (a=1, b=c=d=0), (a=b=1, c=d=0) or (a=c=1, b=d=0).

1-2. Physical Properties of Compound (1)

In compound (1), physical properties such as a clearing point, optical anisotropy and dielectric anisotropy can be arbitrarily adjusted by suitably selecting kinds of $R^1$, ring $A^1$ to ring $A^4$, $W^1$, $W^2$, $L^1$ to $L^5$, $Y^1$ to $Y^5$, $Z^1$ to $Z^5$ and $X^1$, and a combination of a, b, c and d. Compound (1) may contain an isotope such as $^2$H (deuterium) and $^{13}$C in an amount larger than an amount of natural abundance because no significant difference is in the physical properties of the compound. A main effect of kinds of $R^1$ or the like on the physical properties of compound (1) is described below.

When left-terminal group $R^1$ has a straight chain, the temperature range of the liquid crystal phase is wide and viscosity is small. When $R^1$ has a branched chain, the compatibility with other liquid crystal compounds is good. A compound in which $R^1$ is optically active is useful as a chiral dopant. A reverse twisted domain to be generated in the liquid crystal display device can be prevented by adding the compound to the composition. A compound in which $R^1$ is not an optically active is useful as a component of the composition. When $R^1$ is alkenyl, a preferred configuration depends on a position of a double bond. An alkenyl compound having the preferred configuration has the small viscosity, the high maximum temperature or the wide temperature range of the liquid crystal phase. When $R^1$ is alkoxy, the alkenyl compound has the high maximum temperature.

When all of ring $A^1$ to ring $A^4$ are 1,4-cyclohexylene, the clearing point is high and the viscosity is small. When at least one of ring $A^1$ to ring $A^4$ is 1,4-phenylene, or 1,4-phenylene in which at least one of hydrogen is replaced by halogen, the optical anisotropy is comparatively large and the orientational order parameter is comparatively large. When all of ring $A^1$ to ring $A^4$ are 1,4-phenylene, 1,4-phenylene in which at least one of hydrogen is replaced by halogen, pyrimidine-2,5-diyl, pyridine-2,5-diyl or the combination thereof, the optical anisotropy is particularly large. When at least one of ring $A^1$ to ring $A^4$ is 2-fluoro-1,4-phenylene, 2-chloro-1,4-phenylene, 2,6-difluoro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl, the dielectric anisotropy is large. When at least one of ring $A^1$ to ring $A^4$ is 2, 3-difluoro-1,4-phenylene, 2,3-dichloro-1,4-phenylene, 2-chloro-3-fluoro-1,4-phenylene, tetrahydropyran-2,5-diyl or 1,3-dioxane-2,5-diyl, the dielectric constant in the minor axis direction is large.

When $W^1$ is a group represented by formula (1a) and both $Y^1$ and $Y^2$ are fluorine, the clearing point is high and chemical stability is high. When $W^1$ is a group represented by formula (1b), the optical anisotropy is large. When $W^1$ is a group represented by formula (1b) and all of $Y^3$, $Y^4$ and $Y^5$ are fluorine, the dielectric constant in the minor axis direction is particularly large.

When $W^2$ is a group represented by formula (1c) and both $L^1$ and $L^2$ are hydrogen, the clearing point is high. When $W^2$ is a group represented by formula (1c) and either $L^1$ or $L^2$ is fluorine, the dielectric anisotropy is comparatively large, the dielectric constant in the minor axis direction is large and the compatibility with other liquid crystal compounds is good. When $W^2$ is a group represented by formula (1c) and both $L^1$ and $L^2$ are fluorine, the dielectric anisotropy is particularly large. When $W^1$ is a group represented by formula (1d), the optical anisotropy is large. When $W^1$ is a group represented by formula (1d) and all of $L^3$, $L^4$ and $L^5$ are fluorine, the dielectric anisotropy is significantly large.

When bonding groups $Z^1$ to $Z^5$ are a single bond or —$CH_2CH_2$—, the viscosity is small. When $Z^1$ to $Z^5$ are —$(CH_2)_4$—, —$(CH_2)_2CF_2O$—, —$OCH_2CF_2O$—, —$(CH_2)_3O$—, —$O(CH_2)_3$— or —$(CH_2)_2COO$—, the elastic constant (K) is large. When $Z^1$ to $Z^5$ are —COO— or —OCO—, the clearing point is high. When $Z^1$ to $Z^5$ are —COO—, —$(CH_2)_2CF_2O$—, —$OCH_2CF_2O$— or —$(CH_2)_2COO$—, the dielectric anisotropy is large. When $Z^1$ to $Z^5$ are —$OCH_2$—, —$OCH_2CF_2O$— or —$O(CH_2)_3$—, the dielectric constant in the minor axis direction is large. When $Z^1$ to $Z^5$ are a single bond, —$(CH_2)_2$— or —$(CH_2)_4$—, chemical stability is high.

When $X^1$ is fluorine, —C≡N, —N=C=S, —$CF_3$, —CF=CHF, —CH=CHCF$_3$, —CF=CHCF$_3$ or —CF=CFCF3, the dielectric anisotropy is particularly large. When $X^1$ is —C≡N, —N=C=S, —CH=CHF, —CH=CF$_2$, —CF=CHF, —CF=CF$_2$, —CH=CHCH$_2$F, —CH=CHCF$_3$, —CF=CHCF$_3$ or —CF=CFCF$_3$, the clearing point is high and the optical anisotropy is large. When $X^1$ is fluorine, —$OCH_2F$, —$OCHF_2$ or —$OCF_3$, the compatibility with other liquid crystal compounds is good. When $X^1$ is fluorine, —$CF_3$, —$CF_2CF_3$, —$(CF_2)_3$—F, —$(CF_2)_4$—F, —$(CF_2)_5$—F, —$(CF_2)_6$—F, —$(CF_2)_7$—F, —$OCF_3$, —$OCF_2CF_3$, —O—$(CF_2)_3$—F, —O—$(CF_2)_4$—F, —O—$(CF_2)_5$—F or —O—$(CF_2)_6$—F, chemical stability is high.

When the combination of a, b, c and d includes a combination: (a=b=c=d=0), the compatibility with other liquid crystal compounds is good and the viscosity is small. When the combination includes a combination: (a=1, b=c=d=0), or when the combination includes a combination: (c=1, a=b=d=0), the compatibility with other liquid crystal compounds is good, the dielectric anisotropy is large and the dielectric constant in the minor axis direction is particularly large. When the combination includes a combination: (a=b=1, c=d=0), the clearing point is high, the dielectric anisotropy is large and the dielectric constant in the minor axis direction is large. When the combination includes a combination: (a=c=1, b=d=0), the dielectric anisotropy is large and the compatibility with other liquid crystal compounds is good. When the combination includes a combination: (a=b=c=1, d=0), or a combination: (a=1, b=c=d=0), the clearing point is particularly high and the dielectric anisotropy is large.

As described above, a compound having objective physical properties can be obtained by suitably selecting kinds of ring structure, terminal group and bonding group. Accordingly, compound (1) is useful as the component of the liquid crystal composition to be used for the liquid crystal display device having a mode such as a PC, TN, STN, ECB, OCB, IPS, FES and VA.

1-3. Preferred Compound

Preferred examples of compound (1) include compounds represented by formulas (1-1) to (1-8).

(1-1)

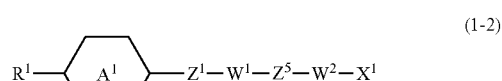

(1-2)

(1-3)

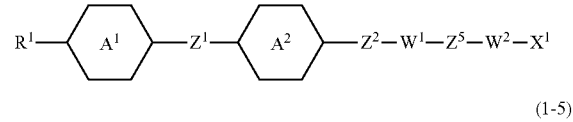

(1-4)

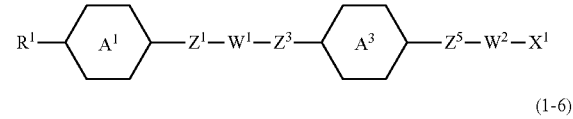

(1-5)


(1-6)

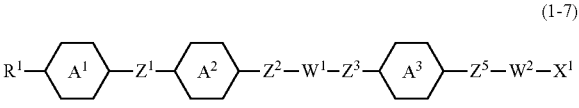

(1-7)

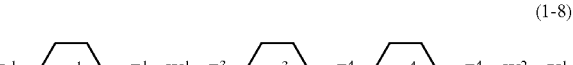

(1-8)

In formulas (1-1) to (1-8), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl, or 1,3-dioxane-2,5-diyl, naphthalene-2,6-diyl, or naphthalene-2,6-diyl in which at least one of hydrogen is replaced by fluorine;

$W^1$ is a group represented by formula (1a) or formula (1b);

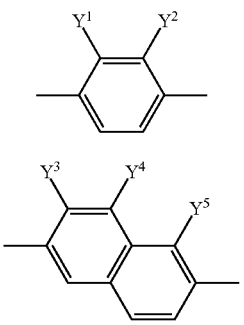
(1a)

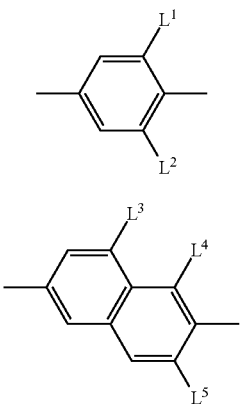
(1b)

wherein, in formula (1a),
Y$^1$ and Y$^2$ are fluorine,
in formula (1b),
Y$^3$, Y$^4$ and Y$^5$ are independently hydrogen or fluorine, and at least two of Y$^3$, Y$^4$ and Y$^5$ are fluorine; and
in formulas (1-1) to (1-8),
W$^2$ is a group represented by formula (1c) or formula (1d);

(1c)

(1d)

wherein, in formula (1c) and (1d),
L$^1$, L$^2$, L$^3$, L$^4$, and L$^5$ are independently hydrogen or fluorine;
in formulas (1-1) to (1-8),
Z$^1$, Z$^2$, Z$^3$, Z$^4$ and Z$^5$ are independently a single bond, —(CH$_2$)$_2$—, —CH$_2$O—, —OCH$_2$—, —(CH$_2$)$_4$—, —(CH$_2$)$_2$CF$_2$O— or —OCH$_2$CF$_2$O—, and at least one of Z$^1$, Z$^2$, Z$^3$, Z$^4$ and Z$^5$ is —(CH$_2$)$_2$—, —CH$_2$O—, —OCH$_2$—, —(CH$_2$)$_4$—, —(CH$_2$)$_2$CF$_2$O— or —OCH$_2$CF$_2$O—; and
X$^1$ is fluorine, —CF$_3$, —CHF$_2$, —OCF$_3$ or —OCHF$_2$.

Further preferred examples of compound (1) include compounds represented by formulas (1-9) to (1-22).

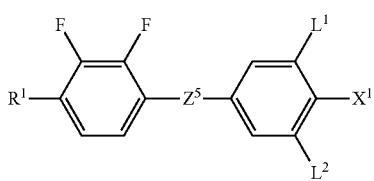
(1-9)

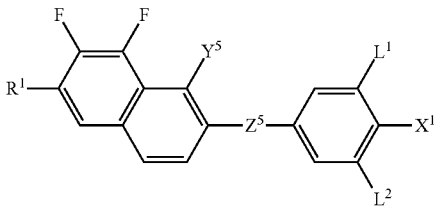
(1-10)

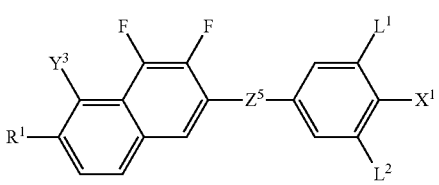
(1-11)

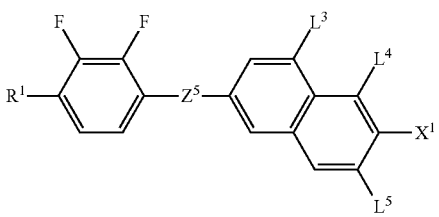
(1-12)

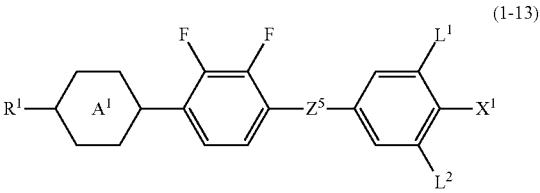
(1-13)

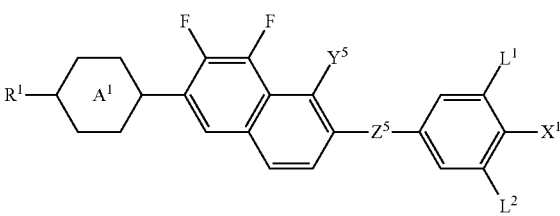
(1-14)

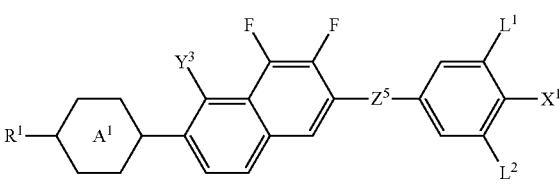
(1-15)

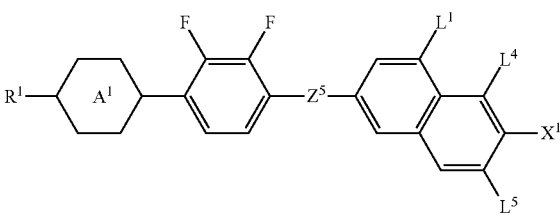
(1-16)

-continued (1-17)
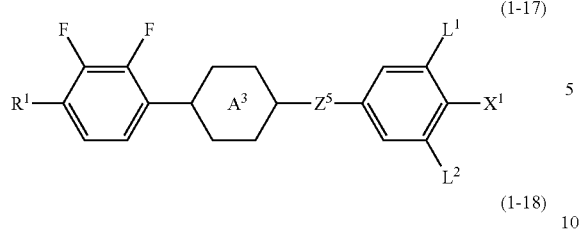

(1-18)
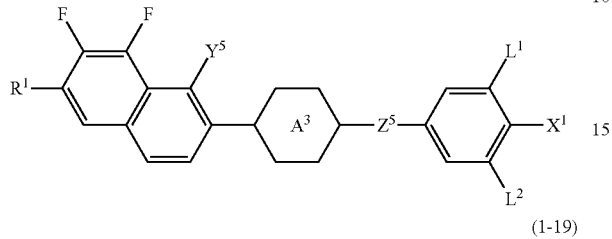

(1-19)
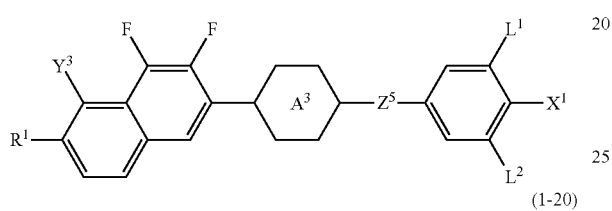

(1-20)
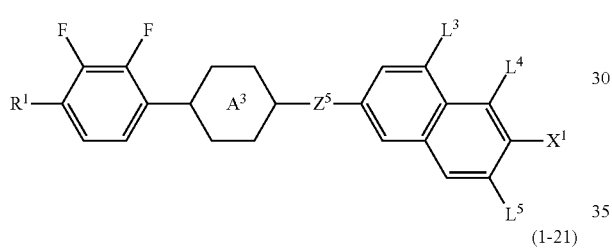

(1-21)
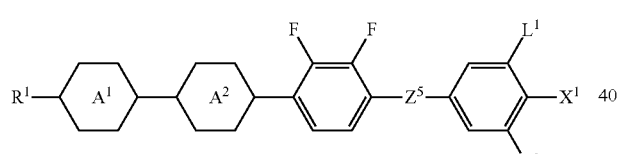

(1-22)
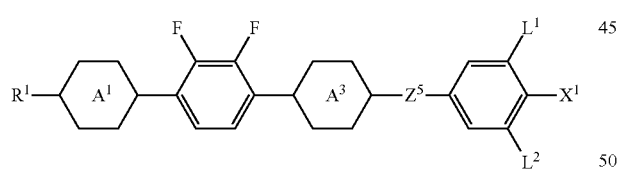

In formulas (1-9) to (1-22),
R$^1$ is alkyl having 1 to 10 carbons or alkenyl having 2 to 10 carbons;
ring A$^1$, ring A$^2$ and ring A$^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;
Z$^5$ is —(CH$_2$)$_2$—, —CH$_2$O—, —OCH$_2$—, —(CH$_2$)$_4$—, —(CH$_2$)$_2$CF$_2$O— or —OCH$_2$CF$_2$O—,
X$^1$ is fluorine, —CF$_3$ or —OCF$_3$; and
L$^1$, L$^2$, L$^3$, L$^4$, L$^5$, Y$^3$ and Y$^5$ are independently hydrogen or fluorine.

Still further preferred examples of compound (1) include compounds represented by formulas (1-23) to (1-36).

(1-23)
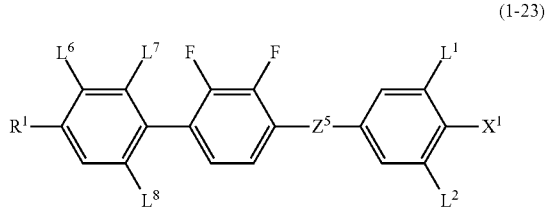

(1-24)
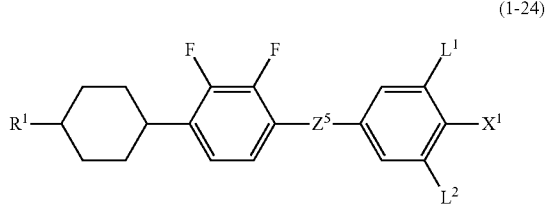

(1-25)
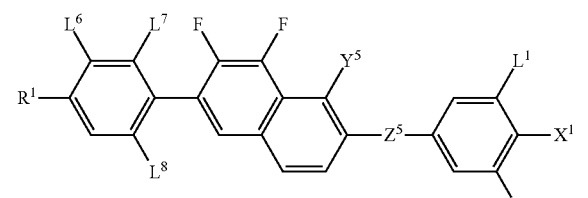

(1-26)
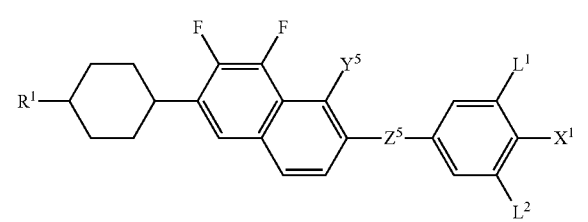

(1-27)
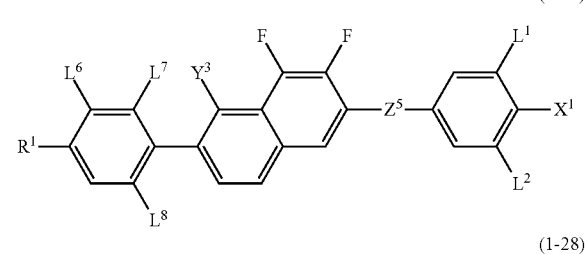

(1-28)
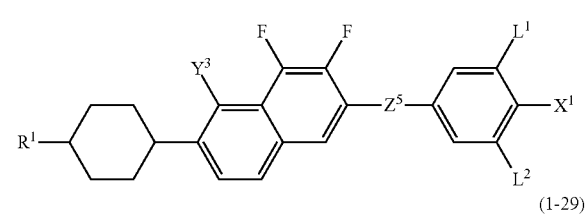

(1-29)
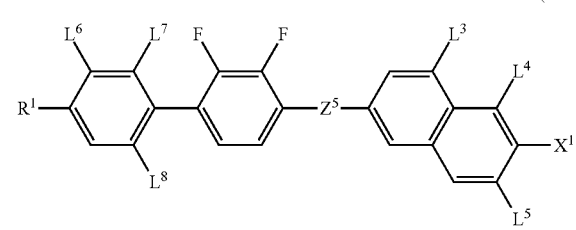

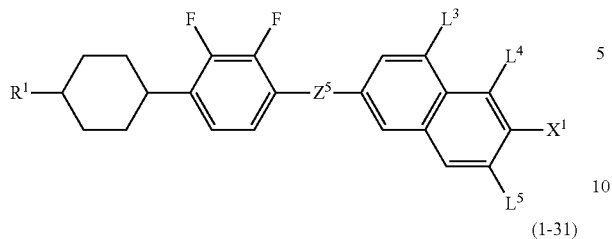
(1-30)
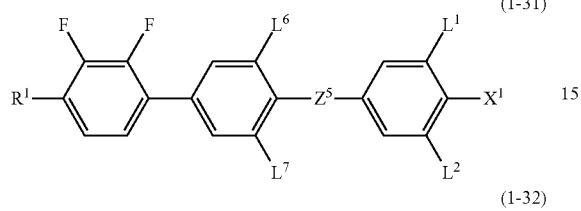
(1-31)
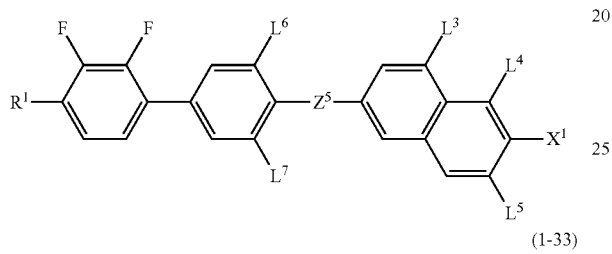
(1-32)
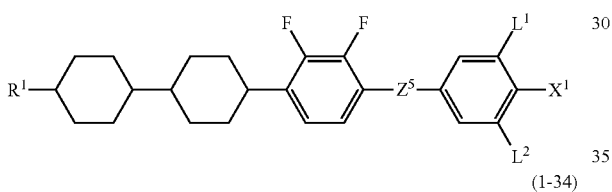
(1-33)
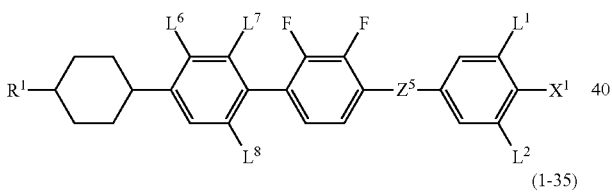
(1-34)
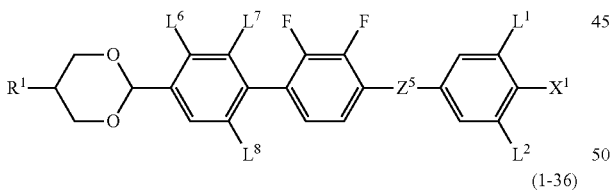
(1-35)
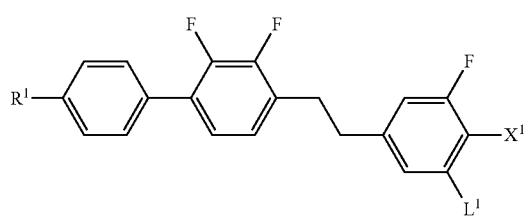
(1-36)
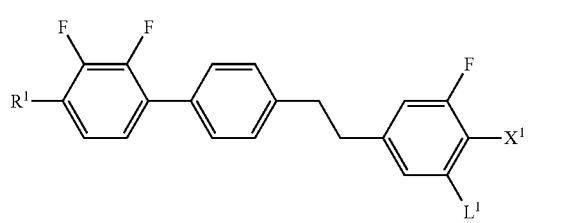
(1-37)
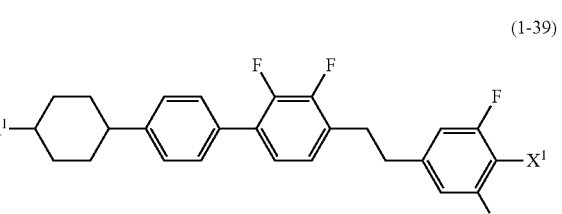
(1-38)
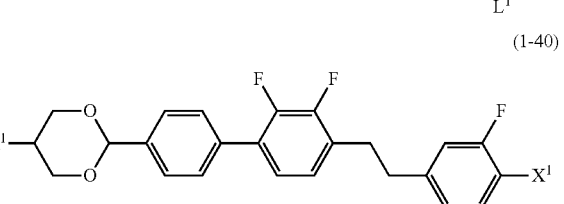
(1-39)
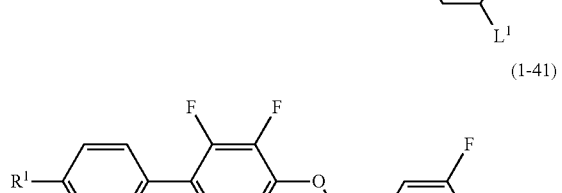
(1-40)
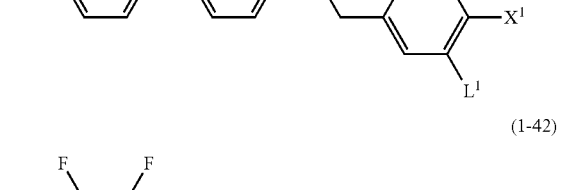
(1-41)
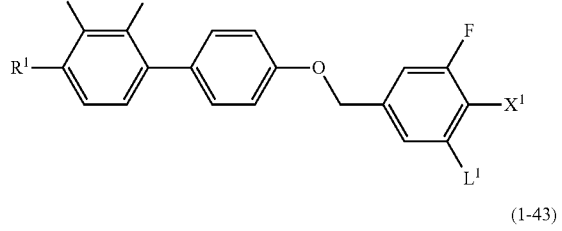
(1-42)
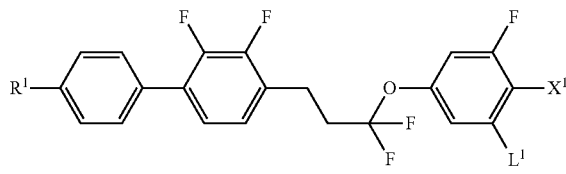
(1-43)
In formulas (1-23) to (1-36), $R^1$ is alkyl having 1 to 10 carbons or alkenyl having 2 to 10 carbons; $Z^5$ is —(CH$_2$)$_2$—, —OCH$_2$—, —(CH$_2$)$_2$CF$_2$O— or —OCH$_2$CF$_2$O—; $X^1$ is fluorine, —CF$_3$ or —OCF$_3$; and $L^1$, $L^2$, $L^3$, $L^4$, $L^5$, $L^6$, $L^7$, $L^8$, $Y^3$ and $Y^5$ are independently hydrogen or fluorine.
Most preferred examples of compound (1) include compounds represented by formulas (1-37) to (1-48).

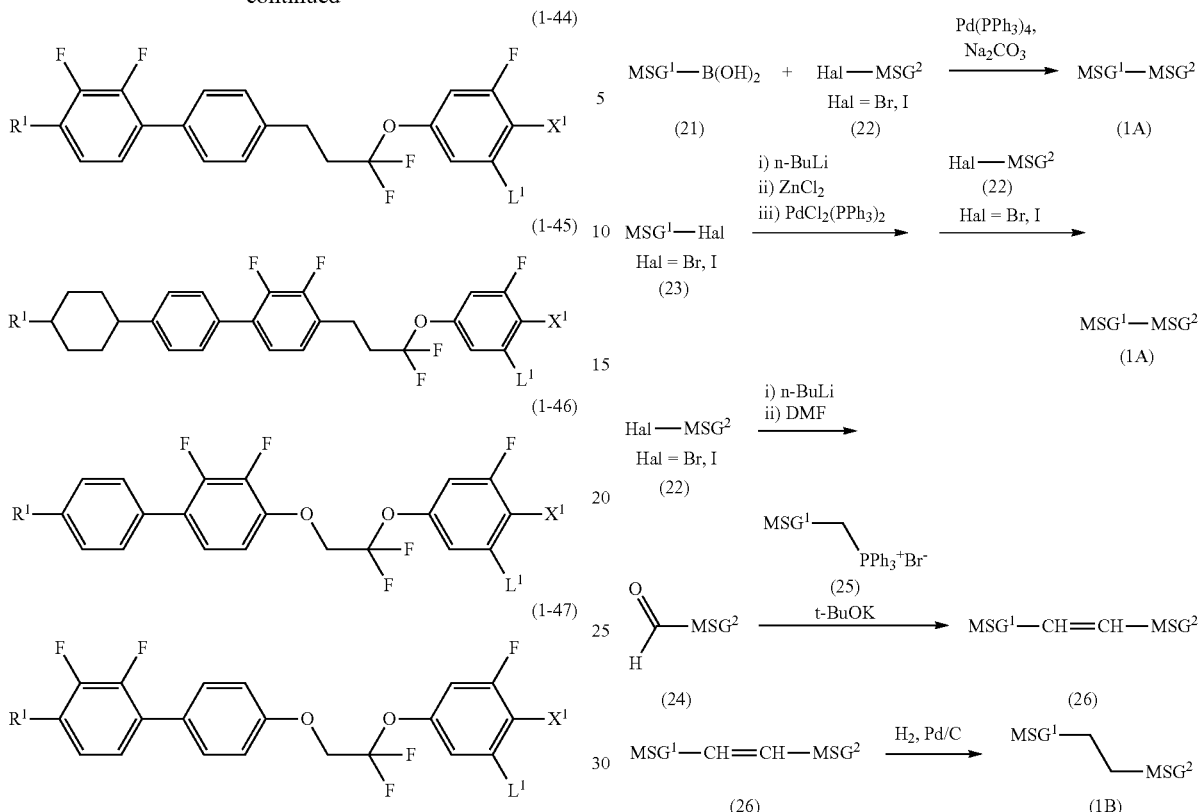

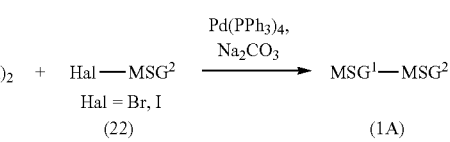

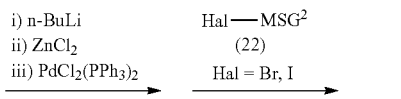

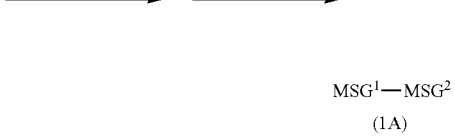


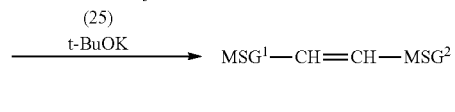

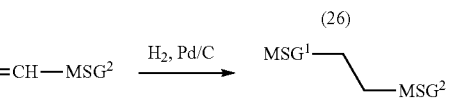

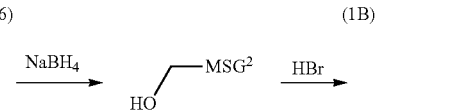


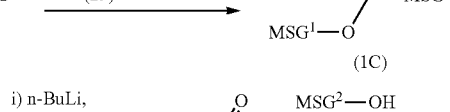


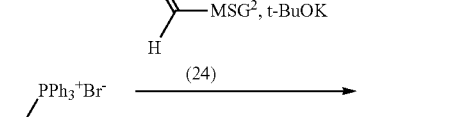

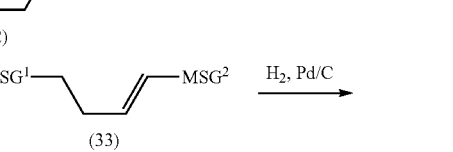

In formulas (1-37) to (1-48), $R^1$ is alkyl having 1 to 10 carbons or alkenyl having 2 to 10 carbons; $X^1$ is fluorine, —$CF_3$ or —$OCF_3$; and $L^1$ is hydrogen or fluorine.

1-4. Synthesis of Compound (1)

A method for preparing compound (1) will be described. Compound (1) can be prepared by suitably combining methods in synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

1-4-1. Formation of a Bonding Group

An example of a method for forming a bonding group in compound (1) is as described in the scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1G) correspond to compound (1) or an intermediate of compound (1).

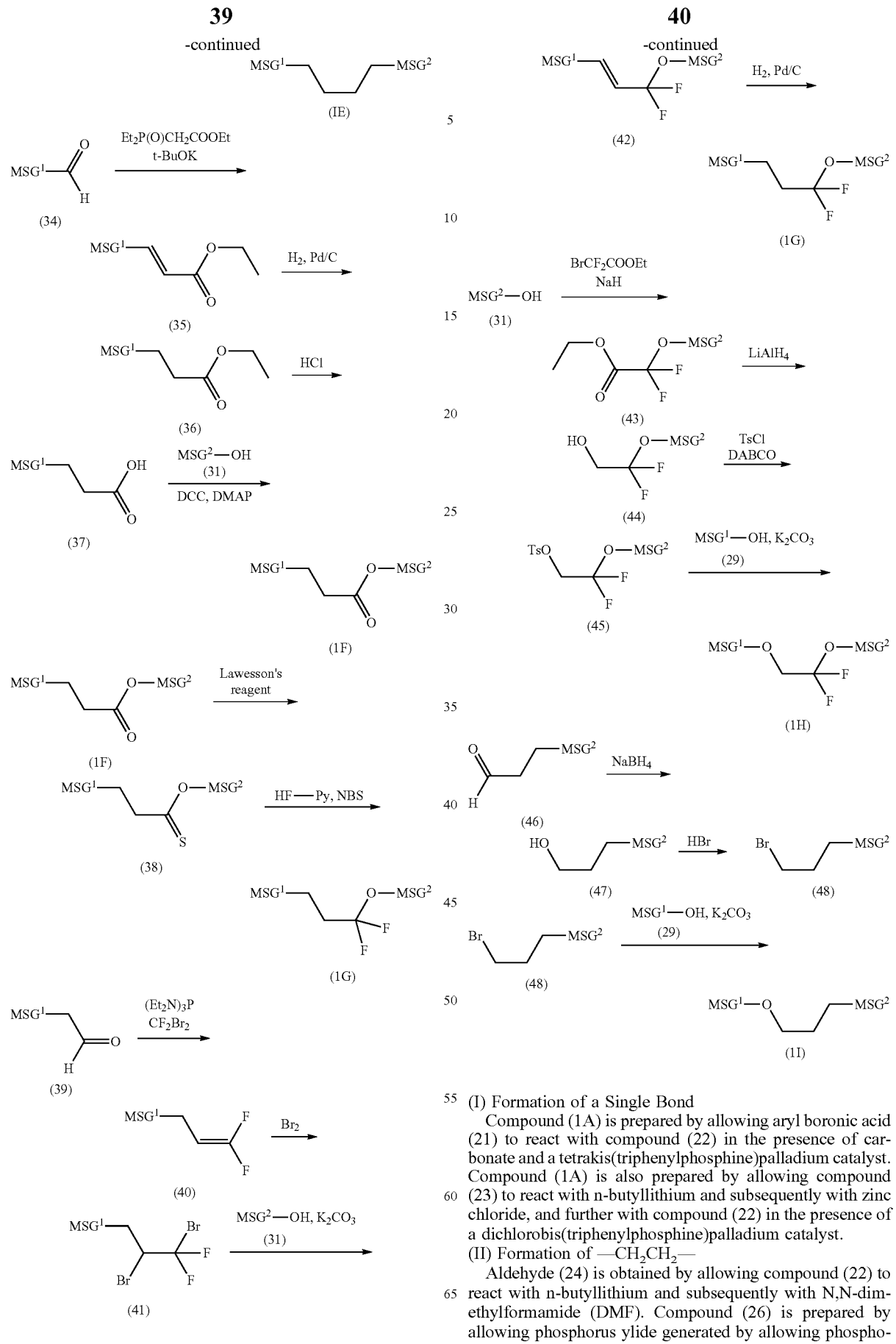

(I) Formation of a Single Bond

Compound (1A) is prepared by allowing aryl boronic acid (21) to react with compound (22) in the presence of carbonate and a tetrakis(triphenylphosphine)palladium catalyst. Compound (1A) is also prepared by allowing compound (23) to react with n-butyllithium and subsequently with zinc chloride, and further with compound (22) in the presence of a dichlorobis(triphenylphosphine)palladium catalyst.

(II) Formation of —CH$_2$CH$_2$—

Aldehyde (24) is obtained by allowing compound (22) to react with n-butyllithium and subsequently with N,N-dimethylformamide (DMF). Compound (26) is prepared by allowing phosphorus ylide generated by allowing phosphonium salt (25) to react with potassium tert-butoxide to react with aldehyde (24). Compound (1B) is prepared by hydrogenating compound (26) in the presence of a palladium on carbon catalyst.

(III) Formation of —OCH$_2$— and —CH$_2$O—

Compound (27) is obtained by reducing compound (24) by sodium borohydride. Compound (28) is obtained by brominating the resulting product with hydrobromic acid. Compound (1C) is prepared by allowing compound (28) to react with compound (29) in the presence of potassium carbonate. A compound having —CH$_2$O— is also prepared according to the method.

(IV) Formation of —COO— and —OCO—

Carboxylic acid (30) is obtained by allowing compound (23) to react with n-butyllithium and subsequently with carbon dioxide. Compound (1D) having —COO— is prepared by dehydrating carboxylic acid (30) and phenol (31) in the presence of 1,3-dicyclohexylcarbodiimide (DCC) and 4-dimethylaminopyridine (DMAP). A compound having —OCO— is also prepared according to the method.

(V) Formation of —(CH$_2$)$_4$—

Compound (1E) is prepared using phosphonium salt (32) according to the method in section (II).

(VI) Formation of —(CH$_2$)$_2$COO—

Compound (35) is obtained by acting ethyl triethylphosphonoacetate and potassium tert-butoxide on aldehyde (34). Compound (36) is obtained by hydrogenating compound (35) in the presence of a palladium on carbon catalyst, and then carboxylic acid (37) is obtained by hydrolyzing compound (36). Compound (1F) is prepared by dehydrating carboxylic acid (37) and phenol (31) in the presence of DCC and DMAP.

(VII) Formation of —(CH$_2$)$_2$CF$_2$O—

Compound (38) is obtained by thionating compound (1F) with a Lawesson's reagent. Compound (1G) having —(CH$_2$)$_2$CF$_2$O— is prepared by fluorinating compound (38) with a hydrogen fluoride pyridine complex and N-bromosuccinimide (NBS). Compound (1G) is also prepared by sequentially performing difluoromethylation, bromination, etherification and hydrogenation to compound (39).

(VIII) Formation of —OCH$_2$CF$_2$O—

Compound (43) is obtained by etherifying phenol (31) and ethyl bromodifluoroacetate in the presence of NaH. Next, alcohol (44) is obtained by reducing compound (43) with lithium aluminum hydride. Compound (45) is obtained by tosylating alcohol (44) using p-toluenesulfonyl chloride and 1,4-diazabicyclo[2.2.2]octane (DABCO), and then compound (1H) is prepared by allowing compound (29) to react with compound (45) in the presence of potassium carbonate.

(IX) Formation of —O(CH$_2$)$_3$— and —(CH$_2$)$_3$O—

Compound (1I) is prepared using aldehyde (46) according to the method in section (III). A compound having —(CH$_2$)$_3$O— is also prepared according to the method.

1-4-2. Formation of Ring A$^1$ and Ring A$^2$

With regard to a ring such as 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl and pyridine-2,5-diyl, a starting material thereof is commercially available or a synthetic method thereof is well known.

1-4-3. Synthesis Examples

An example of a method for preparing compound (1) is as described below. In the compounds, R$^1$, ring A$^1$ to ring A$^4$, Z$^1$ to Z$^5$, L$^1$, L$^2$, Y$^1$, Y$^2$, a, b, c and d are defined in a manner identical with the definitions in item 1 described above.

In compound (1), compound (1-51) in which Z$^5$ is —CH$_2$CH$_2$— can be prepared according to the method described below. Compound (53) is prepared by allowing phosphorus ylide generated by allowing compound (52) to be prepared according to a publicly known method to react with potassium tert-butoxide to react with compound (51) to be prepared according to a publicly known method. Compound (1-51) can be derived from compound (53) by hydrogenating in the presence of a palladium on carbon catalyst.

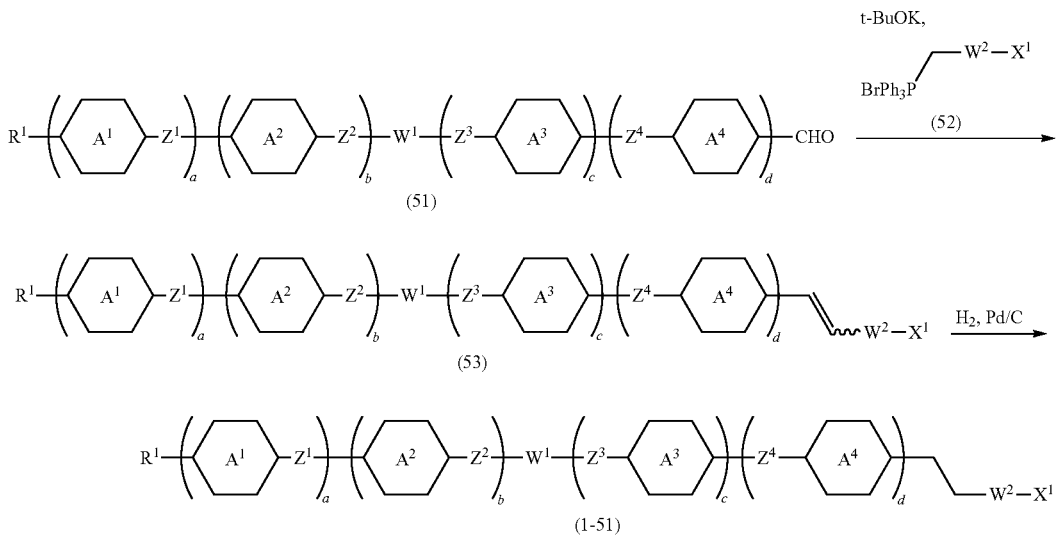

In compound (1), compound (1-52) in which Z$^5$ is —OCH$_2$— can be prepared according to the method described below. Compound (1-52) can be derived from compound (54) to be prepared according to a publicly known method by allowing compound (55) to be prepared according to a publicly known method to react in the presence of potassium carbonate.

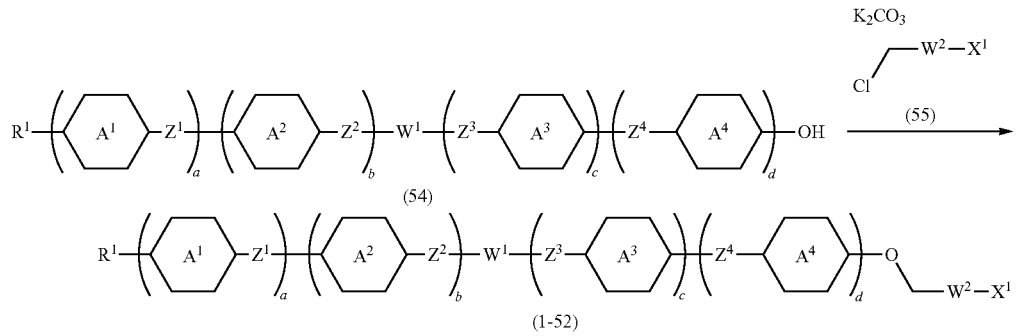

In compound (1), compound (1-53) in which $Z^5$ is —$(CH_2)_2CF_2O$— can be prepared according to the method described below. Compound (57) is obtained by acting trisdiethylamino phosphine and dibromodifluoromethane on compound (56) to be prepared according to a publicly known method. Next, compound (58) is obtained by acting bromine on compound (57), and then compound (60) is obtained by allowing compound (59) to be prepared according to a publicly known method to react with compound (58) in the presence of potassium carbonate. Compound (1-53) can be derived from compound (60) by hydrogenating in the presence of a palladium on carbon catalyst.

In compound (1), compound (1-54) in which $Z^5$ is —$OCH_2CF_2O$— can be prepared according to the method described below. Compound (62) is obtained by acting sodium hydride and ethyl bromodifluoroacetate on compound (61) to be prepared according to a publicly known method. Next, compound (63) is obtained by acting lithium aluminum hydride on compound (62), and then compound (64) is obtained by acting P-toluenesulfonyl chloride and DABCO on compound (63). Compound (1-54) can be derived from compound (65) to be prepared according to a publicly known method by allowing compound (64) to react in the presence of potassium carbonate.

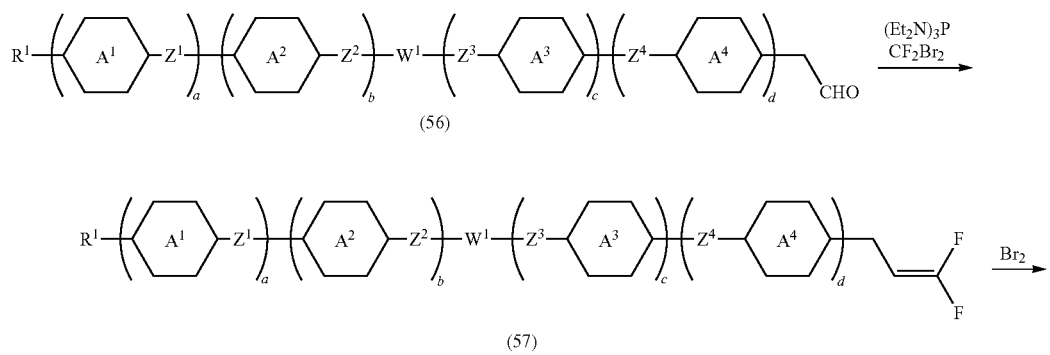

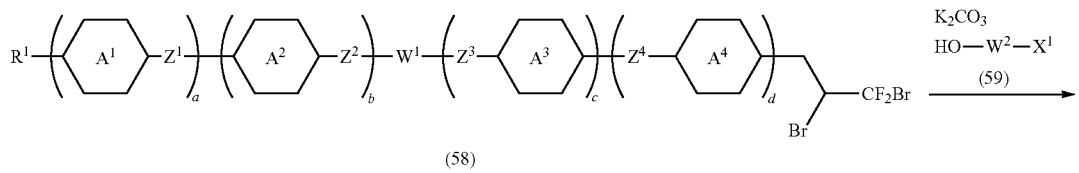

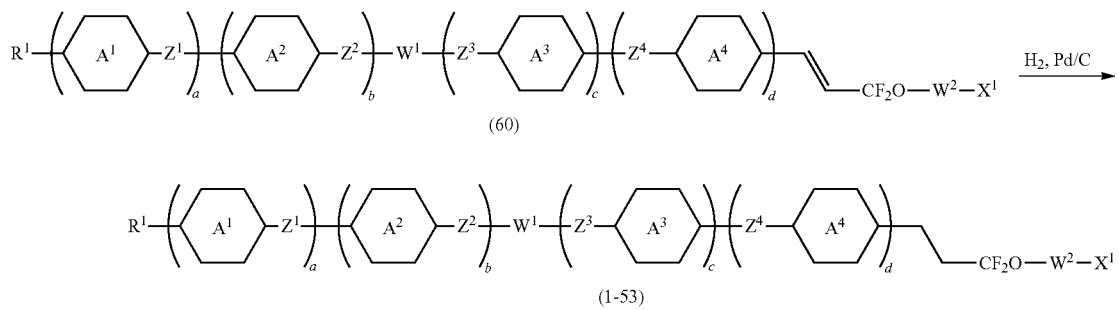

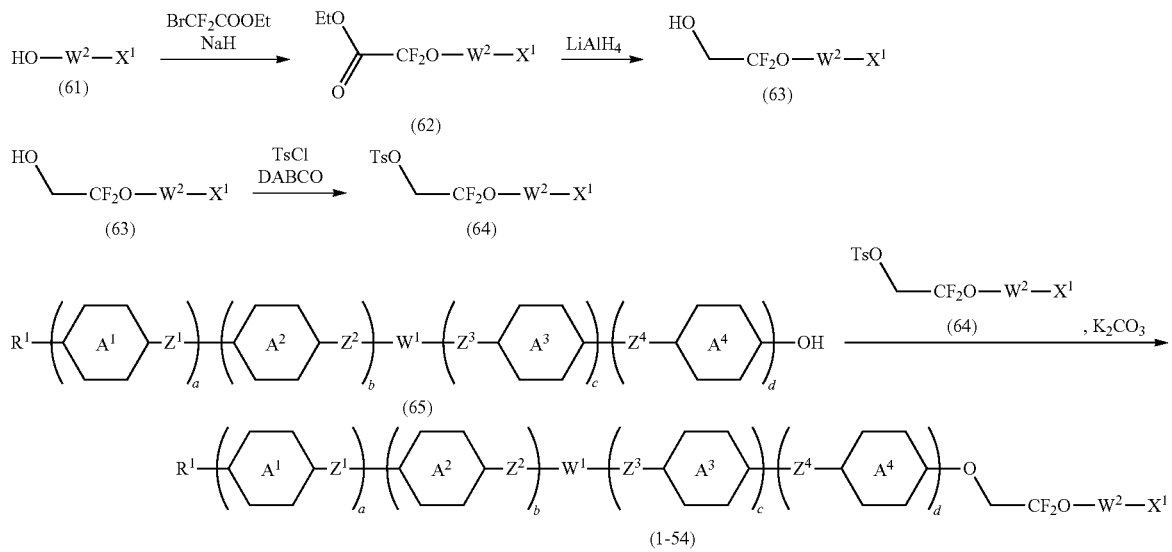

2. Composition

A liquid crystal composition of the invention is described. The composition contains at least one compound (1) as component A. The composition may contain two or more compounds (1). A component in the liquid crystal compound may be compound (1) only. In order to develop excellent physical properties, the composition preferably contains at least one of compounds (1) in the range of approximately 1 to approximately 99% by weight. In a composition having a positive dielectric anisotropy, a preferred content of compound (1) is in the range of approximately 5 to approximately 60% by weight. In a composition having a negative dielectric anisotropy, a preferred content of compound (1) is approximately 30% by weight or less. Composition (1) may also contain compound (1) and various kinds of liquid crystal compounds that are not described herein.

A preferred composition contains compounds selected from components B, C, D and E shown below. When a composition is prepared, components can be selected by taking the dielectric anisotropy of compound (1) into consideration, for example. When a composition having a positive dielectric anisotropy is prepared for a mode such as TFT, IPS and FFS, a main component includes components A, B and E. When a composition having the positive dielectric anisotropy is prepared for a mode such as STN and TN, a main component includes components A, C and E. When a composition having the negative dielectric anisotropy is prepared for a mode such as VA and PSA, a main component includes components D and E, and component A is added for the purpose of adjusting a voltage-transmittance curve of a device. A composition in which the component is suitably selected has a high maximum temperature, a low minimum temperature, the small viscosity, a suitable optical anisotropy, the large dielectric anisotropy and a suitable elastic constant.

Component B includes compounds (2) to (4). Component C includes compound (5). Component D includes compounds (6) to (12). Component E includes compounds (13) to (15). The components are described in the order.

Component B is a compound having a halogen-containing group or a fluorine-containing group at a right terminal. Preferred examples of component B include compounds (2-1) to (2-16), compounds (3-1) to (3-113) and compounds (4-1) to (4-57). In the compounds, $R^{11}$ and $X^{11}$ are defined in a manner identical with the definitions in item 9 described above.

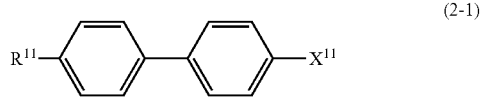
(2-1)

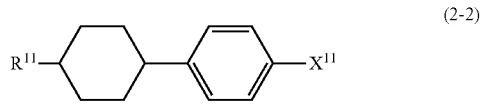
(2-2)

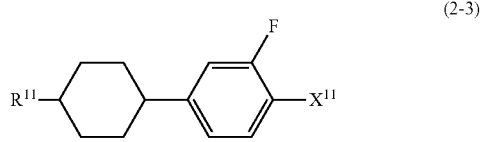
(2-3)

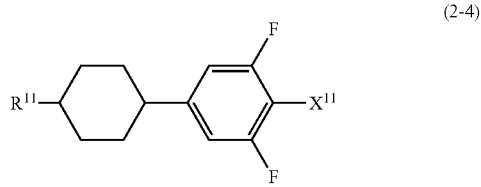
(2-4)

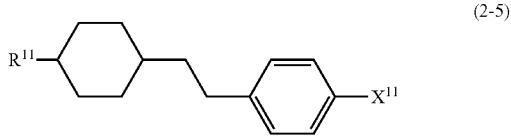
(2-5)

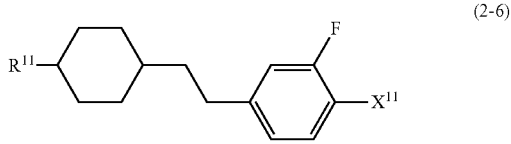
(2-6)

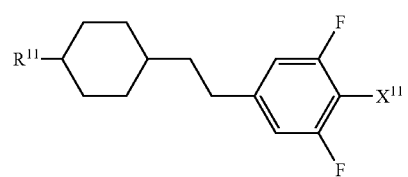
(2-7)
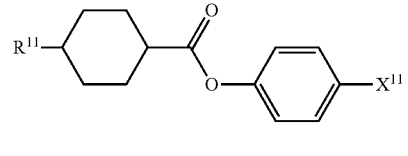
(2-8)
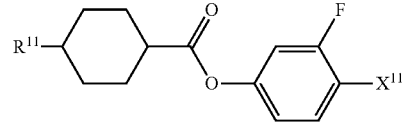
(2-9)
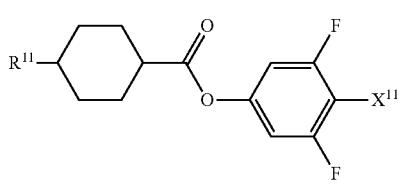
(2-10)
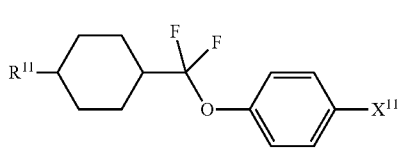
(2-11)
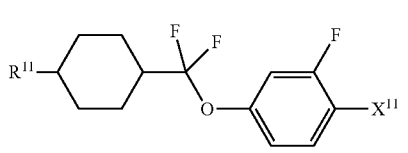
(2-12)
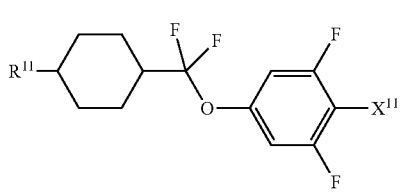
(2-13)
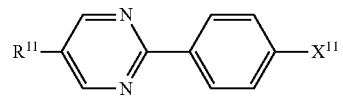
(2-14)
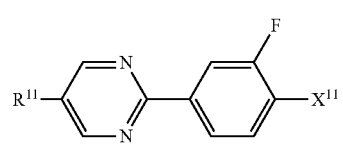
(2-15)
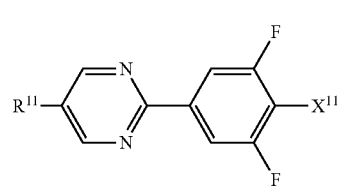
(2-16)
(3-1)
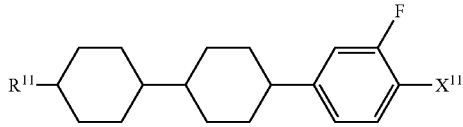
(3-2)
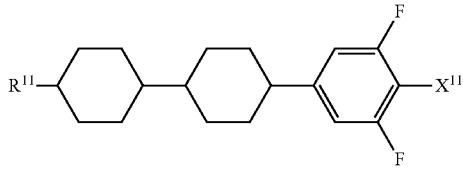
(3-3)
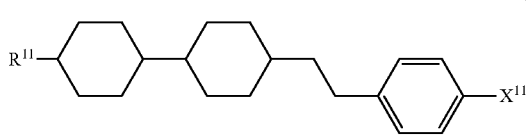
(3-4)
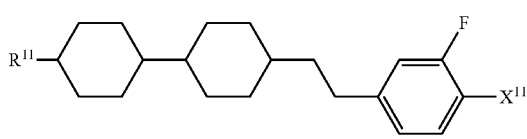
(3-5)
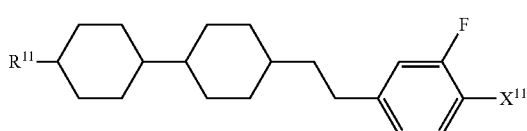
(3-6)
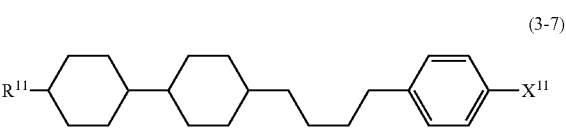
(3-7)
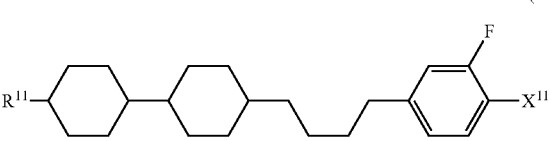
(3-8)
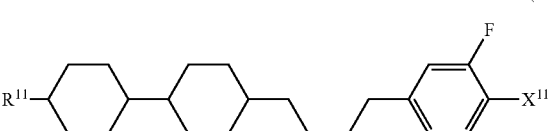
(3-9)
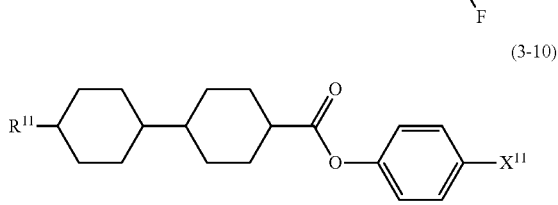
(3-10)

(3-11) 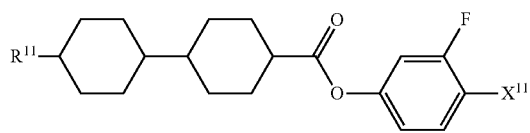
(3-12) 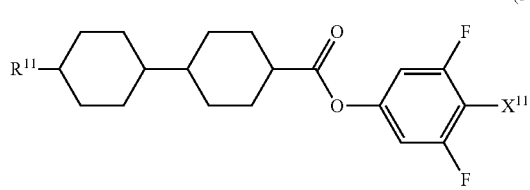
(3-13) 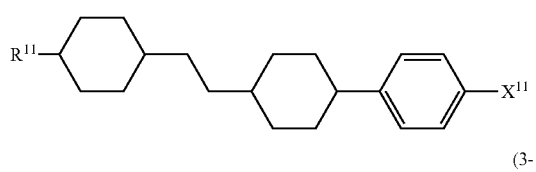
(3-14) 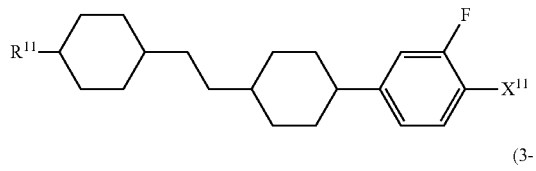
(3-15) 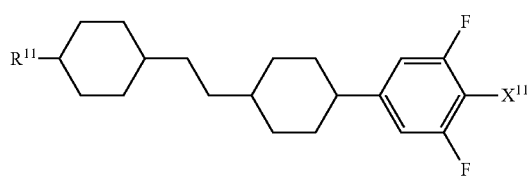
(3-16) 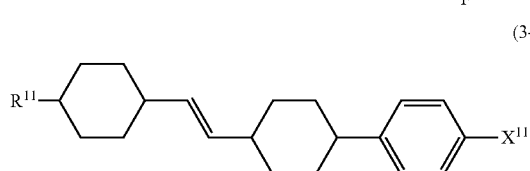
(3-17) 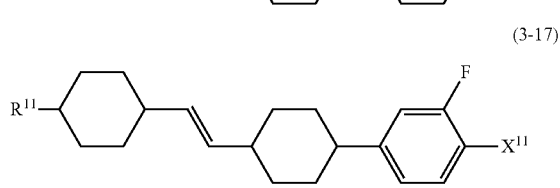
(3-18) 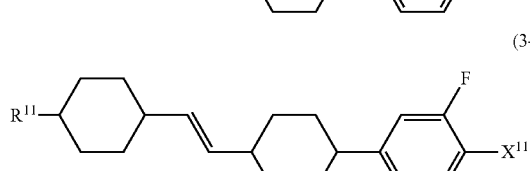
(3-19) 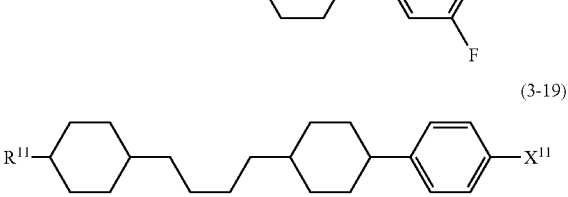
(3-20) 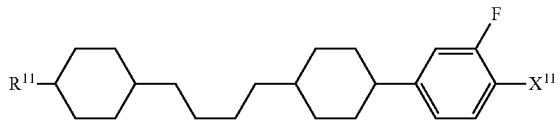
(3-21) 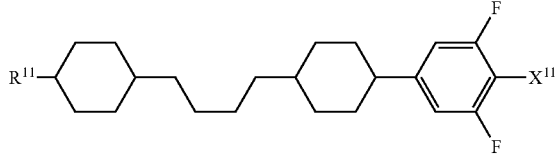
(3-22) 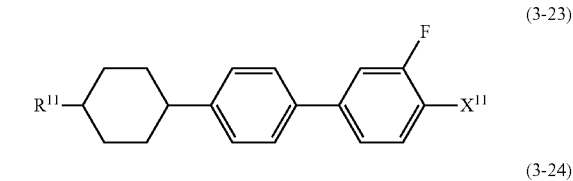
(3-23) 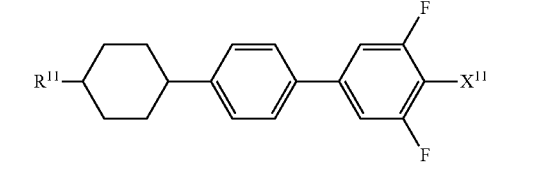
(3-24) 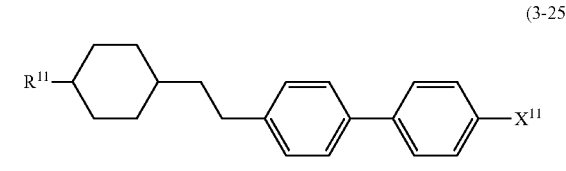
(3-25) 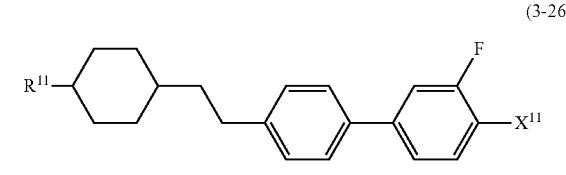
(3-26) 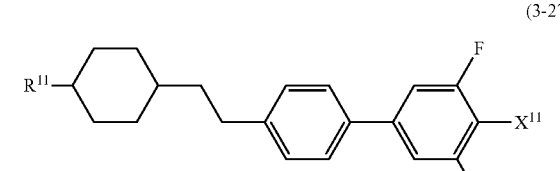
(3-27) 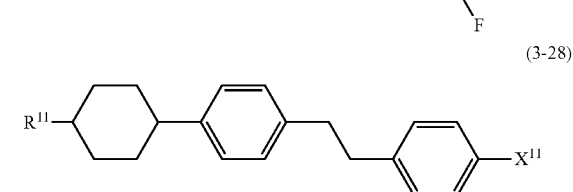
(3-28) 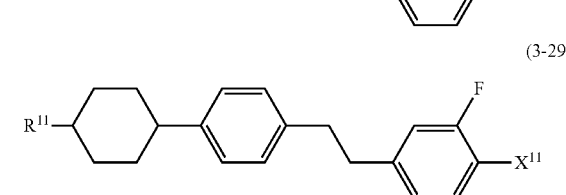
(3-29)

(3-30)
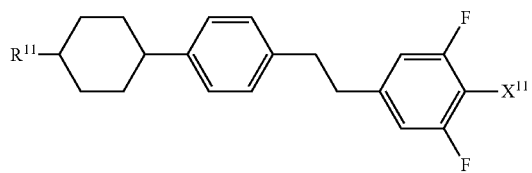
(3-31)
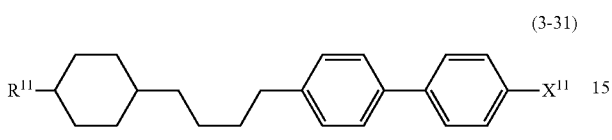
(3-32)
(3-33)
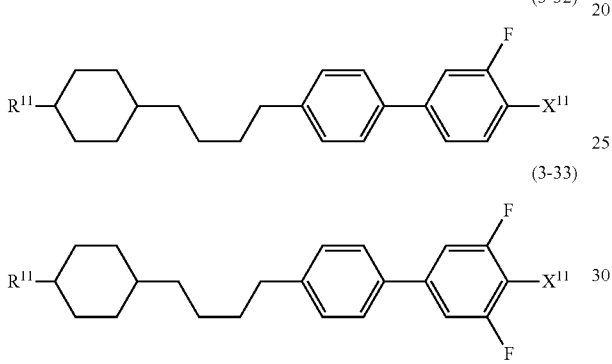
(3-34)
(3-35)
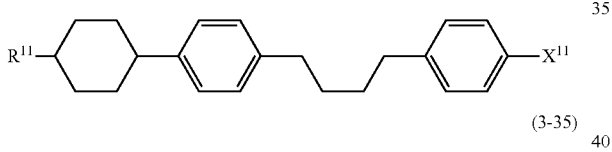
(3-36)
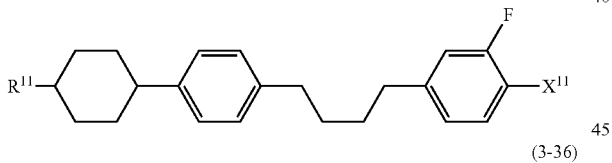
(3-37)
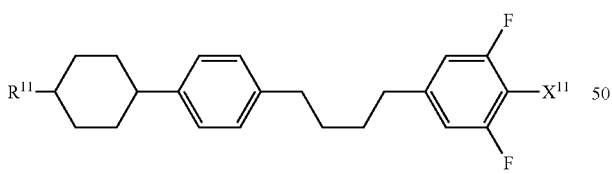
(3-38)
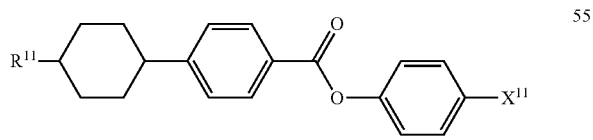
(3-39)
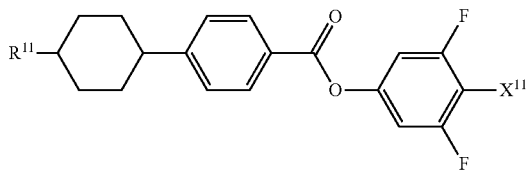
(3-40)
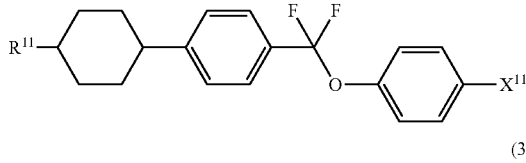
(3-41)
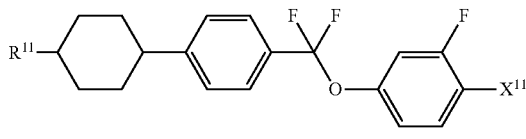
(3-42)
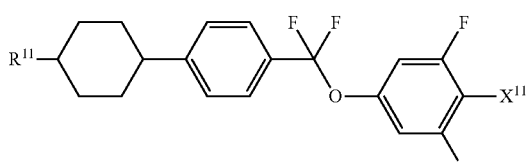
(3-43)
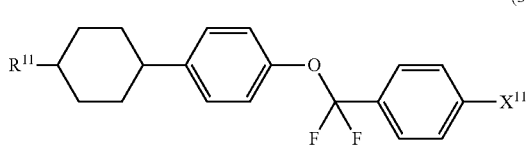
(3-44)
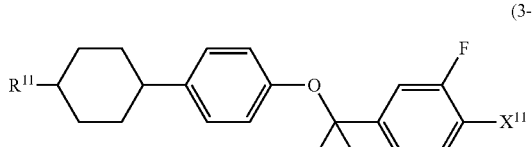
(3-45)
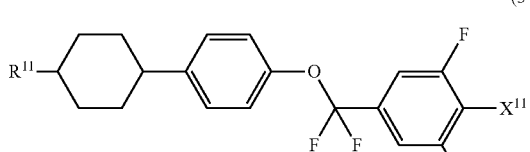
(3-46)
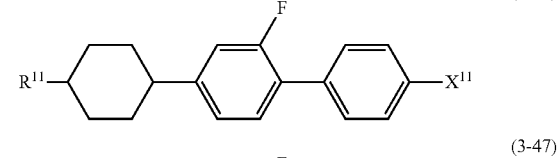
(3-47)

(3-48) 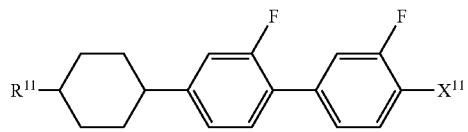
(3-49) 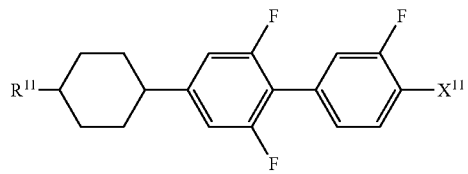
(3-50) 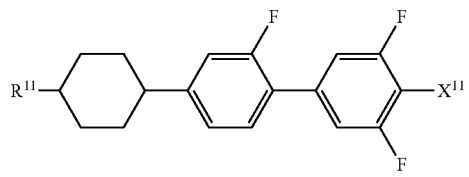
(3-51) 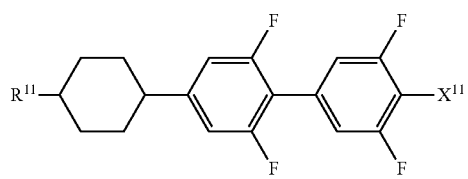
(3-52) 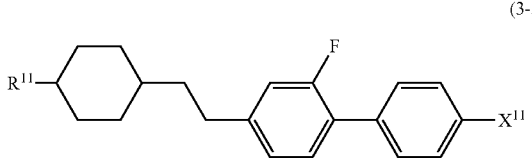
(3-53) 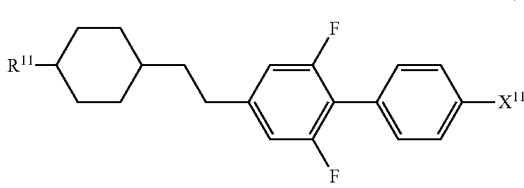
(3-54) 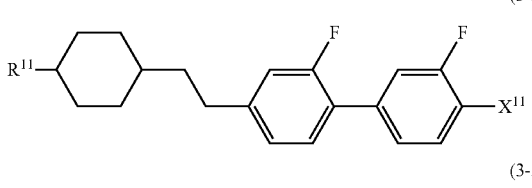
(3-55) 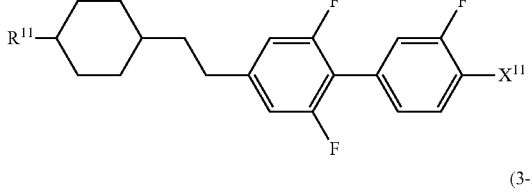
(3-56) 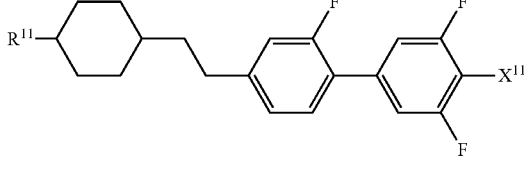
(3-57) 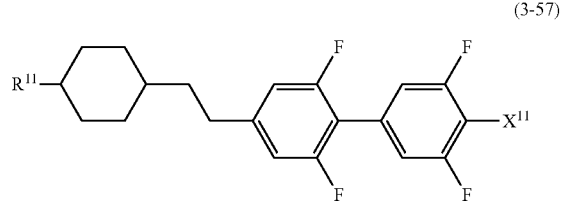
(3-58) 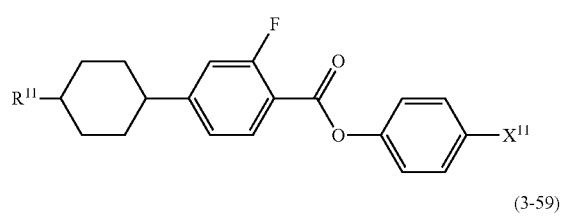
(3-59) 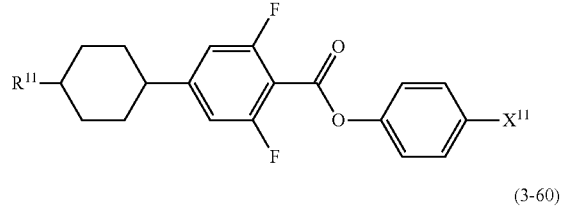
(3-60) 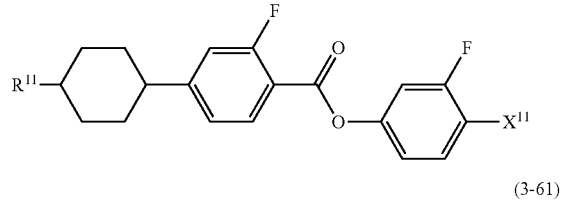
(3-61) 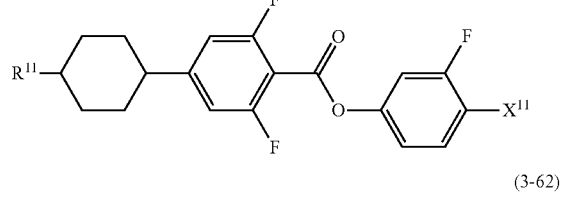
(3-62) 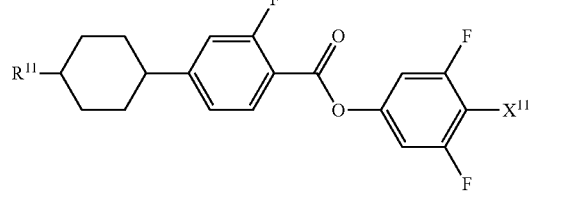
(3-63) 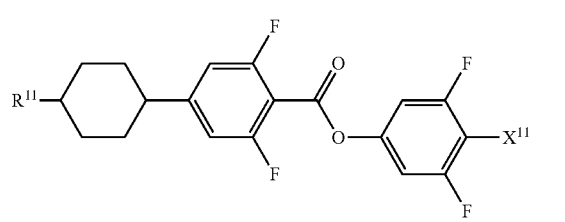
(3-64) 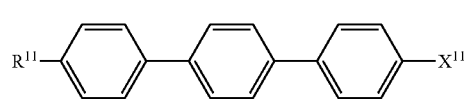

(3-65)
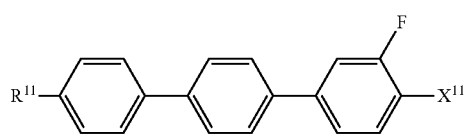
(3-66)
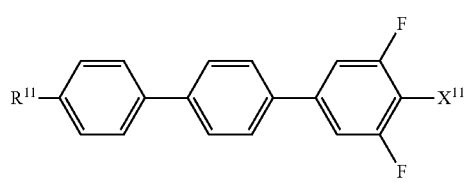
(3-67)
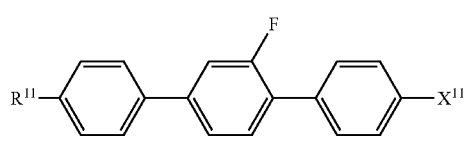
(3-68)
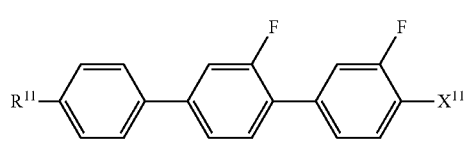
(3-69)
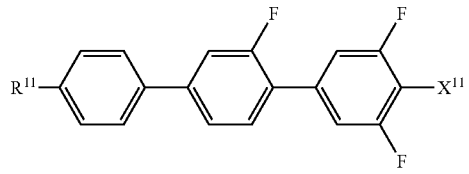
(3-70)
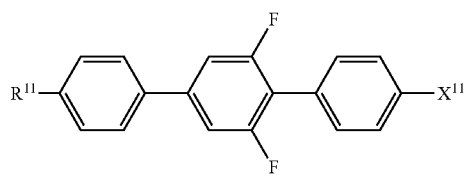
(3-71)
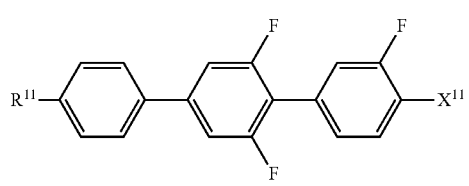
(3-72)
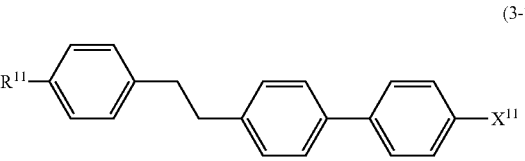
(3-73)
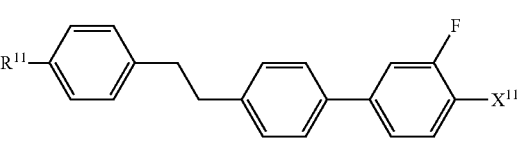
(3-74)
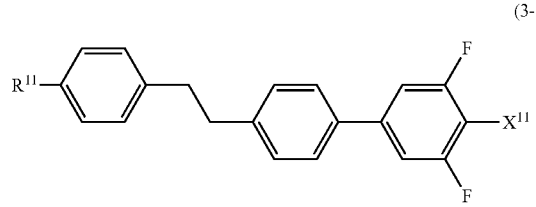
(3-75)
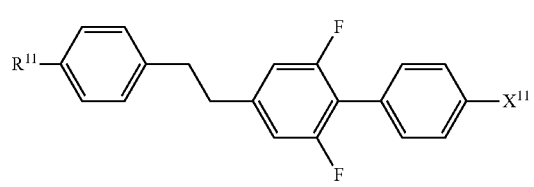
(3-76)
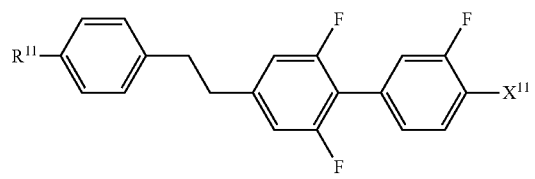
(3-77)
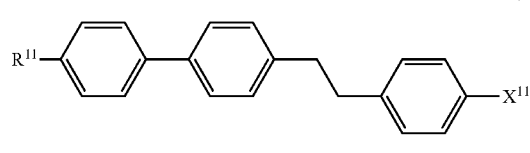
(3-78)
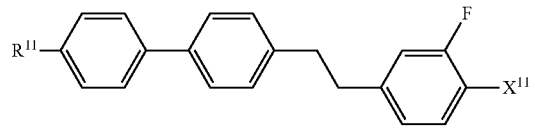
(3-79)
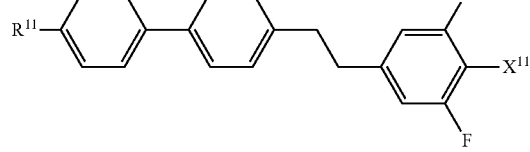
(3-80)
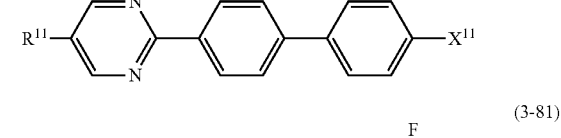
(3-81)
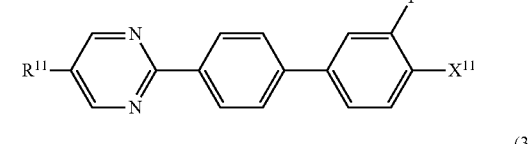
(3-82)
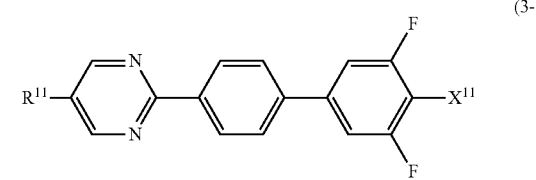

(3-83)
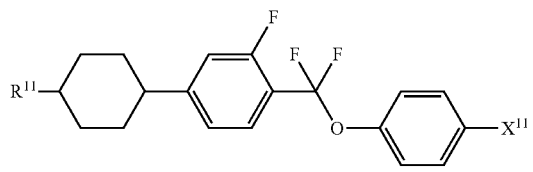
(3-84)
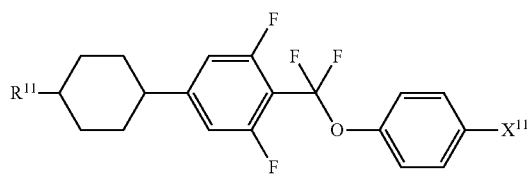
(3-85)
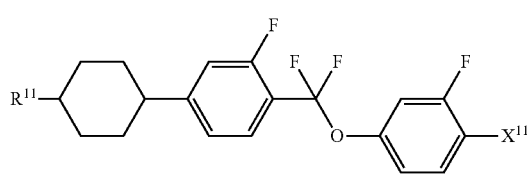
(3-86)
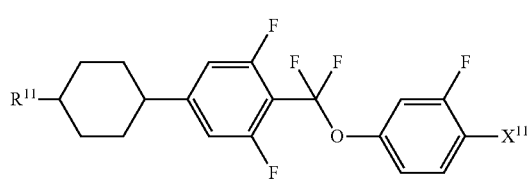
(3-87)
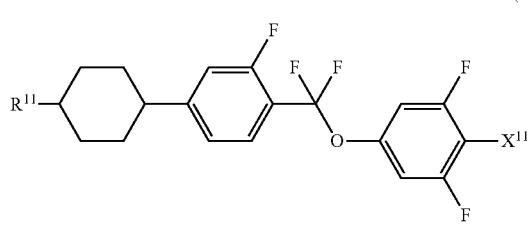
(3-88)
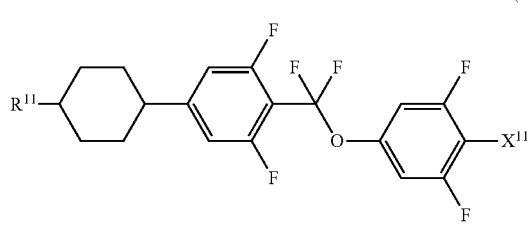
(3-89)
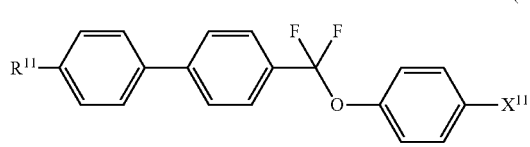
(3-90)
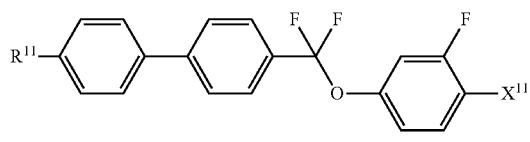
(3-91)
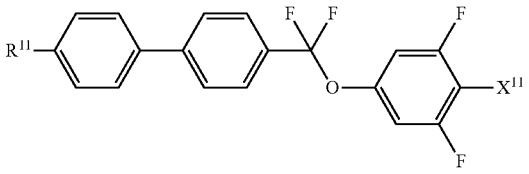
(3-92)
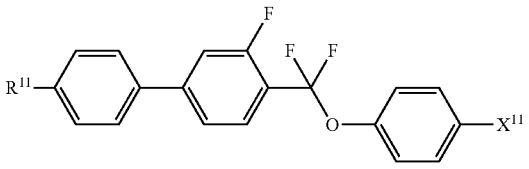
(3-93)
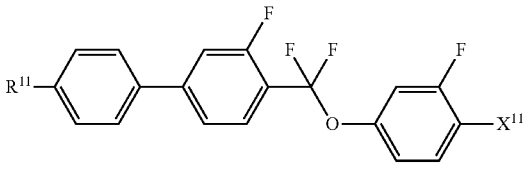
(3-94)
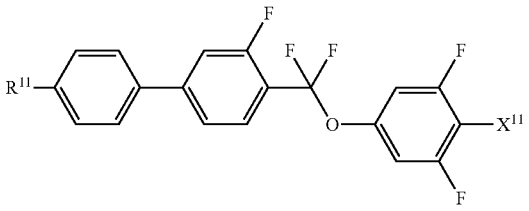
(3-95)
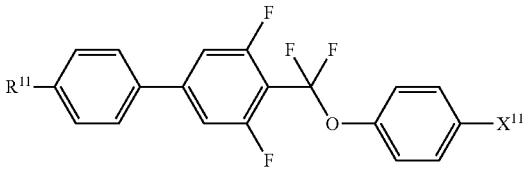
(3-96)
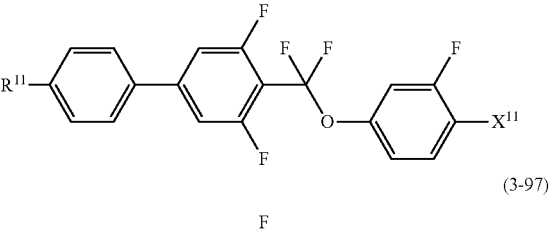
(3-97)
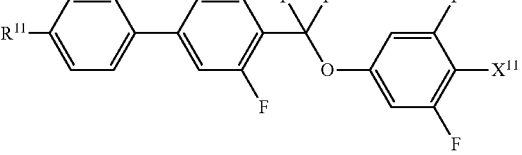
(3-98)
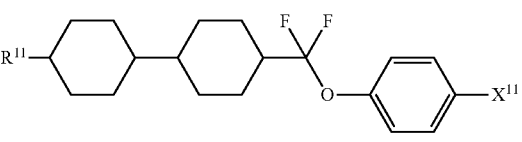

(3-99) 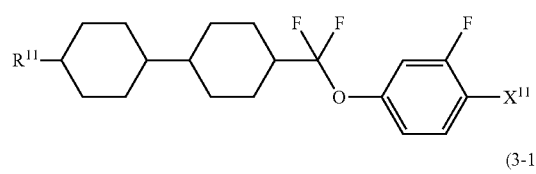
(3-100) 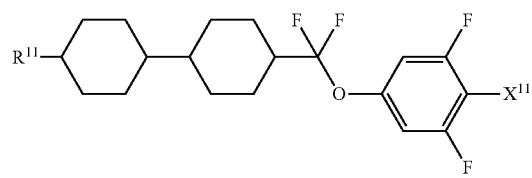
(3-101) 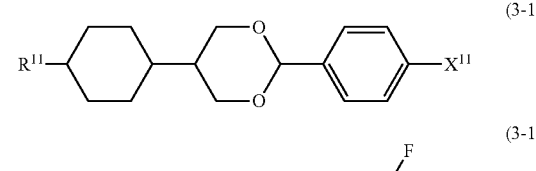
(3-102) 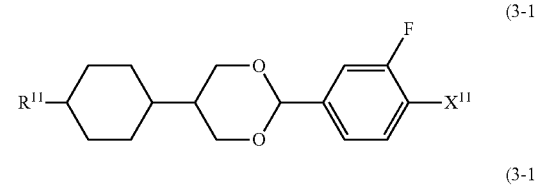
(3-103) 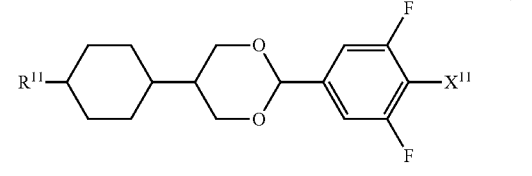
(3-104) 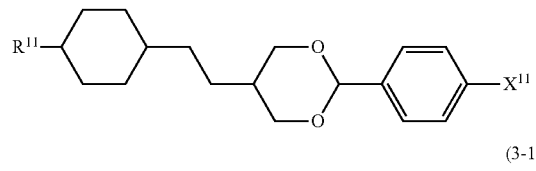
(3-105) 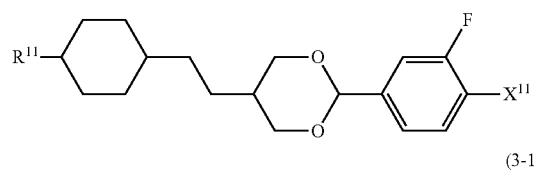
(3-106) 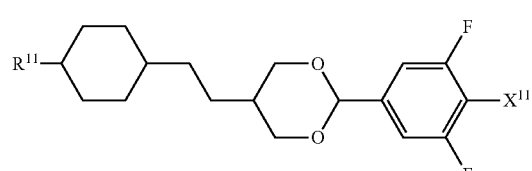
(3-107) 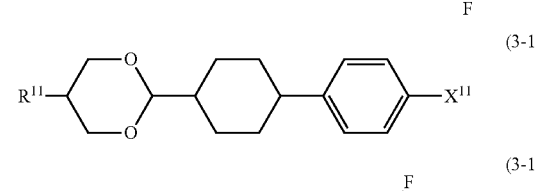
(3-108) 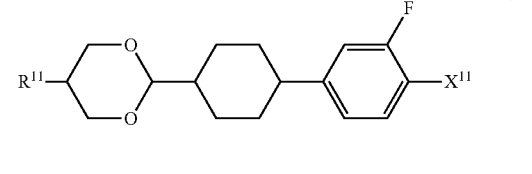
(3-109) 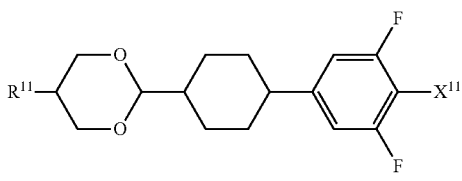
(3-110) 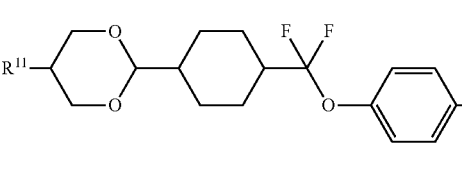
(3-111) 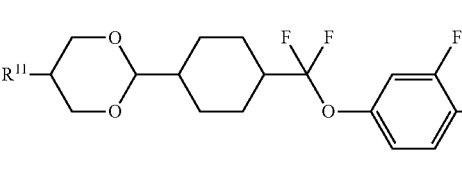
(3-112) 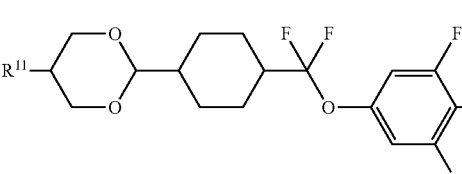
(3-113) 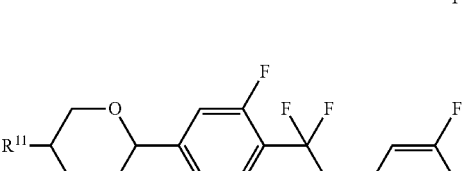
(4-1) 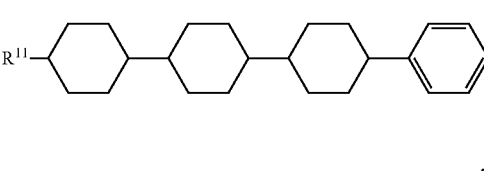
(4-2) 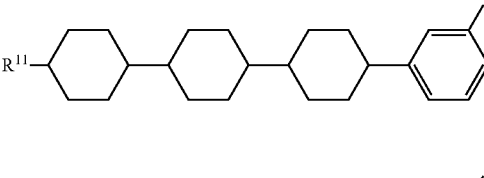
(4-3) 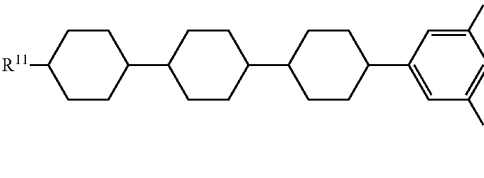
(4-4) 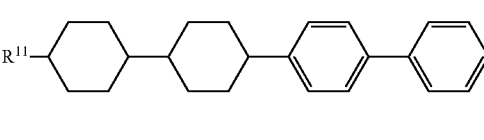

(4-5) 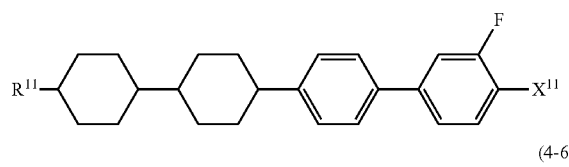
(4-6) 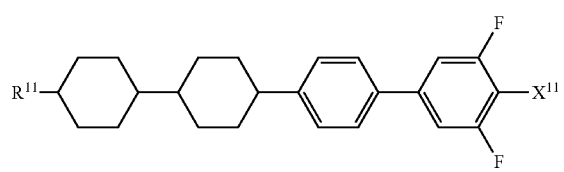
(4-7) 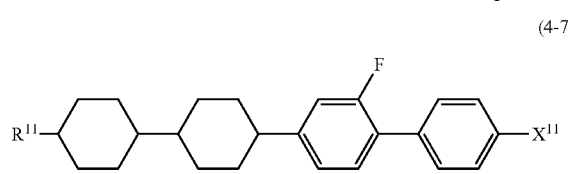
(4-8) 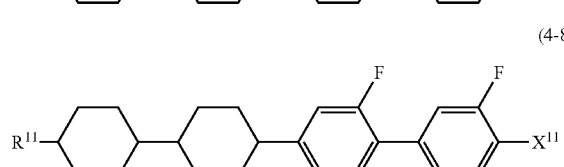
(4-9) 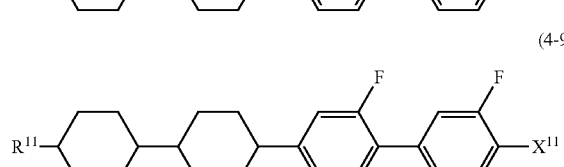
(4-10) 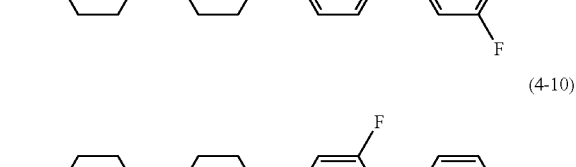
(4-11) 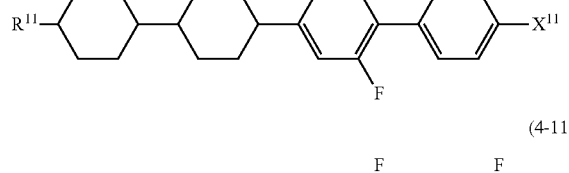
(4-12) 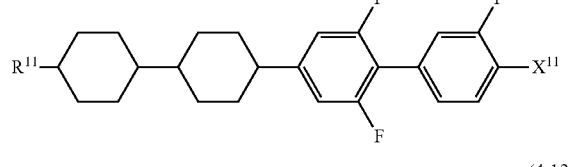
(4-13) 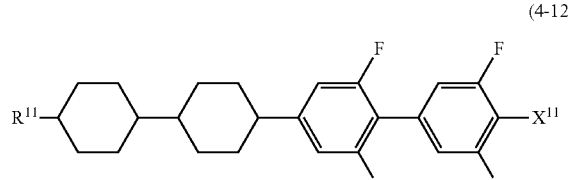
(4-14) 
(4-15) 
(4-16) 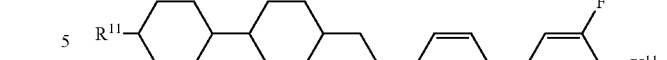
(4-17) 
(4-18) 
(4-19) 
(4-20) 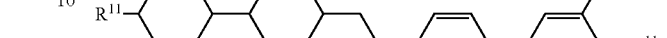
(4-21) 
(4-22) 
(4-23) 

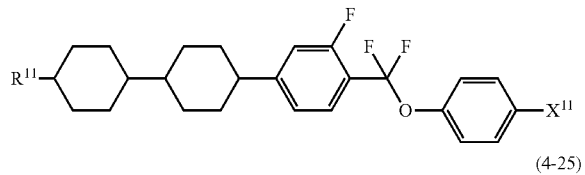 (4-24)
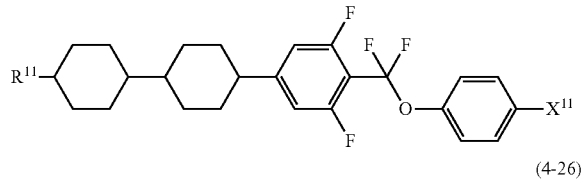 (4-25)
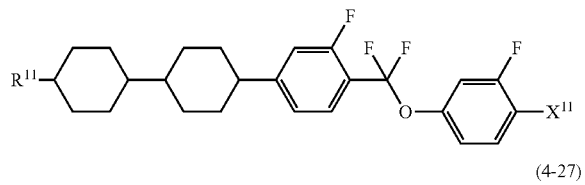 (4-26)
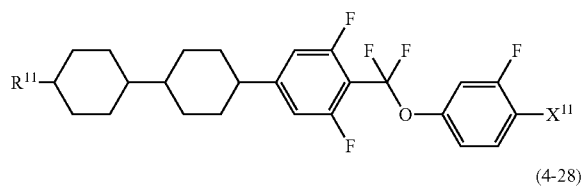 (4-27)
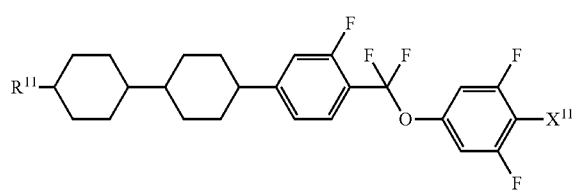 (4-28)
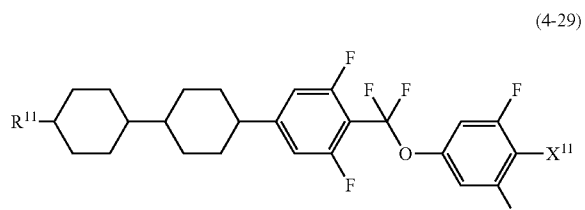 (4-29)
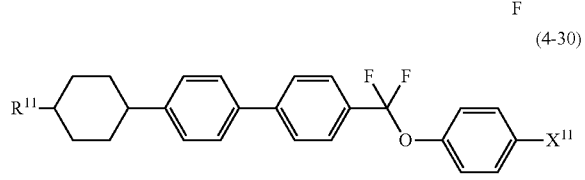 (4-30)
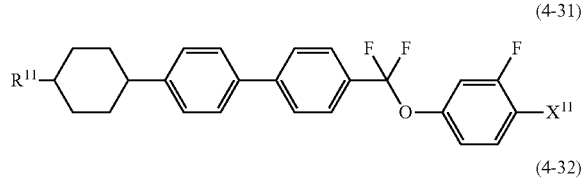 (4-31)
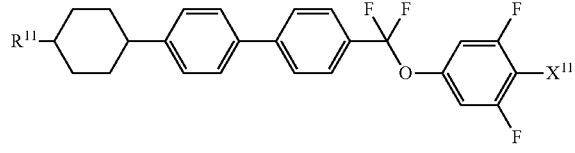 (4-32)
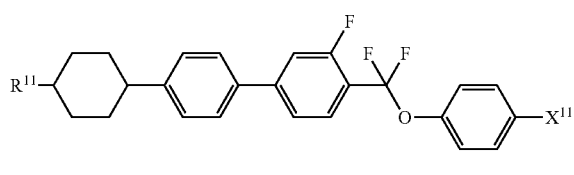 (4-33)
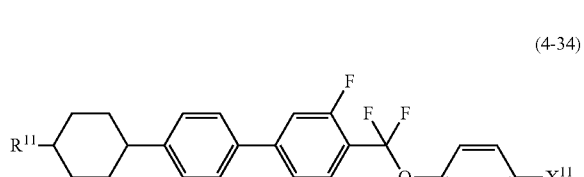 (4-34)
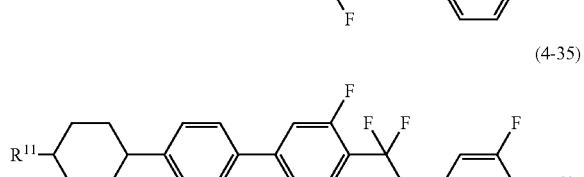 (4-35)
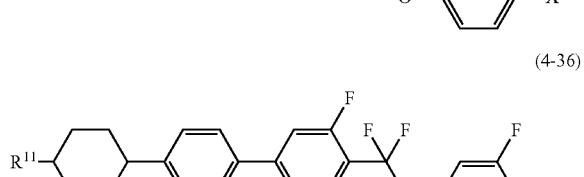 (4-36)
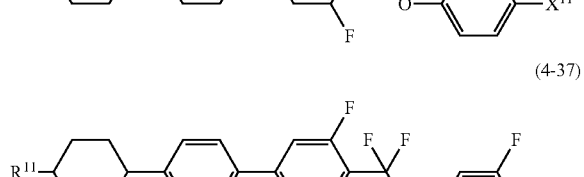 (4-37)
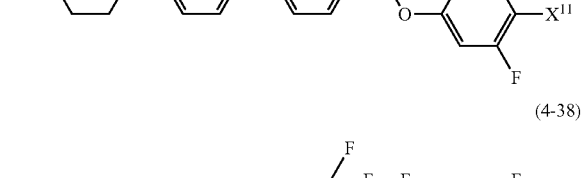 (4-38)
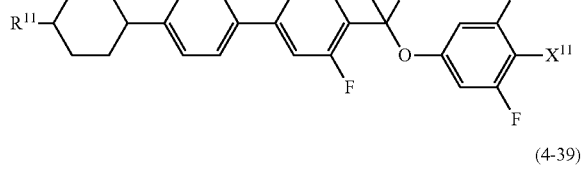 (4-39)
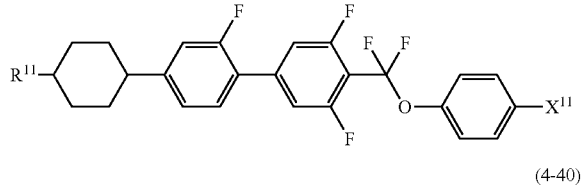 (4-40)
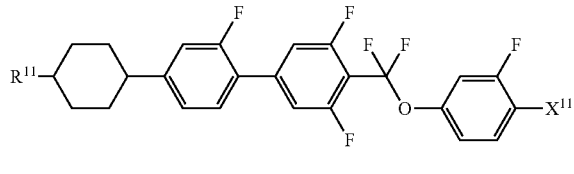

(4-41)
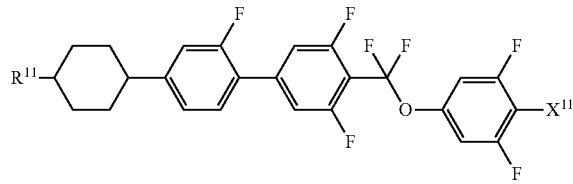
(4-42)
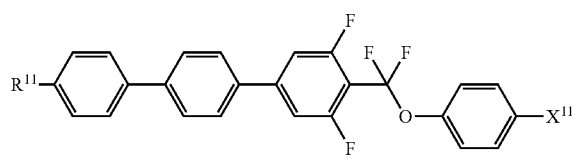
(4-43)
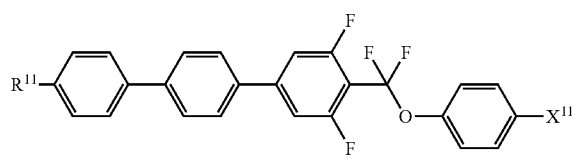
(4-44)
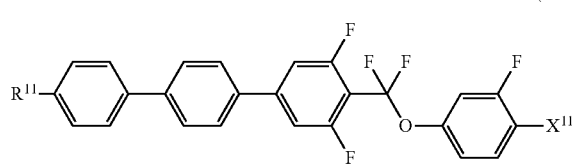
(4-45)
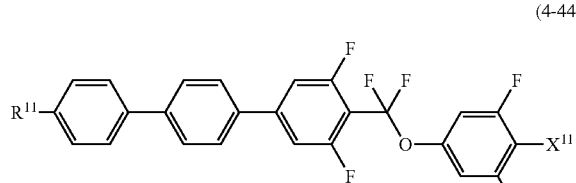
(4-46)
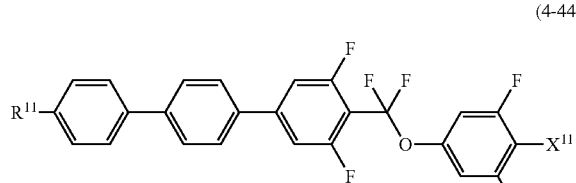
(4-47)
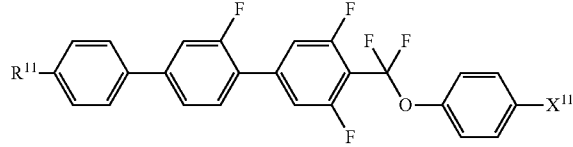
(4-48)
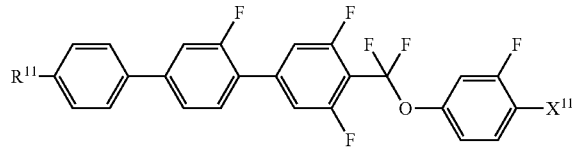
(4-49)
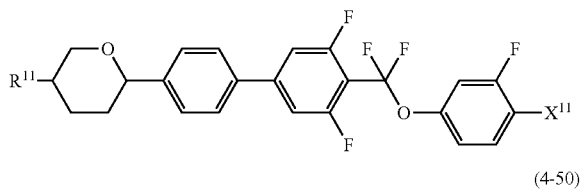
(4-50)
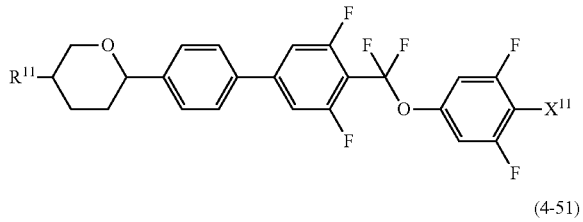
(4-51)
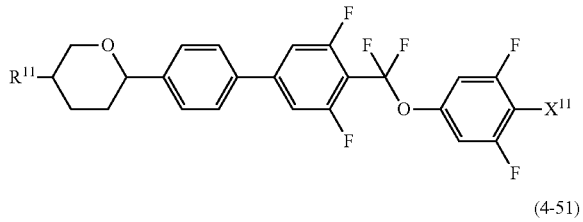
(4-52)
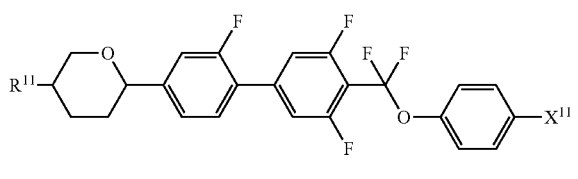
(4-53)
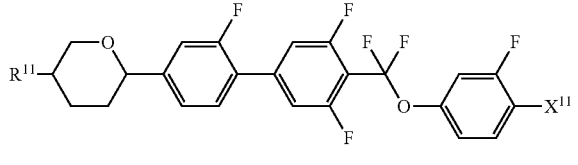
(4-54)
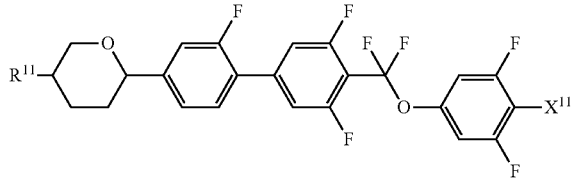
(4-55)
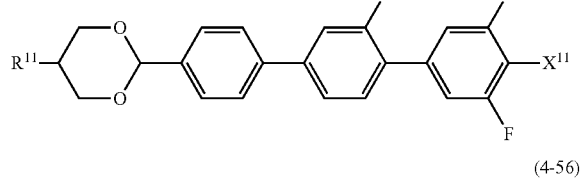
(4-56)
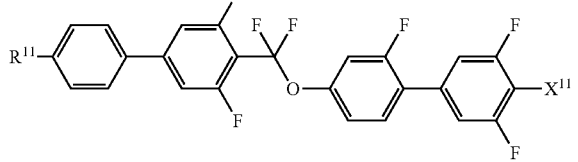

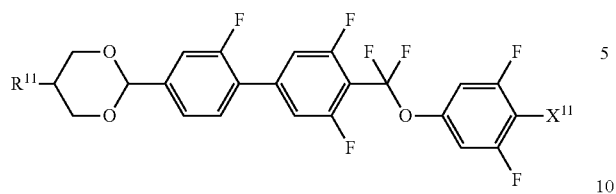
(4-57)

Component B has the positive dielectric anisotropy, and superb stability to heat, light and so forth, and therefore is used when a composition for a mode such as TFT, IPS and FFS is prepared. A content of component B is suitably in the range of approximately 1 to approximately 99% by weight, preferably in the range of approximately 10 to approximately 97% by weight, and further preferably in the range of approximately 40 to approximately 95% by weight, based on the weight of the composition. The viscosity of the composition can be adjusted by further adding compounds (13) to (15) (Component E).

Component C is compound (5) in which a right-terminal group is —C≡N or —C≡C—C≡N. Preferred examples of component C include compounds (5-1) to (5-64). In the compounds (component C), $R^{12}$ and $X^{12}$ are defined in a manner identical with the definitions in item 10 described above.

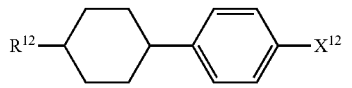
(5-1)

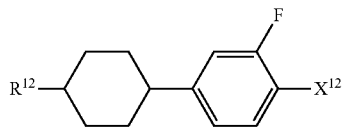
(5-2)

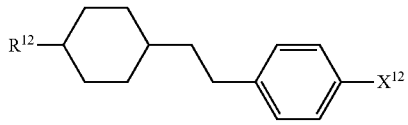
(5-3)

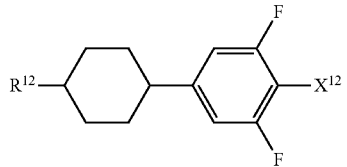
(5-4)

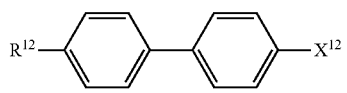
(5-5)

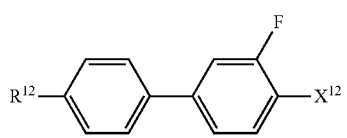
(5-6)

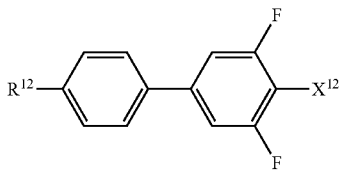
(5-7)

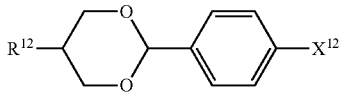
(5-8)

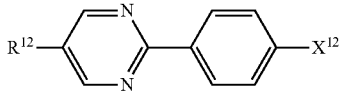
(5-9)

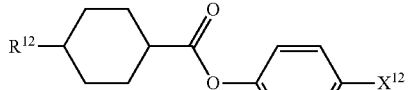
(5-10)

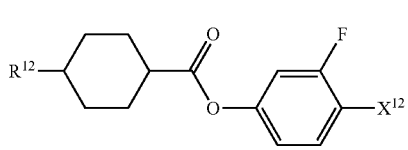
(5-11)

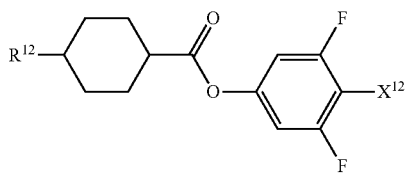
(5-12)

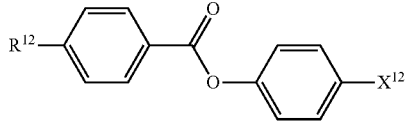
(5-13)

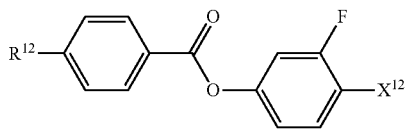
(5-14)

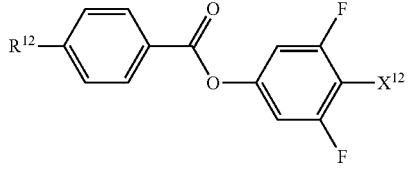
(5-15)

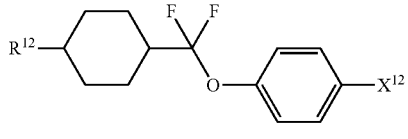
(5-16)

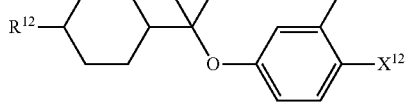
(5-17)

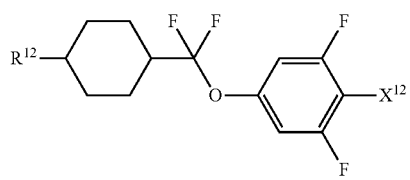 (5-18)
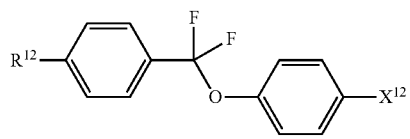 (5-19)
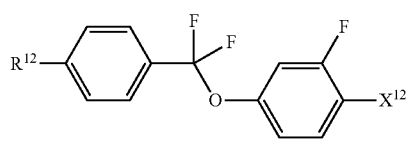 (5-20)
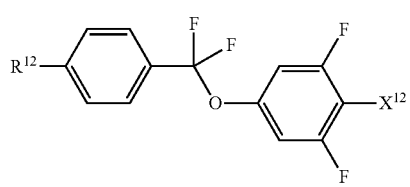 (5-21)
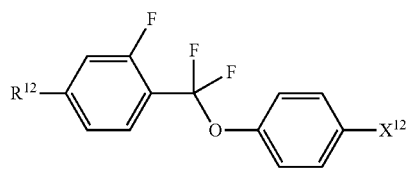 (5-22)
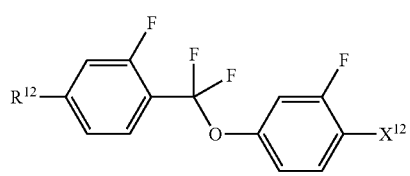 (5-23)
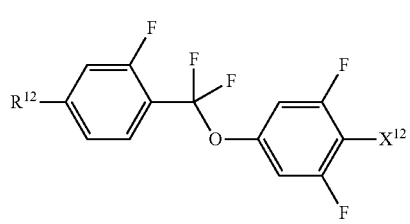 (5-24)
 (5-25)
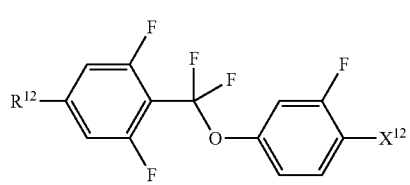 (5-26)
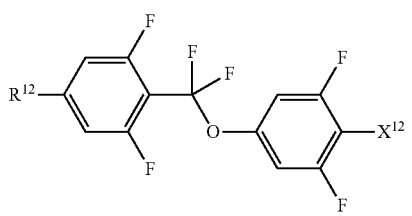 (5-27)
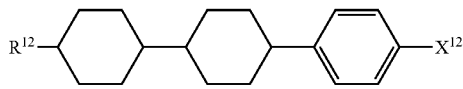 (5-28)
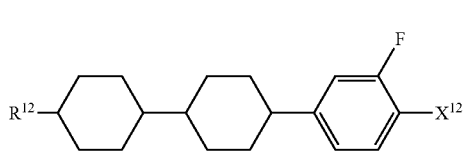 (5-29)
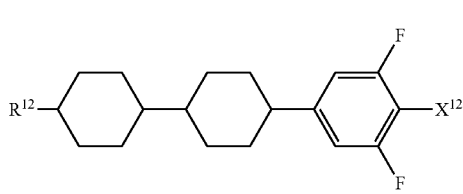 (5-30)
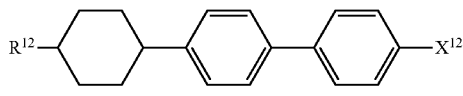 (5-31)
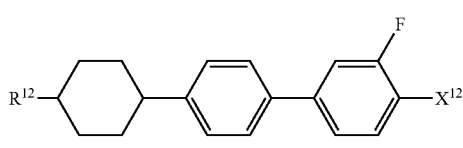 (5-32)
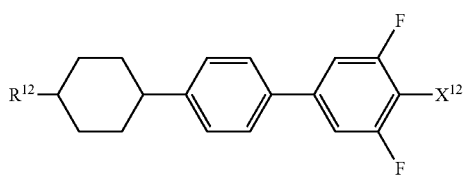 (5-33)
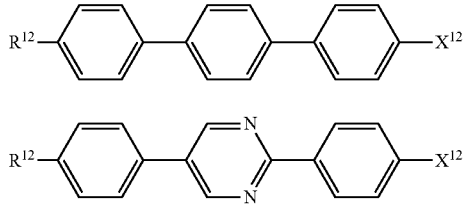 (5-34)
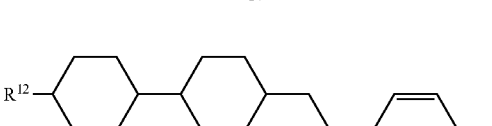 (5-35)
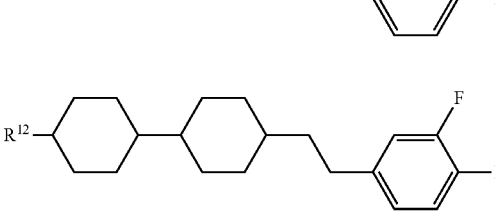 (5-36)
 (5-37)

-continued
(5-38)
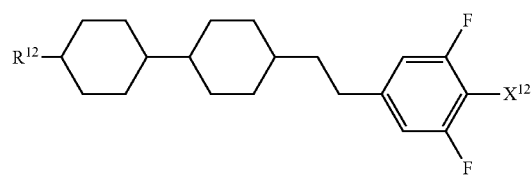
(5-39)
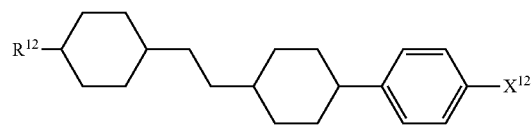
(5-40)
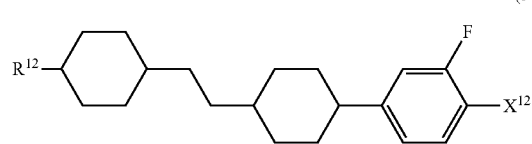
(5-41)
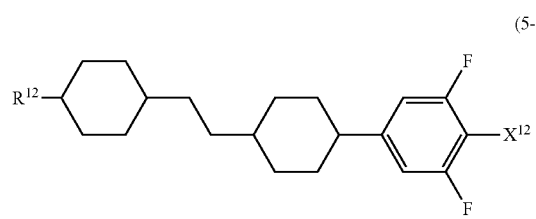
(5-42)
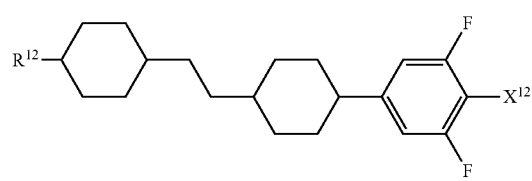
(5-43)
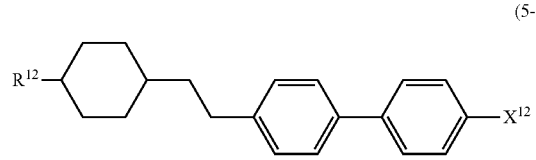
(5-44)
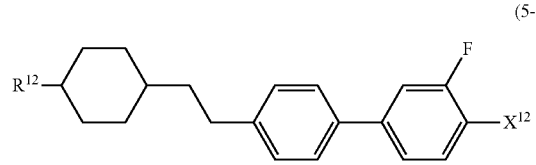
(5-45)
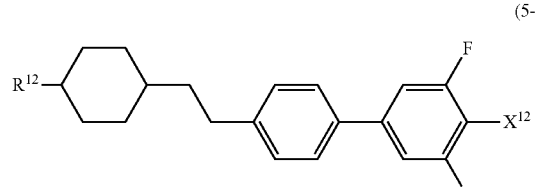
(5-46)
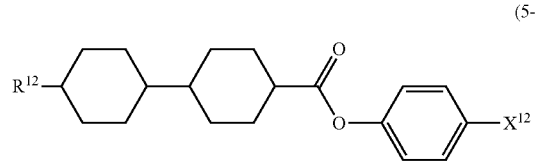
-continued
(5-47)
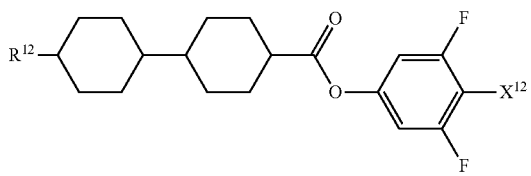
(5-48)
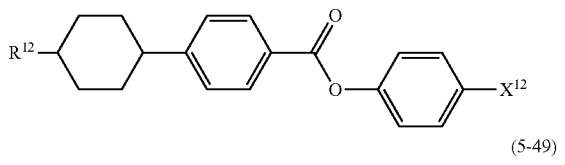
(5-49)
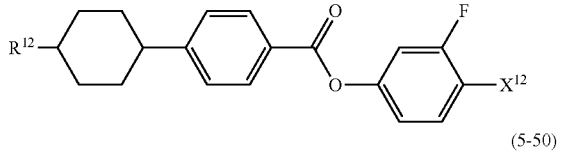
(5-50)
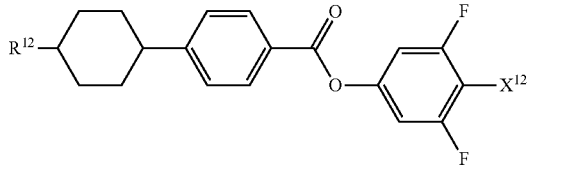
(5-51)
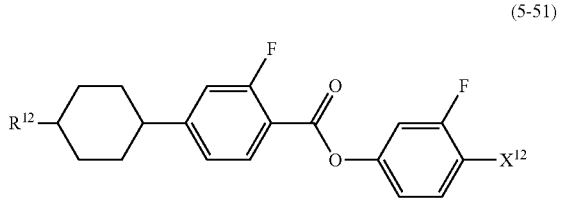
(5-52)
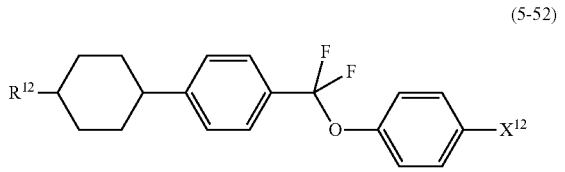
(5-53)
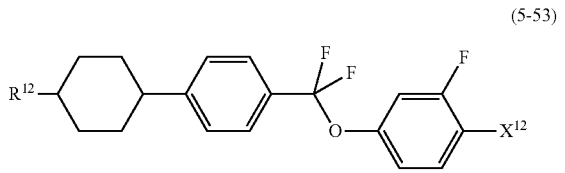
(5-54)
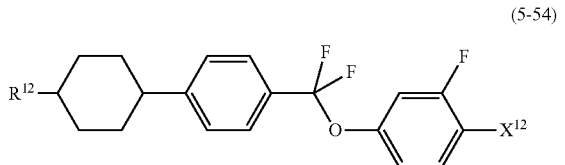
(5-55)
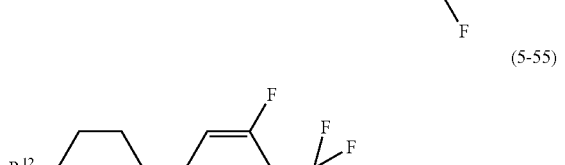

-continued (5-56) 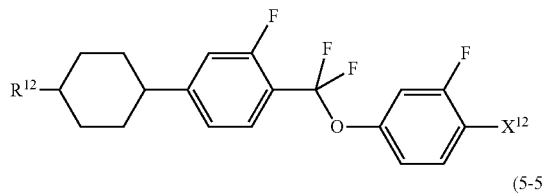

(5-57) 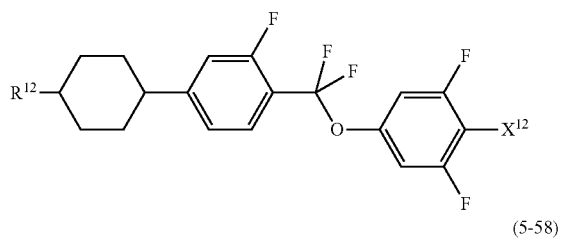

(5-58) 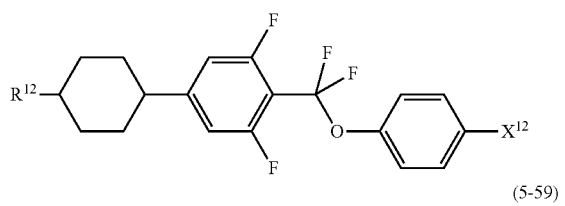

(5-59) 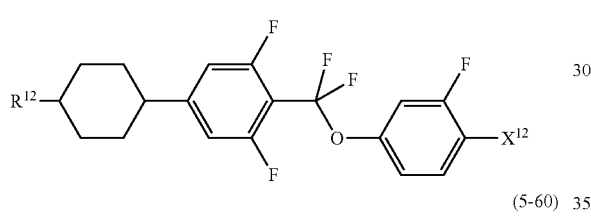

(5-60) 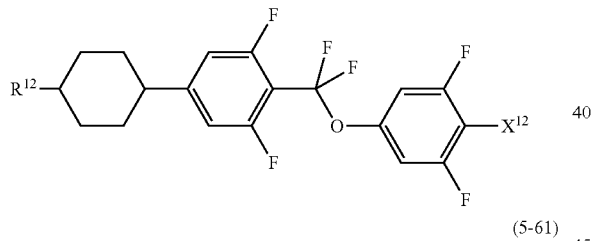

(5-61) 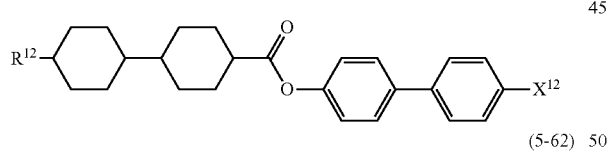

(5-62) 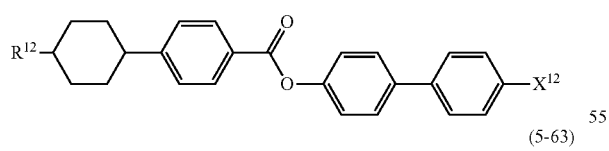

(5-63) 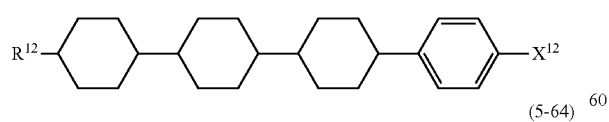

(5-64) 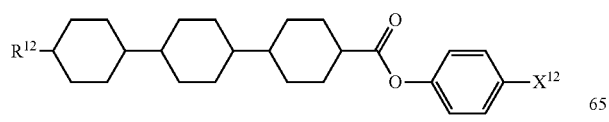

Component C has the positive dielectric anisotropy and a value thereof is large, and therefore is mainly used when a composition for the STN mode, the TN mode or the PSA mode is prepared. The dielectric anisotropy of the composition can be increased by adding component C. Component C is effective in extending the temperature range of the liquid crystal phase, adjusting the viscosity or adjusting the optical anisotropy. Component C is also useful for adjustment of the voltage-transmittance curve of the device.

When a composition for the STN mode or the TN mode is prepared, a content of component C is suitably in the range of approximately 1 to approximately 99% by weight, preferably, in the range of approximately 10 to approximately 97% by weight, and further preferably, in the range of approximately 40 to approximately 95% by weight, based on the weight of the composition. In the composition, the temperature range of the liquid crystal phase, the viscosity, the optical anisotropy, the dielectric anisotropy and so forth can be adjusted by adding component E.

Component D includes compounds (6) to (12). The compounds have a benzene ring in which hydrogen in lateral positions are replaced by two of halogen, such as 2,3-difluoro-1,4-phenylene. Preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3). In the compounds (component D), $R^{13}$, $R^{14}$ and $R^{15}$ are defined in a manner identical with the definitions in item 11 described above.

(6-1) 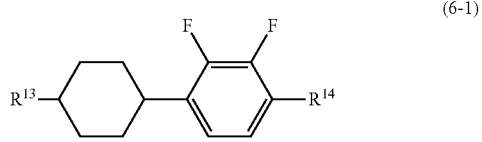

(6-2) 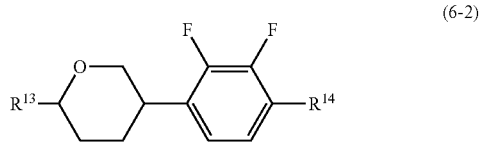

(6-3) 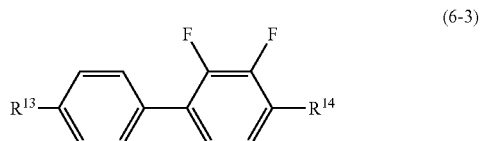

(6-4) 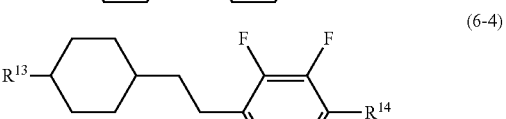

(6-5) 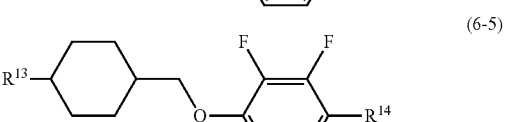

(6-6) 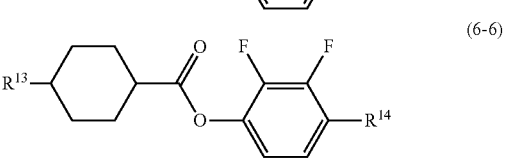

(6-7) 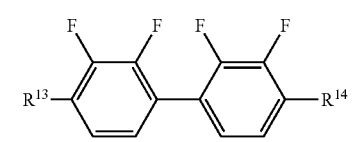
(6-8) 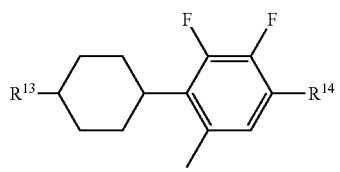
(7-1) 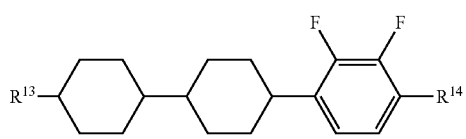
(7-2) 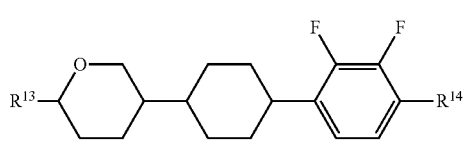
(7-3) 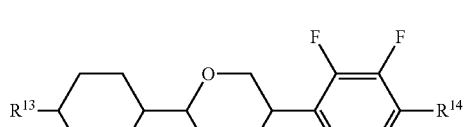
(7-4) 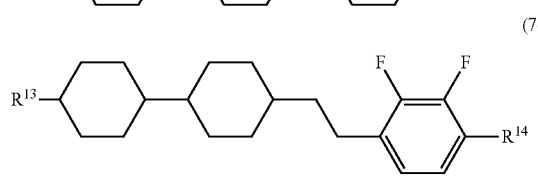
(7-5) 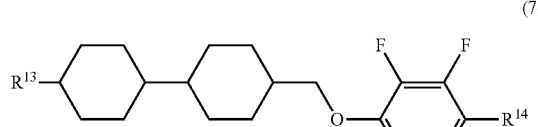
(7-6) 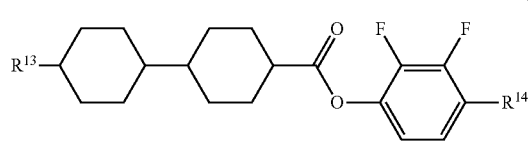
(7-7) 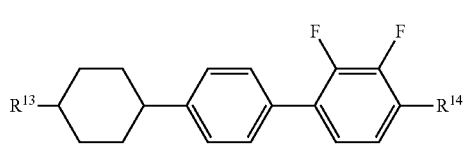
(7-8) 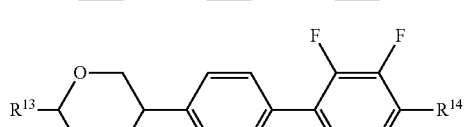
(7-9) 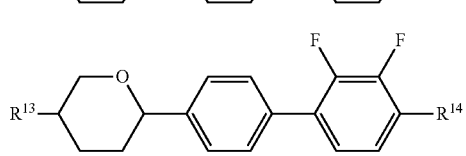
(7-10) 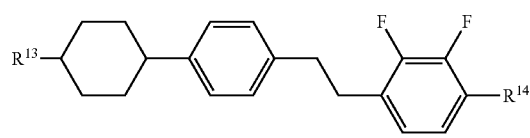
(7-11) 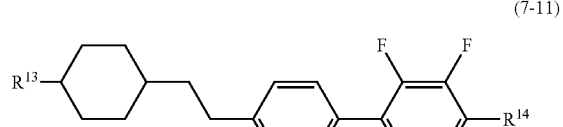
(7-12) 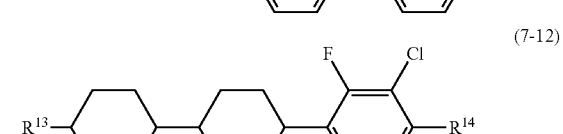
(7-13) 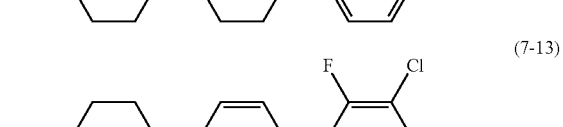
(7-14) 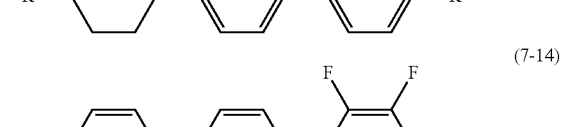
(7-15) 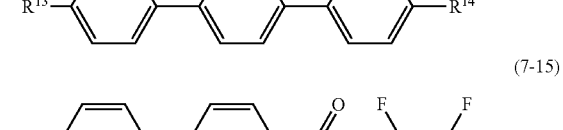
(7-16) 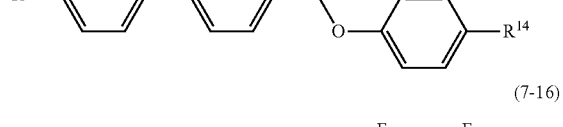
(7-17) 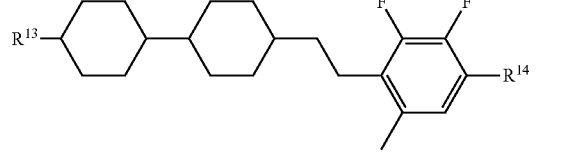
(8-1) 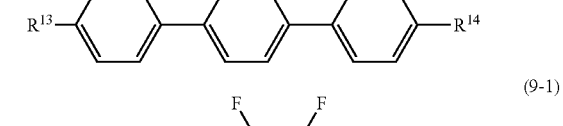
(9-1) 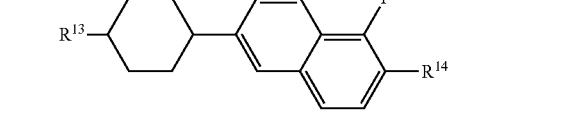

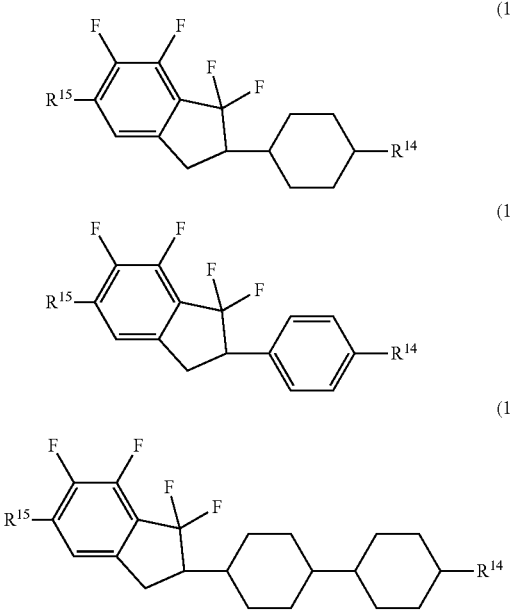

Component D is a compound having the negative dielectric anisotropy. Component D is mainly used when a composition for a VA mode or the PSA mode is prepared. Among types of component D, compound (6) is a bicyclic compound, and therefore is effective mainly in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When a liquid crystal composition for the VA mode or the PSA mode is prepared, a content of component D is preferably approximately 40% by weight or more, and further preferably in the range of approximately 50 to approximately 95% by weight, based on the weight of the composition. When component D is added to a composition having the positive dielectric anisotropy, a content of component D is preferably approximately 30% by weight or less based on the weight of the composition. Addition of component D allows adjustment of the voltage-transmittance curve of the device.

Component E is a compound in which two terminal groups are alkyl or the like. Preferred examples of component E include compounds (13-1) to (13-11), compounds (14-1) to (14-19) and compounds (15-1) to (15-7). In the compounds (component E), $R^{16}$ and $R^{17}$ are defined in a manner identical with the definitions in item 12 described above.

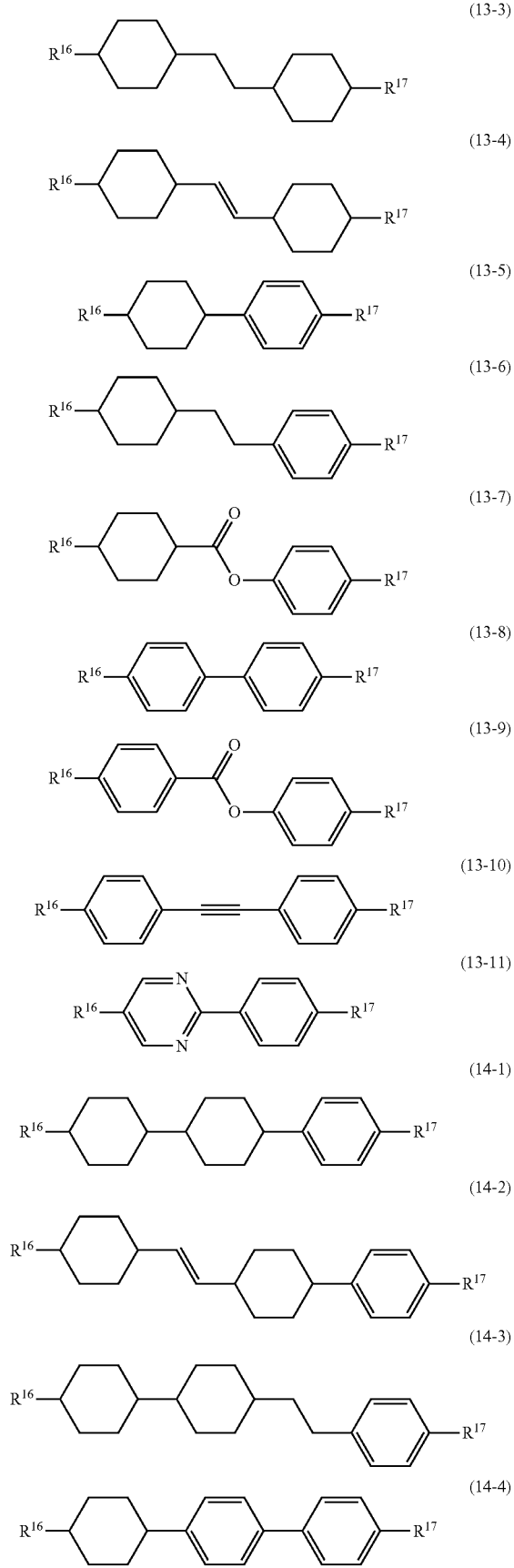

(14-5) 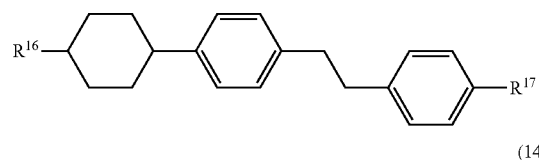
(14-6) 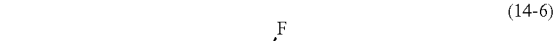
(14-7) 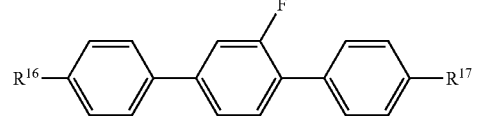
(14-8) 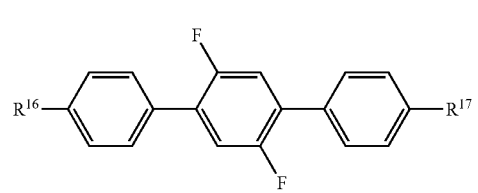
(14-9) 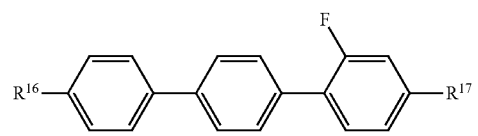
(14-10) 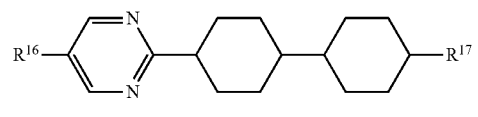
(14-11) 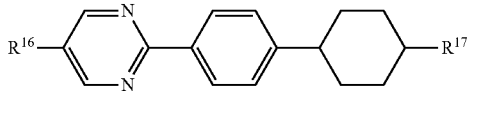
(14-12) 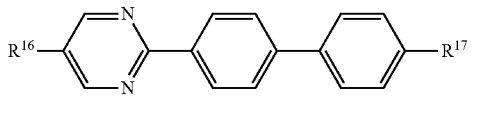
(14-13) 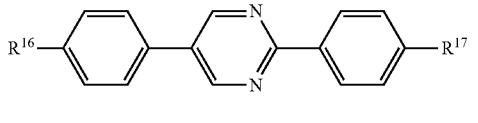
(14-14) 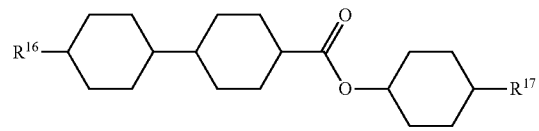
(14-15) 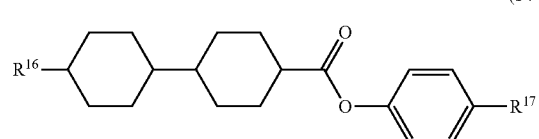
(14-16) 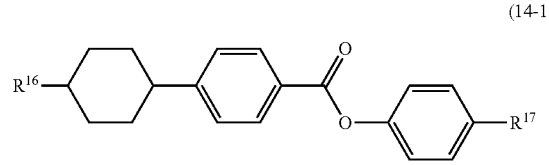
(14-16) 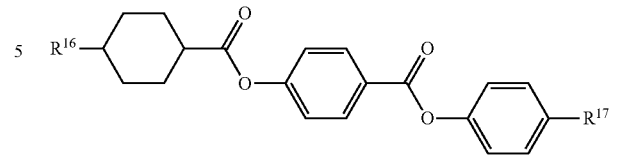
(14-17) 
(14-18) 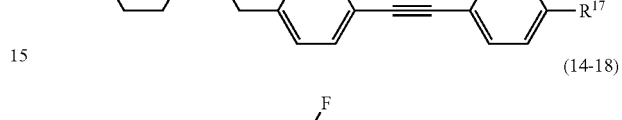
(14-19) 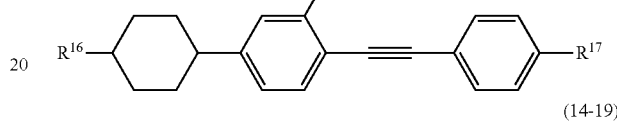
(15-1) 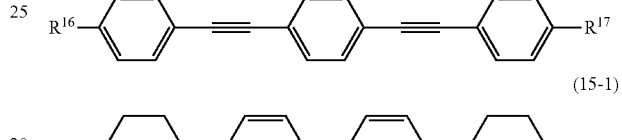
(15-2) 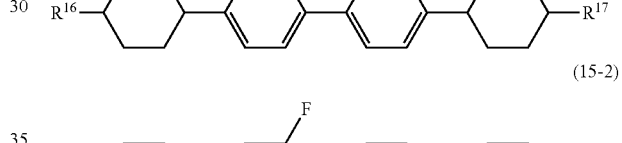
(15-3) 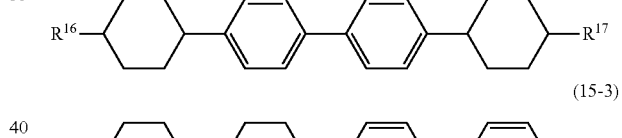
(15-4) 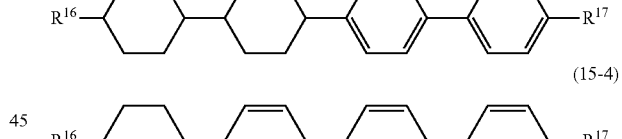
(15-5) 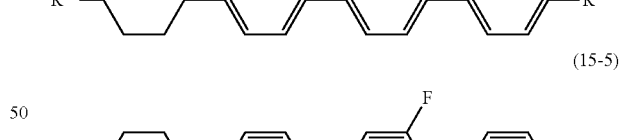
(15-6) 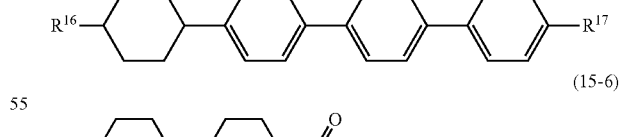
(15-7) 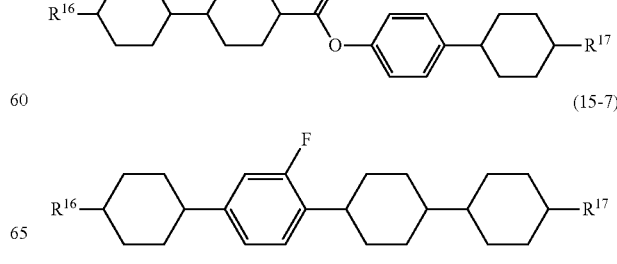

Component E has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or effective in adjusting the optical anisotropy.

When a content of component E is increased, the dielectric anisotropy of the composition decreases, but the viscosity also decreases. Thus, as long as a desired value of threshold voltage of the device is met, the content is preferably as large as possible. Accordingly, when the composition is prepared, the content of component E is preferably approximately 30% by weight or more, and further preferably approximately 40% by weight or more, based on the weight of the composition.

Preparation of composition (1) is performed by a method of dissolving required components at a high temperature, or the like. According to an application, an additive may be added to the composition. Specific examples of the additive include the optically active compound, the polymerizable compound, the polymerization initiator, the antioxidant, the ultraviolet light absorber, the light stabilizer, the heat stabilizer, the antifoaming agent and the dye. Such additives are well known to those skilled in the art, and described in literature.

Composition (1) may further contain at least one optically active compound. The optically active compound is effective in inducing helical structure in liquid crystal molecules to give a required twist angle, thereby being effective in preventing a reverse twist. Preferred examples of the optically active compound include compounds (Op-1) to (Op-18) described below.

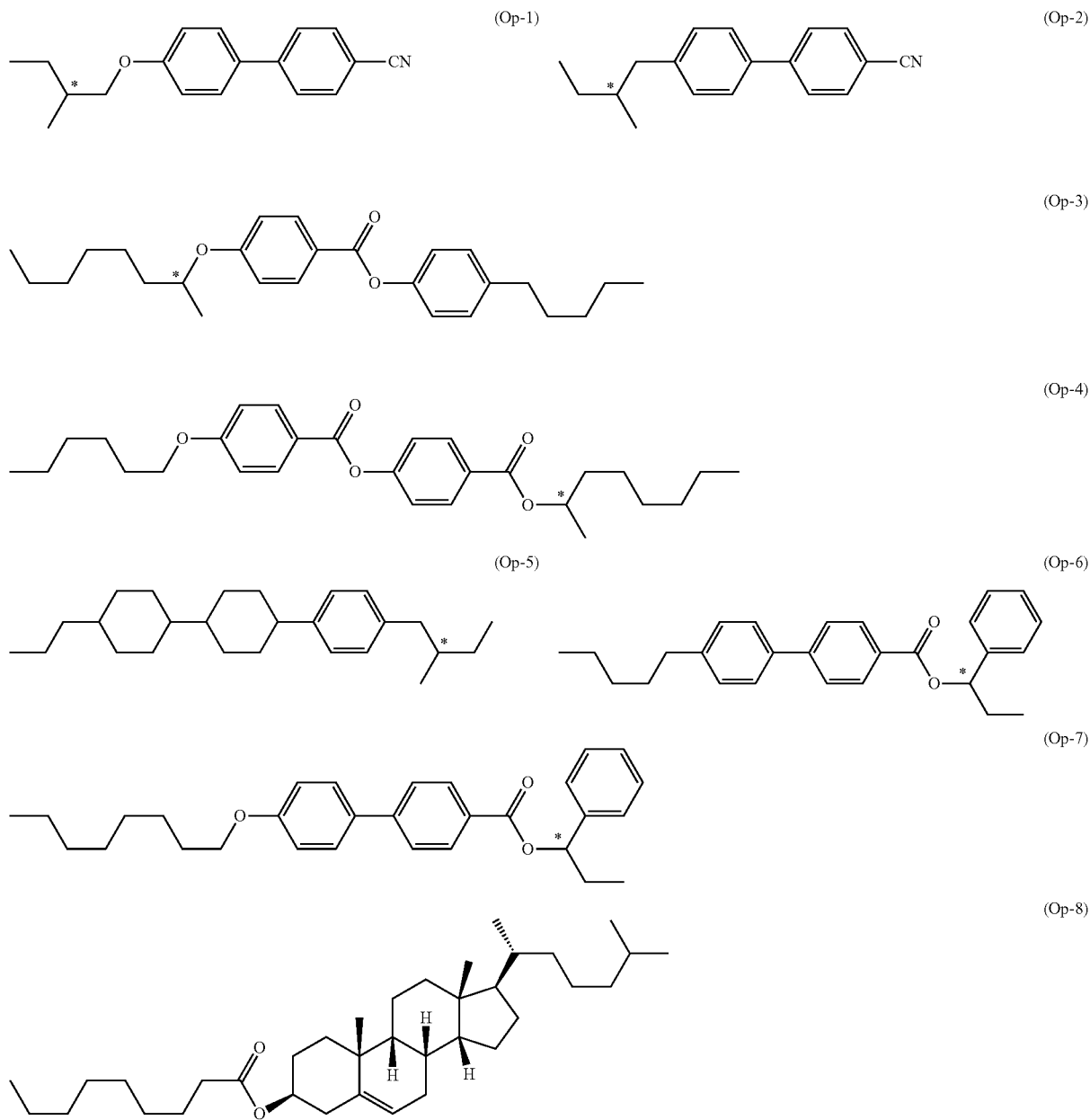

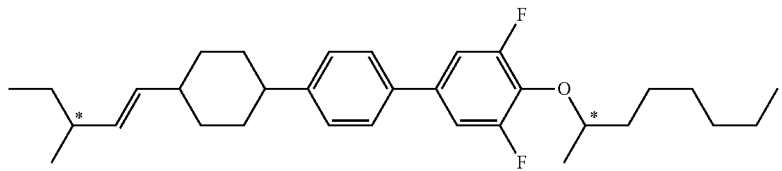 (Op-9)
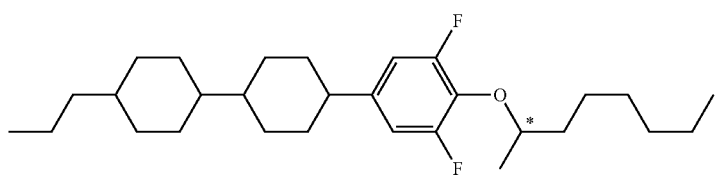 (Op-10)
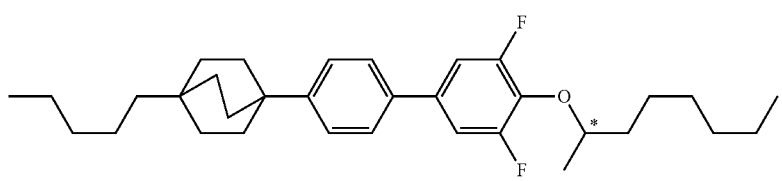 (Op-11)
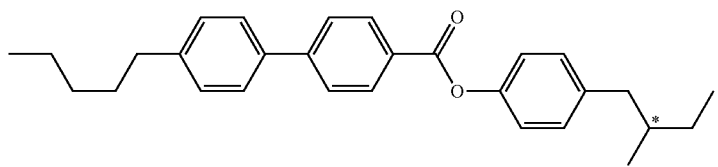 (Op-12)
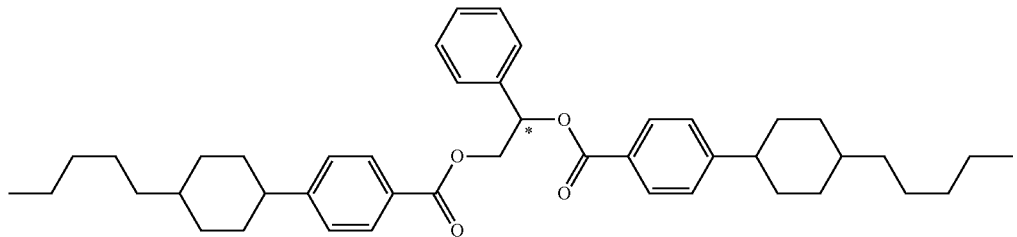 (Op-13)
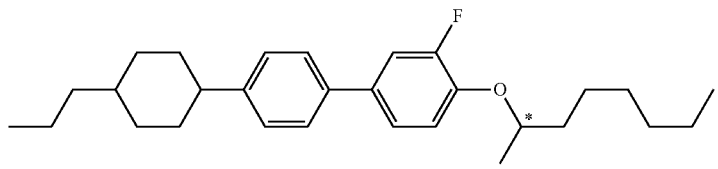 (Op-14)
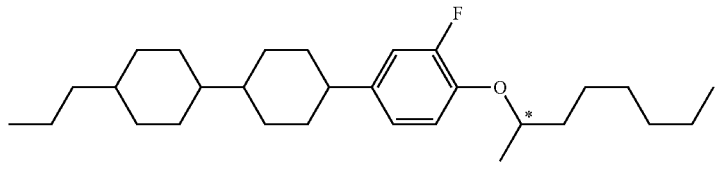 (Op-15)
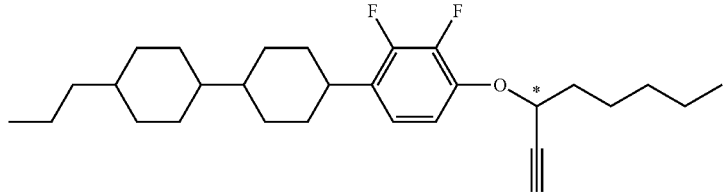 (Op-16)

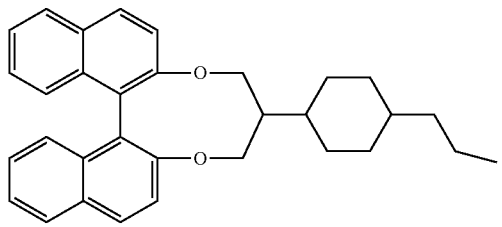

(Op-17)

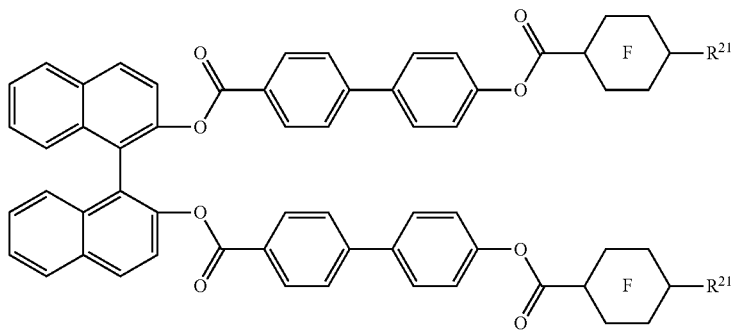

(Op-18)

In compound (Op-18), ring F is 1,4-cyclohexylene or 1,4-phenylene, and $R^{21}$ is alkyl having 1 to 10 carbons.

In composition (1), a helical pitch is adjusted by adding such an optically active compound. The helical pitch is preferably adjusted in the range of approximately 40 to approximately 200 micrometers in a liquid crystal composition for the TFT mode and the TN mode. In a composition for the STN mode, the helical pitch is preferably adjusted in the range of approximately 6 to approximately 20 micrometers. In the case of a composition for a BTN mode, the helical pitch is preferably adjusted in the range of approximately 1.5 to approximately 4 micrometers. Two or more optically active compounds may be added for the purpose of adjusting temperature dependence of the helical pitch.

A composition can also be used for the PSA mode by adding the polymerizable compound. Examples of the polymerizable compound include acrylate, methacrylate, a vinyl compound, a vinyloxy compound, propenyl ether, an epoxy compound (oxirane, oxetane) and vinyl ketone. The polymerizable compound is polymerized by irradiation with ultraviolet light or the like. An initiator such as a photopolymerization initiator may be added. Suitable conditions for polymerization, suitable types of the initiator and suitable amounts thereof are known to those skilled in the art and are described in literature. Specific preferred examples of the polymerizable compound include compounds (M-1) to (M-12).

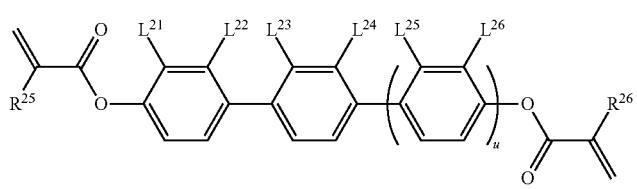

(M-1)

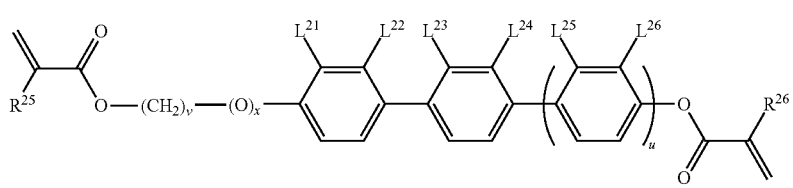

(M-2)

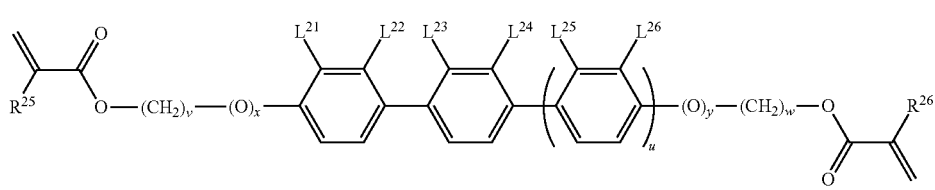

(M-3)

-continued
(M-4)
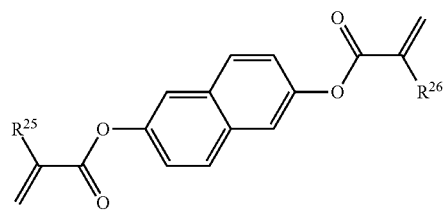
(M-5)
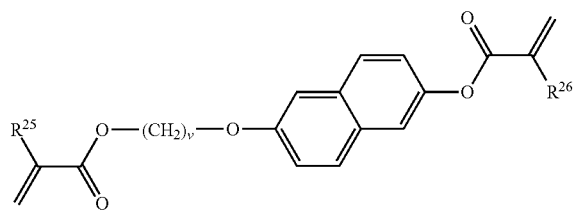
(M-6)
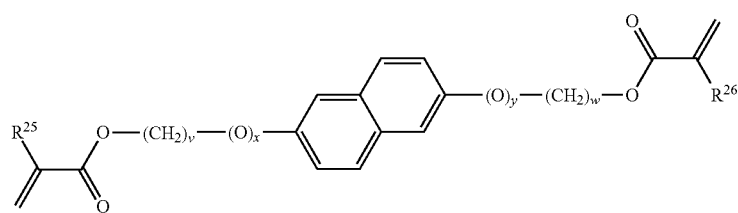
(M-7)
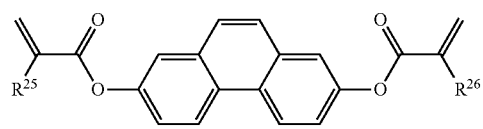
(M-8)
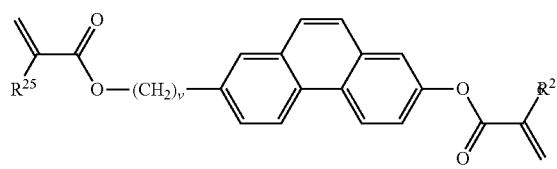
(M-9)
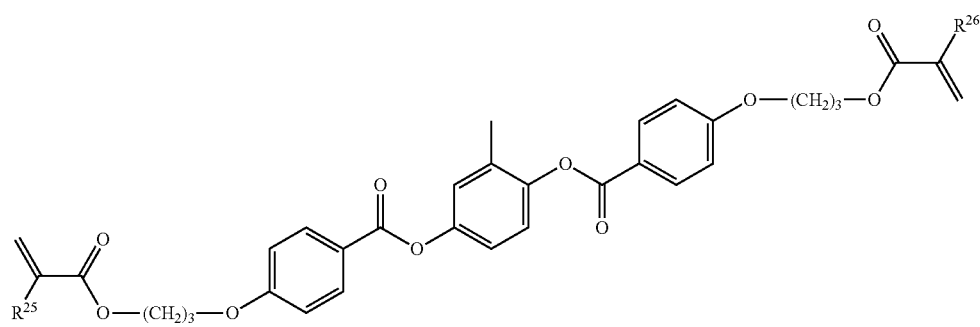
(M-10)
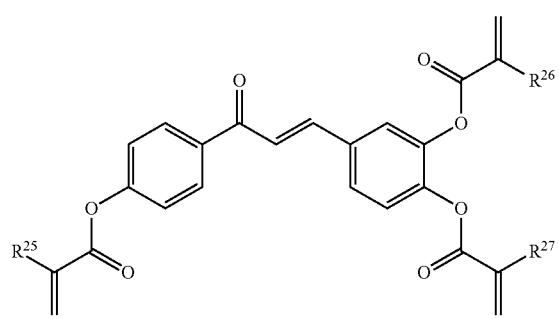
(M-11)
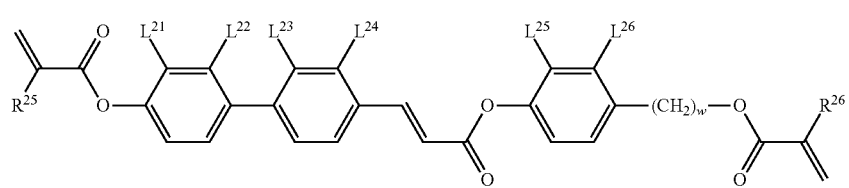

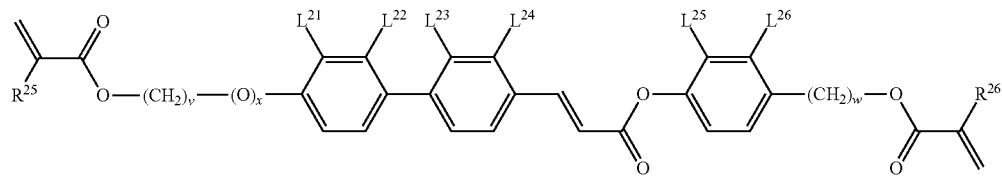

(M-12)

In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

The antioxidant is effective for maintaining a large voltage holding ratio. Preferred examples of the antioxidant include compounds (AO-1) and (AO-2) described below, IRGANOX 415, IRGANOX 565, IRGANOX 1010, IRGANOX 1035, IRGANOX 3114, and IRGANOX 1098 (trade names: BASF SE). The ultraviolet light absorber is effective for preventing a decrease of the maximum temperature. Preferred examples of the ultraviolet light absorbent include a benzophenone derivative, a benzoate derivative, a triazole derivative. Specific examples includes compound (AO-3) and (AO-4) described below, TINUVIN329, TINUVIN P, TINUVIN 326, TINUVIN 234, TINUVIN 213, TINUVIN 400, TINUVIN 328, TINUVIN 99-2 (trade names: BASF SE), and 1,4-diazabicyclo[2.2.2]octane (DABCO). A light stabilizer such as an amine having steric hindrance is preferred for maintaining the large voltage holding ratio. Preferred examples of the light stabilizers include compounds (AO-5) and (AO-6) described below, TINUVIN 144, TINUVIN 765 and TINUVIN 770DF (trade names: BASF SE). The heat stabilizer is also effective for maintaining the large voltage holding ratio, and specific preferred examples include IRGAFOS 168 (trade names: BASF SE). The antifoaming agent is effective for preventing foam formation. Preferred examples of the antifoaming agent include dimethyl silicone oil and methylphenyl silicone oil.

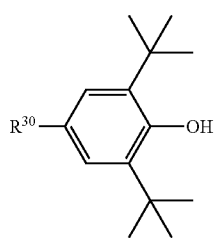

(AO-1)

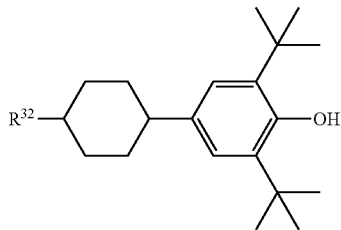

(AO-2)

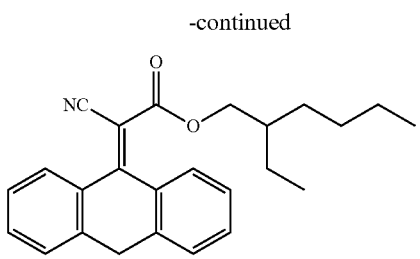

(AO-3)

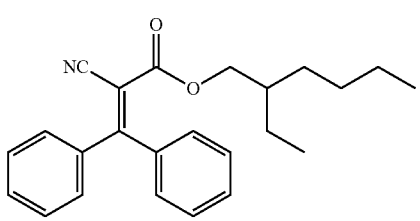

(AO-4)

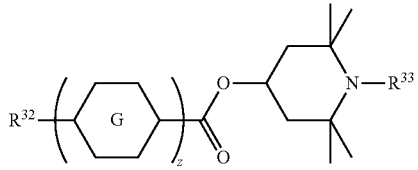

(AO-5)

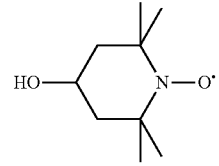

(AO-6)

In compound (AO-1), $R^{30}$ is alkyl having 1 to 20 carbons, alkoxy having 1 to 20 carbons, —COOR$^{31}$ or —CH$_2$CH$_2$COOR$^{31}$, and $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl or O$^-$ (oxygen radical); ring G is 1,4-cyclohexylene or 1,4-phenylene; and z is 1, 2 or 3.

Composition (1) can be also used for a guest host (GH) mode by addition of a dichroic dye such as a merocyanine type, a stylyl type, an azo type, an azomethine type, an azoxy type, a quinophthalone type, an anthraquinone type and a tetrazine type.

3. Liquid Crystal Display Device

Composition (1) can be used for a liquid crystal display device having an operating mode such as the PC mode, the TN mode, the STN mode, the OCB mode and the PSA mode, and driven by an active matrix (AM mode). Composition (1) can also be used for a liquid crystal display device having the operating mode such as the PC mode, the TN mode, the STN mode, the OCB mode, the VA mode and the IPS mode, and driven by a passive matrix (PM) mode. The AM mode and the PM mode devices can be applied to any of a reflective type, a transmissive type and transflective type.

Composition (1) can also be used for a nematic curvilinear aligned phase (NCAP) device prepared by microencapsulating a nematic liquid crystal, a polymer dispersed liquid crystal display device (PDLCD) and a polymer network liquid crystal display device (PNLCD), in which a three-dimensional network polymer is formed in the liquid crystal.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. However, the invention is not limited by the Examples.

1-1. Example of Compound (1)

Compound (1) was prepared according to the procedures described below. The thus prepared compound was identified by methods such as an NMR analysis. Physical properties of the compound were measured by methods described below.

NMR Analysis

For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. $^{19}$F-NMR measurement was carried out using $CFCl_3$ as an internal standard and under conditions of 24 times of accumulation. In the explanation of nuclear magnetic resonance spectra, symbols s, d, t, q, quin, sex, m and br stand for a singlet, a doublet, a triplet, a quartet, a quintet, a sextet, a multiplet and being broad, respectively.

Sample for Measurement

When phase structure and transition temperature were measured, a liquid crystal compound itself was used as a sample. When physical properties such as a maximum temperature of a nematic phase, viscosity, optical anisotropy and dielectric anisotropy were measured, a composition prepared by mixing the compound with a base liquid crystal was used as the sample.

When the sample in which the compound was mixed with the base liquid crystal was used, measurement was carried out as follows. The sample was prepared by mixing 15% by weight of the compound and 85% by weight of the base liquid crystal. Then, extrapolated values were calculated from measured values of the sample, according to an extrapolation method, expressed by an equation below, and the extrapolated values were described. {Extrapolated value}={100×(measured value of a sample)−(% by weight of a base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and physical properties of the sample at a ratio at which no crystals (or the smectic phase) precipitated at 25° C. were measured. In addition, unless otherwise noted, the ratio of the compound to the base liquid crystal was 15% by weight:85% by weight.

As the base liquid crystal, base liquid crystal (i) described below was used. Ratios of components of the base liquid crystal (i) are expressed in terms of weight percent (% by weight).

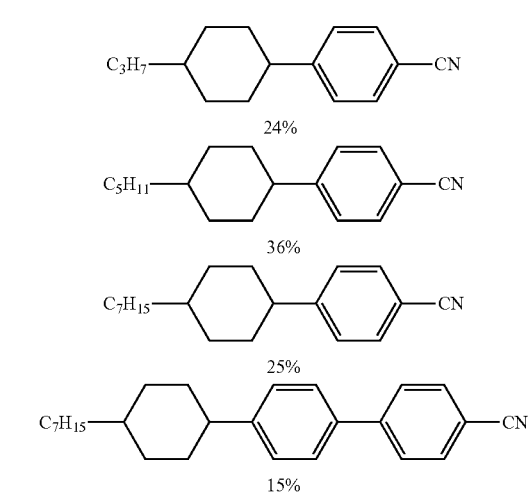

Measurement Methods

Physical properties were measured according to methods described below. Most of the methods are applied as described in the Standard of the Japan Electronics and Information Technology Industries Association (hereinafter, abbreviated as JEITA) (JEITA ED-2521B) discussed and established by JEITA, or as modified thereon. No TFT was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high-sensitivity differential scanning calorimeter, X-DSC7000, made by SR NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. Temperature at which a compound undergoes transition from a solid to a liquid crystal phase such as the smectic phase and the nematic phase may be occasionally abbreviated as "minimum temperature of the liquid crystal phase." Temperature at which a compound undergoes transition from the liquid crystal phase to the isotropic liquid may be occasionally abbreviated as "clearing point."

The crystals were expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at a Low Temperature

Samples in which the base liquid crystal and the compound were mixed for the compound to be 20% by weight, 15% by weight, 10% by weight, 5% by weight, 3% by weight and 1% by weight were prepared, and placed in glass vials. After the glass vials were kept in freezers at −10° C. or −20° C. for a predetermined period of time, whether or not crystals or a smectic phase precipitated was observed.

(4) Maximum Temperature of a Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. A higher limit of the temperature range of the nematic phase may be occasionally abbreviated as "maximum temperature." When the sample was a mixture of a compound and the mother liquid crystal, the maximum temperature was expressed using a symbol $T_{NI}$. When the sample was a mixture of a compound and component B, the maximum temperature was expressed using a symbol NI.

(5) Minimum Temperature of a Nematic Phase ($T_C$; ° C.)

Samples each having a nematic phase were kept in freezers at temperatures of 0° C., −10° C., −20° C., −30° C. and −40° C. for 10 days, and then the liquid crystal phases were observed. For example, when the sample maintained the nematic phase at −20° C. and changed to the crystals or the smectic phase at −30° C., $T_c$ was expressed as $T_c \leq -20°$ C. A lower limit of the temperature range of the nematic phase may be occasionally abbreviated as "minimum temperature."

(6) Viscosity (Bulk Viscosity; η; Measured at 20° C.; mPa·s)

A cone-plate (E type) rotational viscometer made by TOKYO KEIKI INC. was used for measurement.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values according to calculating equation (8) on page 40 of the paper presented by M. Imai et al. A value of dielectric anisotropy required for the calculation was determined using the device by which the rotational viscosity was measured and by a method described below.

(8) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=nμ−n⊥.

(9) Dielectric Constant in a Minor Axis Direction (∈⊥) and Dielectric Anisotropy (Δ∈; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant in the major axis direction (∈∥) of liquid crystal molecules was measured. Sine waves (0.5 V, 1 kHz) were applied to the device, and after 2 seconds, a dielectric constant in the minor axis direction (∈⊥) of the liquid crystal molecules was measured. A value of dielectric anisotropy was calculated from an equation: Δ∈=∈∥−∈⊥.

(10) Elastic Constant (K; Measured at 25° C.; pN)

For measurement, HP4284A LCR Meter made by Yokogawa-Hewlett-Packard Co. was used. A sample was put in a horizontal alignment device in which a distance (cell gap) between two glass substrates was approximately 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is expressed using a mean value of the thus determined $K_{11}$, $K_{22}$ and $K_{33}$.

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was approximately 0.45/Δn (μm) and a twist angle was approximately 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 90% transmittance.

(12) Voltage Holding Ratio (VHR-1; Measured at 25° C.; %)

A TN device used for measurement had a polyimide alignment film and a distance (cell gap) between two glass substrates was approximately 5 micrometers. A sample was put in the device, and the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(13) Voltage Holding Ratio (VHR-2; Measured at 80° C.; %)

A voltage holding ratio (VHR-2) was determined in a manner similar to the method for measuring VHF-1 except that measurement was carried out at 80° C.

Raw Material

Solmix A-11 (trade name) is a mixture of ethanol (85.5%), methanol (13.4%) and isopropanol (1.1%), and was purchased from Japan Alcohol Trading Co., Ltd.

Example 1

Synthesis of Compound (1-2-2)

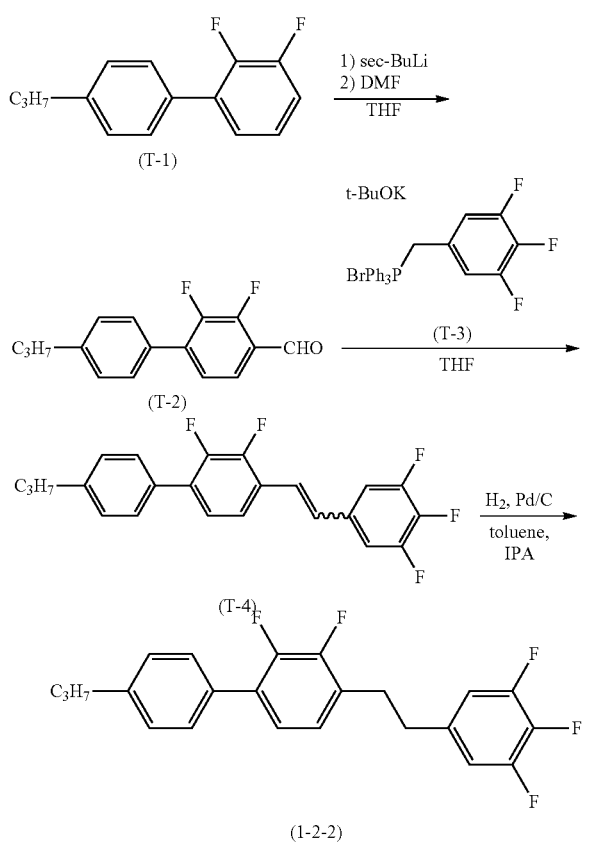

First Step

Under a nitrogen atmosphere, compound (T-1) (3.29 g) and THF (65.0 mL) were put in a reaction vessel, and the resulting mixture was cooled to −70° C. Thereto, sec-butyl lithium (1.03 M; cyclohexane, n-hexane solution; 16.5 mL) was slowly added, and resulting mixture was stirred for 1 hour. Next, DMF (2.19 mL) was slowly added thereto, and the resulting mixture was stirred for 8 hours while the mixture was returned to room temperature. The resulting reaction mixture was poured into a saturated aqueous solution of ammonium chloride, and the resulting aqueous layer was subjected to extraction with toluene. Then, organic layers combined were washed with brine, and dried over anhydrous magnesium sulfate. The resulting solution was concentrated under reduced pressure, and the residue was purified by silica gel chromatography (heptane:toluene=1:1 in a volume ratio) to give compound (T-2) (3.00 g; 81%).

Second Step

Under a nitrogen atmosphere, compound (T-3) (7.02 g) and THF (25.0 mL) were put in a reaction vessel, and the resulting mixture was cooled to −30° C. Thereto, potassium t-butoxide (1.55 g) was slowly added, and the resulting mixture was stirred for 30 minutes. Next, a THF (20.0 mL) solution of compound (T-1) (3.00 g) was slowly added thereto, and the resulting mixture was stirred for 8 hours while the mixture was returned to room temperature. The resulting reaction mixture was poured into ice water, and the resulting aqueous layer was subjected to extraction with toluene. Then, organic layers combined were washed with brine, and dried over anhydrous magnesium sulfate. The resulting solution was concentrated under reduced pressure, and the residue was purified by silica gel chromatography (heptane:toluene=8:1 in a volume ratio) to give compound (T-4) (4.48 g; 100%).

Third Step

Compound (T-4) (4.48 g), a palladium on carbon catalyst (0.224 g; NX type of 5% Pd/C (50% wet basis); made by N.E. CHEMCAT Corporation), toluene (23.0 mL) and IPA (23.0 mL) were put in a reaction vessel, and the resulting mixture was stirred for 8 hours under a hydrogen atmosphere. The catalyst was removed by filtration, and then the resulting mixture was concentrated under reduced pressure, and the residue was purified by silica gel chromatography (heptane). The resulting product was further purified by recrystallization from Solmix (registered trade name) A-11 to give compound (1-2-2) (2.94 g; 65%).

Chemical shifts δ (ppm; CDCl$_3$): 7.47-7.42 (m, 2H), 7.30-7.24 (m, 2H), 7.13-7.07 (m, 1H), 6.91-6.85 (m, 1H), 6.84-6.76 (m, 2H), 3.00-2.86 (m, 4H), 2.64 (t, J=7.8 Hz, 2H), 1.74-1.63 (m, 2H) and 0.98 (t, J=7.3 Hz, 3H).

Physical properties of compound (1-2-2) were as described below.

Transition temperature: C 65.8 I.

Maximum temperature ($T_{NI}$)=1.0° C.; optical anisotropy (Δn)=0.130; dielectric anisotropy (Δ∈)=14.1; dielectric constant in a minor axis direction (∈⊥)=9.2; viscosity (η)=57.2 mPa·s.

Example 2

Synthesis of Compound (1-2-51)

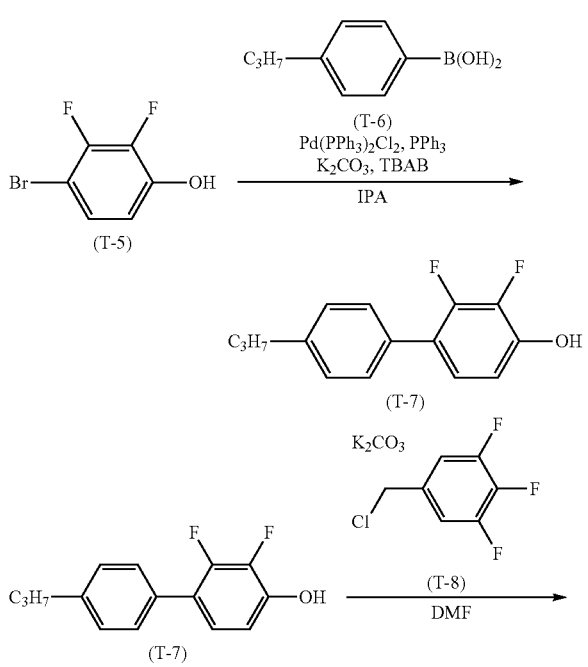

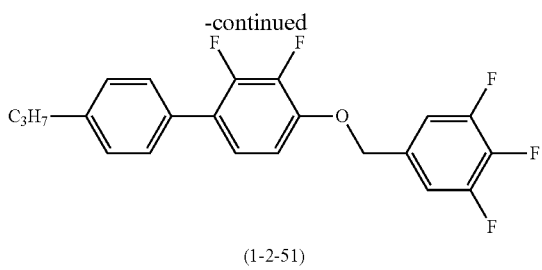

(1-2-51)

First Step

Under a nitrogen atmosphere, compound (T-5) (10.0 g), compound (T-6) (9.42 g), dichlorobis(triphenylphosphine) palladium (1.28 g), triphenyl phosphine (0.960 g), potassium carbonate (16.9 g), TBAB (3.93 g) and IPA (150 mL) were put in a reaction vessel, and the resulting mixture was heated under reflux for 3 hours. The resulting reaction mixture was poured into water, and the resulting aqueous layer was subjected to extraction with toluene. Then, organic layers combined were washed with water, and dried over anhydrous magnesium sulfate. The resulting solution was concentrated under reduced pressure, and the residue was purified by silica gel chromatography (toluene) to give compound (T-7) (9.96 g; 84%).

Second Step

Under a nitrogen atmosphere, compound (T-7) (4.95 g), compound (T-8) (3.00 g), potassium carbonate (4.59 g), TBAB (1.07 g) and DMF (30.0 mL) were put in a reaction vessel, and the resulting mixture was stirred at 115° C. for 3 hours. The resulting reaction mixture was poured into water, and the resulting aqueous layer was subjected to extraction with ethyl acetate. Then, organic layers combined were washed with brine, and dried over anhydrous magnesium sulfate. The resulting solution was concentrated under reduced pressure, and the residue was purified by silica gel chromatography (heptane:toluene=3:1 in a volume ratio). The resulting product was further purified by recrystallization from Solmix (registered trade name) A-11 to give compound (1-2-51) (5.31 g; 81%).

Chemical shifts δ (ppm; CDCl$_3$): 7.44-7.39 (m, 2H), 7.27-7.23 (m, 2H), 7.14-7.06 (m, 3H), 6.81-6.75 (m, 1H), 5.10 (s, 2H), 2.63 (t, J=7.5 Hz, 2H), 1.73-1.63 (m, 2H) and 0.97 (t, J=7.2 Hz, 3H).

Physical properties of compound (1-2-51) were as described below.

Transition temperature: C 114 I.

Maximum temperature (T$_{NI}$)=−0.3° C.; optical anisotropy (Δn)=0.157; dielectric anisotropy (Δ∈)=16.1; dielectric constant in a minor axis direction (∈⊥)=12.5; viscosity (η)=57.2 mPa·s.

Example 3

Synthesis of Compound (1-2-81)

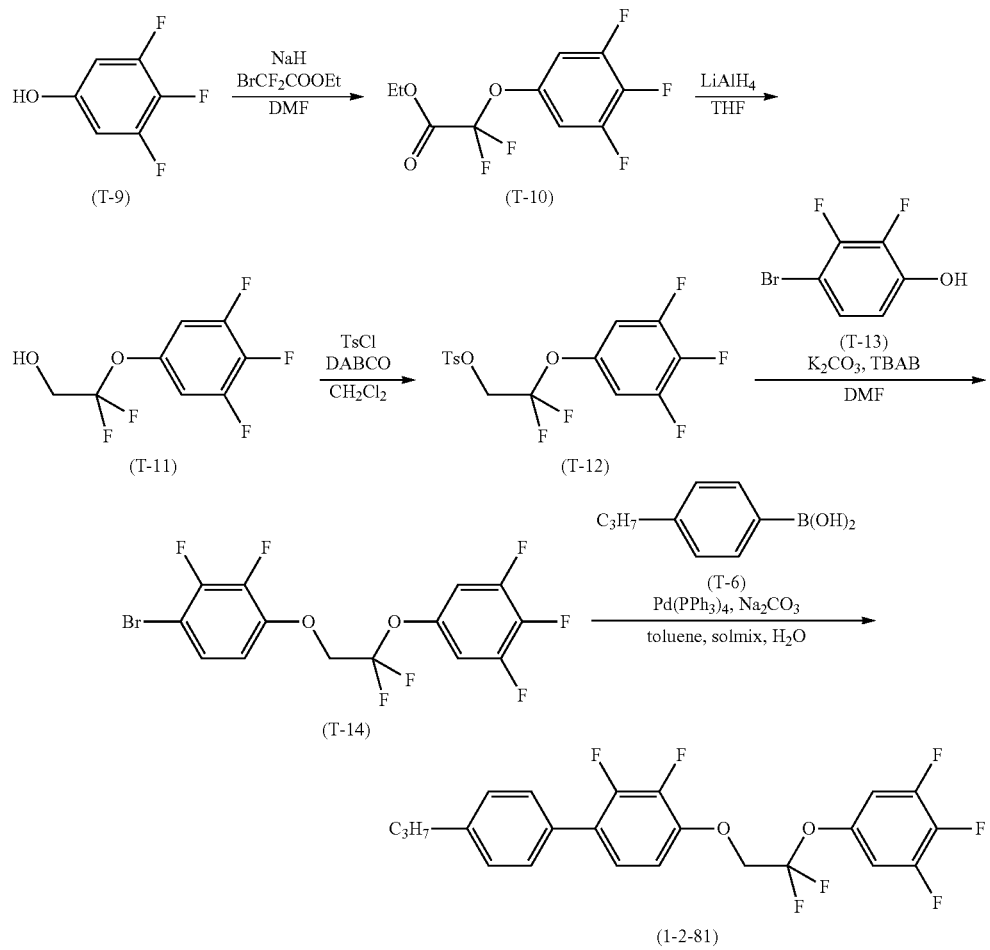

First Step

Under a nitrogen atmosphere, compound (T-9) (36.5 g) and DMF (350 mL) were put in a reaction vessel, and the resulting mixture was stirred at room temperature for 1 hour. Thereto, a DMF (50.0 mL) solution of ethyl bromodifluoroacetate (50.0 g) was slowly added, and the resulting mixture was further stirred at room temperature for 1 hour. The resulting reaction mixture was poured into ice water, and the resulting aqueous layer was subjected to extraction with diethyl ether. Then, organic layers combined were washed with brine, and dried over anhydrous magnesium sulfate. The resulting solution was concentrated under reduced pressure, and the residue was purified by silica gel chromatography (hexane:THF=4:1 in a volume ratio) to give compound (T-10) (45.9 g; 69%).

Second Step

Under a nitrogen atmosphere, lithium aluminum hydride (2.81 g) and THF (150 mL) were put in a reaction vessel, and the resulting mixture was cooled to 0° C. Thereto, a THF (100 mL) solution of compound (T-10) (20.0 g) was slowly added, and the resulting mixture was stirred for 3 hours while the mixture was returned to room temperature. The resulting reaction mixture was poured into a saturated aqueous solution of ammonium chloride, and the resulting insoluble matter was removed by filtration, and then the resulting aqueous layer was subjected to extraction with ethyl acetate. Then, organic layers combined were washed with brine, and dried over anhydrous magnesium sulfate. The resulting solution was concentrated under reduced pressure to give compound (T-11) (16.9 g; 100%).

Third Step

Under a nitrogen atmosphere, compound (T-11) (16.9 g), p-toluene sulfonyl chloride (14.1 g) and dichloromethane (150 mL) were put in a reaction vessel, and the resulting mixture was cooled to 0° C. Thereto, a dichloromethane (150 mL) solution of DABCO (33.2 g) was slowly added, and the resulting mixture was stirred for 8 hours while the mixture was returned to room temperature. The resulting reaction mixture was poured into 6 N hydrochloric acid, and the resulting aqueous layer was subjected to extraction with dichloromethane. Then, organic layers combined were washed with brine, and dried over anhydrous magnesium sulfate. The resulting solution was concentrated under reduced pressure, and the residue was purified by silica gel chromatography (heptane:toluene=4:6 in a volume ratio) to give compound (T-12) (22.9 g; 81%).

Fourth Step

Under a nitrogen atmosphere, compound (T-12) (22.3 g), compound (T-13) (10.2 g), potassium carbonate (8.07 g), TBAB (1.88 g) and DMF (300 mL) were put in a reaction vessel, and the resulting mixture was stirred at 115° C. for 4 hours. The resulting reaction mixture was poured into water, and the resulting aqueous layer was subjected to extraction with toluene. Then, organic layers combined were washed with brine, and dried over anhydrous magnesium sulfate. The resulting solution was concentrated under reduced pressure, and the residue was purified by silica gel chromatography (heptane:toluene=4:1 in a volume ratio) to give compound (T-14) (14.5 g; 71%).

Fifth Step

Under a nitrogen atmosphere, compound (T-14) (3.00 g), compound (T-6) (1.41 g), tetrakis(triphenylphosphine)palladium (0.414 g), sodium carbonate (1.52 g), toluene (80.0 mL), Solmix (registered trade name) A-11 (60.0 mL) and water (40.0 mL) were put in a reaction vessel, and the resulting mixture was heated under reflux for 4 hours. The resulting reaction mixture was poured into water, and the resulting aqueous layer was subjected to extraction with toluene. Then, organic layers combined were washed with water, and dried over anhydrous magnesium sulfate. The resulting solution was concentrated under reduced pressure, and the residue was purified by silica gel chromatography (heptane: toluene=7:3 in a volume ratio). The resulting product was further purified by recrystallization from a mixed solvent of heptane and Solmix (registered trade name) A-11 (1:2 in a volume ratio) to give compound (1-2-81) (1.85 g; 56%).

Chemical shifts δ (ppm; $CDCl_3$): 7.45-7.39 (m, 2H), 7.30-7.24 (m, 2H), 7.17-7.10 (m, 1H), 6.97-6.85 (m, 3H), 4.50 (t, J=8.3 Hz, 2H), 2.63 (t, J=7.8 Hz, 2H), 1.73-1.63 (m, 2H) and 0.97 (t, J=7.3 Hz, 3H).

Physical properties of compound (1-2-81) were as described below.

Transition temperature: C 55.6 I.

Maximum temperature $(T_{NI})$=−25.0° C.; optical anisotropy (Δn)=0.097; dielectric anisotropy (Δ∈)=12.8; dielectric constant in a minor axis direction (∈⊥)=13.2; viscosity (η)=59.4 mPa·s.

Example 4

Synthesis of Compound (1-4-82)

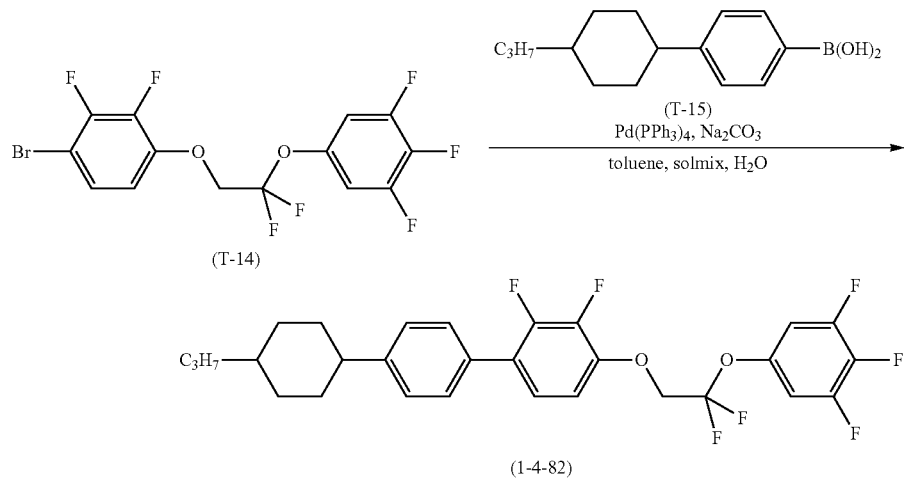

(T-14)

(1-4-82)

First Step

Compound (1-4-82) (2.07 g; 53%) was obtained by using compound (T-5) (2.11 g) in a manner similar to the procedures in the fifth step in Example 3.

Chemical shifts δ (ppm; CDCl$_3$): 7.45-7.39 (m, 2H), 7.31-7.25 (m, 2H), 7.17-7.10 (m, 1H), 6.97-6.85 (m, 3H), 4.50 (t, J=8.3 Hz, 2H), 2.51 (tt, J=12.1 Hz, J=3.1 Hz, 1H), 1.97-1.84 (m, 4H), 1.54-1.43 (m, 2H), 1.41-1.18 (m, 5H), 1.13-1.01 (m, 2H) and 0.91 (t, J=7.4 Hz, 3H).

Physical properties of compound (1-4-82) were as described below.

Transition temperature: C 74.7 S$_A$ 80.1 N 123 I.

Maximum temperature (T$_{NI}$)=88.4° C.; optical anisotropy (Δn)=0.137; dielectric anisotropy (Δ∈)=11.1; dielectric constant in a minor axis direction (∈⊥)=9.7; viscosity (η)=89.6 mPa·s.

Example 5

Synthesis of Compound (1-2-72)

First Step

Under a nitrogen atmosphere, methoxymethyltriphenylphosphonium chloride (32.9 g) and THF (250 mL) were put in a reaction vessel, and the resulting mixture was cooled to −30° C. Thereto, potassium t-butoxide (10.3 g) was slowly added, and the resulting mixture was stirred for 30 minutes. Next, a THF (70 mL) solution of compound (T-2) (20.0 g) was slowly added thereto, and the resulting mixture was stirred for 8 hours while the mixture was returned to room temperature. The resulting reaction mixture was poured into ice water, and the resulting aqueous layer was subjected to extraction with toluene. Then, organic layers combined were washed with brine, and dried over anhydrous magnesium sulfate. The resulting solution was concentrated under reduced pressure, and the residue was purified by silica gel chromatography (heptane:ethyl acetate=20:1 in a volume ratio) to give compound (T-16) (22.2 g; 100%).

Second Step

Under a nitrogen atmosphere, compound (T-3) (22.2 g), formic acid (67.0 mL) and toluene (110 mL) were put in a

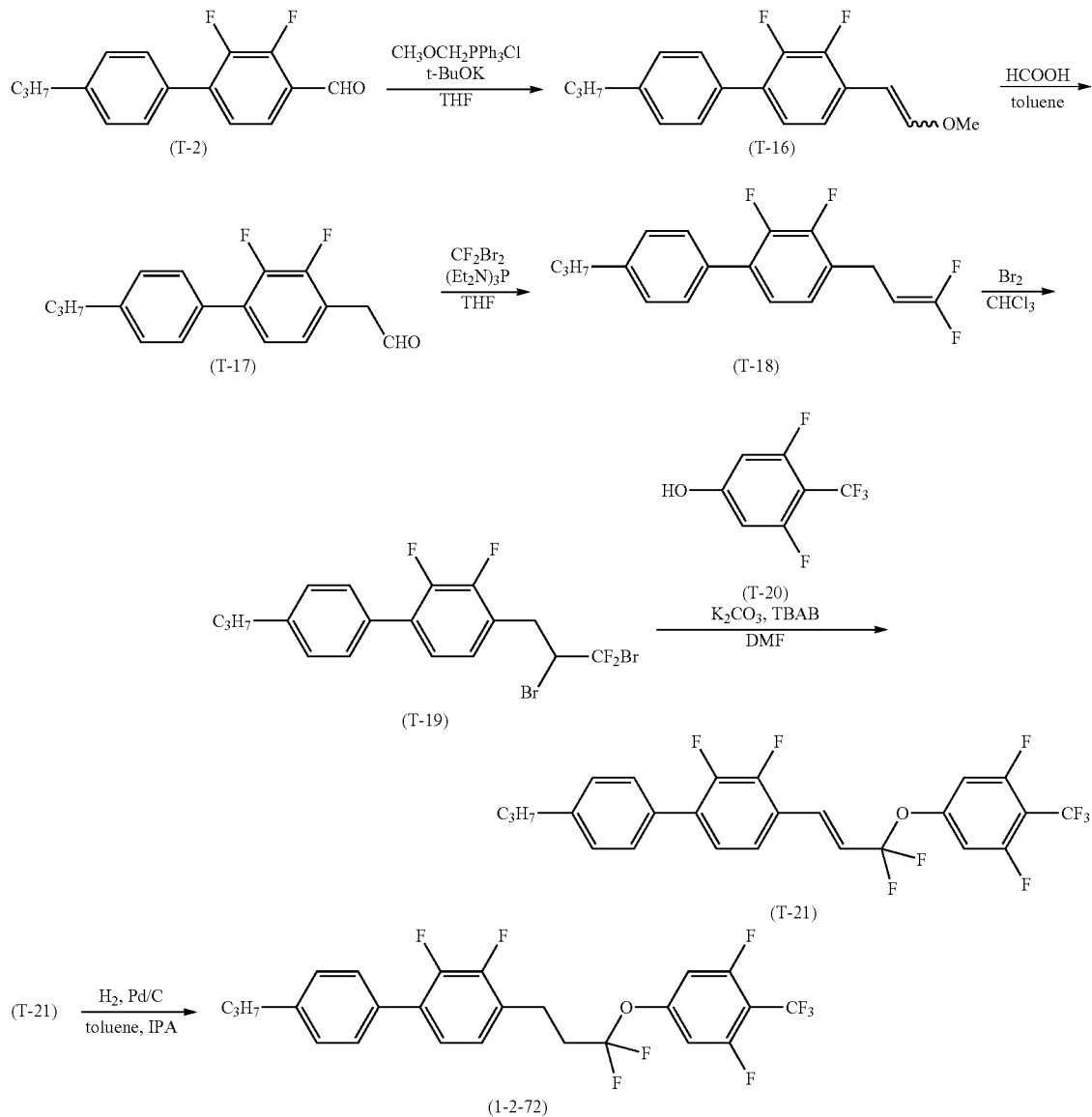

reaction vessel, and the resulting mixture was heated under reflux for 3 hours. The resulting reaction mixture was poured into ice water, and the resulting aqueous layer was subjected to extraction with toluene. Then organic layers combined were sequentially washed with a saturated aqueous solution of sodium hydrogencarbonate, water and brine, and dried over anhydrous magnesium sulfate. The resulting solution was concentrated under reduced pressure, and the residue was purified by silica gel chromatography (toluene) to give compound (T-17) (19.7 g; 92%).

Third Step

Under a nitrogen atmosphere, dibromodifluoromethane (30.1 g) and THF (300 mL) were put in a reaction vessel, and the resulting mixture was cooled to 0° C. Thereto, a THF (150 mL) solution of tris diethylamino phosphine (71.1 g) was slowly added, and the resulting mixture was stirred for 1 hour. Next, a THF (50.0 mL) solution of compound (T-17) (19.7 g) was slowly added thereto, and the resulting mixture was stirred for 5 hours while the mixture was returned to room temperature. The resulting reaction mixture was poured into ice water, and the resulting aqueous layer was subjected to extraction with heptane. Then, organic layers combined were washed with brine, and dried over anhydrous magnesium sulfate. The resulting solution was concentrated under reduced pressure, and the residue was purified by silica gel chromatography (heptane) to give compound (T-18) (7.21 g; 33%).

Fourth Step

Under a nitrogen atmosphere, compound (T-18) (7.20 g) and chloroform (40.0 mL) were put in a reaction vessel, and the resulting mixture was cooled to −10° C. Thereto, a chloroform (20.0 mL) solution of bromine (4.85 g) was slowly added thereto, and the resulting mixture was stirred for 1 hour while the mixture was returned to room temperature. The resulting reaction mixture was poured into water, and the resulting aqueous layer was subjected to extraction with dichloromethane. Then, organic layers combined were sequentially washed with water, a saturated aqueous solution of sodium thiosulfate and brine, and dried over anhydrous magnesium sulfate. The resulting solution was concentrated under reduced pressure, and the residue was purified by silica gel chromatography (heptane) to give compound (T-19) (6.00 g; 55%).

Fifth Step

Under a nitrogen atmosphere, compound (T-20) (1.33 g), potassium carbonate (2.66 g), TBAB (0.413 g) and DMF (40.0 mL) were put in a reaction vessel, and the resulting mixture was stirred at 90° C. for 30 minutes. Thereto, a DMF (20.0 mL) solution of compound (T-19) (3.00 g) was slowly added, and the resulting mixture was stirred at 90° C. for 2 hours. The reaction mixture was poured into ice water, and the resulting aqueous layer was subjected to extraction with toluene. Then, organic layers combined were washed with brine, and dried over anhydrous magnesium sulfate. The resulting solution was concentrated under reduced pressure, and the residue was purified by silica gel chromatography (heptane) to give compound (T-21) (1.22 g; 38%).

Sixth Step

Compound (1-2-72) (0.300 g; 25%) was obtained by using compound (T-21) as a raw material in a manner similar to the procedures in the third step in Example 1.

Chemical shifts δ (ppm; CDCl$_3$): 7.48-7.43 (m, 2H), 7.30-7.24 (m, 2H), 7.18-7.13 (m, 1H), 7.05-7.00 (m, 1H), 6.90-6.84 (m, 2H), 3.03 (t, J=7.7 Hz, 2H), 2.64 (t, J=7.9 Hz, 2H), 2.60-2.49 (m, 2H), 1.74-1.64 (m, 2H) and 0.98 (t, J=7.3 HZ, 3H).

Physical properties of compound (1-2-72) were as described below.

Transition temperature: C 46.0 I.

Maximum temperature (T$_{NI}$)=9.7° C.; optical anisotropy (Δn)=0.117; dielectric anisotropy (Δ∈)=21.4; dielectric constant in a minor axis direction (∈⊥)=8.5; viscosity (η)=59.1 mPa·s.

Example 6

Synthesis of Compound (1-5-62)

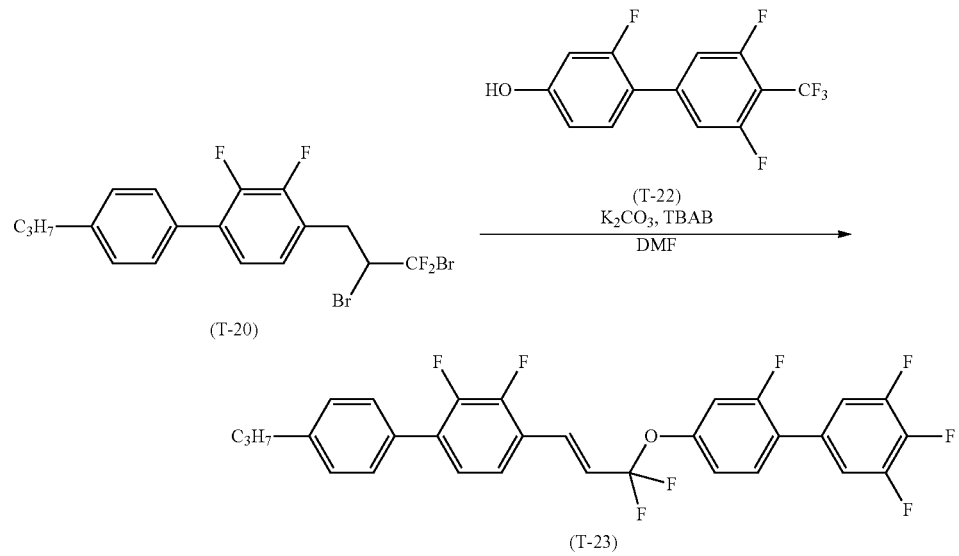

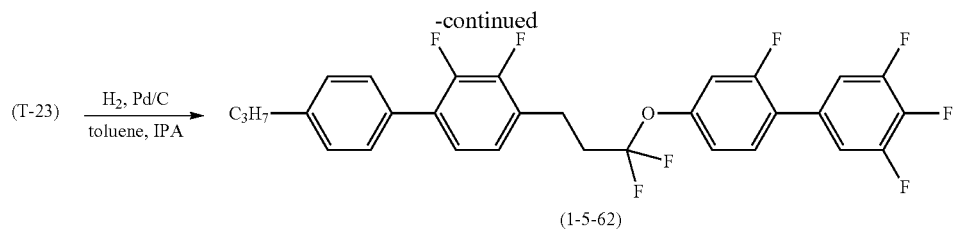

(1-5-62)

First Step

Compound (T-23) (2.19 g; 62%) was obtained by using compound (T-22) in a manner similar to the procedures in the fifth step in Example 5.

Second Step

Compound (1-5-62) (1.79 g; 82%) was obtained by using compound (T-23) as a raw material in a manner similar to the procedures in the third step in Example 1.

Chemical shifts δ (ppm; $CDCl_3$): 7.48-7.44 (m, 2H), 7.38-7.32 (m, 1H), 7.30-7.25 (m, 2H), 7.20-7.13 (m, 3H), 7.10-7.02 (m, 3H), 3.06 (t, J=7.9 Hz, 2H), 2.64 (t, J=7.5 Hz, 2H), 2.60-2.49 (m, 2H), 1.74-1.65 (m, 2H) and 0.98 (t, J=7.3 Hz, 3H).

Physical properties of compound (1-5-62) were as described below.

Transition temperature: C 86.8 N 107 I.

Maximum temperature ($T_{NI}$)=77.7° C.; optical anisotropy (Δn)=0.170; dielectric anisotropy (Δ∈)=19.9; dielectric constant in a minor axis direction (∈⊥)=7.7; viscosity (η)=76.5 mPa·s.

Compounds (No. 1-1-1) to (No. 1-1-20), compounds (No. 1-2-1) to (No. 1-2-120), compounds (No. 1-3-1) to (No. 1-3-80), compounds (No. 1-4-1) to (No. 1-4-100), compounds (No. 1-5-1) to (No. 1-5-80), compounds (No. 1-6-1) to (No. 1-6-40), compounds (No. 1-7-1) to (No. 1-7-10) and compounds (No. 1-8-1) to (No. 1-8-10) as shown below can be prepared according to the synthetic method of compound (1) as already described and the synthetic procedure as described in Examples 1 to 6.

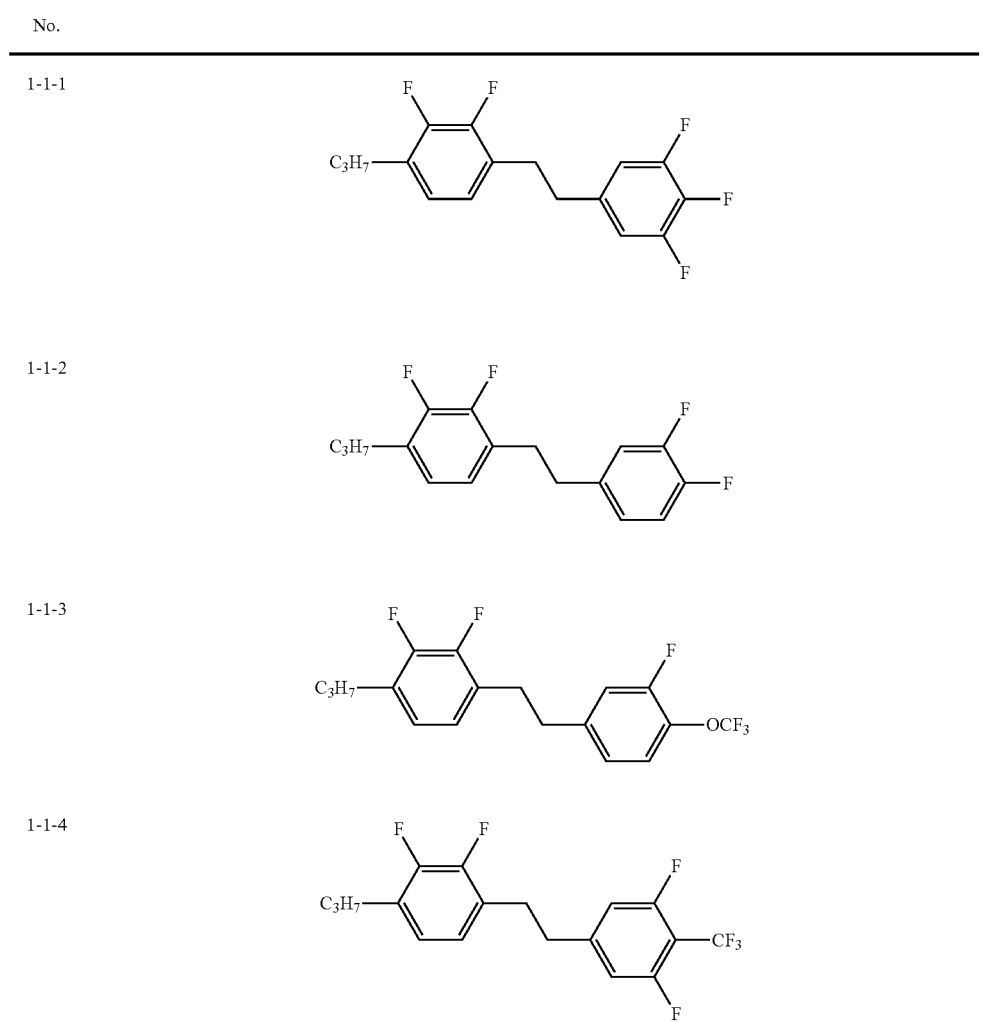

| No. | |
|---|---|
| 1-1-5 | 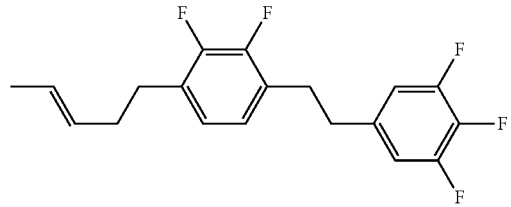 |
| 1-1-6 | 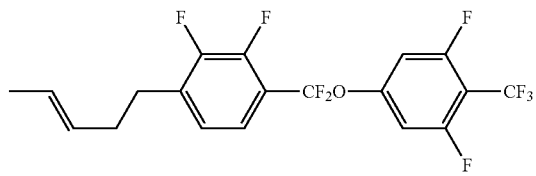 |
| 1-1-7 | 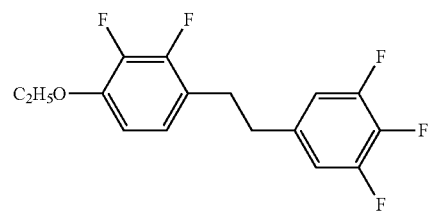 |
| 1-1-8 | 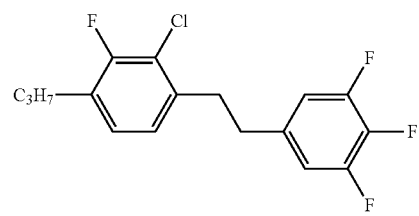 |
| 1-1-9 | 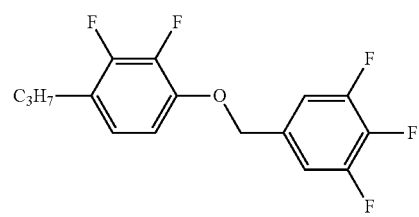 |
| 1-1-10 | 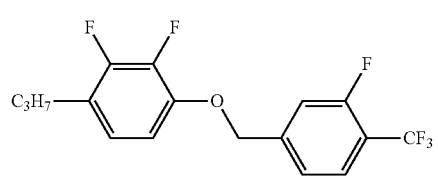 |
| 1-1-11 | 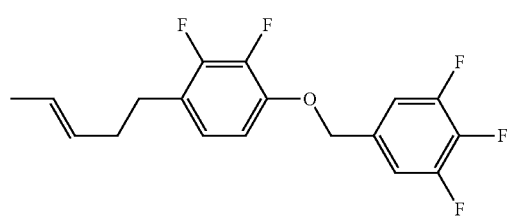 [SMILES: C/C=C/CCc1ccc(OCc2cc(F)c(F)c(F)c2)c(F)c1F] |

-continued
| No. | |
|---|---|
| 1-1-12 | 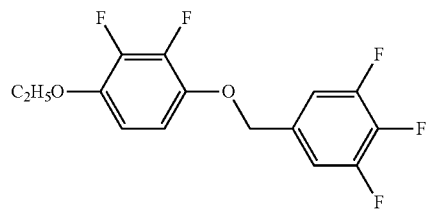 |
| 1-1-13 | 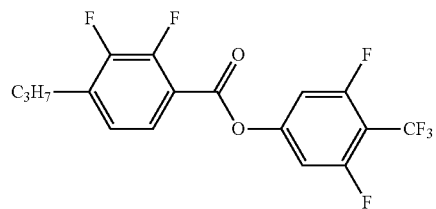 |
| 1-1-14 | 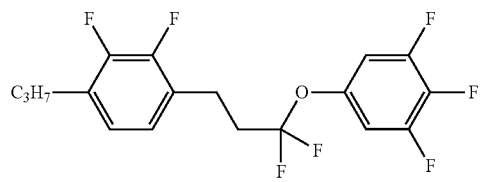 |
| 1-1-15 | 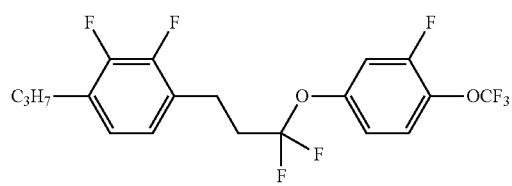 |
| 1-1-16 | 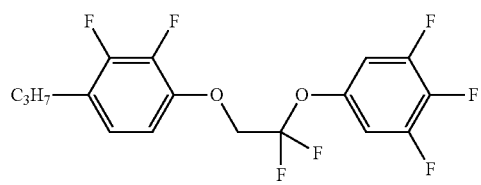 |
| 1-1-17 | 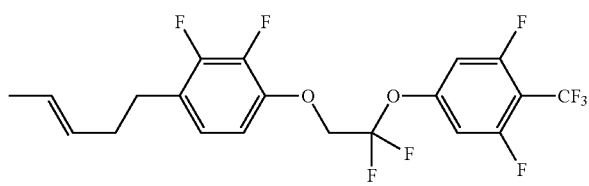 [SMILES: C/C=C/CCc1ccc(OCC(F)(F)Oc2cc(F)c(C(F)(F)F)c(F)c2)c(F)c1F] |
| 1-1-18 | 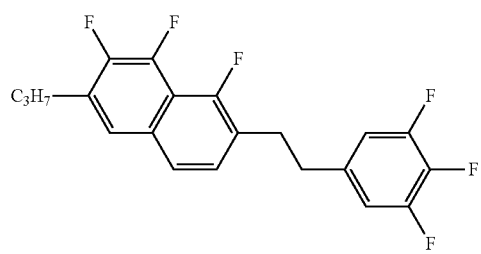 |

| No. | |
|---|---|
| 1-1-19 | 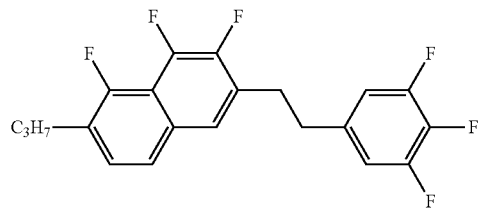 |
| 1-1-20 | 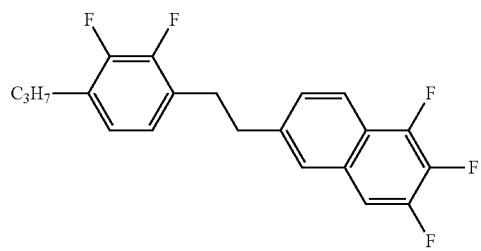 |
| 1-2-1 | 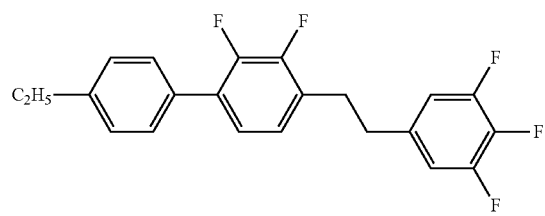 |
| 1-2-2 | 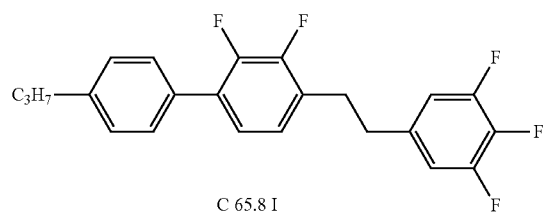<br>C 65.8 I<br>$T_{NI} = 1.0°$ C., $\Delta n = 0.130$, $\Delta\varepsilon = 14.1$, $\varepsilon (\perp) = 9.2$ |
| 1-2-3 | 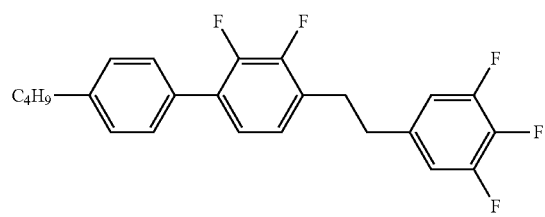 |
| 1-2-4 | 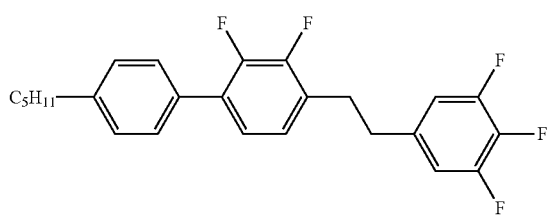 |

| No. | |
|---|---|
| 1-2-5 | 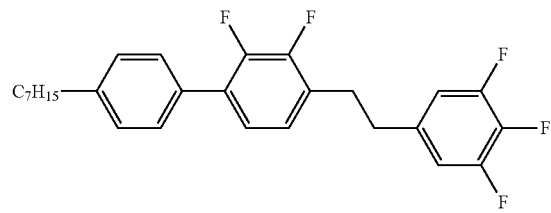 |
| 1-2-6 | 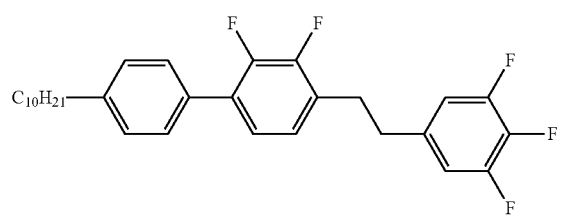 |
| 1-2-7 | 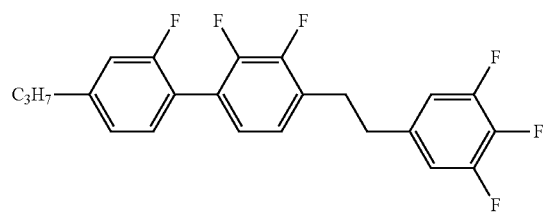 |
| 1-2-8 | 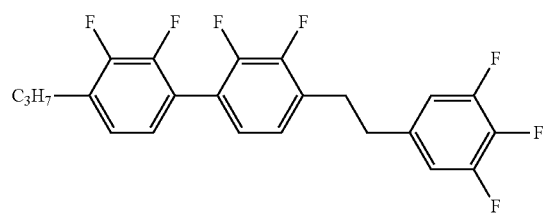 |
| 1-2-9 | 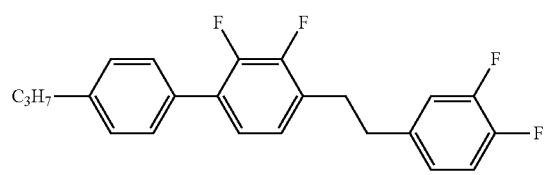 |
| 1-2-10 | 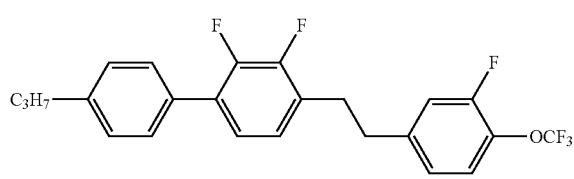 |
| 1-2-11 | 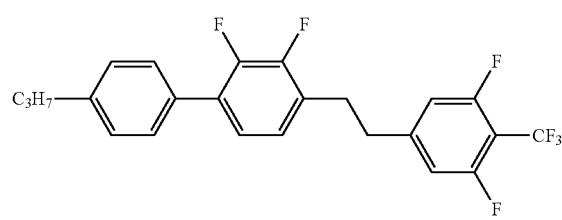 |

| No. |  |
|---|---|
| 1-2-12 | 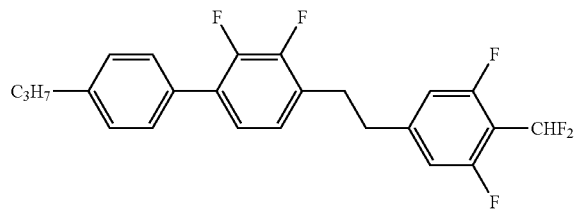 |
| 1-2-13 | 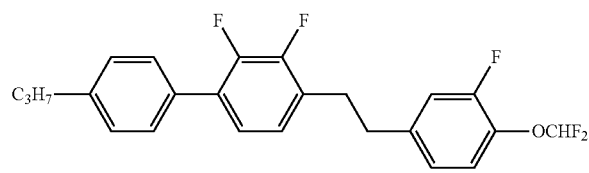 |
| 1-2-14 | 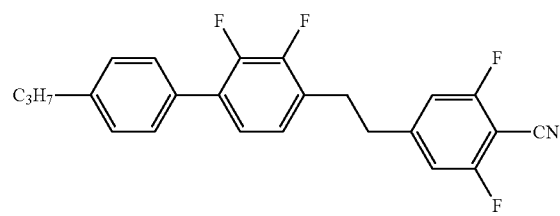 |
| 1-2-15 | 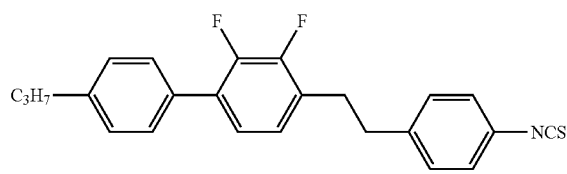 |
| 1-2-16 | 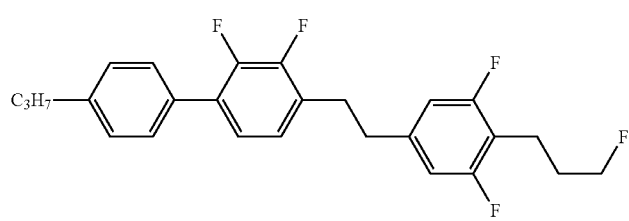 |
| 1-2-17 | 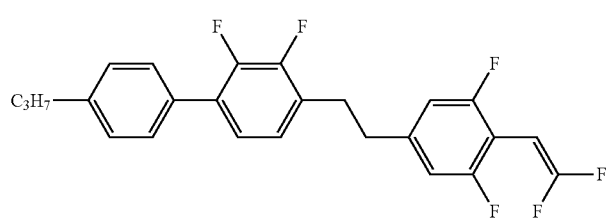 |
| 1-2-18 | 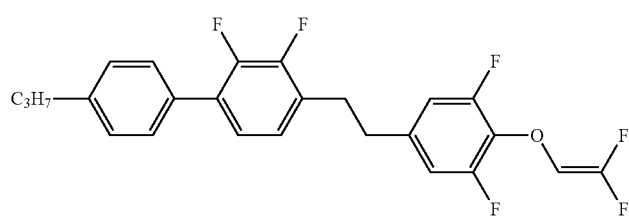 |

| No. | |
|---|---|
| 1-2-19 | 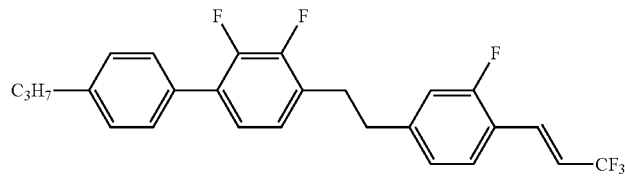 |
| 1-2-20 | 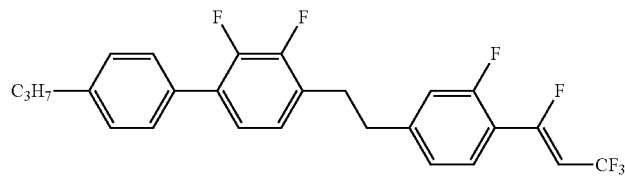 |
| 1-2-21 | 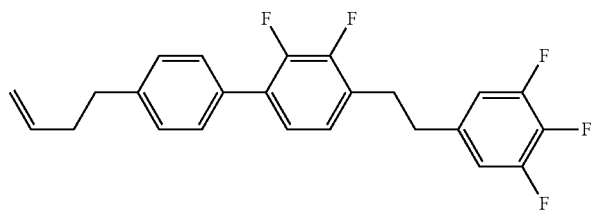 |
| 1-2-22 | 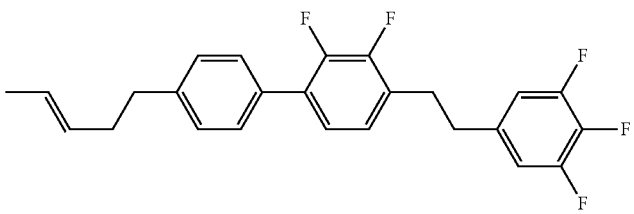 |
| 1-2-23 | 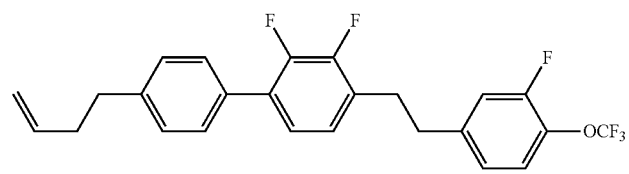 [SMILES: C=CCCc1ccc(-c2ccc(CCc3ccc(OC(F)(F)F)c(F)c3)c(F)c2F)cc1] |
| 1-2-24 | 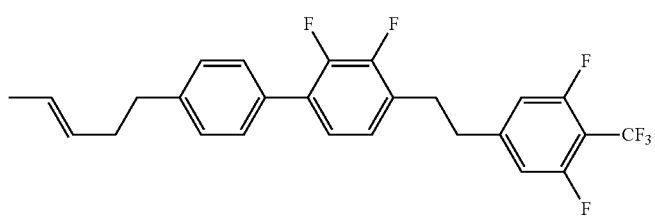 [SMILES: C/C=C/CCc1ccc(-c2ccc(CCc3cc(F)c(C(F)(F)F)c(F)c3)c(F)c2F)cc1] |
| 1-2-25 | 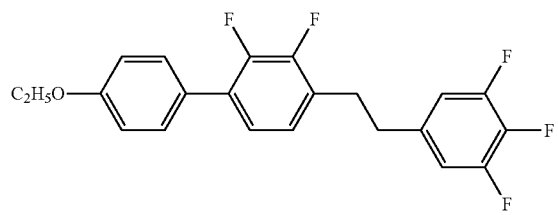 |

| No. | |
|---|---|
| 1-2-26 | 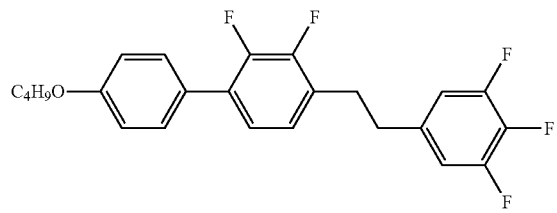 |
| 1-2-27 | 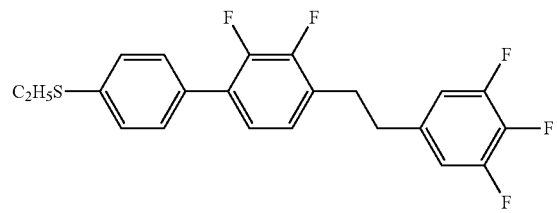 |
| 1-2-28 | 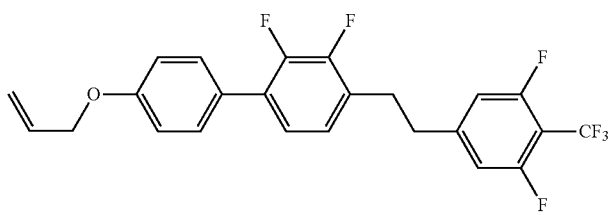 [SMILES: C=CCOc1ccc(-c2ccc(CCc3cc(F)c(C(F)(F)F)c(F)c3)c(F)c2F)cc1] |
| 1-2-29 | 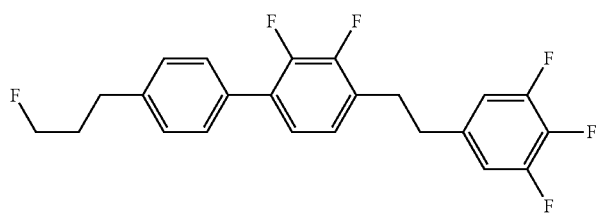 [SMILES: FCCCc1ccc(-c2ccc(CCc3cc(F)c(F)c(F)c3)c(F)c2F)cc1] |
| 1-2-30 | 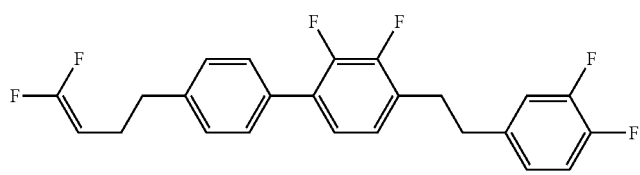 [SMILES: FC(F)=CCCc1ccc(-c2ccc(CCc3ccc(F)c(F)c3)c(F)c2F)cc1] |
| 1-2-31 | 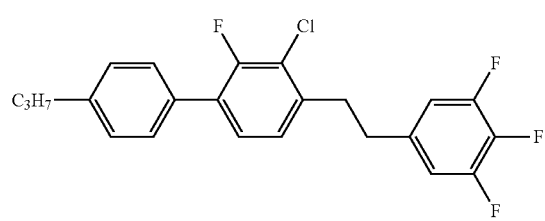 |
| 1-2-32 | 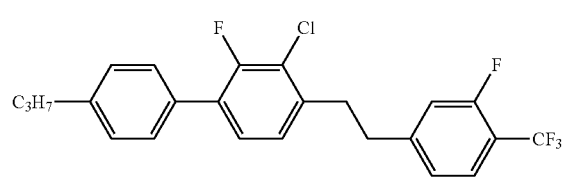 |

| No. | |
|---|---|
| 1-2-33 | 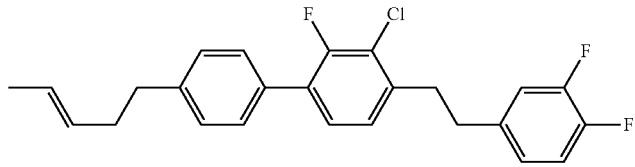 [SMILES: C/C=C/CCc1ccc(-c2ccc(CCc3ccc(F)c(F)c3)c(Cl)c2F)cc1] |
| 1-2-34 | 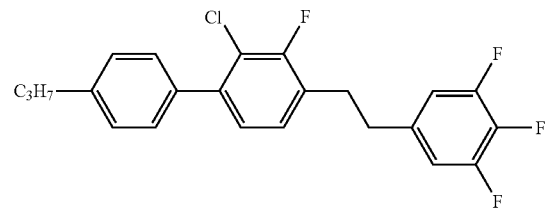 |
| 1-2-35 | 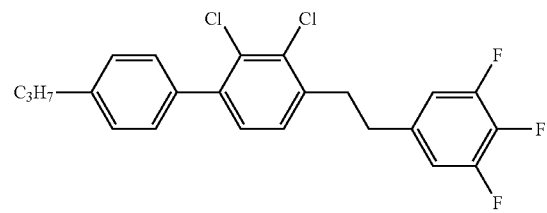 |
| 1-2-36 | 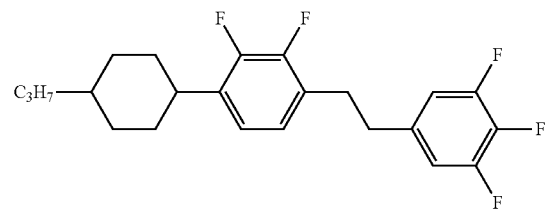 |
| 1-2-37 | 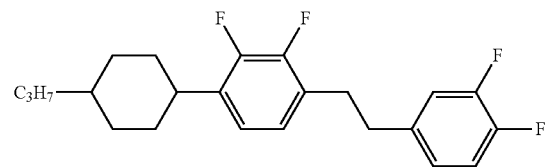 |
| 1-2-38 | 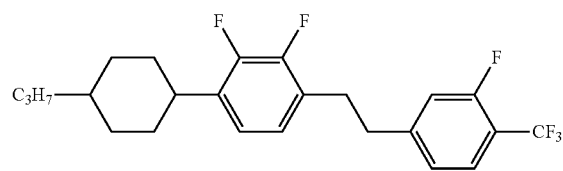 |
| 1-2-39 | 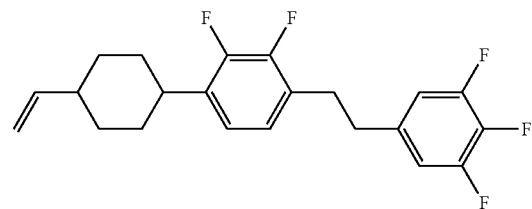 [SMILES: C=CC1CCC(c2ccc(CCc3cc(F)c(F)c(F)c3)c(F)c2F)CC1] |

| No. | |
|---|---|
| 1-2-40 | 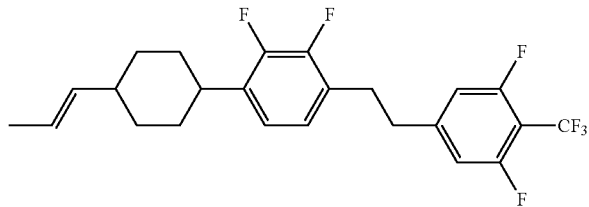 [SMILES: C/C=C/C1CCC(c2ccc(CCc3cc(F)c(C(F)(F)F)c(F)c3)c(F)c2F)CC1] |
| 1-2-41 | 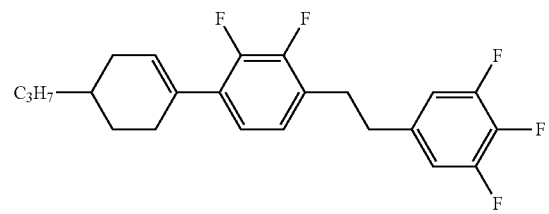 |
| 1-2-42 | 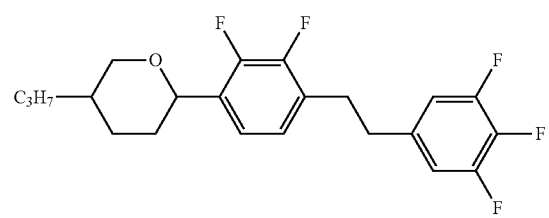 |
| 1-2-43 | 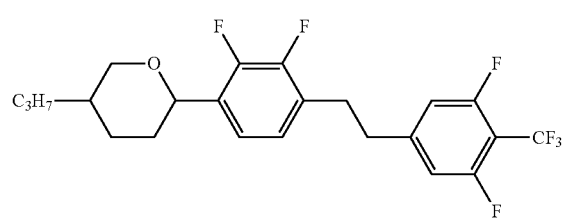 |
| 1-2-44 | 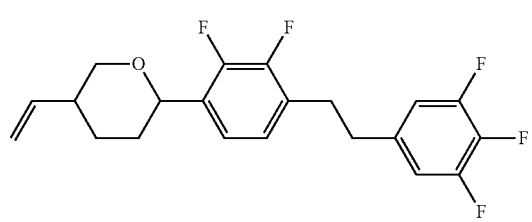 [SMILES: C=CC1CCC(c2ccc(CCc3cc(F)c(F)c(F)c3)c(F)c2F)OC1] |
| 1-2-45 | 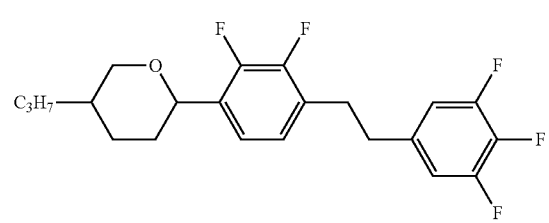 |
| 1-2-46 | 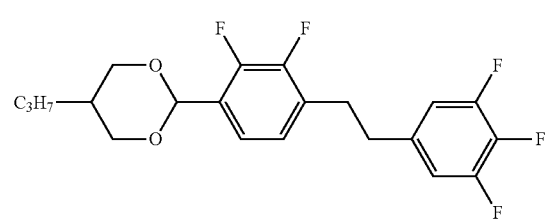 |

-continued
| No. | |
|---|---|
| 1-2-47 | 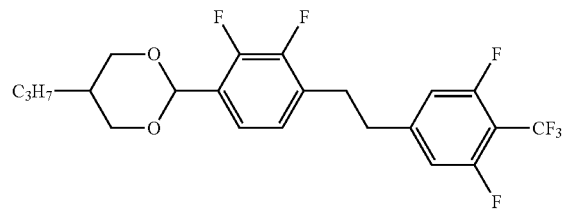 |
| 1-2-48 | 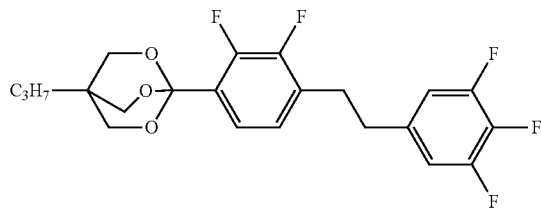 |
| 1-2-49 | 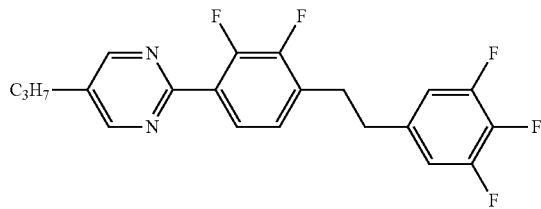 |
| 1-2-50 | 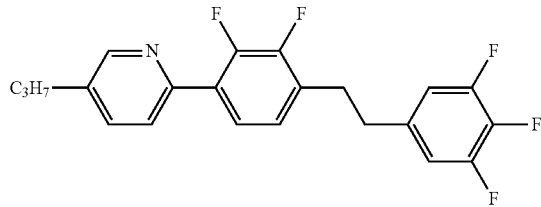 |
| 1-2-51 | 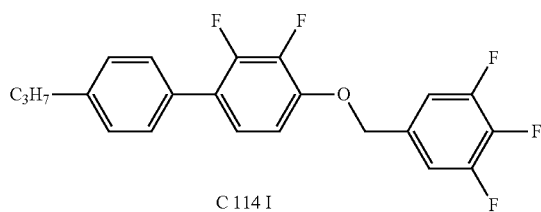<br>C 114 I<br>$T_{NI} = -0.3°$ C., $\Delta n = 0.157$, $\Delta\varepsilon = 16.1$, $\varepsilon (\perp) = 12.5$ |
| 1-2-52 | 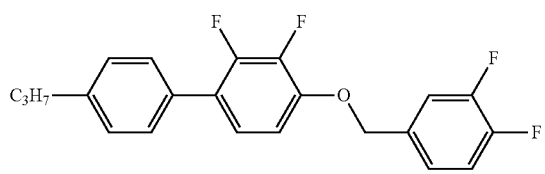 |
| 1-2-53 | 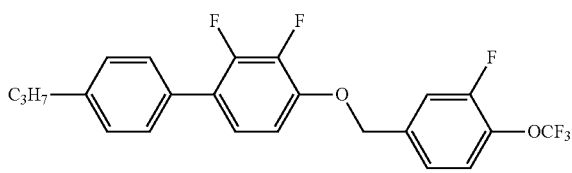 |

| No. | |
|---|---|
| 1-2-54 | 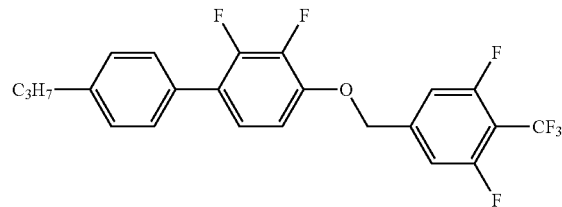 |
| 1-2-55 | 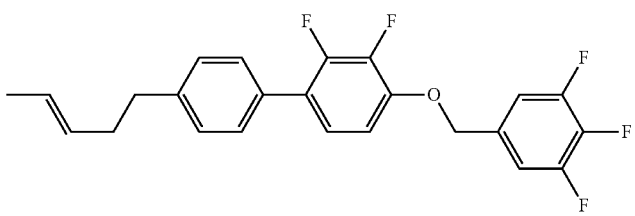 [SMILES: C/C=C/CCc1ccc(-c2ccc(OCc3cc(F)c(F)c(F)c3)c(F)c2F)cc1] |
| 1-2-56 | 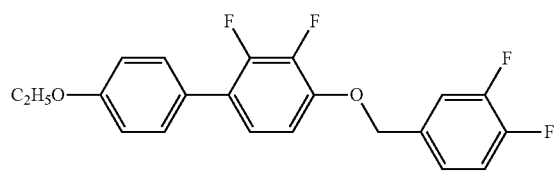 |
| 1-2-57 | 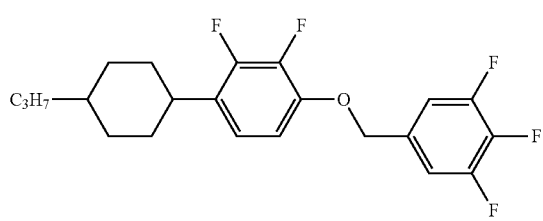 |
| 1-2-58 | 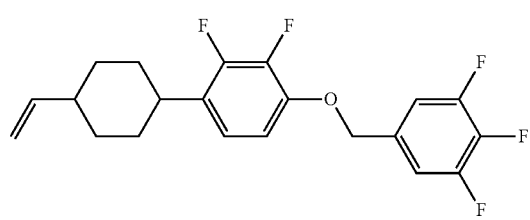 [SMILES: C=CC1CCC(c2ccc(OCc3cc(F)c(F)c(F)c3)c(F)c2F)CC1] |
| 1-2-59 | 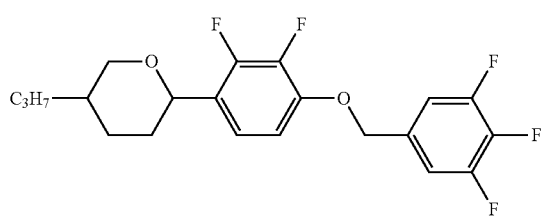 |
| 1-2-60 | 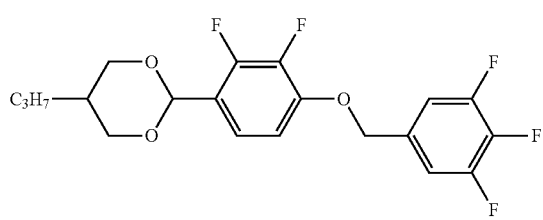 |

| No. | |
|---|---|
| 1-2-61 | 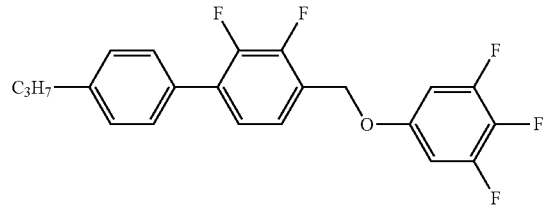 |
| 1-2-62 | 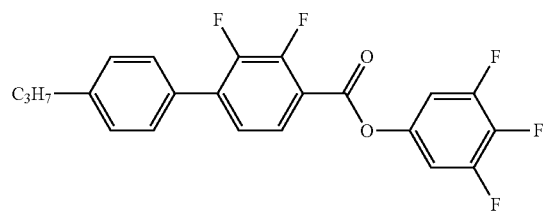 |
| 1-2-63 | 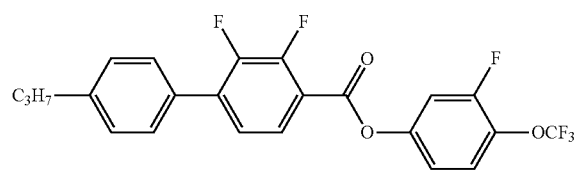 |
| 1-2-64 | 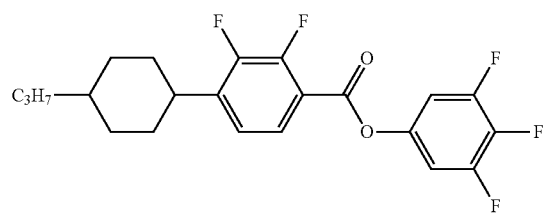 |
| 1-2-65 | 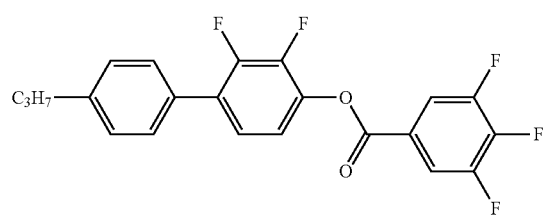 |
| 1-2-66 | 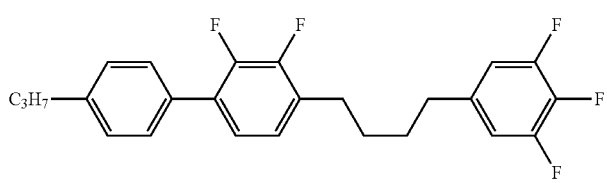 |
| 1-2-67 | 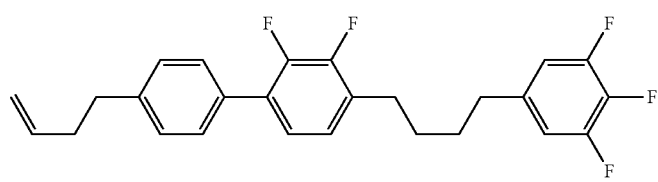 [SMILES: C=CCCc1ccc(-c2ccc(CCCCc3cc(F)c(F)c(F)c3)c(F)c2F)cc1] |

-continued
| No. | |
|---|---|
| 1-2-68 | 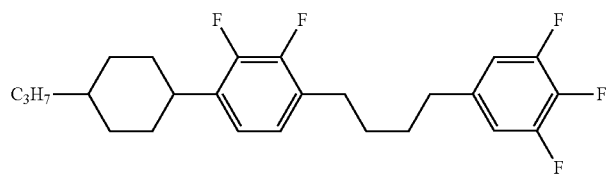 |
| 1-2-69 | 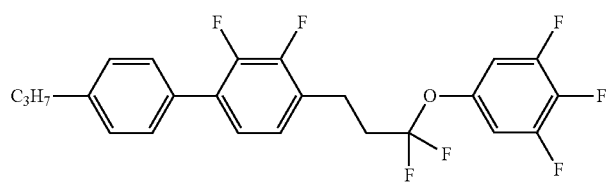 |
| 1-2-70 | 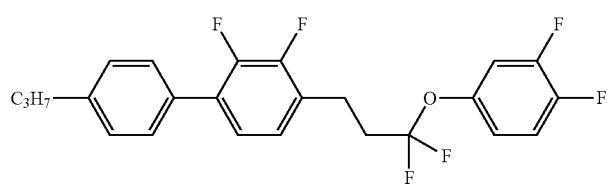 |
| 1-2-71 | 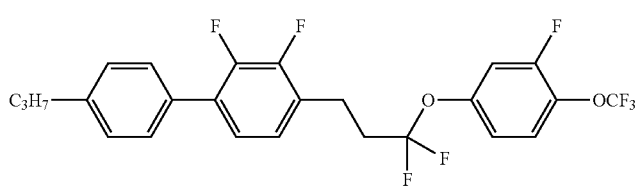 |
| 1-2-72 | 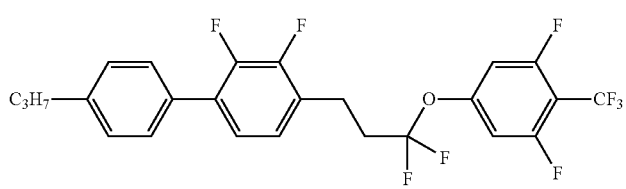 <br> C 46.0 I <br> $T_{NI}$ = 9.7° C., $\Delta n$ = 0.117, $\Delta\varepsilon$ = 21.4, $\varepsilon$ ($\perp$) = 8.5 |
| 1-2-73 | 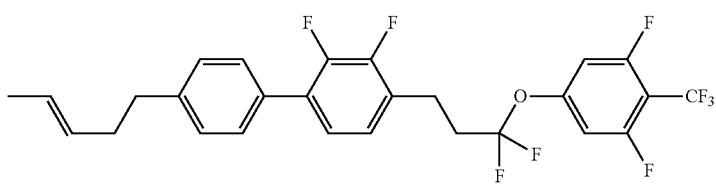 [SMILES: C/C=C/CCc1ccc(-c2ccc(CCC(F)(F)Oc3cc(F)c(C(F)(F)F)c(F)c3)c(F)c2F)cc1] |
| 1-2-74 | 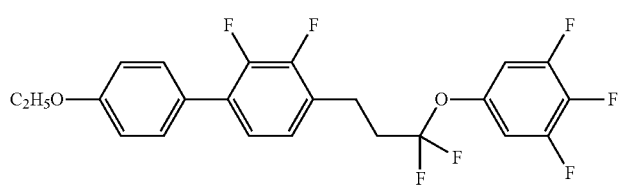 |

| No. | |
|---|---|
| 1-2-75 | 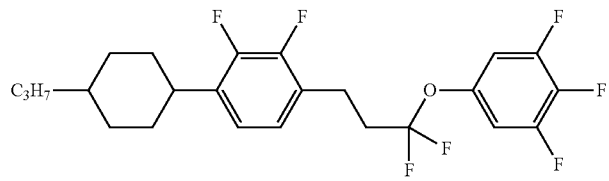 |
| 1-2-76 | 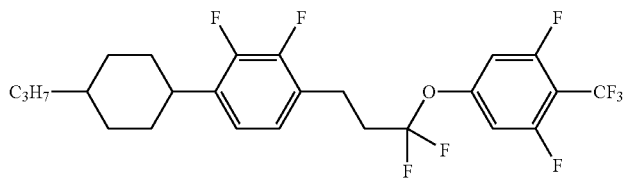 |
| 1-2-77 | 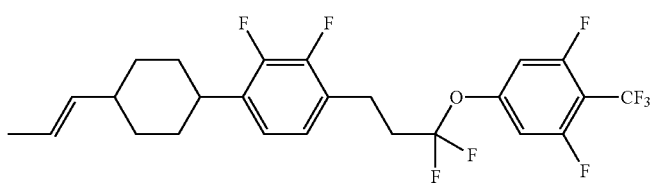 [SMILES: C/C=C/C1CCC(c2ccc(CCC(F)(F)Oc3cc(F)c(C(F)(F)F)c(F)c3)c(F)c2F)CC1] |
| 1-2-78 | 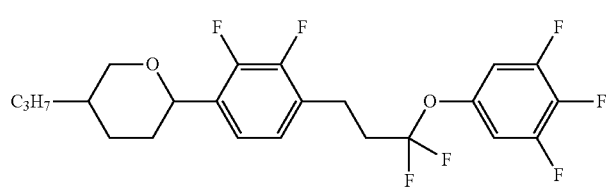 |
| 1-2-79 | 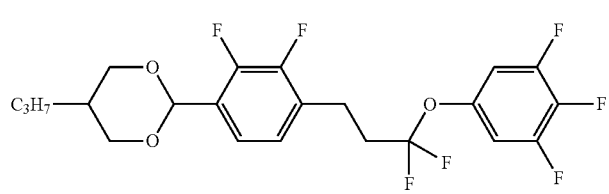 |
| 1-2-80 | 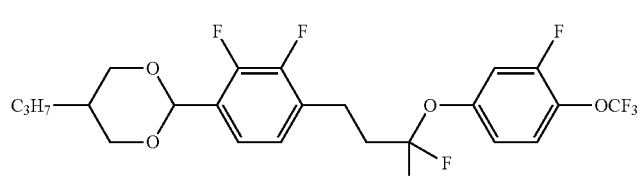 |
| 1-2-81 | 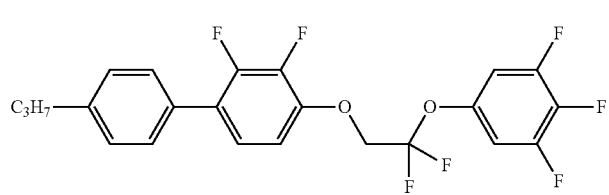 |
C 55.6 I
$T_{NI}$ = −25.0° C., Δn = 0.097, Δε = 12.8, ε (⊥) = 13.2

-continued
| No. | |
|---|---|
| 1-2-82 | 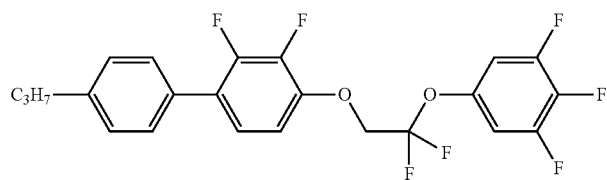 |
| 1-2-83 | 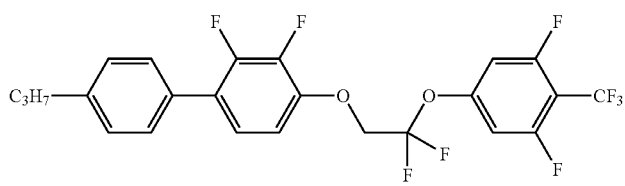 |
| 1-2-84 | 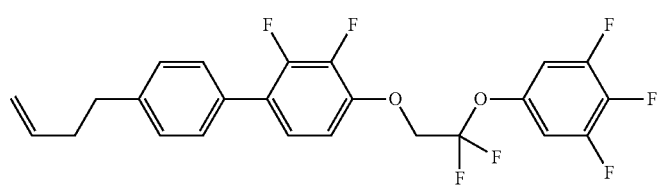 [SMILES: C=CCCc1ccc(-c2ccc(OCC(F)(F)Oc3cc(F)c(F)c(F)c3)c(F)c2F)cc1] |
| 1-2-85 | 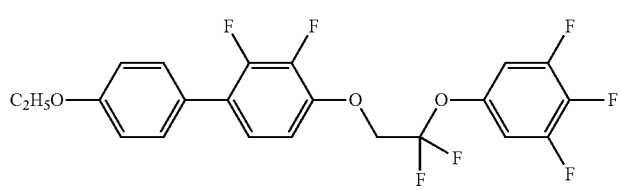 |
| 1-2-86 | 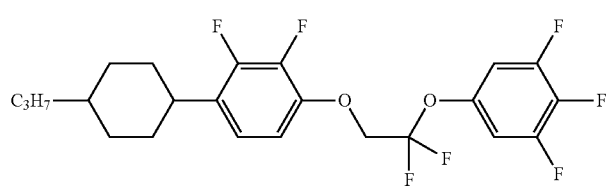 |
| 1-2-87 | 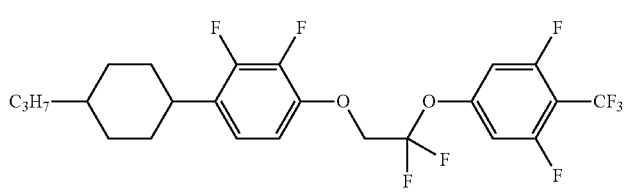 |
| 1-2-88 | 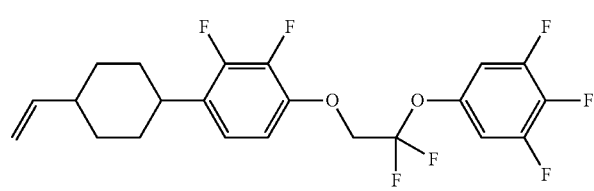 [SMILES: C=CC1CCC(c2ccc(OCC(F)(F)Oc3cc(F)c(F)c(F)c3)c(F)c2F)CC1] |
| 1-2-89 | 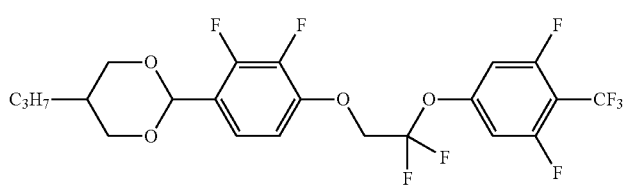 |

| No. | |
|---|---|
| 1-2-90 | 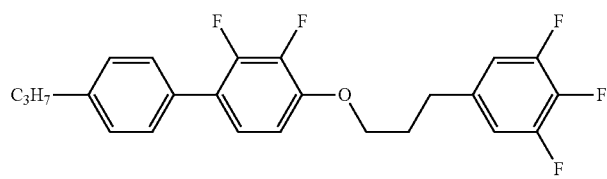 |
| 1-2-91 | 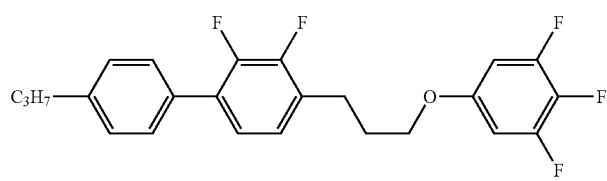 |
| 1-2-92 | 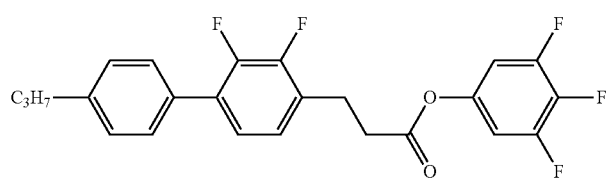 |
| 1-2-93 | 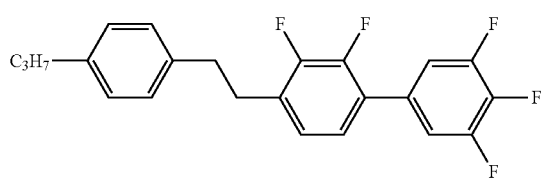 |
| 1-2-94 | 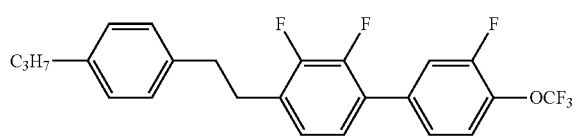 |
| 1-2-95 | 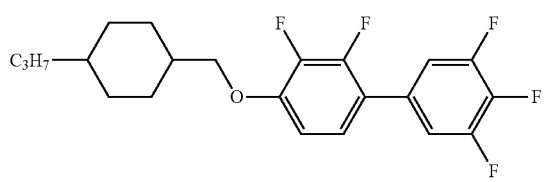 |
| 1-2-96 | 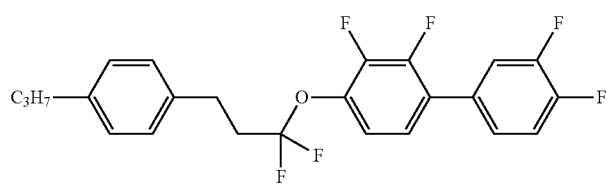 |
| 1-2-97 | 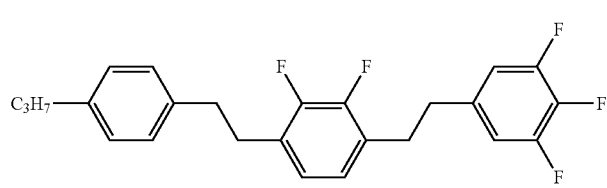 |

-continued
| No. |
|---|
| 1-2-98 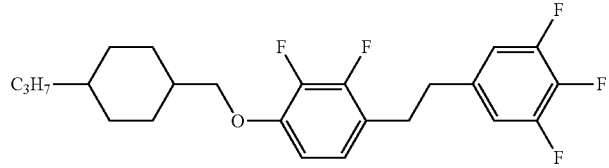 |
| 1-2-99 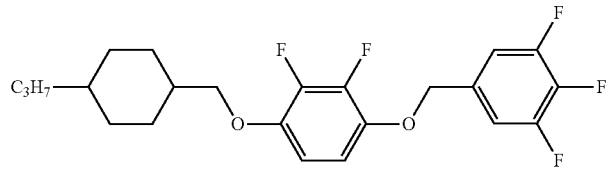 |
| 1-2-100 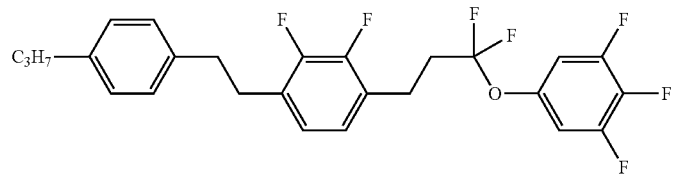 |
| 1-2-101 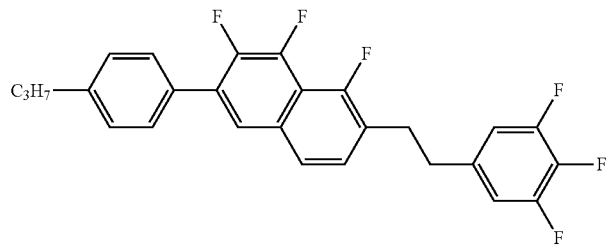 |
| 1-2-102 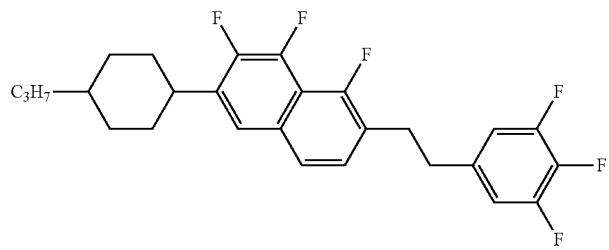 |
| 1-2-103 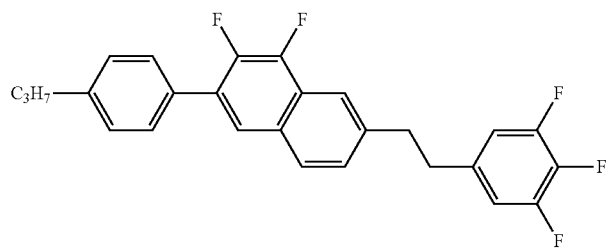 |

| No. | |
|---|---|
| 1-2-104 | 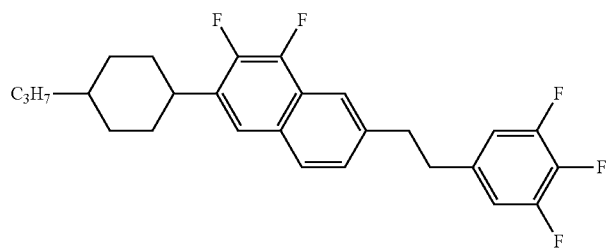 |
| 1-2-105 | 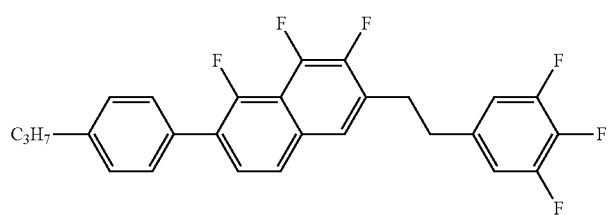 |
| 1-2-106 | 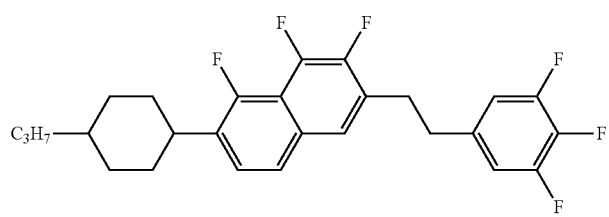 |
| 1-2-107 | 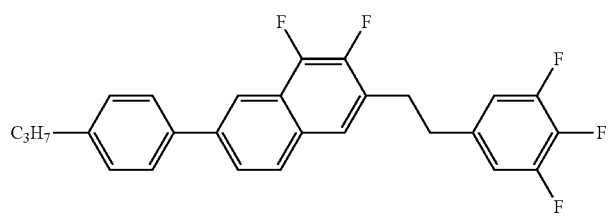 |
| 1-2-108 | 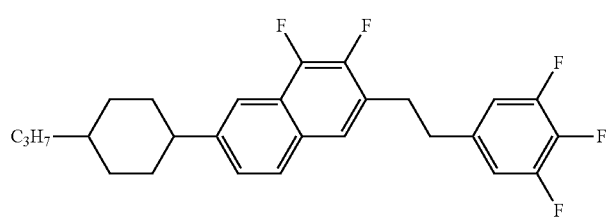 |
| 1-2-109 | 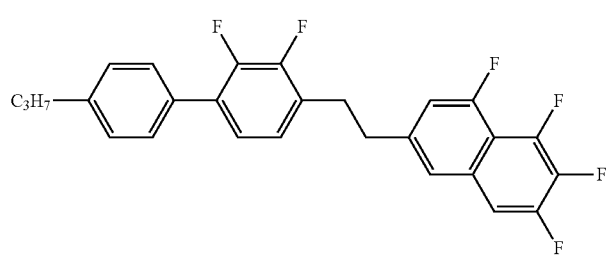 |

-continued
| No. | |
|---|---|
| 1-2-110 | 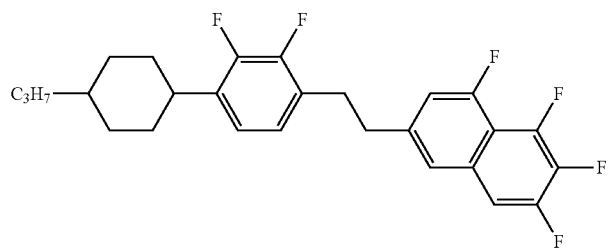 |
| 1-2-111 | 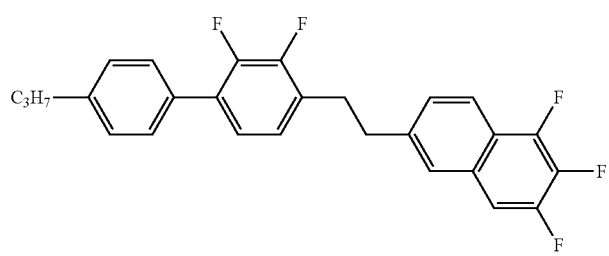 |
| 1-2-112 | 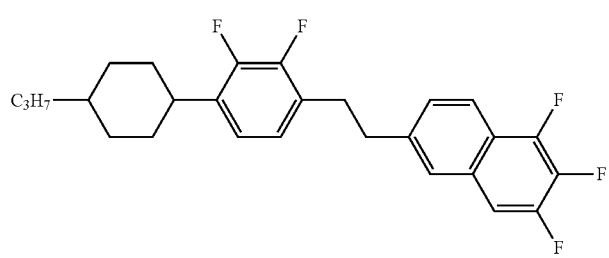 |
| 1-2-113 | 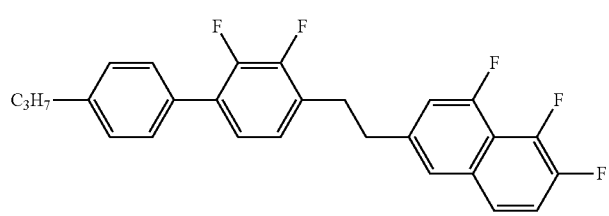 |
| 1-2-114 | 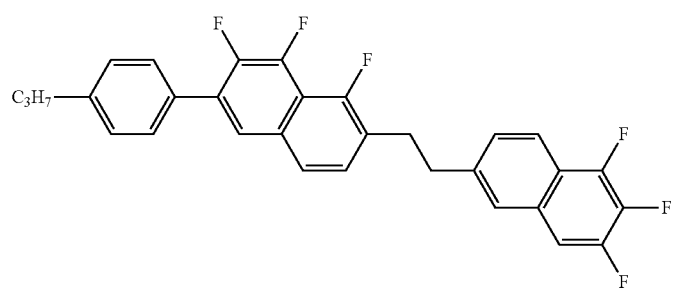 |
| 1-2-115 | 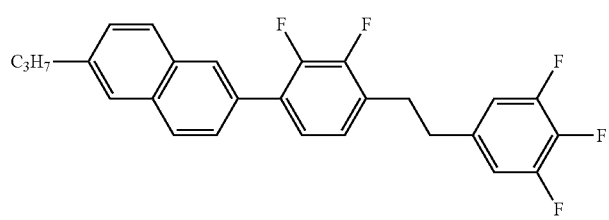 |

-continued
| No. | |
|---|---|
| 1-2-116 | 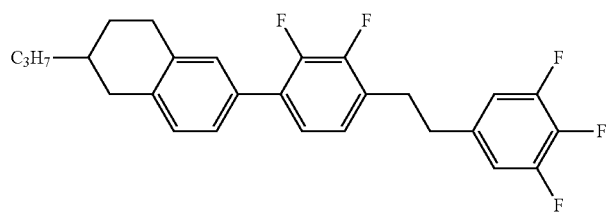 |
| 1-2-117 | 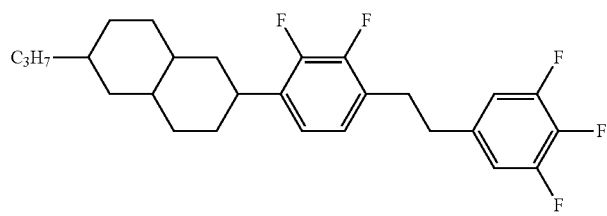 |
| 1-2-118 | 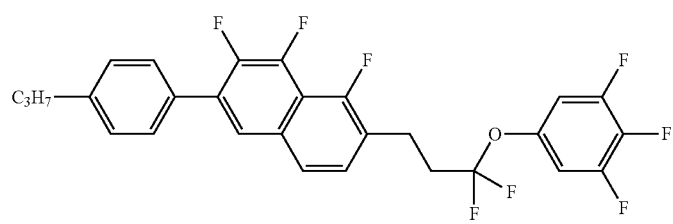 |
| 1-2-119 | 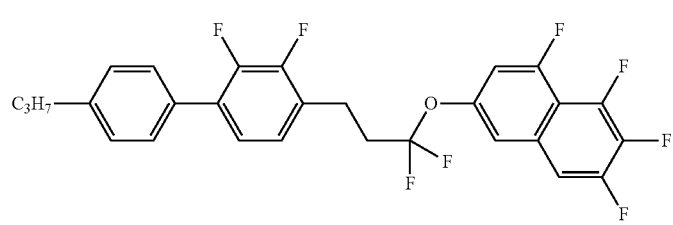 |
| 1-2-120 | 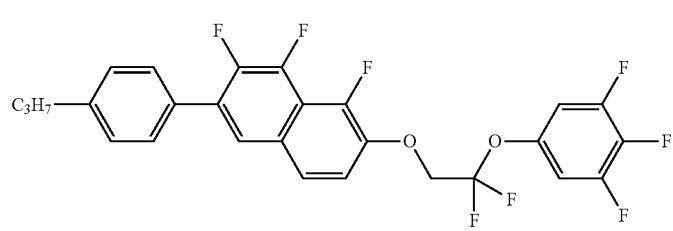 |
| 1-3-1 | 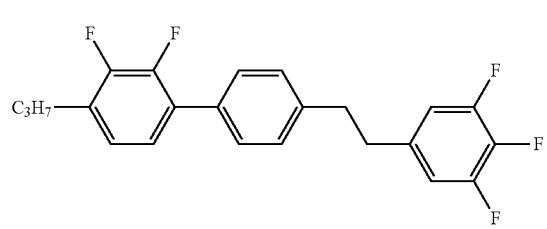 |
| 1-3-2 | 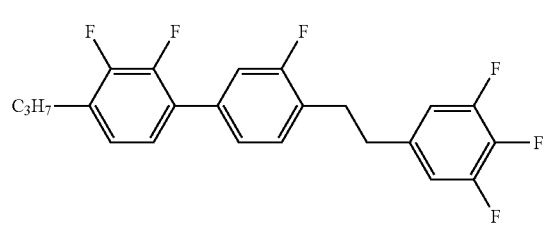 |

-continued
| No. | |
|---|---|
| 1-3-3 | 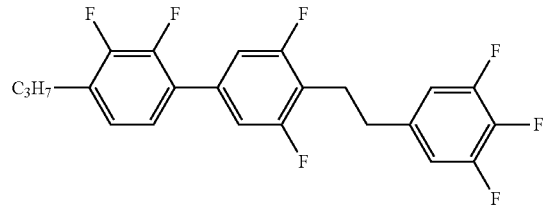 |
| 1-3-4 | 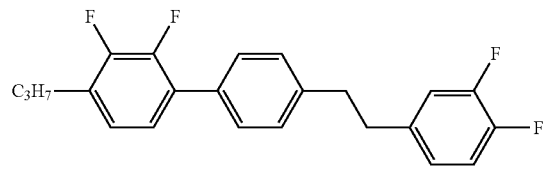 |
| 1-3-5 | 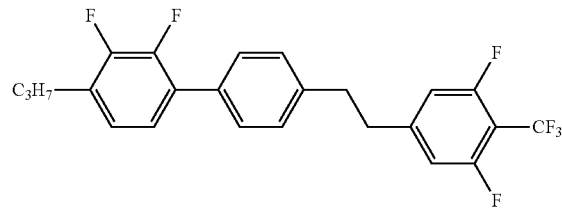 |
| 1-3-6 | 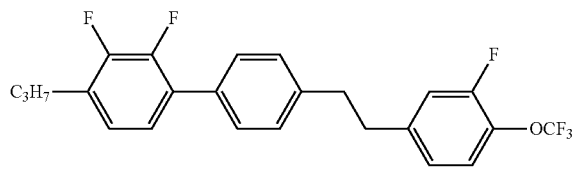 |
| 1-3-7 | 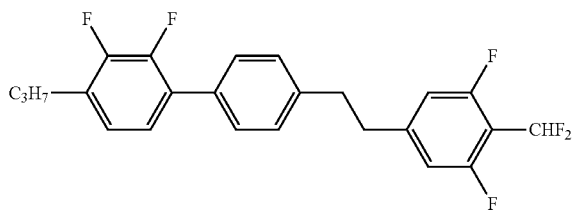 |
| 1-3-8 | 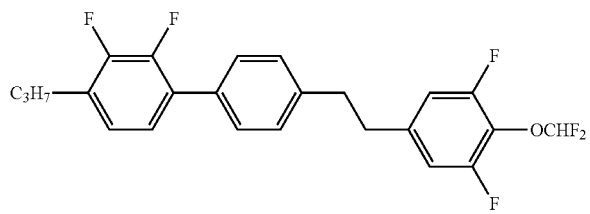 |
| 1-3-9 | 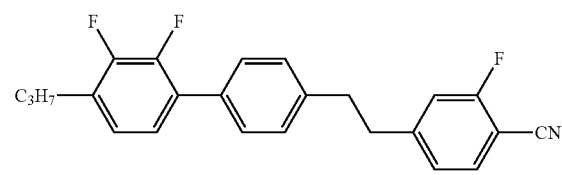 |

-continued
| No. | |
|---|---|
| 1-3-10 | 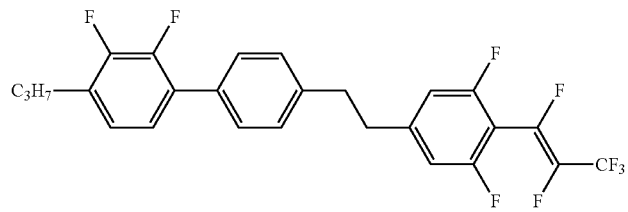 |
| 1-3-11 | 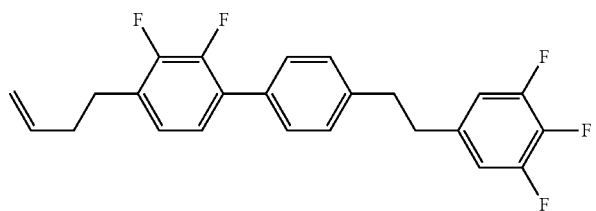 [SMILES: C=CCCc1ccc(-c2ccc(CCc3cc(F)c(F)c(F)c3)cc2)c(F)c1F] |
| 1-3-12 | 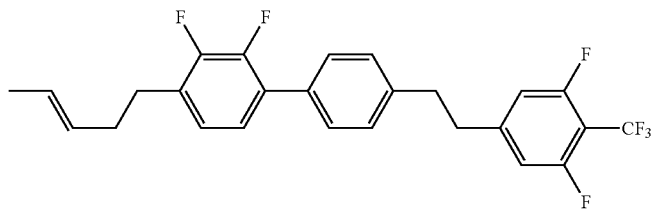 [SMILES: C/C=C/CCc1ccc(-c2ccc(CCc3cc(F)c(C(F)(F)F)c(F)c3)cc2)c(F)c1F] |
| 1-3-13 | 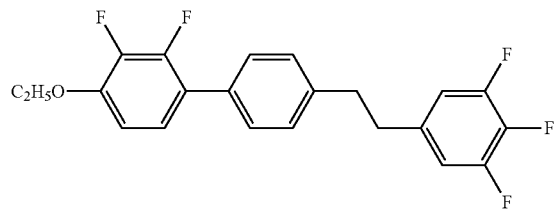 |
| 1-3-14 | 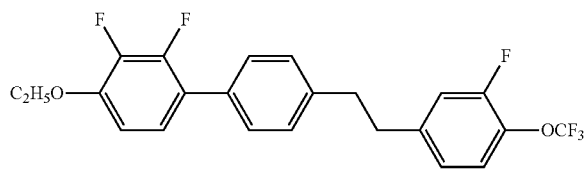 |
| 1-3-15 | 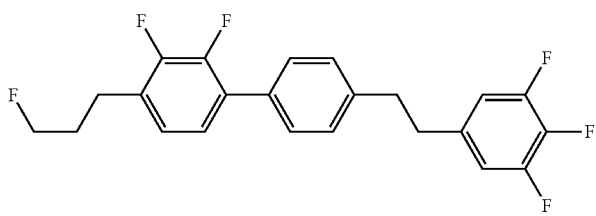 [SMILES: FCCCc1ccc(-c2ccc(CCc3cc(F)c(F)c(F)c3)cc2)c(F)c1F] |
| 1-3-16 | 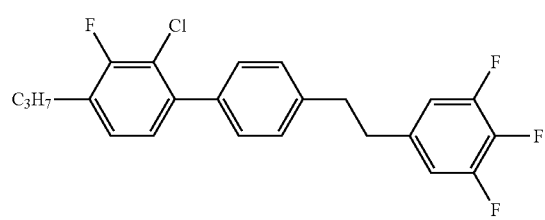 |

-continued
| No. | |
|---|---|
| 1-3-17 | 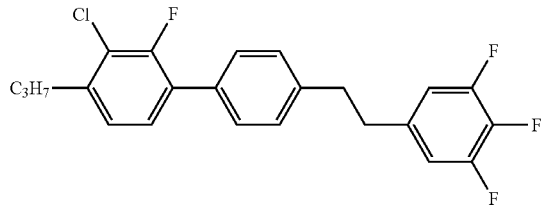 |
| 1-3-18 | 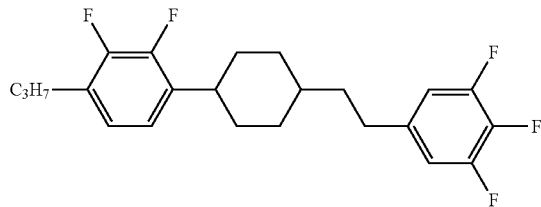 |
| 1-3-19 | 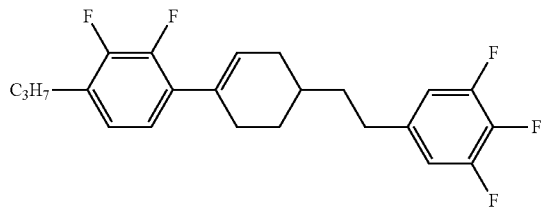 |
| 1-3-20 | 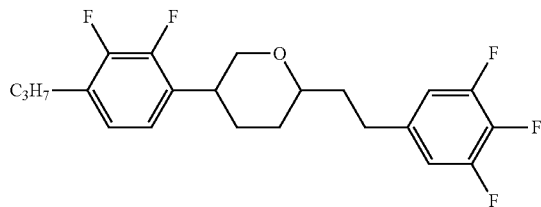 |
| 1-3-21 | 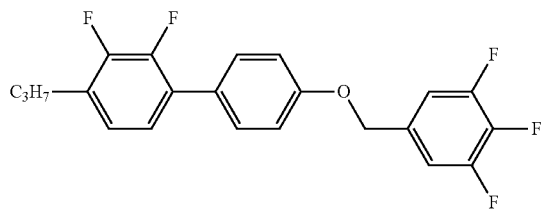 |
| 1-3-22 | 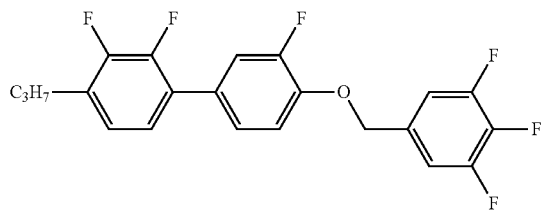 |
| 1-3-23 | 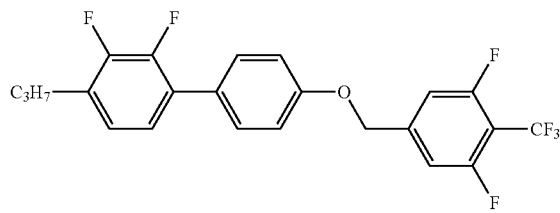 |

| No. | |
|---|---|
| 1-3-24 | 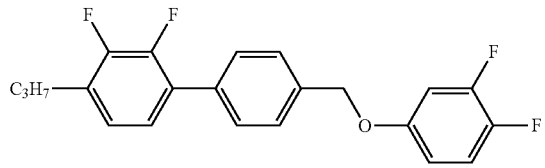 |
| 1-3-25 | 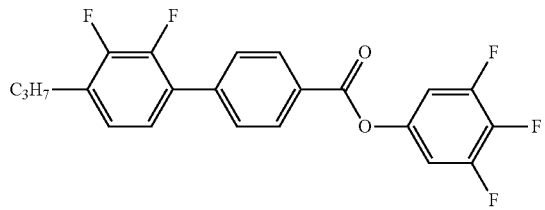 |
| 1-3-26 | 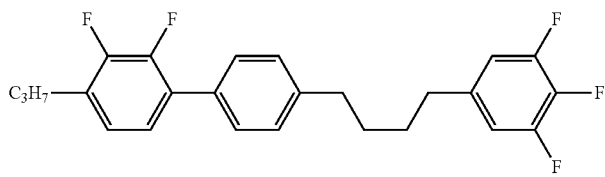 |
| 1-3-27 | 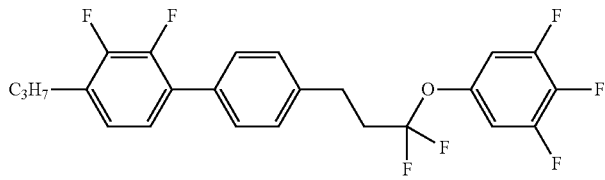 |
| 1-3-28 | 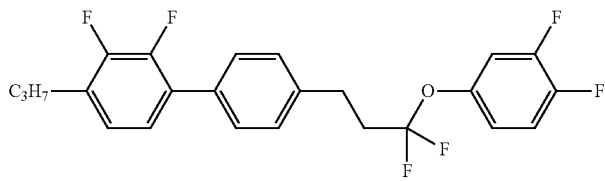 |
| 1-3-29 | 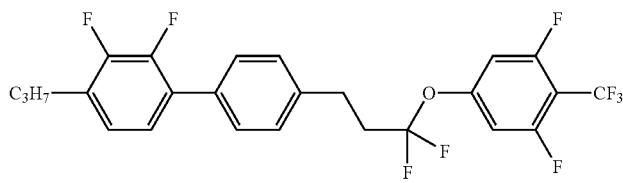 |
| 1-3-30 | 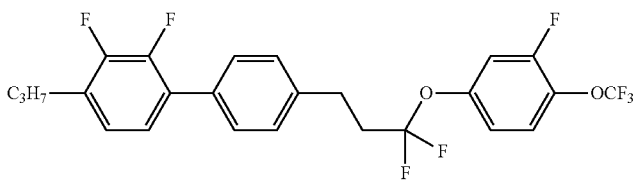 |
| 1-3-31 | 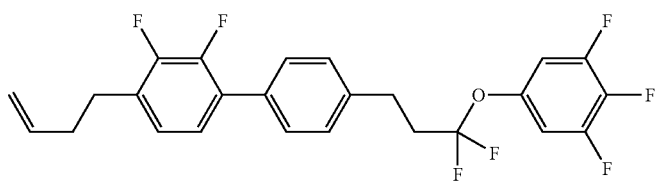 [SMILES: C=CCCc1ccc(-c2ccc(CCC(F)(F)Oc3cc(F)c(F)c(F)c3)cc2)c(F)c1F] |

| No. | |
|---|---|
| 1-3-32 | 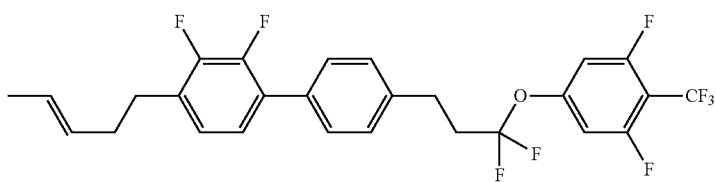 [SMILES: C/C=C/CCc1ccc(-c2ccc(CCC(F)(F)Oc3cc(F)c(C(F)(F)F)c(F)c3)cc2)c(F)c1F] |
| 1-3-33 | 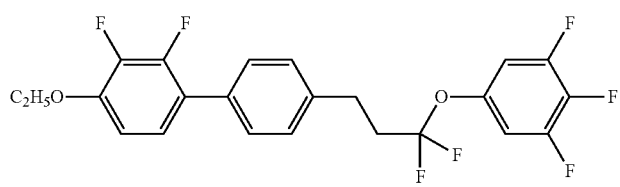 |
| 1-3-34 | 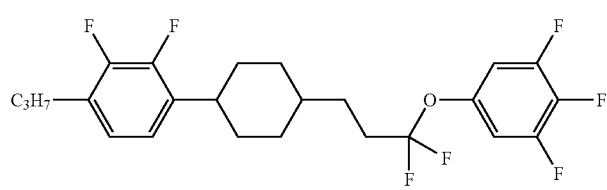 |
| 1-3-35 | 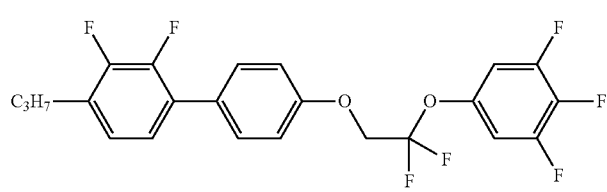 |
| 1-3-36 | 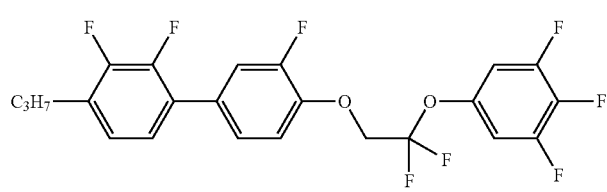 |
| 1-3-37 | 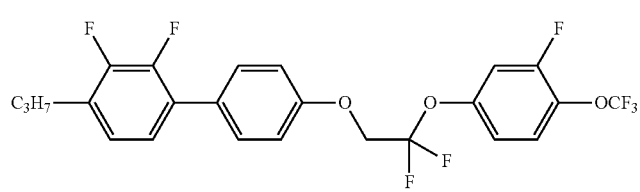 |
| 1-3-38 | 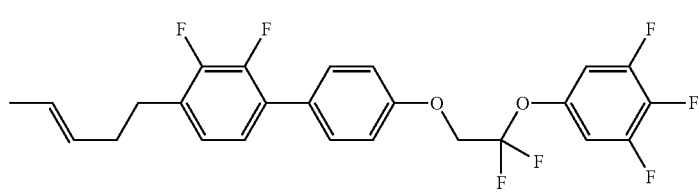 [SMILES: C/C=C/CCc1ccc(-c2ccc(OCC(F)(F)Oc3cc(F)c(F)c(F)c3)cc2)c(F)c1F] |
| 1-3-39 | 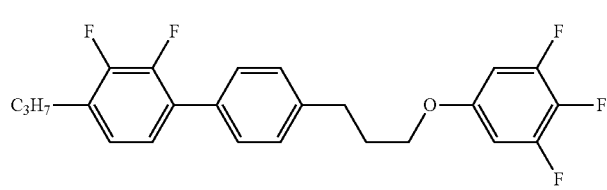 |

| No. | |
|---|---|
| 1-3-40 | 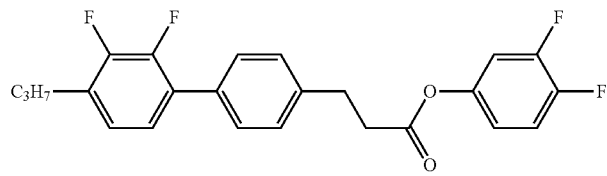 |
| 1-3-41 | 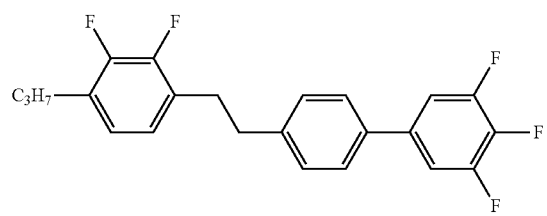 |
| 1-3-42 | 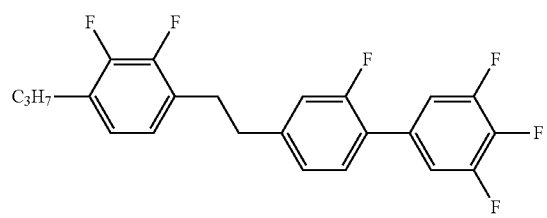 |
| 1-3-43 | 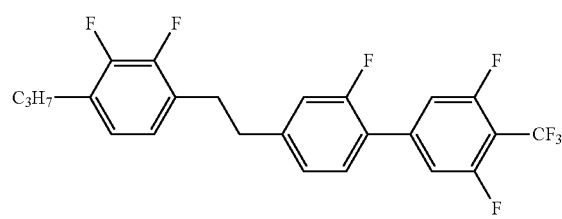 |
| 1-3-44 | 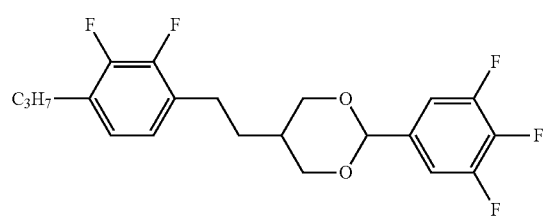 |
| 1-3-45 | 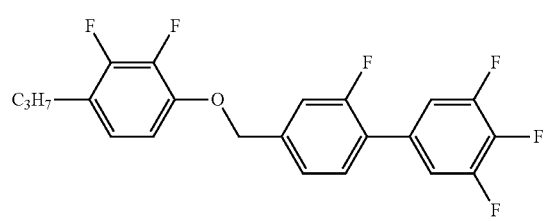 |
| 1-3-46 | 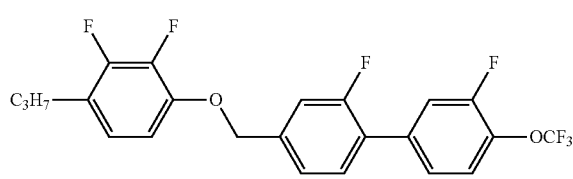 |

| No. | |
|---|---|
| 1-3-47 | 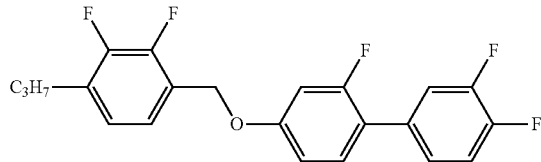 |
| 1-3-48 | 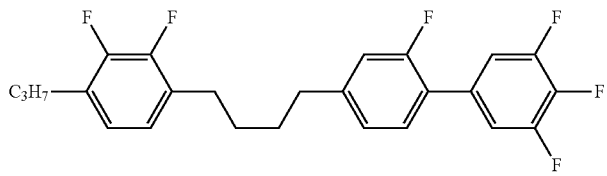 |
| 1-3-49 | 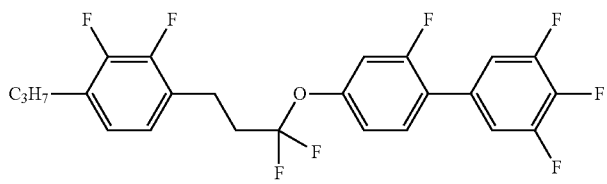 |
| 1-3-50 | 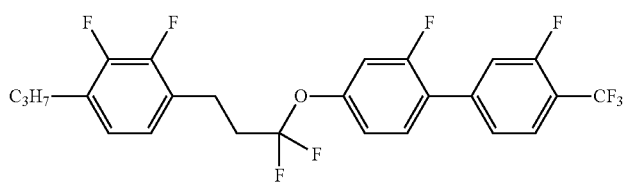 |
| 1-3-51 | 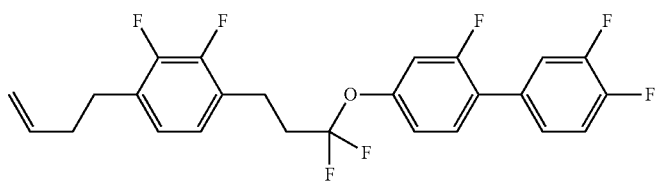 [SMILES: C=CCCc1ccc(CCC(F)(F)Oc2ccc(-c3ccc(F)c(F)c3)c(F)c2)c(F)c1F] |
| 1-3-52 | 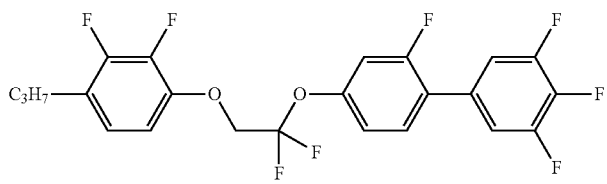 |
| 1-3-53 | 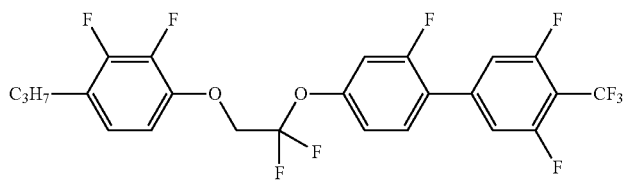 |
| 1-3-54 | 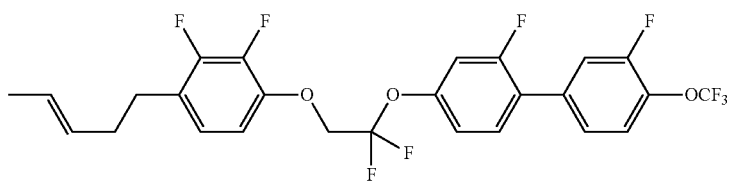 [SMILES: C/C=C/CCc1ccc(OCC(F)(F)Oc2ccc(-c3ccc(OC(F)(F)F)c(F)c3)c(F)c2)c(F)c1F] |

| No. | |
|---|---|
| 1-3-55 | 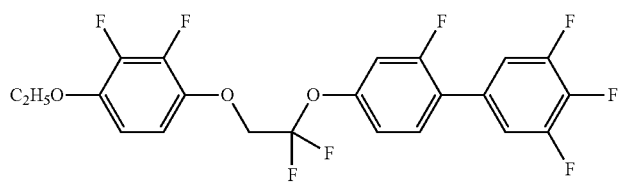 |
| 1-3-56 | 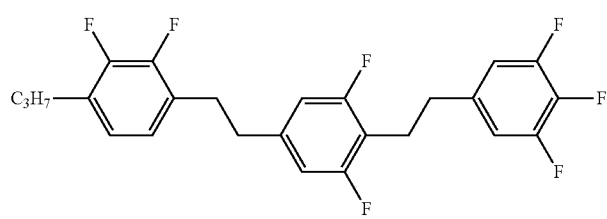 |
| 1-3-57 | 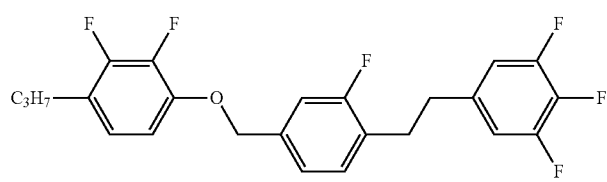 |
| 1-3-58 | 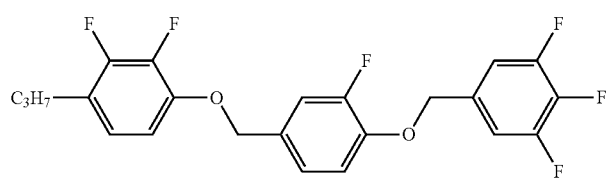 |
| 1-3-59 | 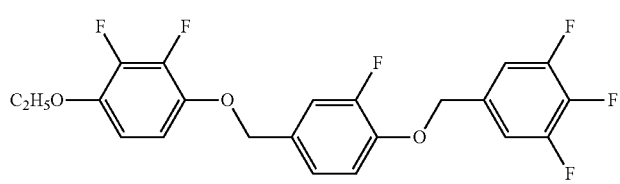 |
| 1-3-60 | 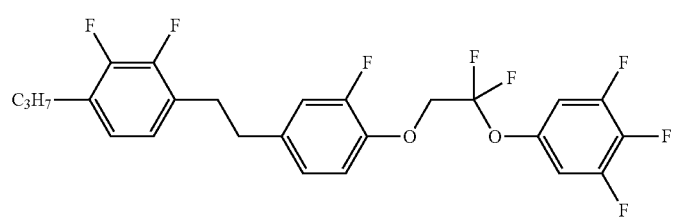 |
| 1-3-61 | 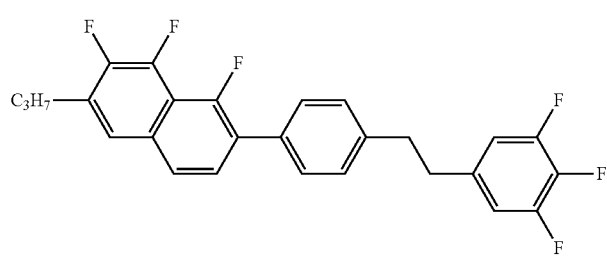 |

| No. | |
|---|---|
| 1-3-62 | 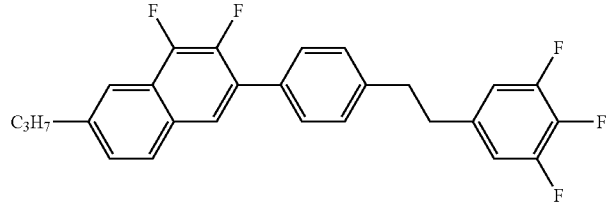 |
| 1-3-63 | 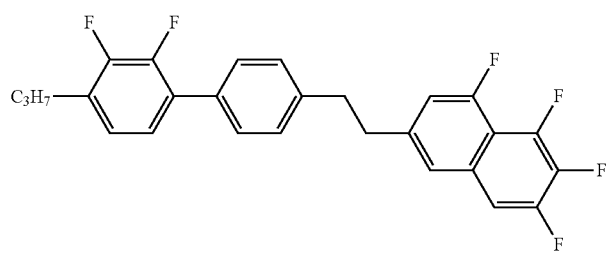 |
| 1-3-64 | 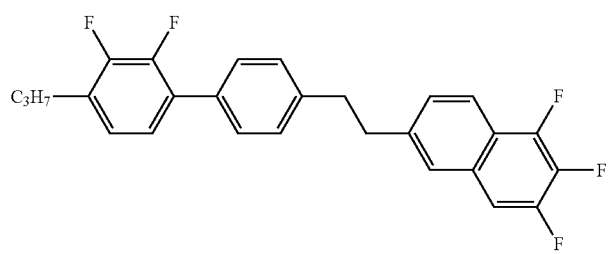 |
| 1-3-65 | 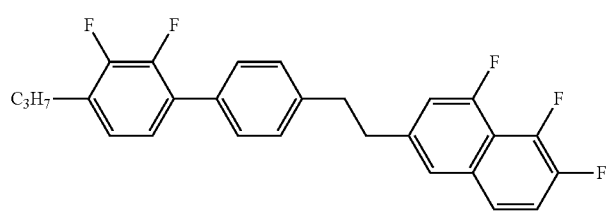 |
| 1-3-66 | 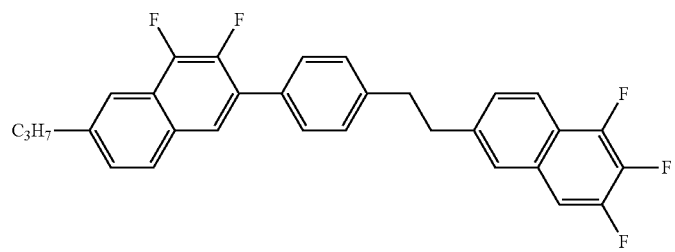 |
| 1-3-67 | 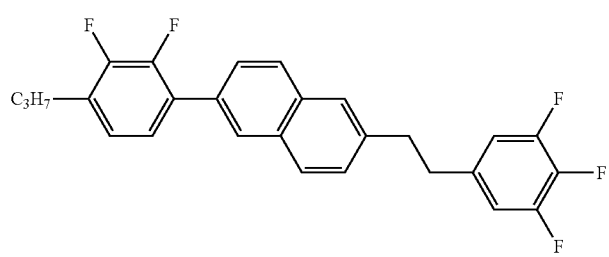 |

| No. | |
|---|---|
| 1-3-68 | 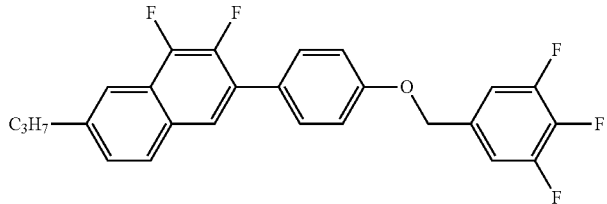 |
| 1-3-69 | 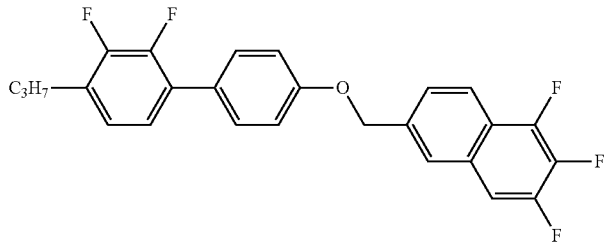 |
| 1-3-70 | 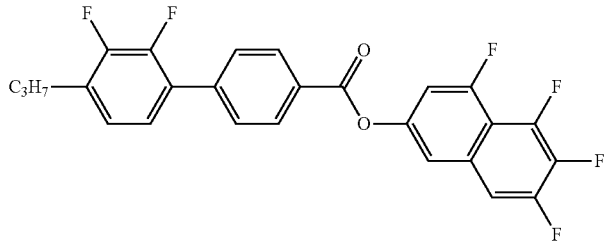 |
| 1-3-71 | 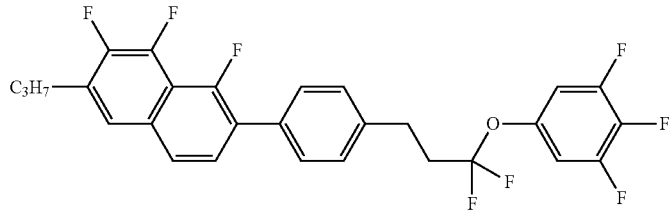 |
| 1-3-72 | 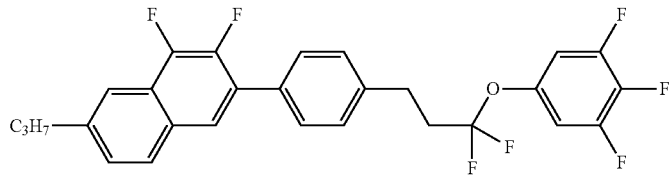 |
| 1-3-73 | 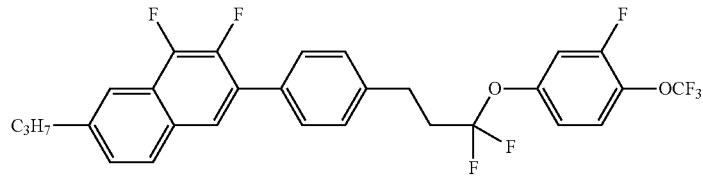 |
| 1-3-74 | 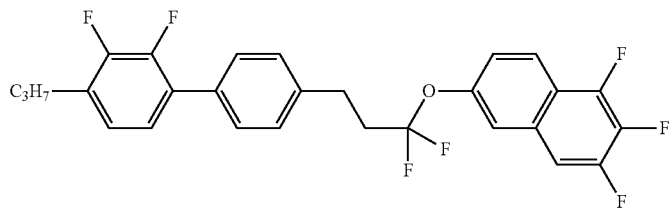 |

| No. | |
|---|---|
| 1-3-75 | 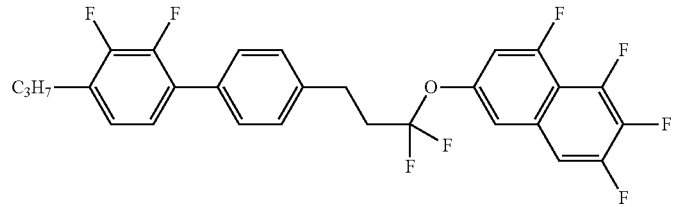 |
| 1-3-76 | 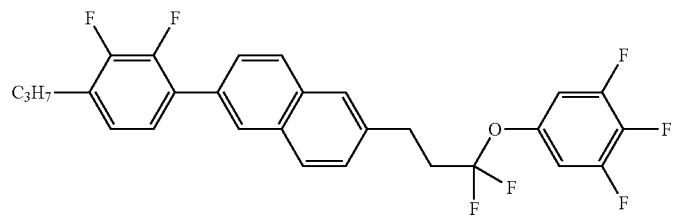 |
| 1-3-77 | 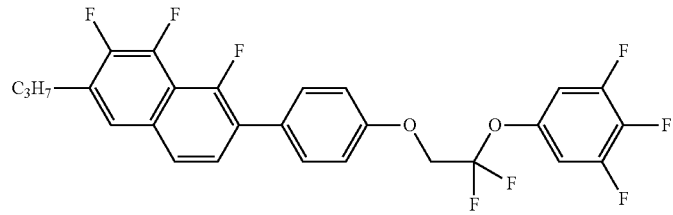 |
| 1-3-78 | 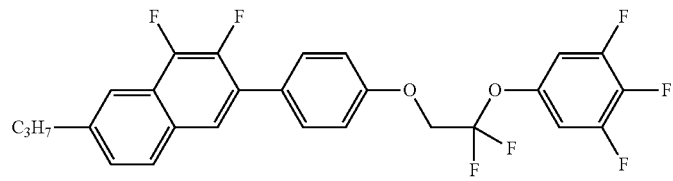 |
| 1-3-79 | 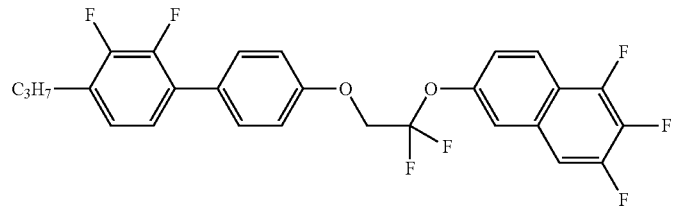 |
| 1-3-80 | 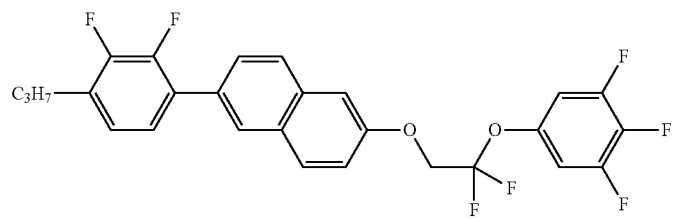 |
| 1-4-1 | 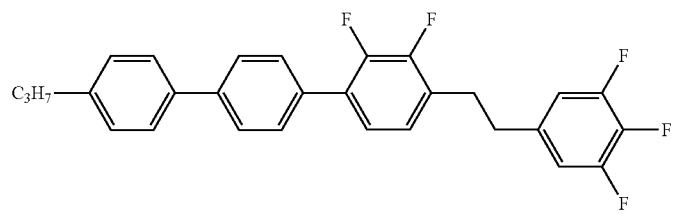 |

-continued
| No. |  |
|---|---|
| 1-4-2 | 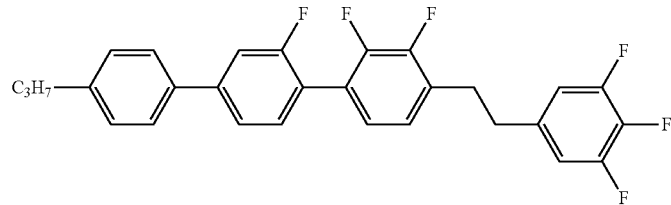 |
| 1-4-3 | 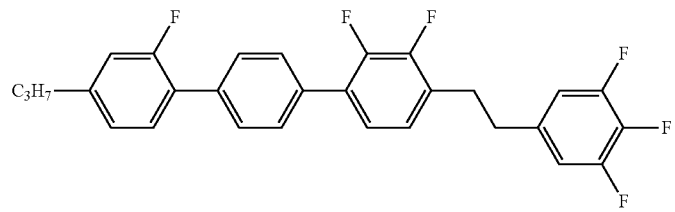 |
| 1-4-4 | 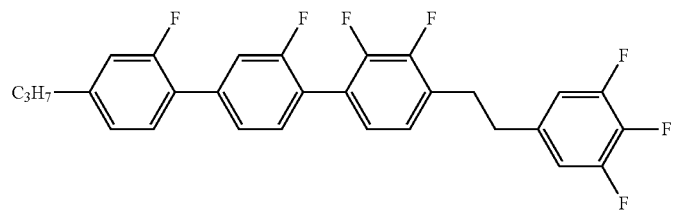 |
| 1-4-5 | 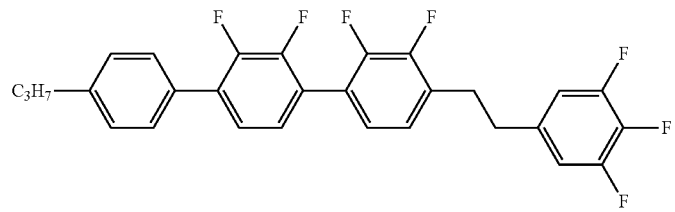 |
| 1-4-6 | 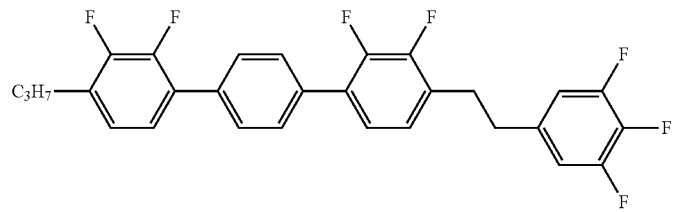 |
| 1-4-7 | 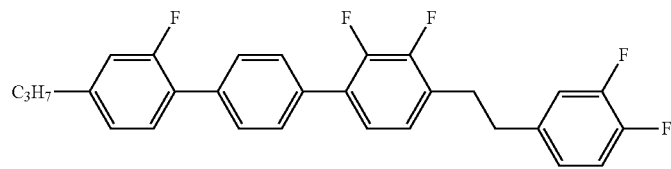 |
| 1-4-8 | 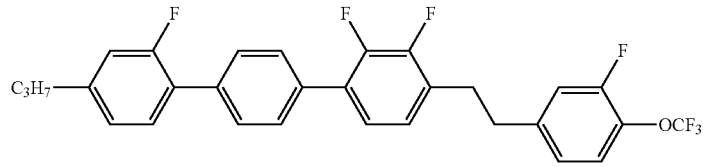 |

| No. | |
|---|---|
| 1-4-9 | 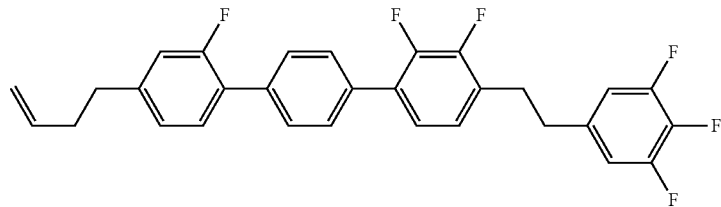 [SMILES: C=CCCc1ccc(-c2ccc(-c3ccc(CCc4cc(F)c(F)c(F)c4)c(F)c3F)cc2)c(F)c1] |
| 1-4-10 | 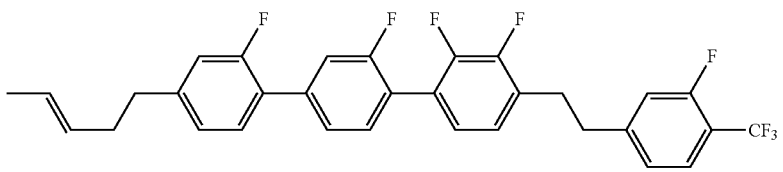 [SMILES: C/C=C/CCc1ccc(-c2ccc(-c3ccc(CCc4ccc(C(F)(F)F)c(F)c4)c(F)c3F)c(F)c2)c(F)c1] |
| 1-4-11 | 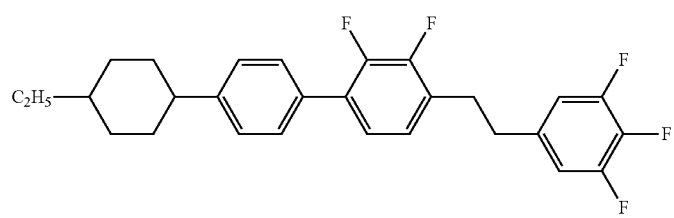 |
| 1-4-12 | 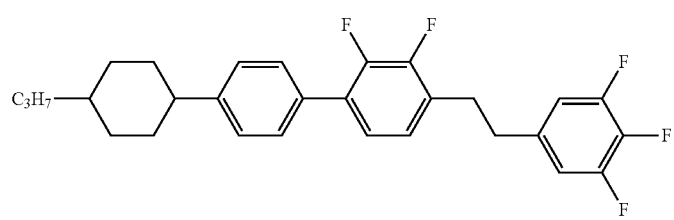 |
| 1-4-13 | 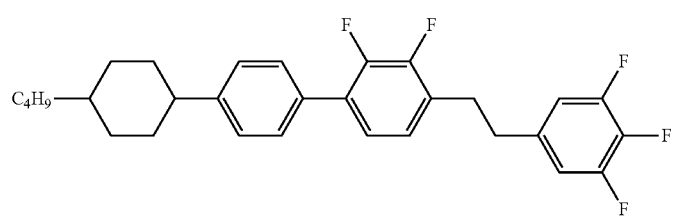 |
| 1-4-14 | 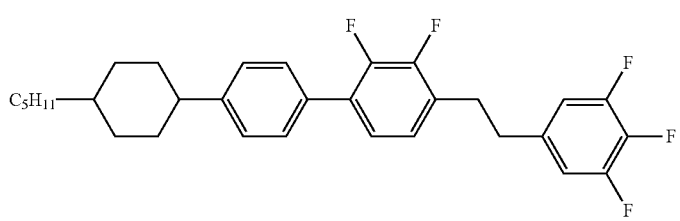 |
| 1-4-15 | 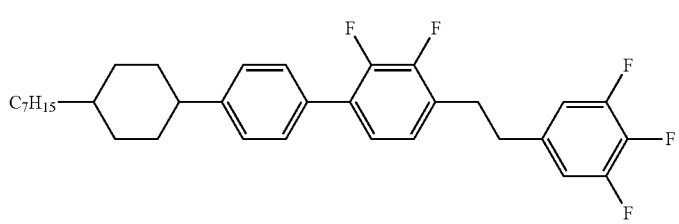 |

| No. |
|---|
| 1-4-16 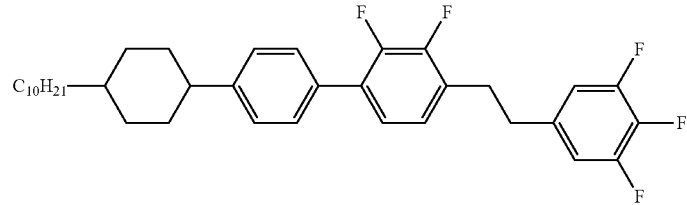 |
| 1-4-17 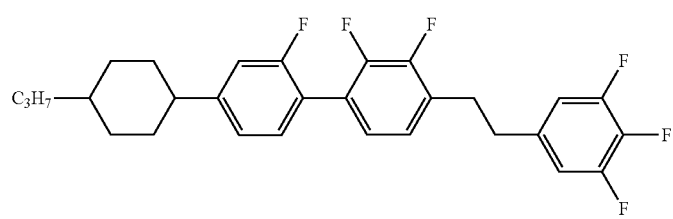 |
| 1-4-18 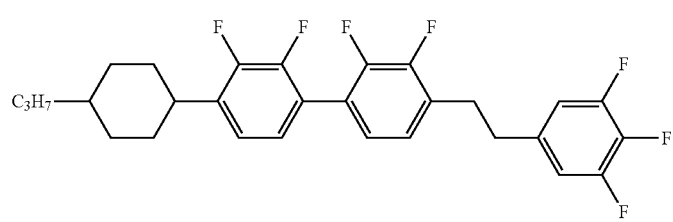 |
| 1-4-19 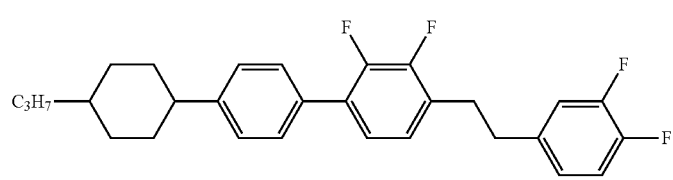 |
| 1-4-20 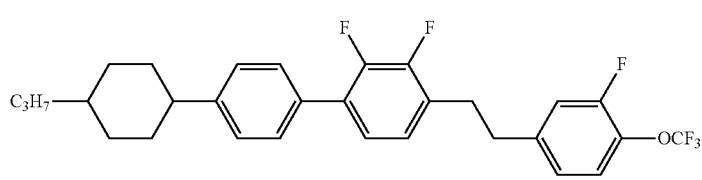 |
| 1-4-21 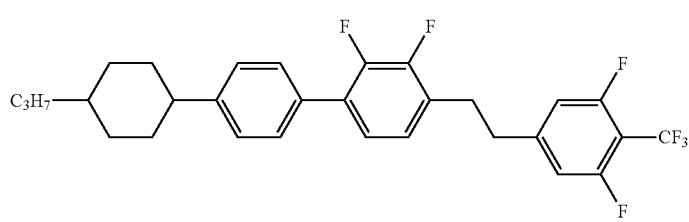 |
| 1-4-22 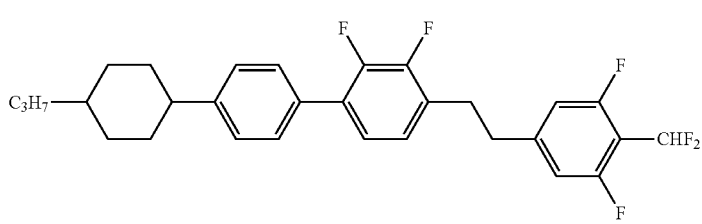 |

| No. |  |
|---|---|
| 1-4-23 | 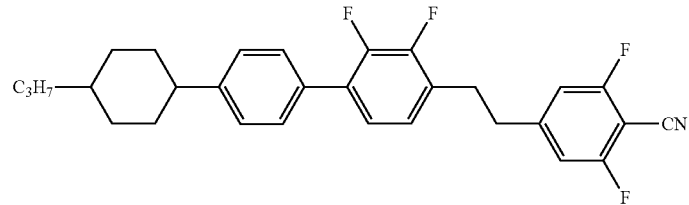 |
| 1-4-24 | 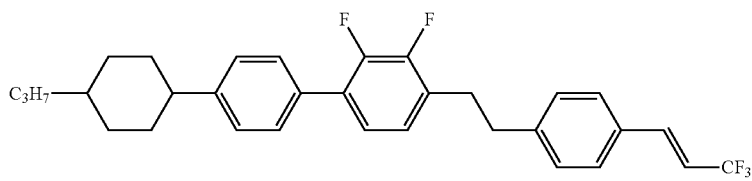 |
| 1-4-25 | 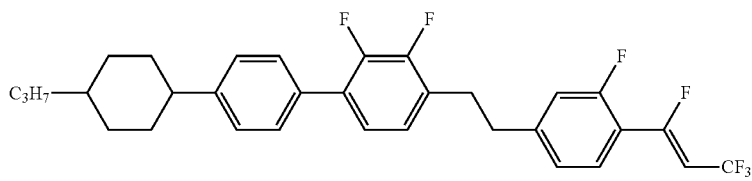 |
| 1-4-26 | 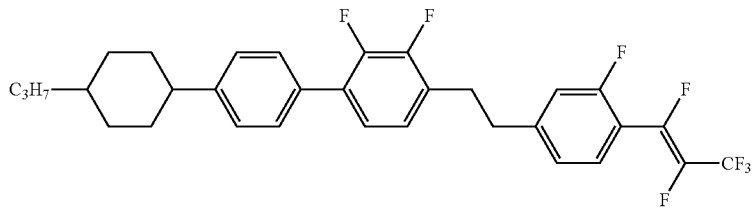 |
| 1-4-27 | 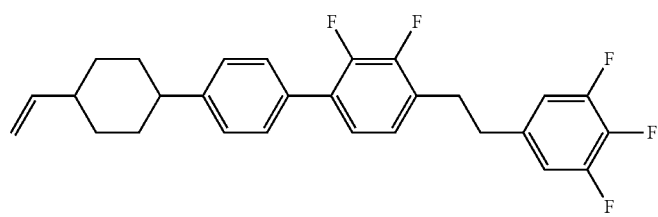 [SMILES: C=CC1CCC(c2ccc(-c3ccc(CCc4cc(F)c(F)c(F)c4)c(F)c3F)cc2)CC1] |
| 1-4-28 | 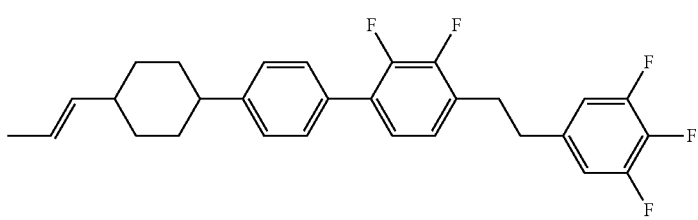 |
| 1-4-29 | 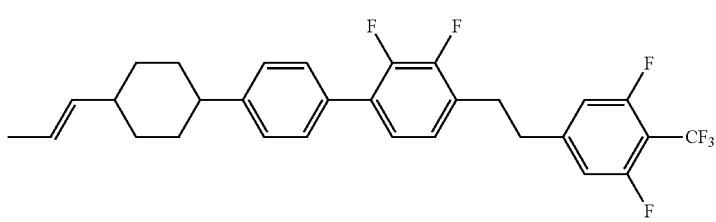 [SMILES: C/C=C/C1CCC(c2ccc(-c3ccc(CCc4cc(F)c(C(F)(F)F)c(F)c4)c(F)c3F)cc2)CC1] |

-continued
| No. | |
|---|---|
| 1-4-30 | 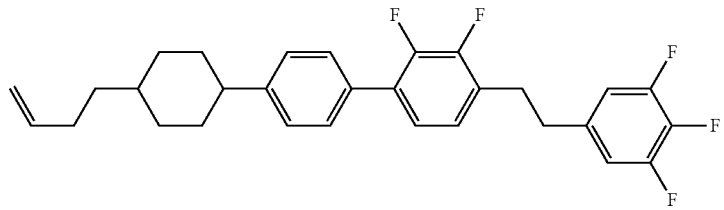 |
| 1-4-31 | 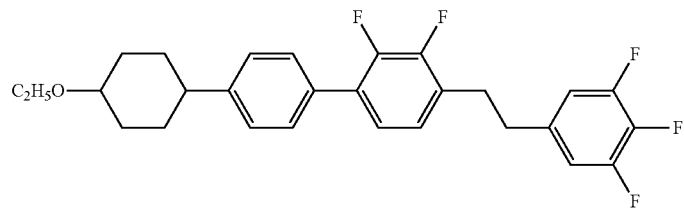 |
| 1-4-32 | 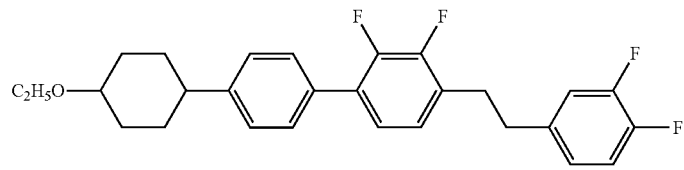 |
| 1-4-33 | 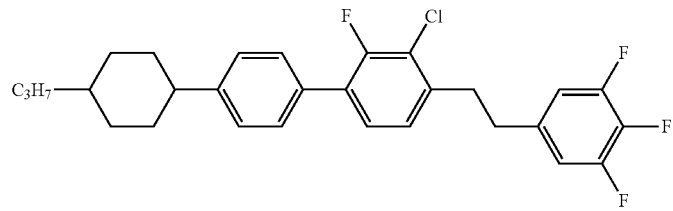 |
| 1-4-34 | 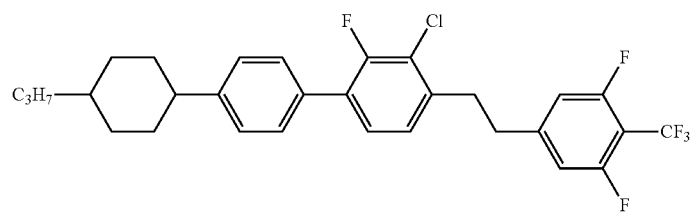 |
| 1-4-35 | 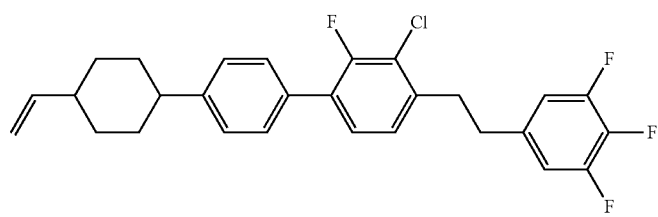 |
| 1-4-36 | 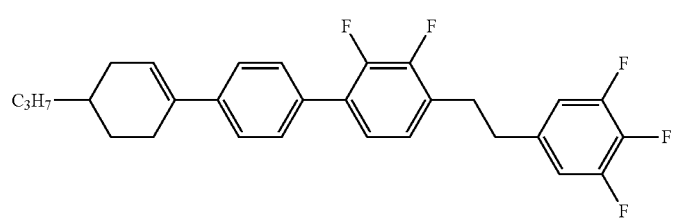 |

| No. | |
|---|---|
| 1-4-37 | 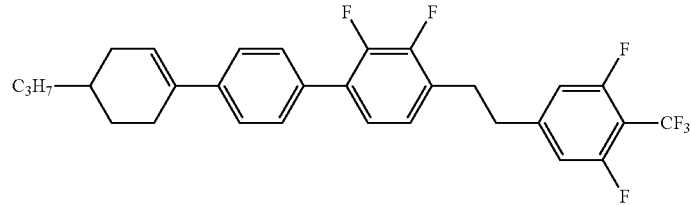 |
| 1-4-38 | 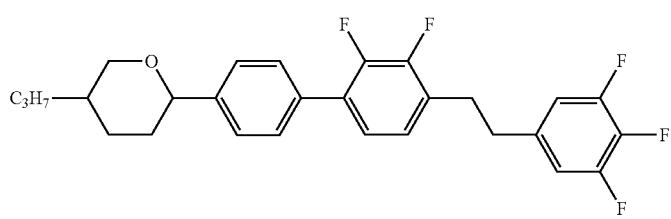 |
| 1-4-39 | 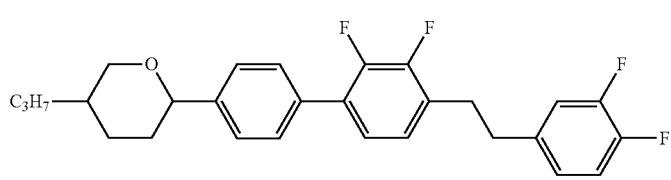 |
| 1-4-40 | 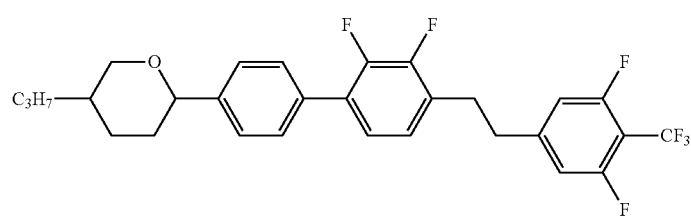 |
| 1-4-41 | 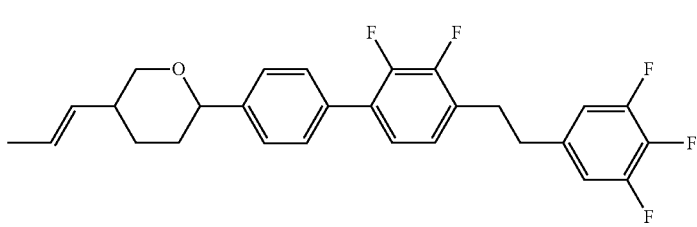 [SMILES: C/C=C/C1CCC(c2ccc(-c3ccc(CCc4cc(F)c(F)c(F)c4)c(F)c3F)cc2)OC1] |
| 1-4-42 | 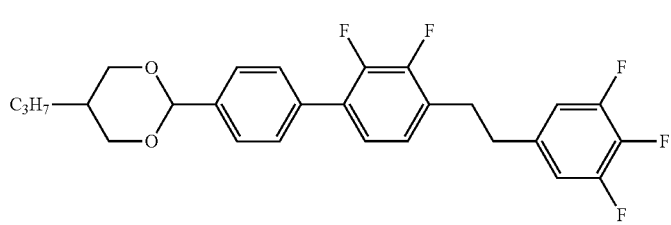 |
| 1-4-43 | 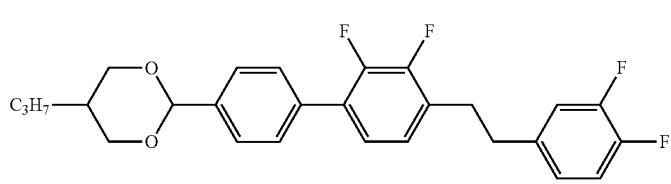 |

-continued
| No. |  |
|---|---|
| 1-4-44 | 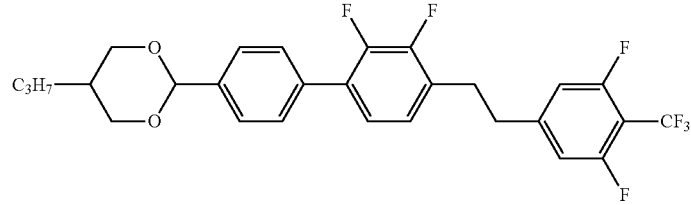 |
| 1-4-45 | 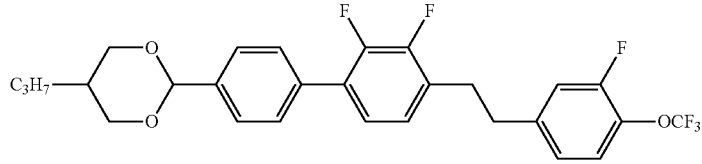 |
| 1-4-46 | 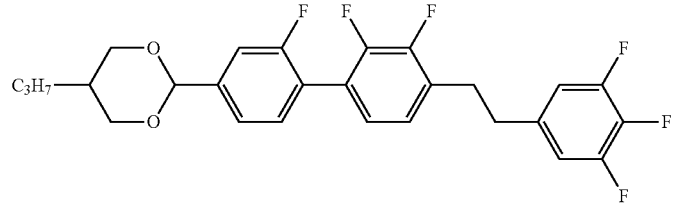 |
| 1-4-47 | 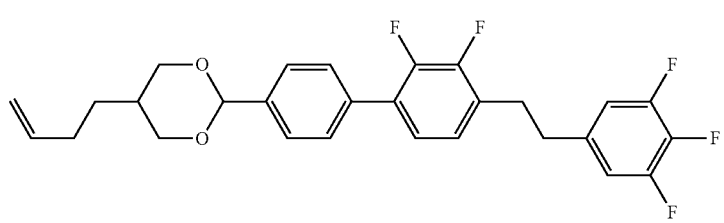 |
| 1-4-48 | 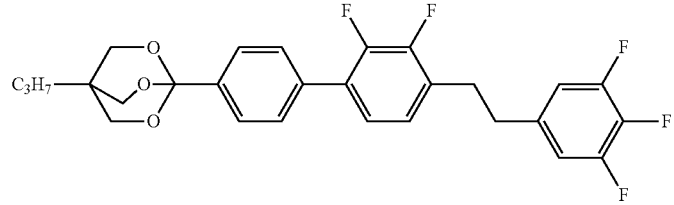 |
| 1-4-49 | 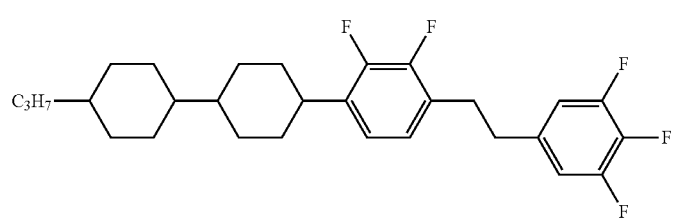 |
| 1-4-50 | 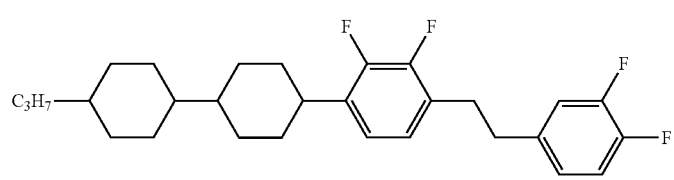 |

| No. | |
|---|---|
| 1-4-51 | 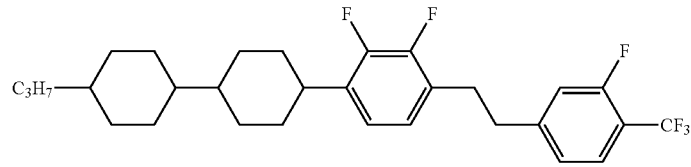 |
| 1-4-52 | 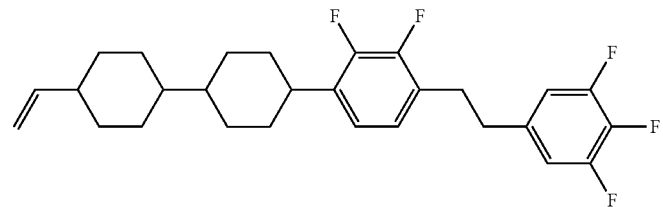 |
| 1-4-53 | 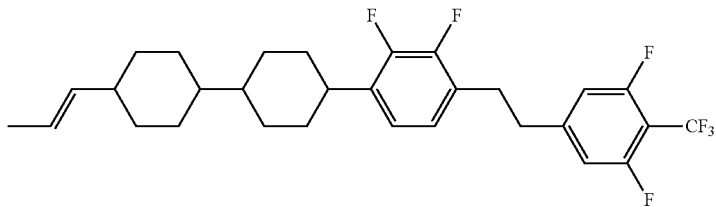 [SMILES: C/C=C/C1CCC(C2CCC(c3ccc(CCc4cc(F)c(C(F)(F)F)c(F)c4)c(F)c3F)CC2)CC1] |
| 1-4-54 | 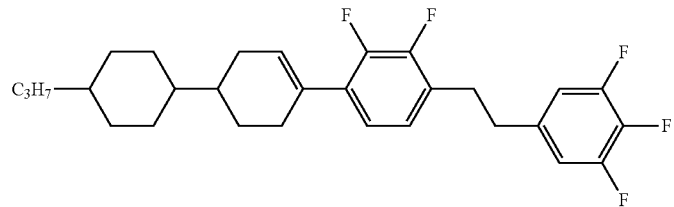 |
| 1-4-55 | 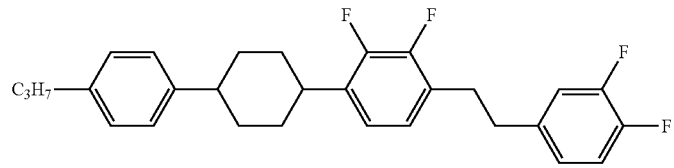 |
| 1-4-56 | 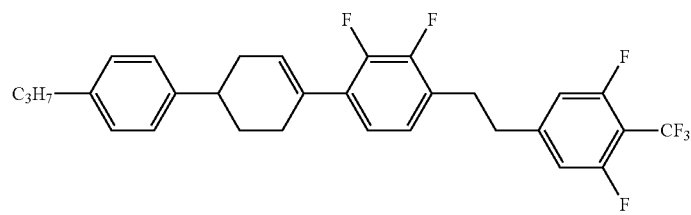 |
| 1-4-57 | 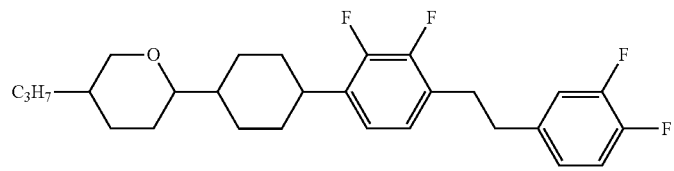 |

| No. | |
|---|---|
| 1-4-58 | 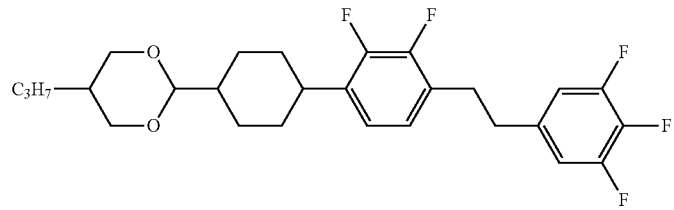 |
| 1-4-59 | 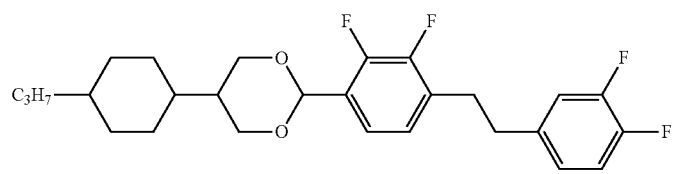 |
| 1-4-60 | 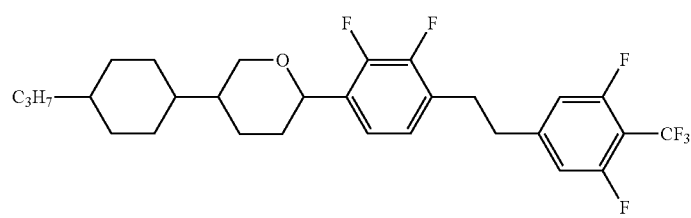 |
| 1-4-61 | 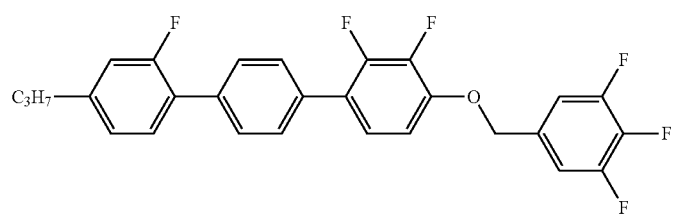 |
| 1-4-62 | 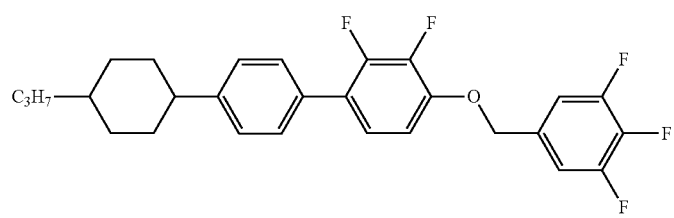 |
| 1-4-63 | 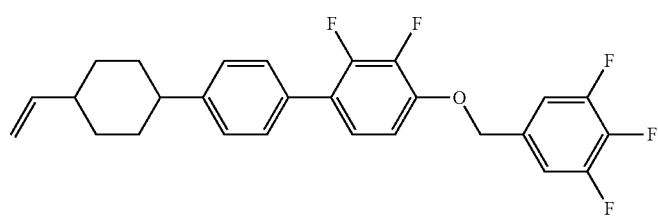 |
| 1-4-64 | 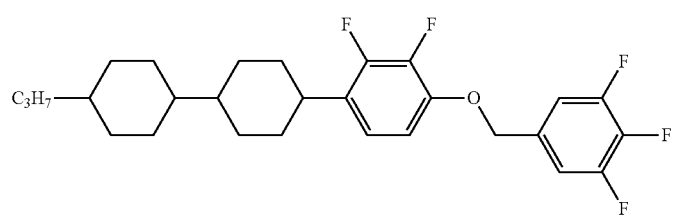 |

| No. | |
|---|---|
| 1-4-65 | 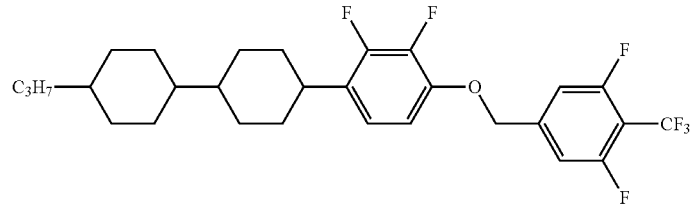 |
| 1-4-66 | 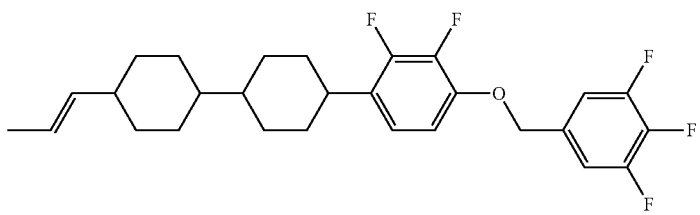 |
| 1-4-67 | 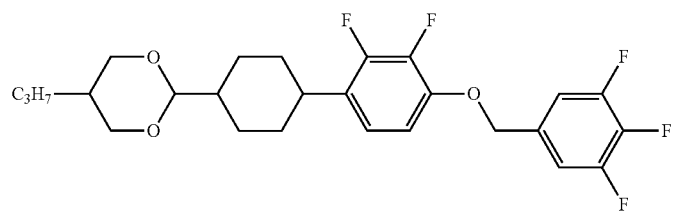 |
| 1-4-68 | 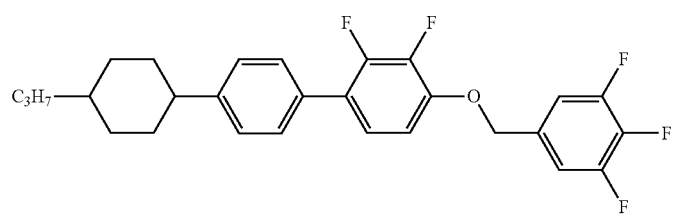 |
| 1-4-69 | 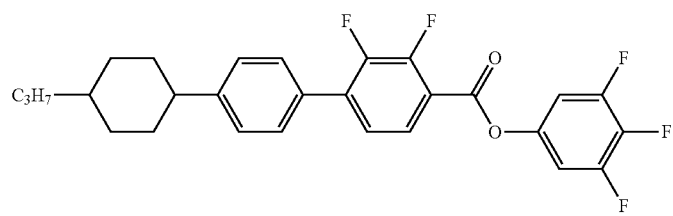 |
| 1-4-70 | 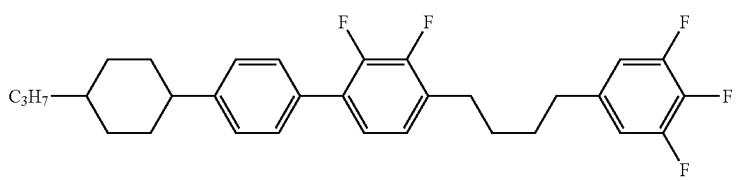 |
| 1-4-71 | 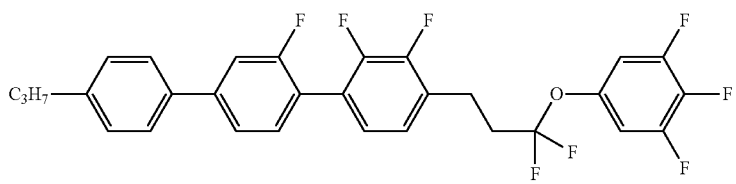 |

| No. | |
|---|---|
| 1-4-72 | 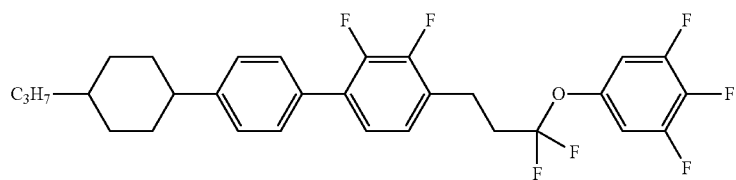 |
| 1-4-73 | 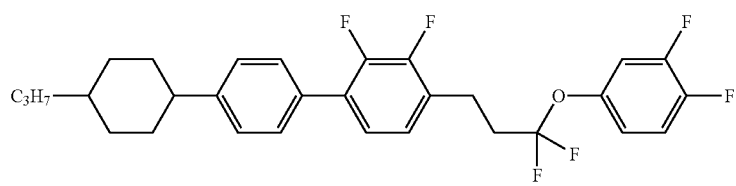 |
| 1-4-74 | 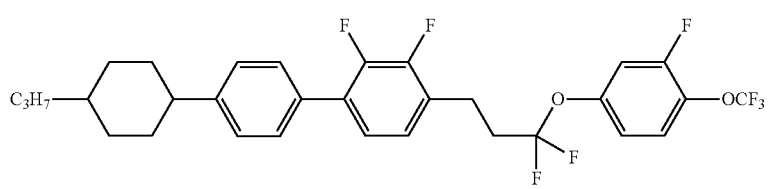 |
| 1-4-75 | 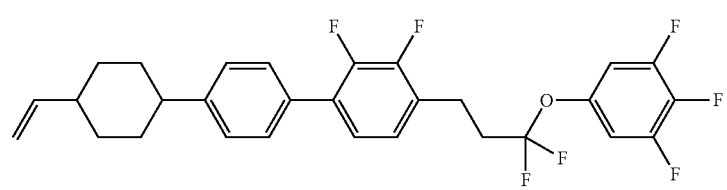 |
| 1-4-76 | 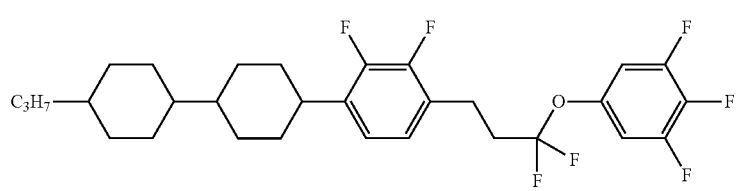 |
| 1-4-77 | 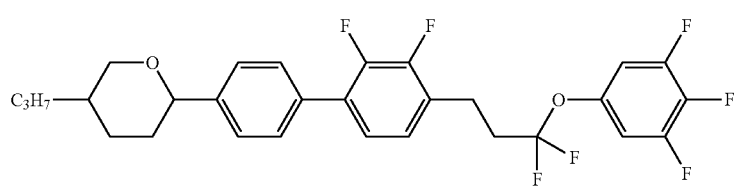 |
| 1-4-78 | 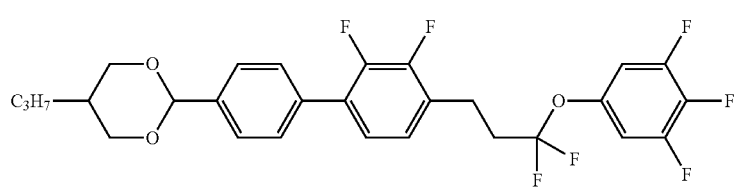 |
| 1-4-79 | 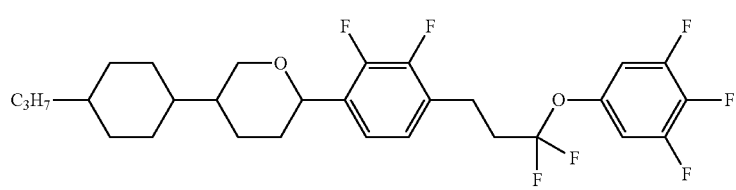 |

| No. | |
|---|---|
| 1-4-80 | 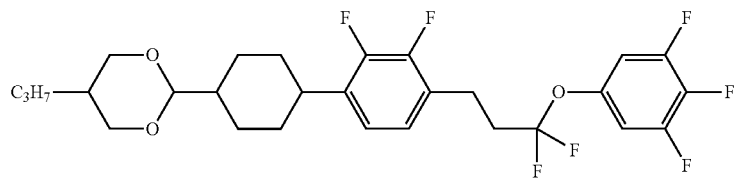 |
| 1-4-81 | 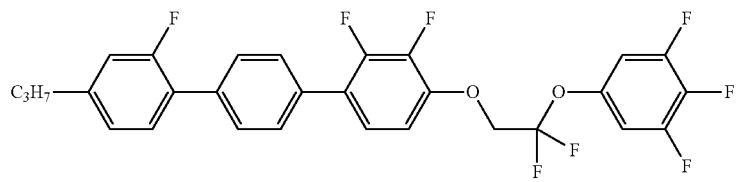 |
| 1-4-82 | 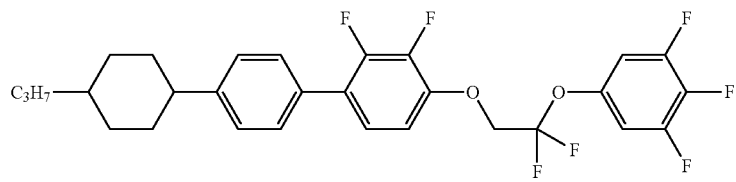 |
| | C 74.7 S$_A$ 80.1 N 123 I<br>T$_{NI}$ = 88.4° C., Δn = 0.137, Δε = 11.1, ε (⊥) = 9.7 |
| 1-4-83 | 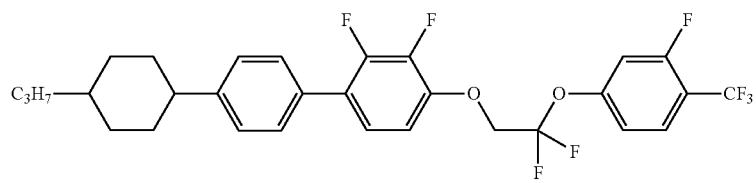 |
| 1-4-84 | 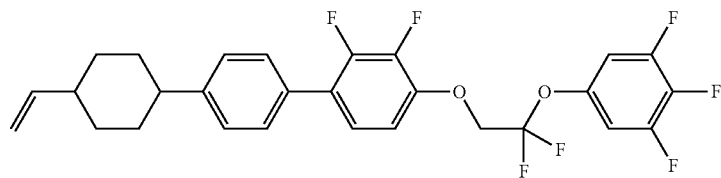 [SMILES: C=CC1CCC(c2ccc(-c3ccc(OCC(F)(F)Oc4cc(F)c(F)c(F)c4)c(F)c3F)cc2)CC1] |
| 1-4-85 | 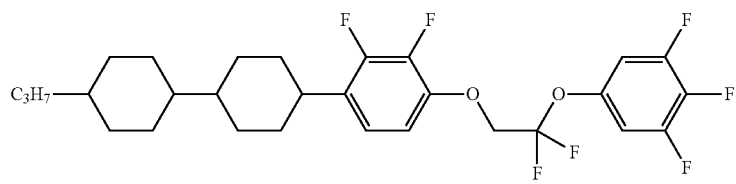 |
| 1-4-86 | 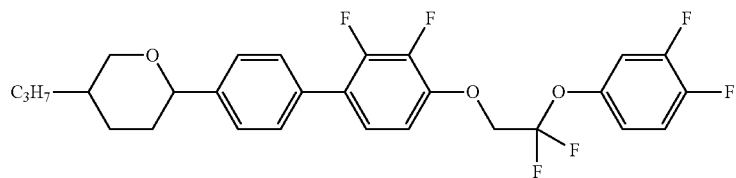 |

| No. | |
|---|---|
| 1-4-87 | 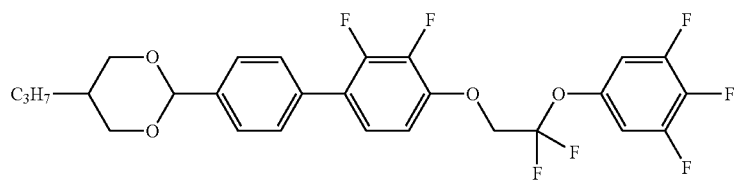 |
| 1-4-88 | 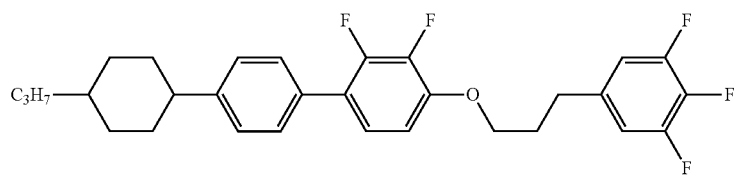 |
| 1-4-89 | 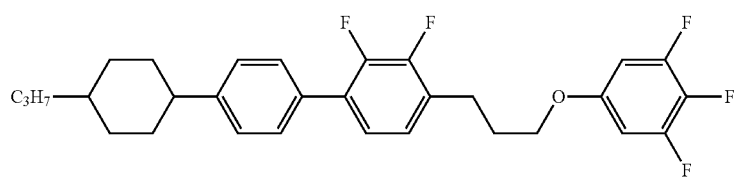 |
| 1-4-90 | 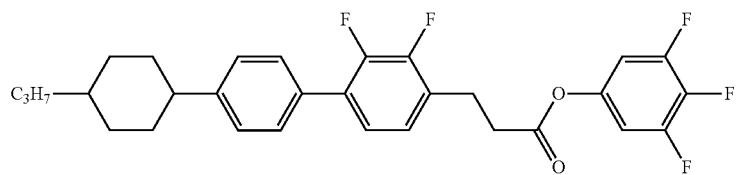 |
| 1-4-91 | 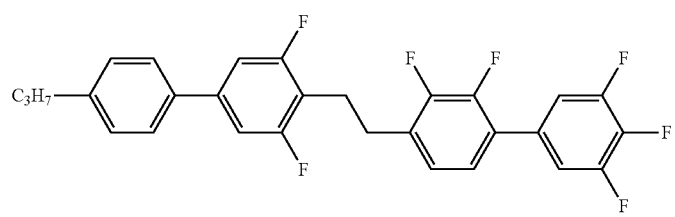 |
| 1-4-92 | 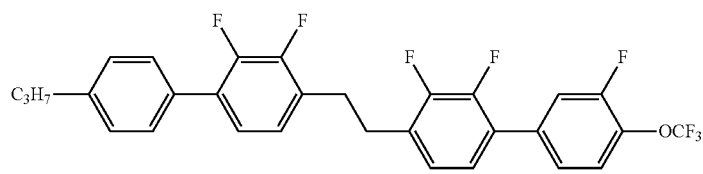 |
| 1-4-93 | 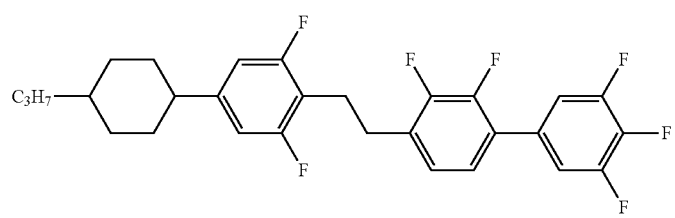 |

| No. |
|---|
| 1-4-94 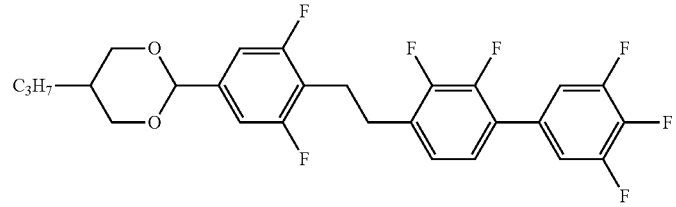 |
| 1-4-95 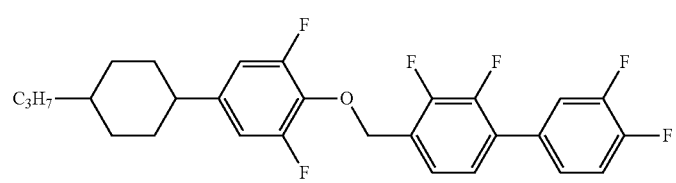 |
| 1-4-96 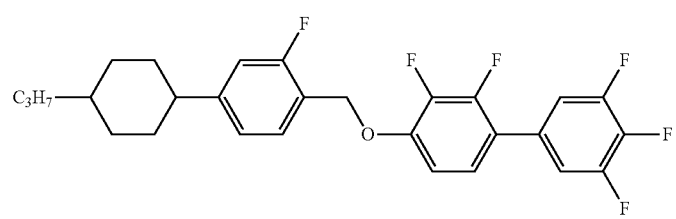 |
| 1-4-97 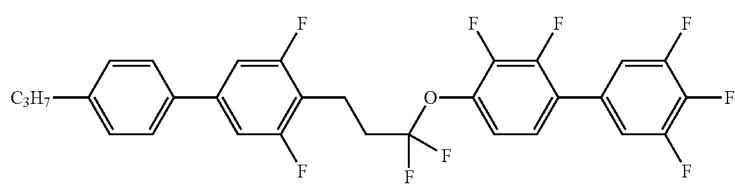 |
| 1-4-98 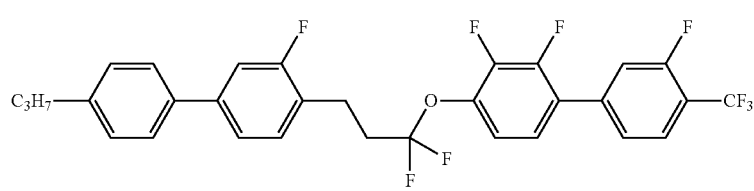 |
| 1-4-99 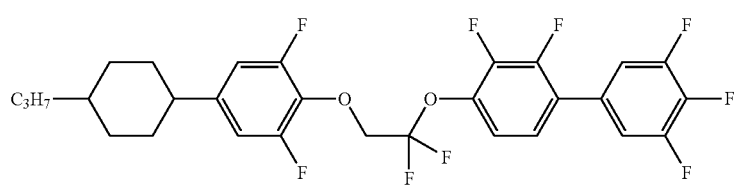 |
| 1-4-100 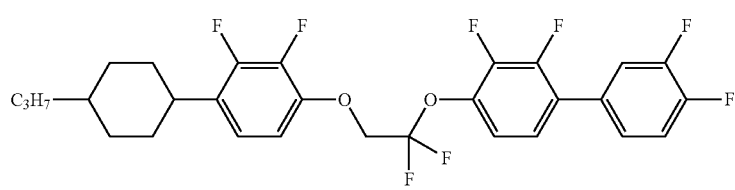 |

| No. | |
|---|---|
| 1-5-1 | 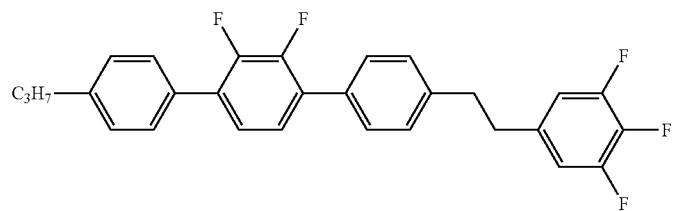 |
| 1-5-2 | 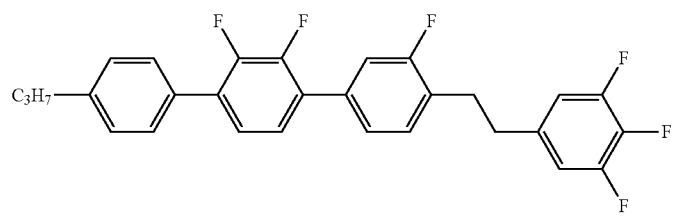 |
| 1-5-3 | 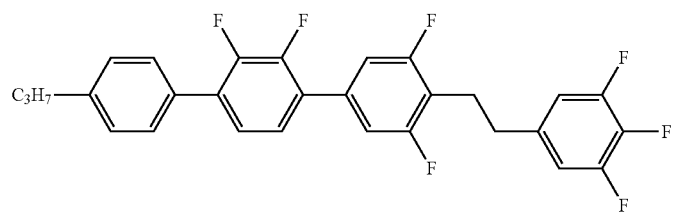 |
| 1-5-4 | 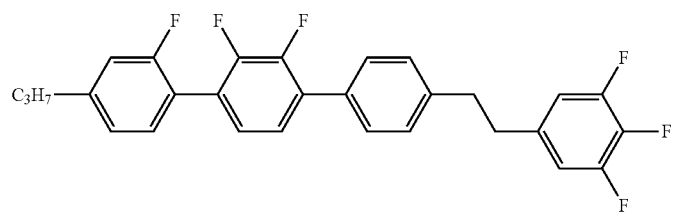 |
| 1-5-5 | 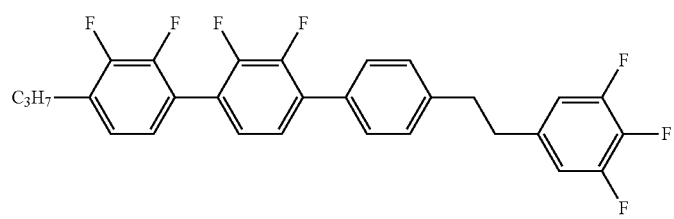 |
| 1-5-6 | 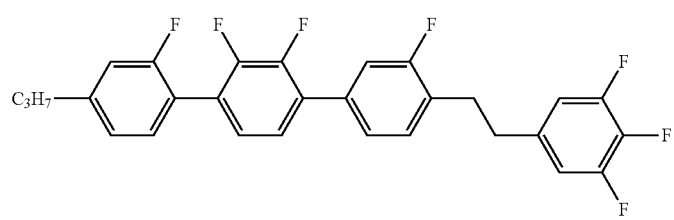 |
| 1-5-7 | 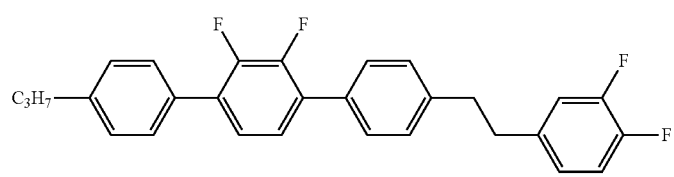 |

| No. | |
|---|---|
| 1-5-8 | 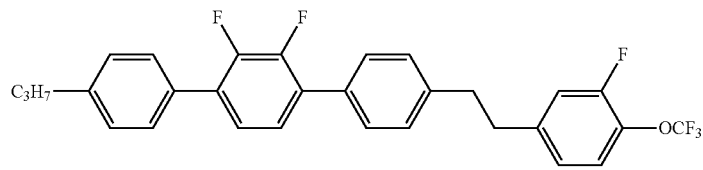 |
| 1-5-9 | 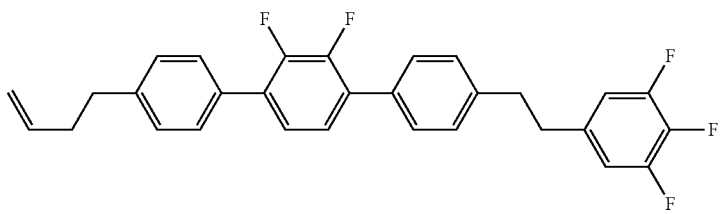 [SMILES: C=CCCc1ccc(-c2ccc(-c3ccc(CCc4cc(F)c(F)c(F)c4)cc3)c(F)c2F)cc1] |
| 1-5-10 | 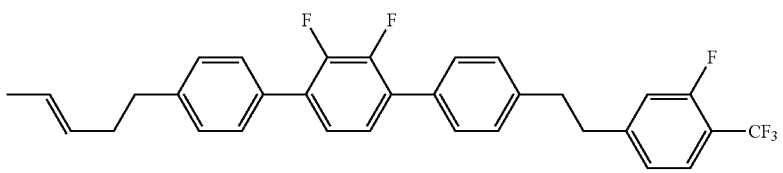 [SMILES: C/C=C/CCc1ccc(-c2ccc(-c3ccc(CCc4ccc(C(F)(F)F)c(F)c4)cc3)c(F)c2F)cc1] |
| 1-5-11 | 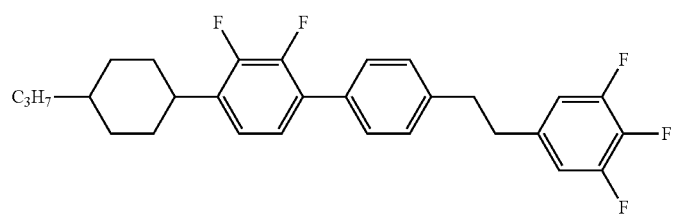 |
| 1-5-12 | 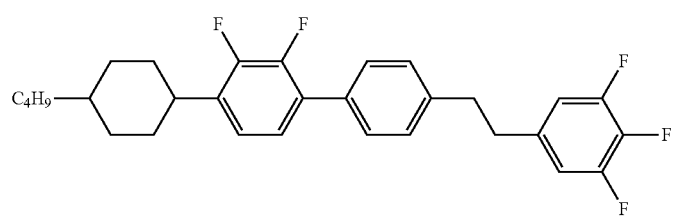 |
| 1-5-13 | 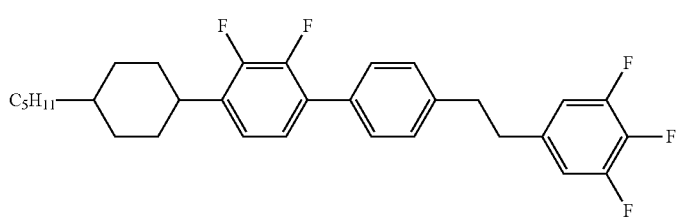 |
| 1-5-14 | 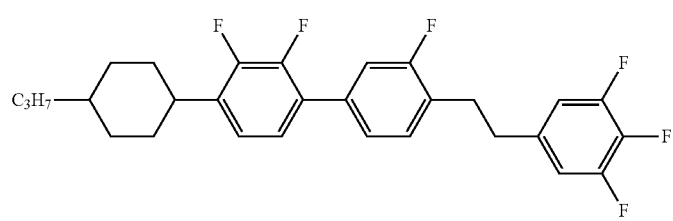 |

| No. |  |
|---|---|
| 1-5-15 | 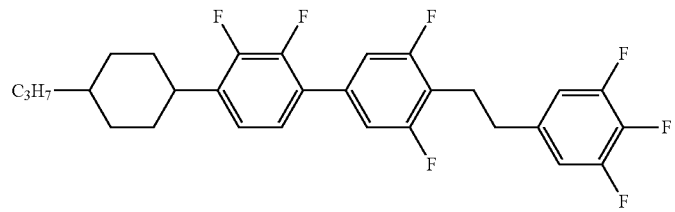 |
| 1-5-16 | 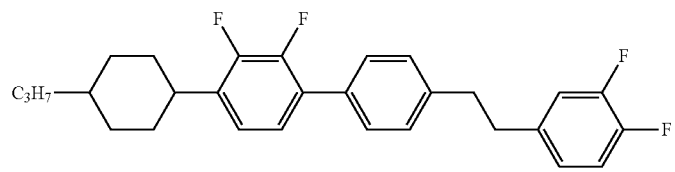 |
| 1-5-17 | 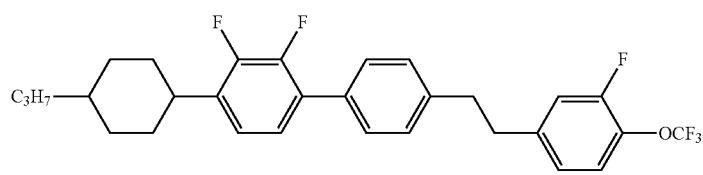 |
| 1-5-18 | 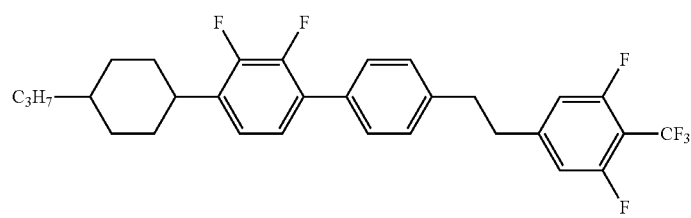 |
| 1-5-19 | 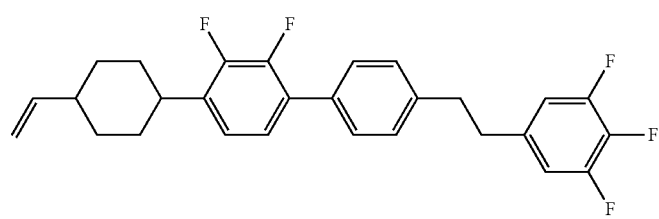 [SMILES: C=CC1CCC(c2ccc(-c3ccc(CCc4cc(F)c(F)c(F)c4)cc3)c(F)c2F)CC1] |
| 1-5-20 | 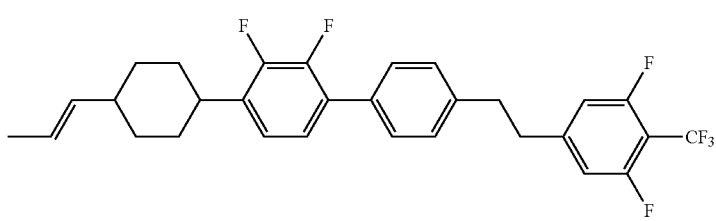 [SMILES: C/C=C/C1CCC(c2ccc(-c3ccc(CCc4cc(F)c(C(F)(F)F)c(F)c4)cc3)c(F)c2F)CC1] |
| 1-5-21 | 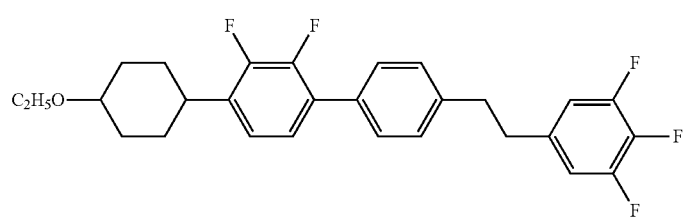 |

-continued
| No. | |
|---|---|
| 1-5-22 | 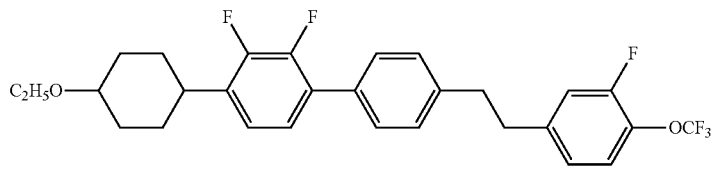 |
| 1-5-23 | 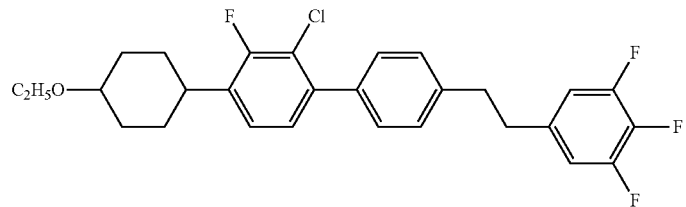 |
| 1-5-24 | 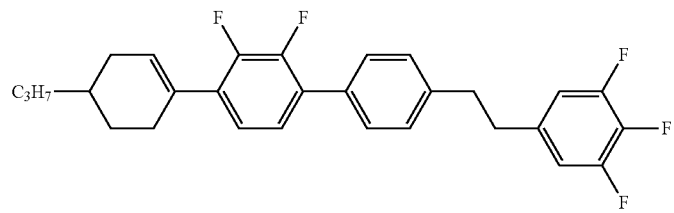 |
| 1-5-25 | 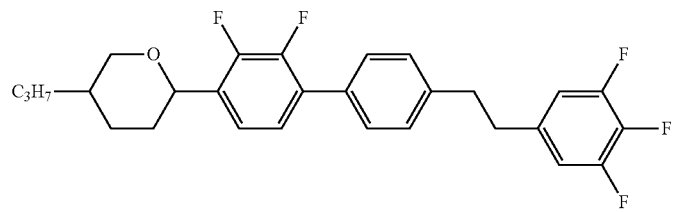 |
| 1-5-26 | 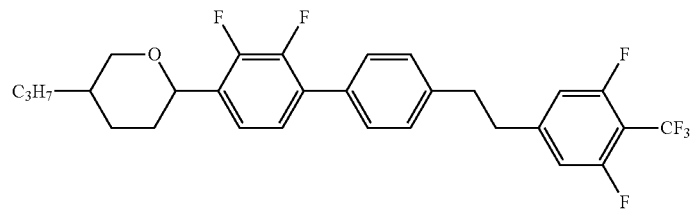 |
| 1-5-27 | 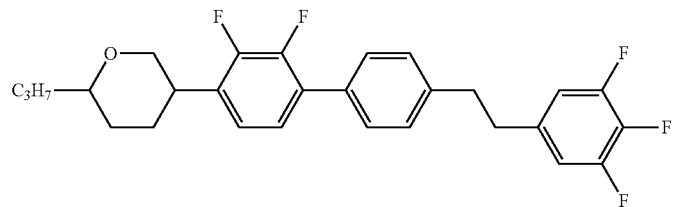 |
| 1-5-28 | 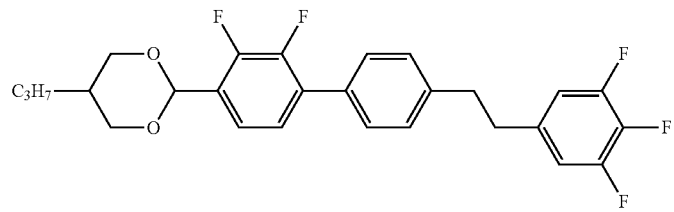 |

-continued
| No. |  |
|---|---|
| 1-5-29 | 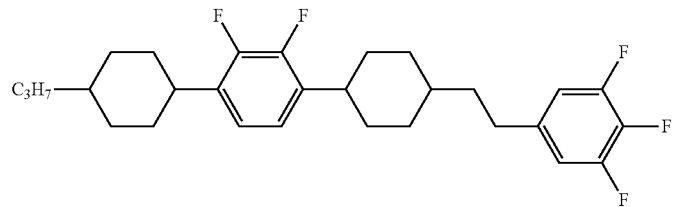 |
| 1-5-30 | 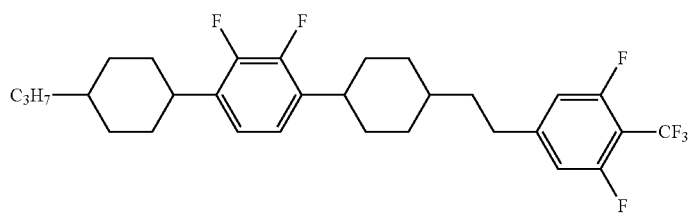 |
| 1-5-31 | 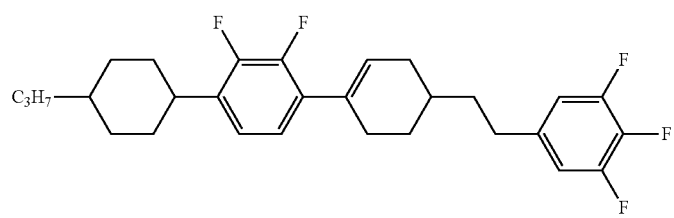 |
| 1-5-32 | 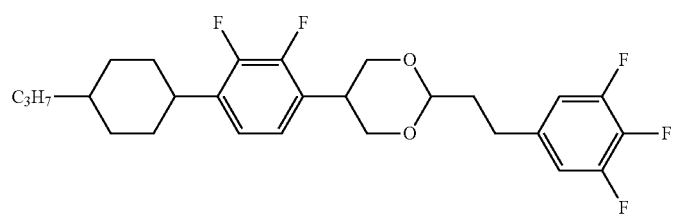 |
| 1-5-33 | 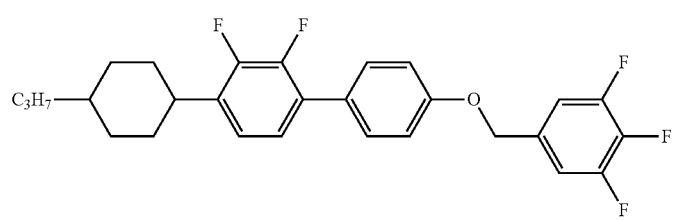 |
| 1-5-34 | 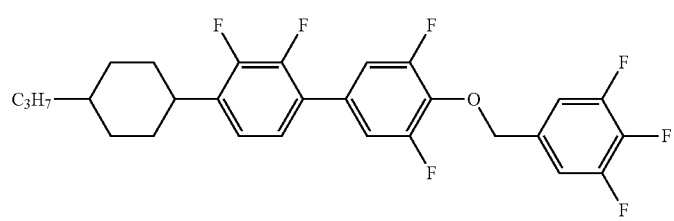 |
| 1-5-35 | 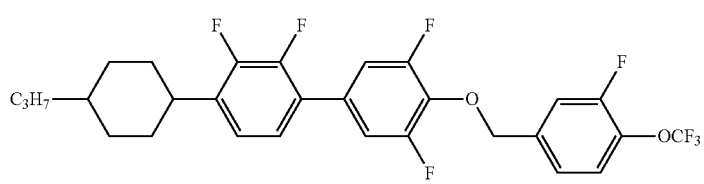 |

| No. | |
|---|---|
| 1-5-36 | 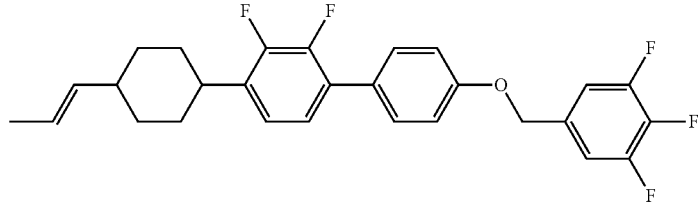 [SMILES: C/C=C/C1CCC(c2ccc(-c3ccc(OCc4cc(F)c(F)c(F)c4)cc3)c(F)c2F)CC1] |
| 1-5-37 | 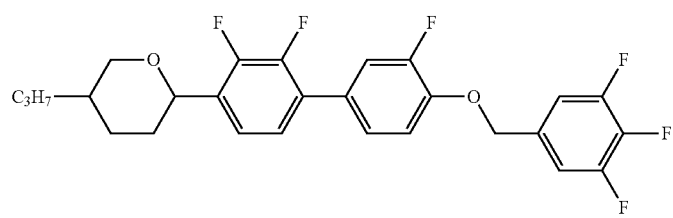 |
| 1-5-38 | 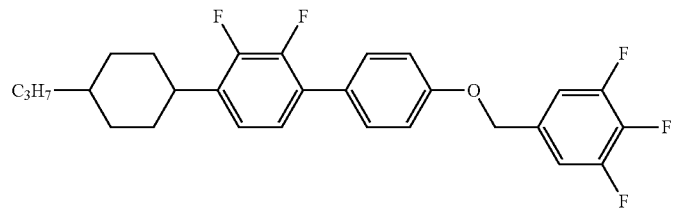 |
| 1-5-39 | 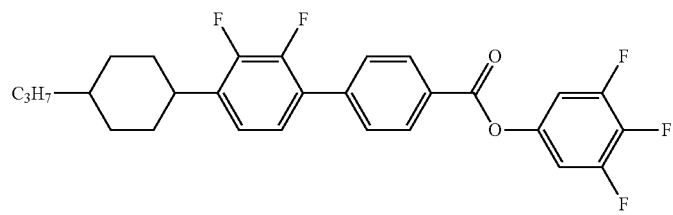 |
| 1-5-40 | 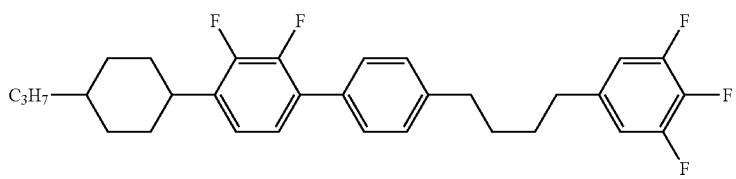 |
| 1-5-41 | 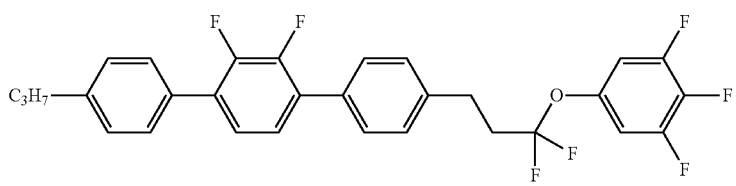 |
| 1-5-42 | 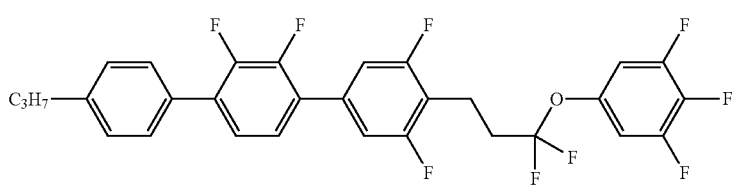 |

| No. | |
|---|---|
| 1-5-43 | 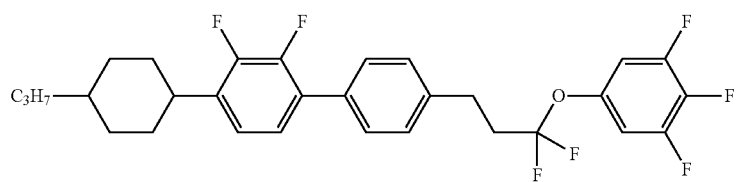 |
| 1-5-44 | 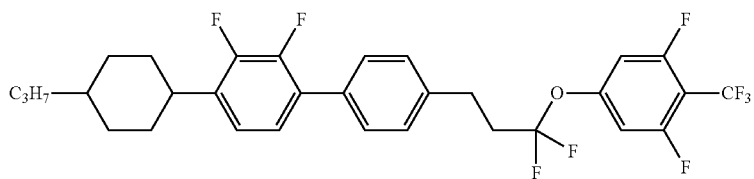 |
| 1-5-45 | 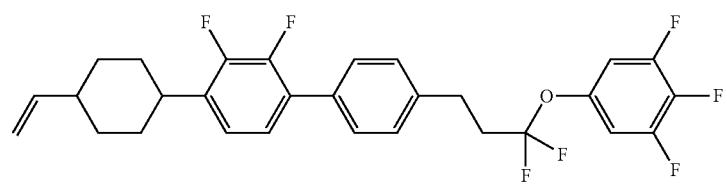 [SMILES: C=CC1CCC(c2ccc(-c3ccc(CCC(F)(F)Oc4cc(F)c(F)c(F)c4)cc3)c(F)c2F)CC1] |
| 1-5-46 | 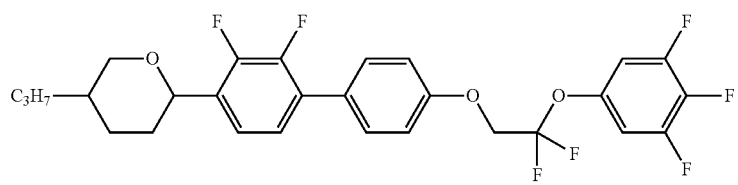 |
| 1-5-47 | 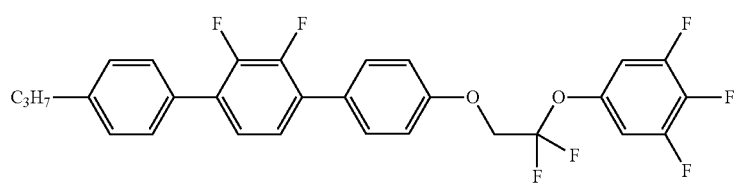 |
| 1-5-48 | 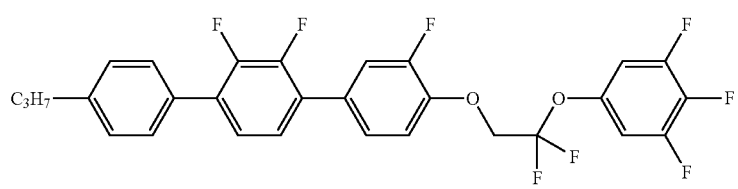 |
| 1-5-49 | 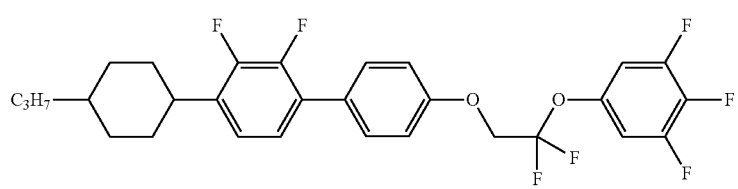 |
| 1-5-50 | 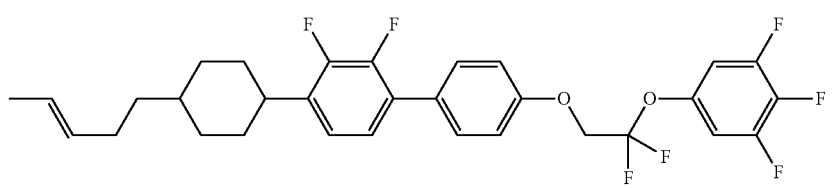 [SMILES: C/C=C/CCC1CCC(c2ccc(-c3ccc(OCC(F)(F)Oc4cc(F)c(F)c(F)c4)cc3)c(F)c2F)CC1] |

| No. | |
|---|---|
| 1-5-51 | 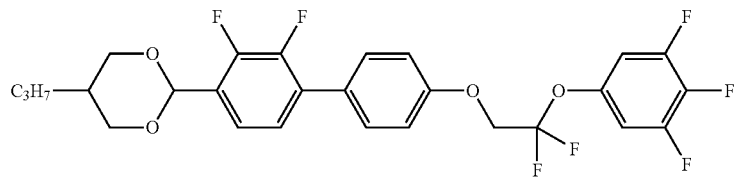 |
| 1-5-52 | 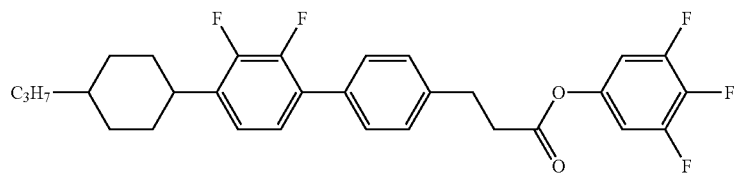 |
| 1-5-53 | 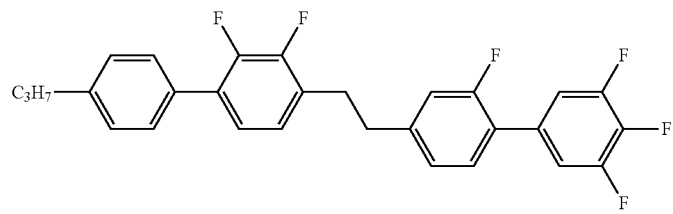 |
| 1-5-54 | 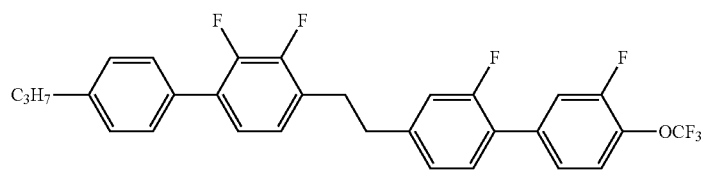 |
| 1-5-55 | 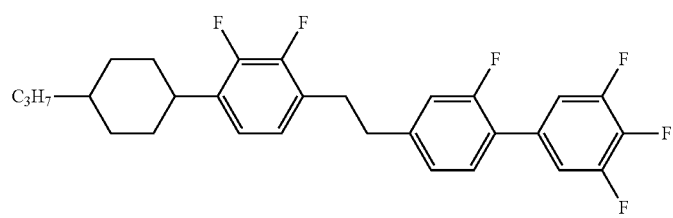 |
| 1-5-56 | 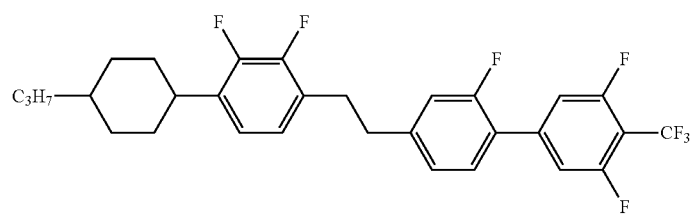 |
| 1-5-57 | 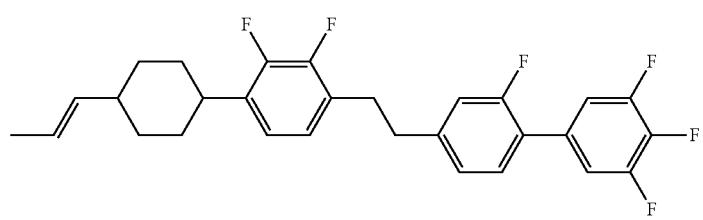 |

| No. | |
|---|---|
| 1-5-58 | 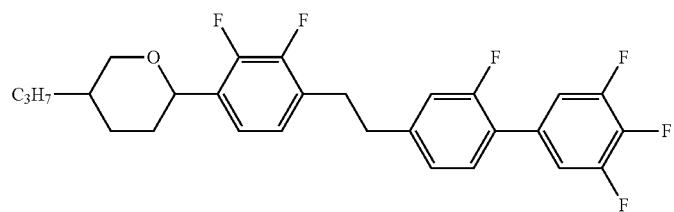 |
| 1-5-59 | 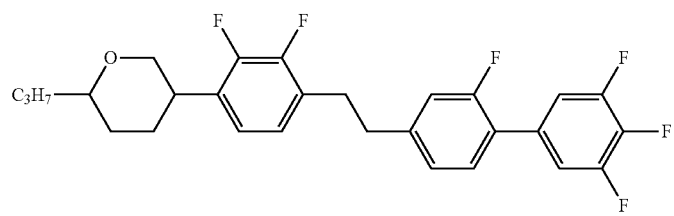 |
| 1-5-60 | 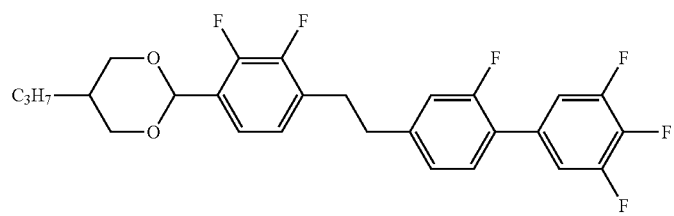 |
| 1-5-61 | 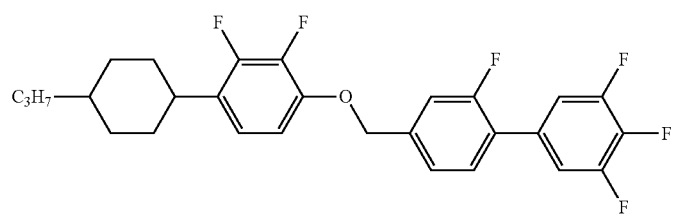 |
| 1-5-62 | 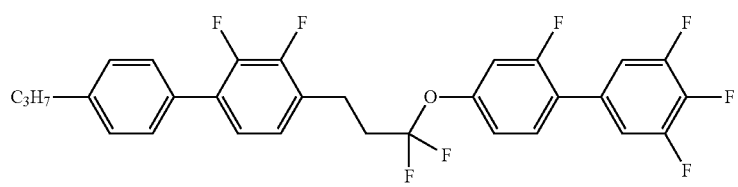<br>C 86.8 N 107 I<br>$T_{NI} = 77.7°$ C., $\Delta n = 0.170$, $\Delta\varepsilon = 19.9$, $\varepsilon\ (\perp) = 7.7$ |
| 1-5-63 | 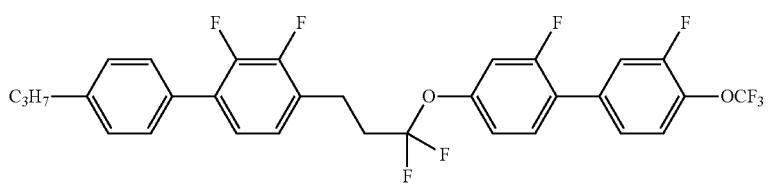 |
| 1-5-64 | 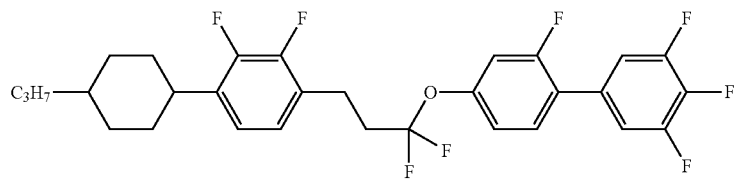 |

| No. | |
|---|---|
| 1-5-65 | 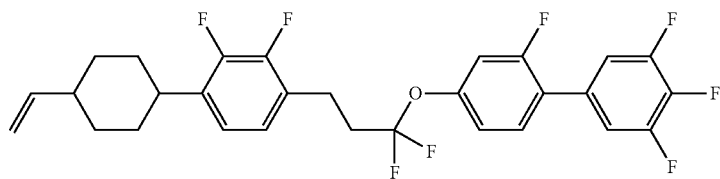 [SMILES: C=CC1CCC(c2ccc(CCC(F)(F)Oc3ccc(-c4cc(F)c(F)c(F)c4)c(F)c3)c(F)c2F)CC1] |
| 1-5-66 | 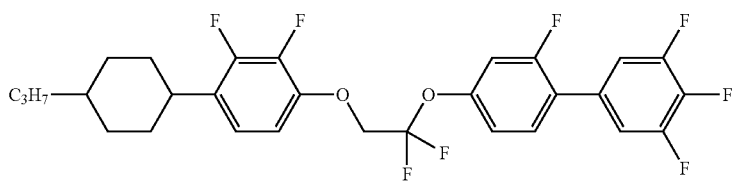 |
| 1-5-67 | 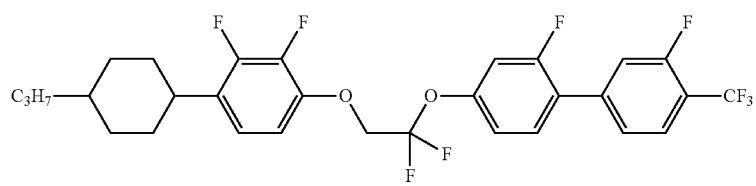 |
| 1-5-68 | 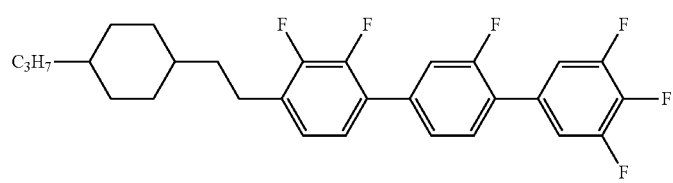 |
| 1-5-69 | 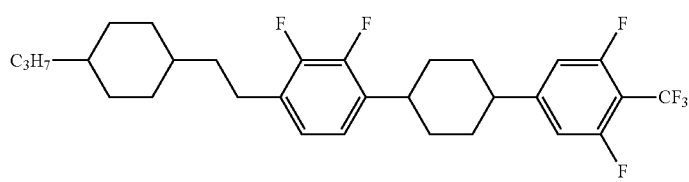 |
| 1-5-70 | 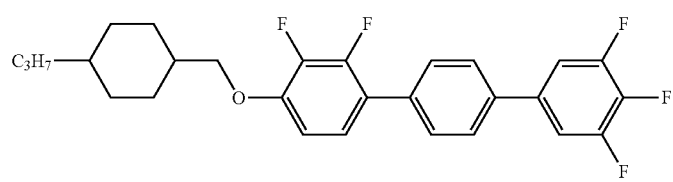 |
| 1-5-71 | 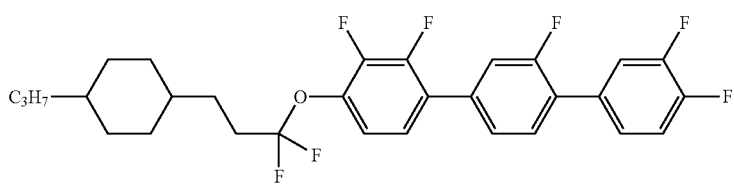 |
| 1-5-72 | 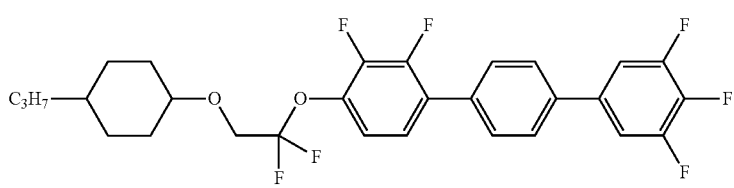 |

-continued
| No. |
|---|
| 1-5-73 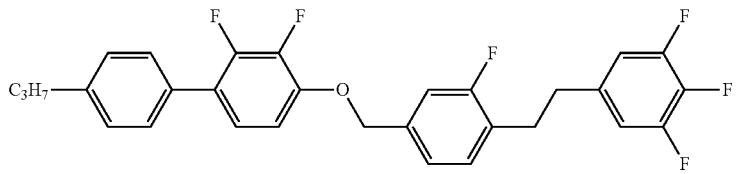 |
| 1-5-74 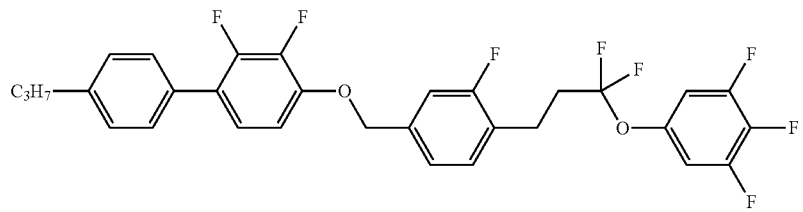 |
| 1-5-75 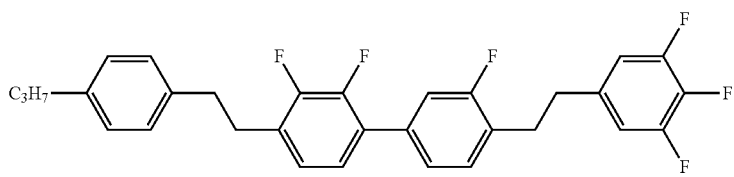 |
| 1-5-76 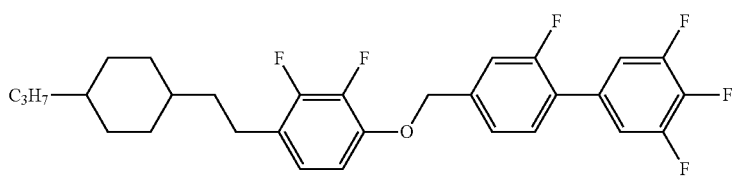 |
| 1-5-77 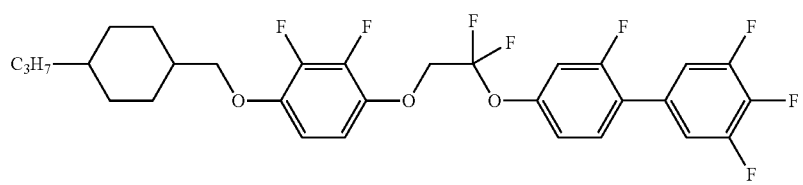 |
| 1-5-78 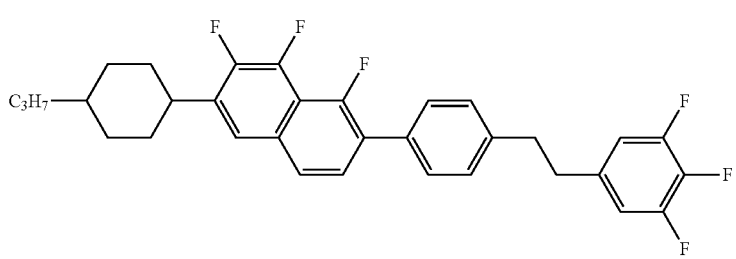 |
| 1-5-79 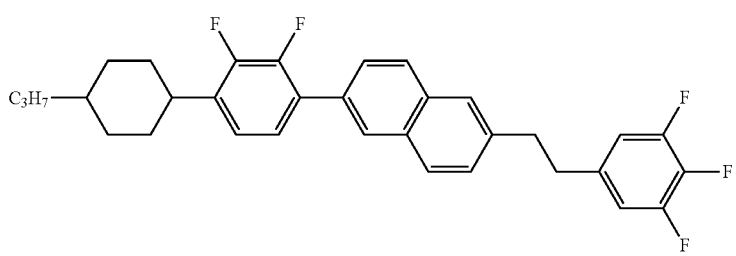 |

-continued
No.
1-5-80 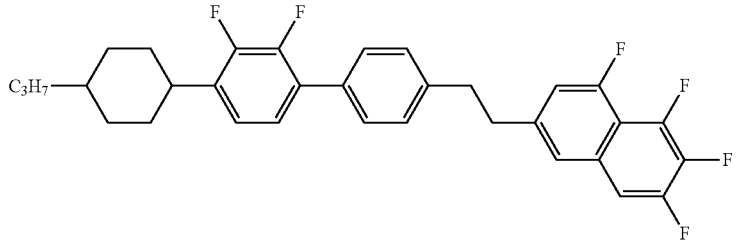
1-6-1 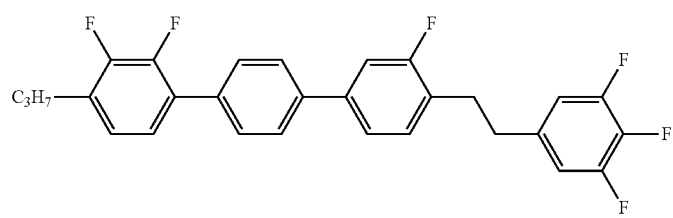
1-6-2 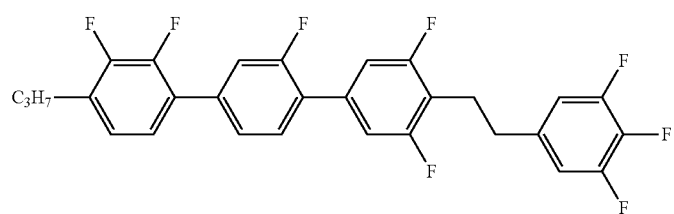
1-6-3 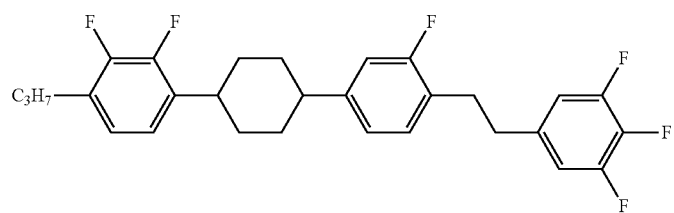
1-6-4 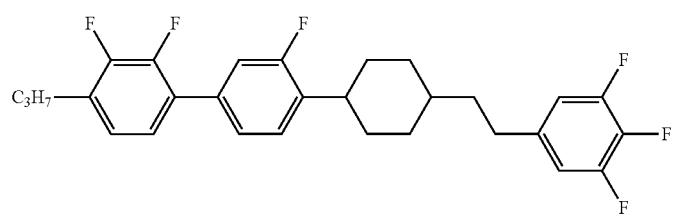
1-6-5 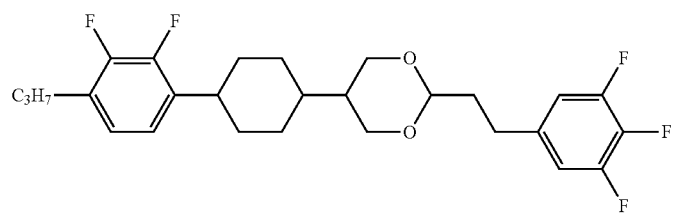

| No. | |
|---|---|
| 1-6-6 | 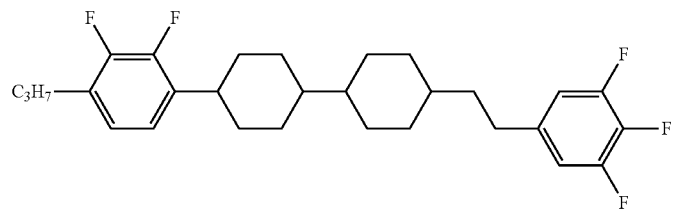 |
| 1-6-7 | 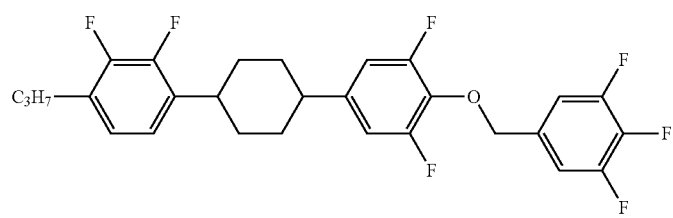 |
| 1-6-8 | 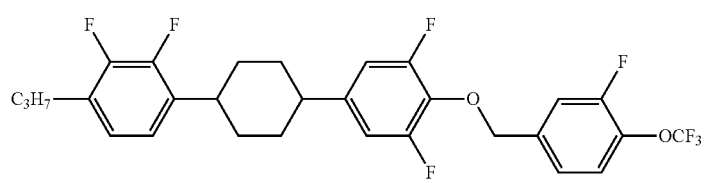 |
| 1-6-9 | 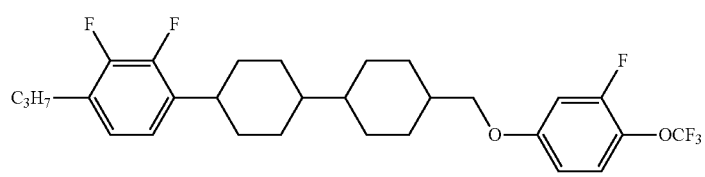 |
| 1-6-10 | 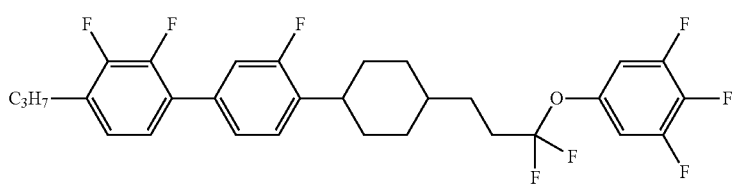 |
| 1-6-11 | 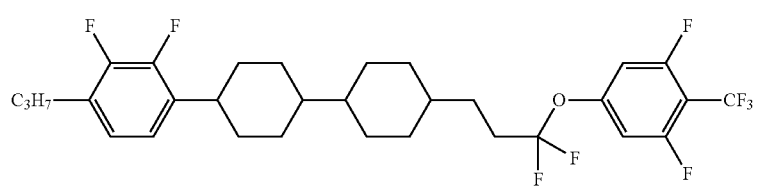 |
| 1-6-12 | 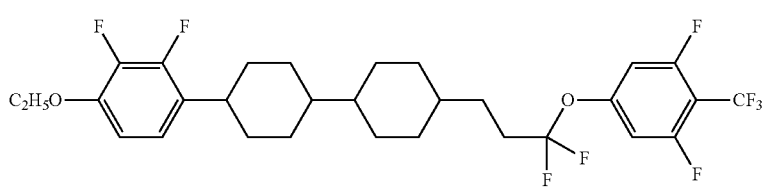 |

| No. | |
|---|---|
| 1-6-13 | 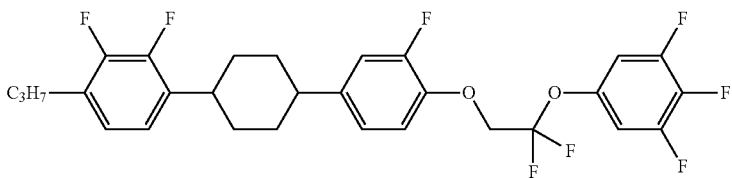 |
| 1-6-14 | 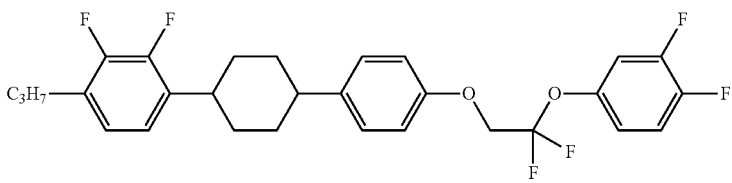 |
| 1-6-15 | 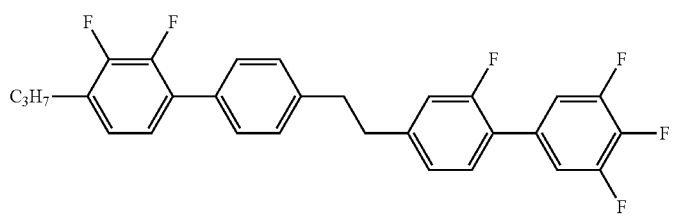 |
| 1-6-16 | 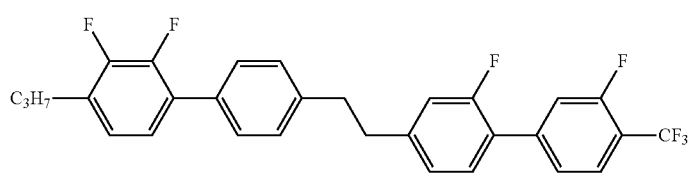 |
| 1-6-17 | 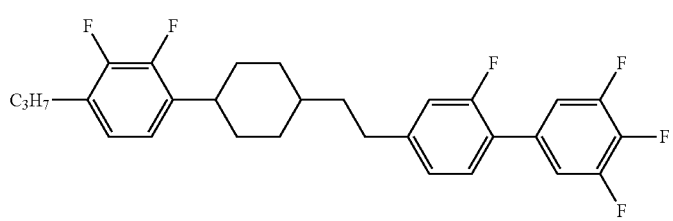 |
| 1-6-18 | 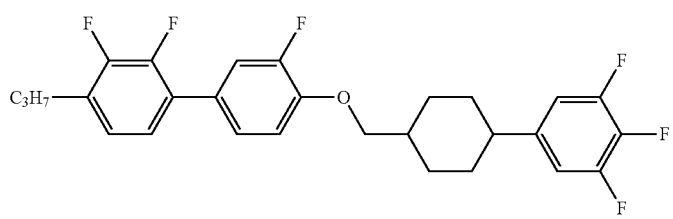 |
| 1-6-19 | 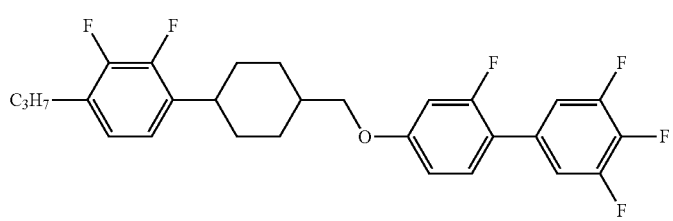 |

-continued
| No. | |
|---|---|
| 1-6-20 | 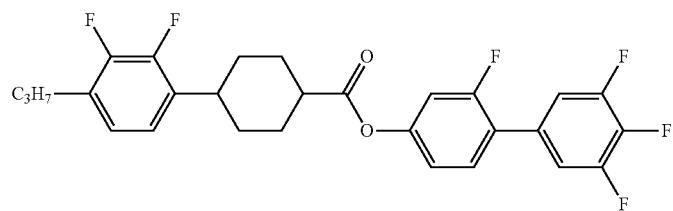 |
| 1-6-21 | 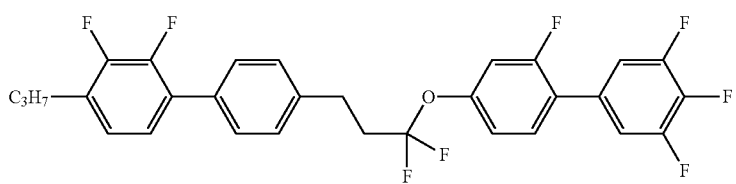 |
| 1-6-22 | 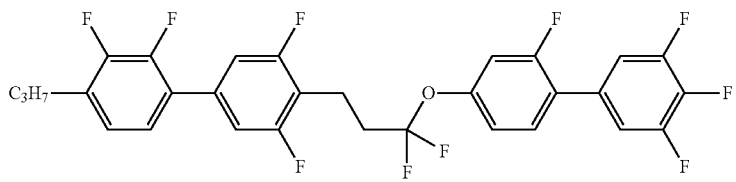 |
| 1-6-23 | 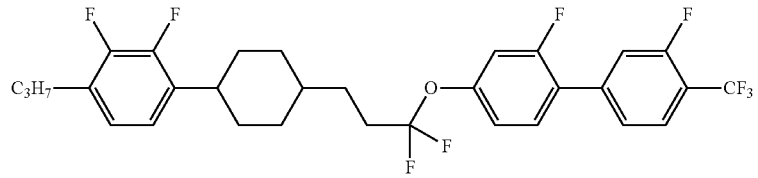 |
| 1-6-24 | 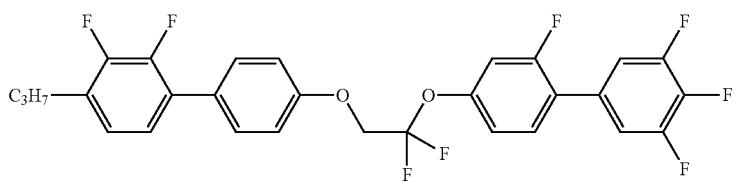 |
| 1-6-25 | 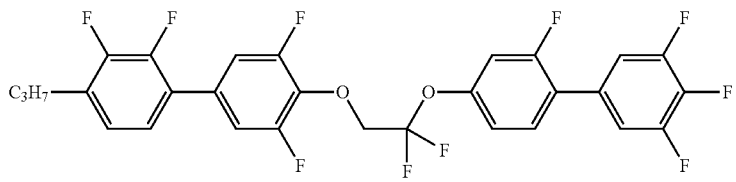 |
| 1-6-26 | 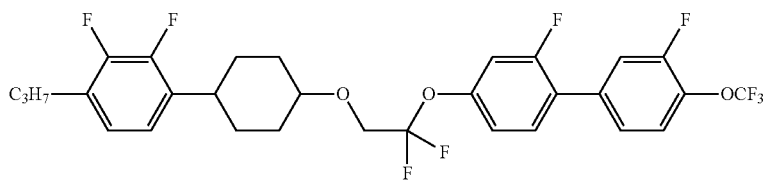 |

-continued
| No. |  |
|---|---|
| 1-6-27 | 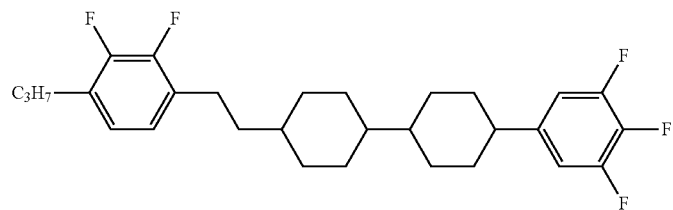 |
| 1-6-28 | 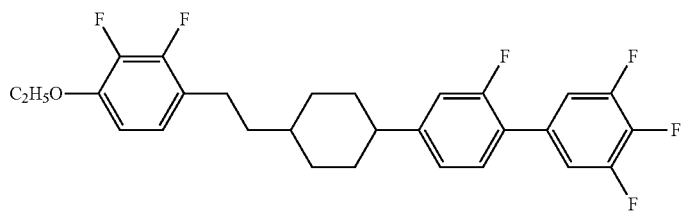 |
| 1-6-29 | 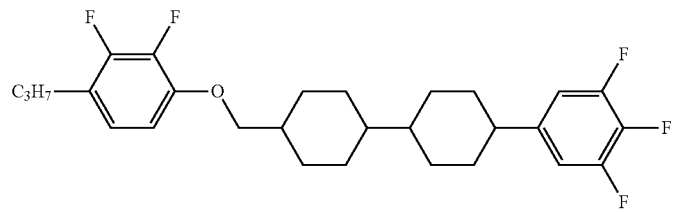 |
| 1-6-30 | 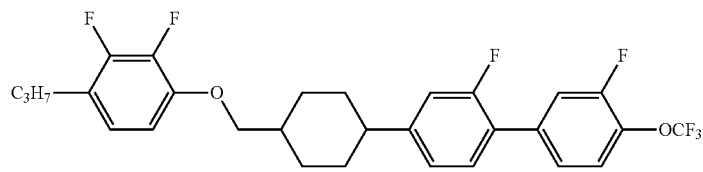 |
| 1-6-31 | 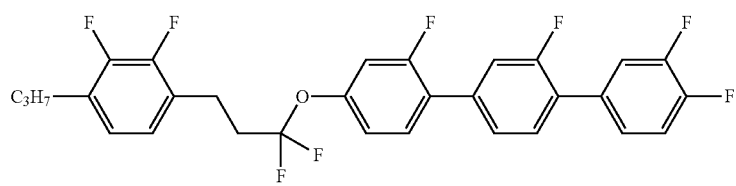 |
| 1-6-32 | 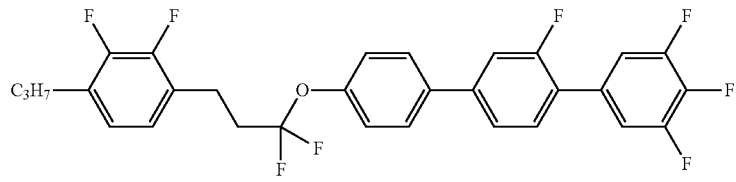 |
| 1-6-33 | 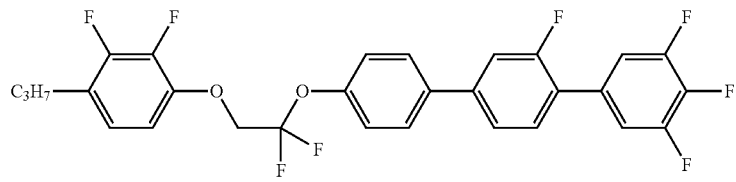 |

| No. | |
|---|---|
| 1-6-34 | 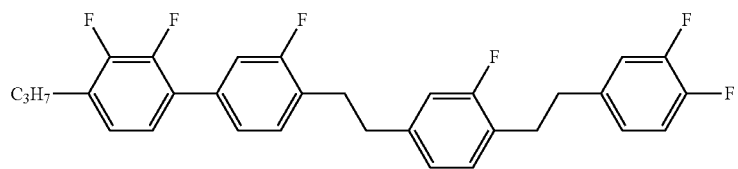 |
| 1-6-35 | 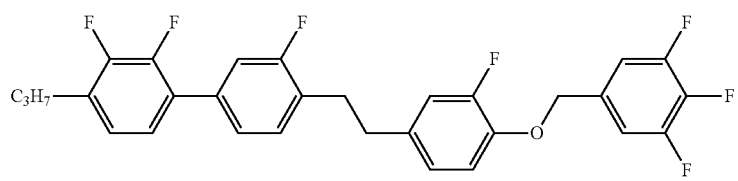 |
| 1-6-36 | 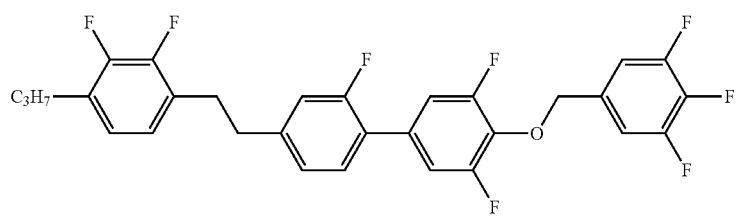 |
| 1-6-37 | 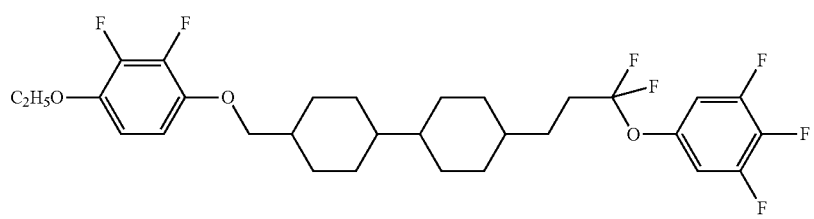 |
| 1-6-38 | 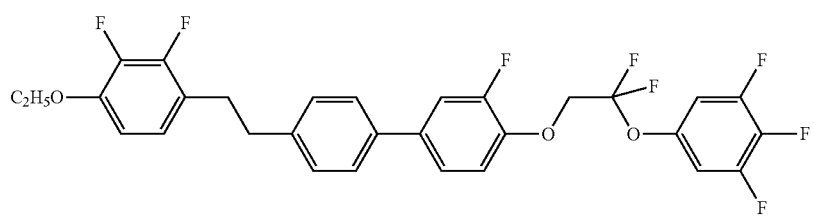 |
| 1-6-39 | 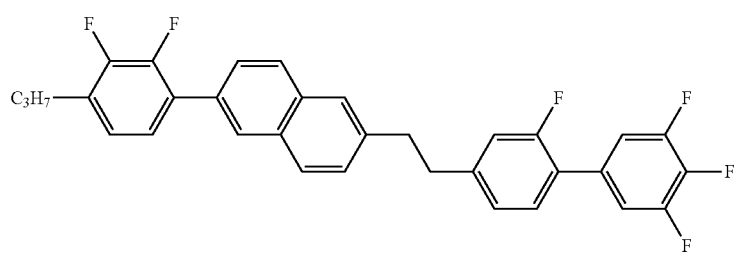 |
| 1-6-40 | 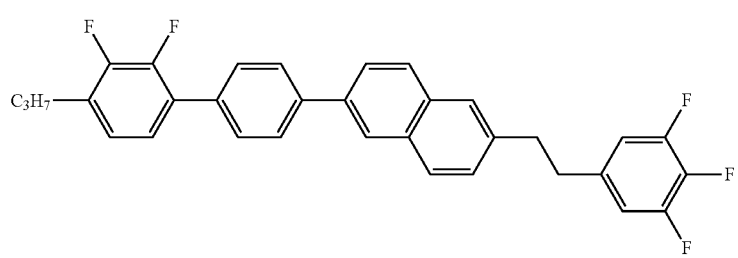 |

| No. | |
|---|---|
| 1-7-1 | 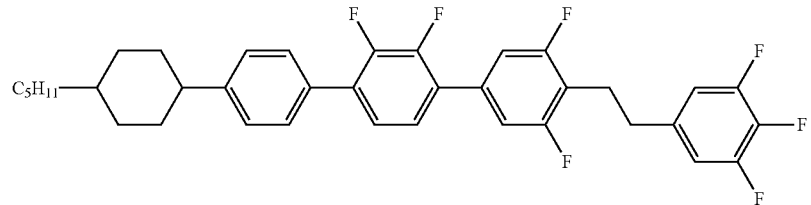 |
| 1-7-2 | 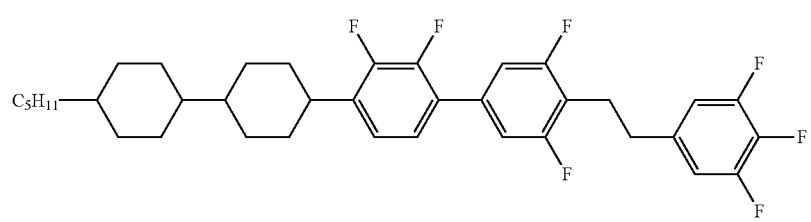 |
| 1-7-3 | 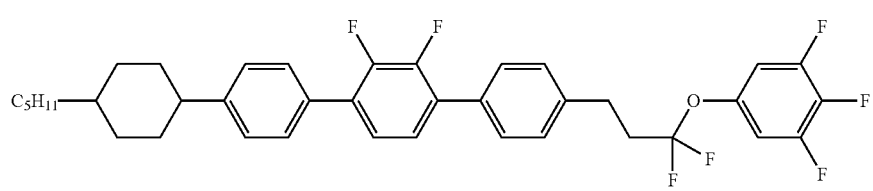 |
| 1-7-4 | 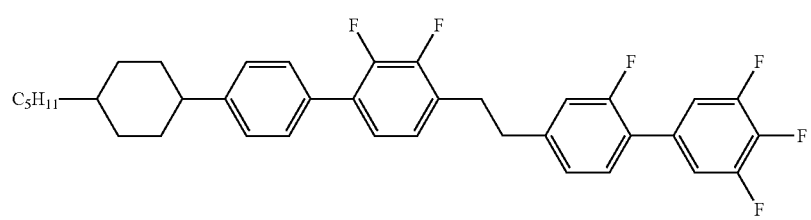 |
| 1-7-5 | 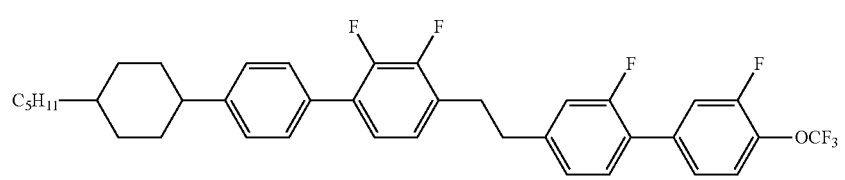 |
| 1-7-6 | 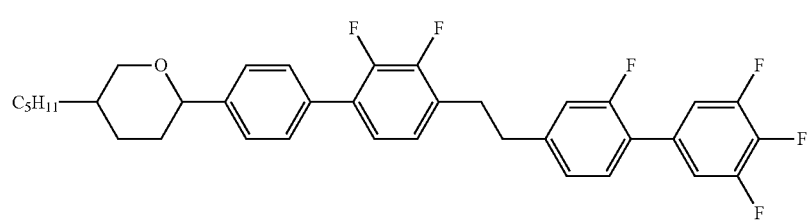 |
| 1-7-7 | 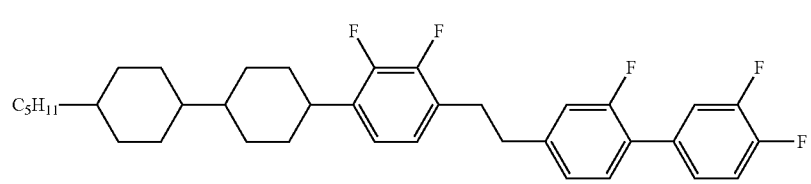 |

| No. | |
|---|---|
| 1-7-8 | 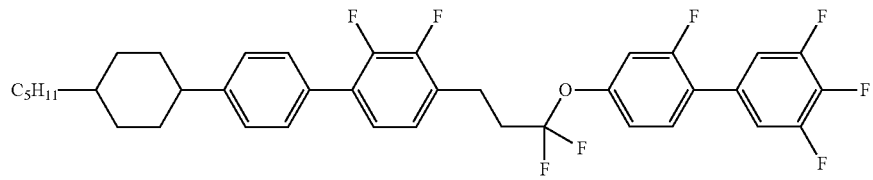 |
| 1-7-9 | 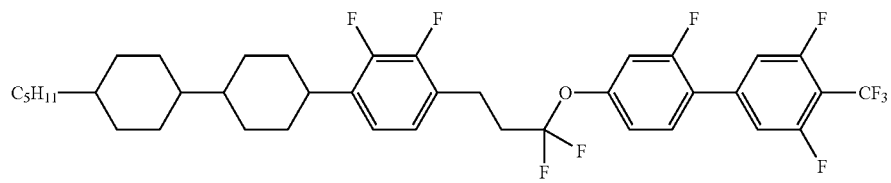 |
| 1-7-10 | 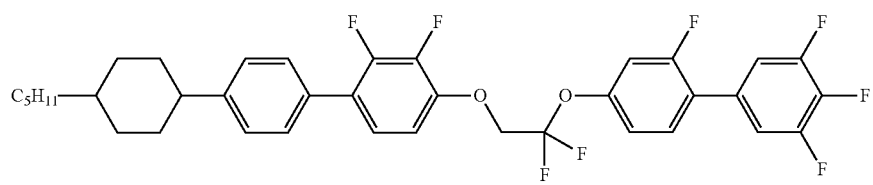 |
| 1-8-1 | 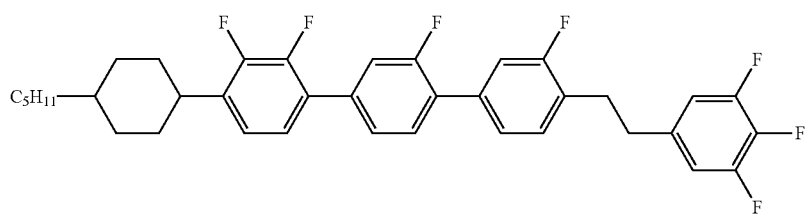 |
| 1-8-2 | 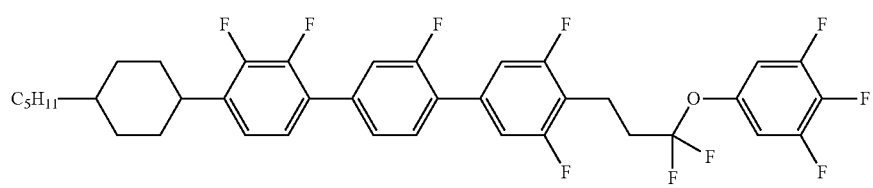 |
| 1-8-3 | 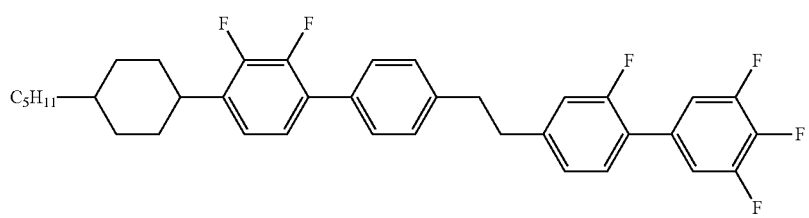 |
| 1-8-4 | 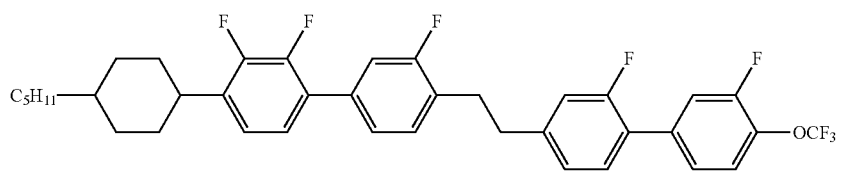 |

| No. | |
|---|---|
| 1-8-5 | 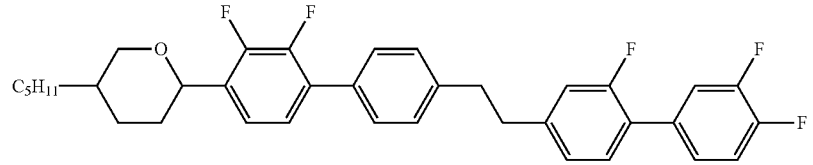 |
| 1-8-6 | 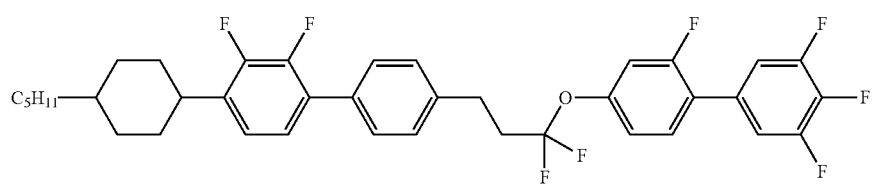 |
| 1-8-7 | 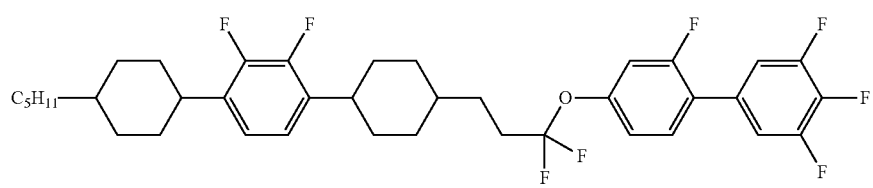 |
| 1-8-8 | 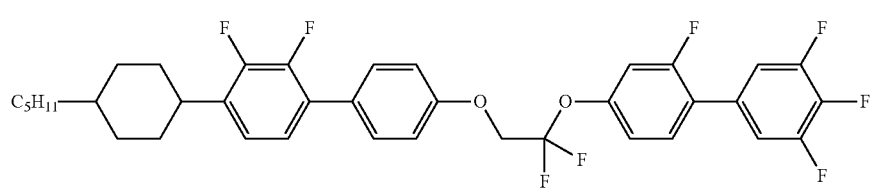 |
| 1-8-9 | 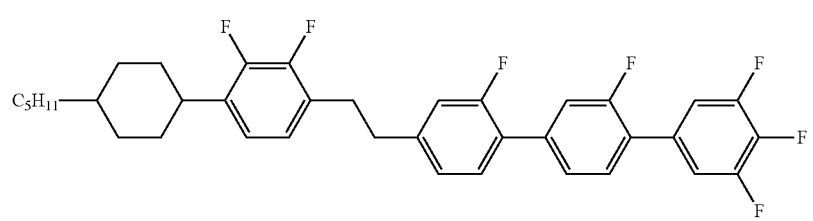 |
| 1-8-10 | 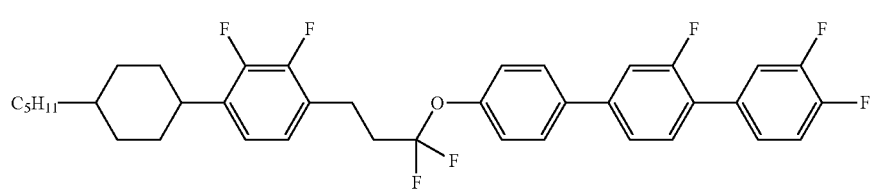 |

Comparative Example 1

As a comparative compound, compound (S-1) was prepared. The reason is that the compound is described in JP 2002-327175 A and similar to the compound of the invention.

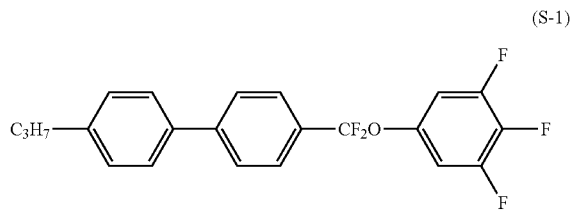

(S-1)

Chemical shifts δ (ppm; CDCl$_3$): 7.75 (d, J=8.4 Hz, 2H), 7.68 (d, J=8.4 Hz, 2H), 7.53 (d, J=8.1 Hz, 2H), 7.29 (d, J=8.1 Hz, 2H), 7.02-6.94 (m, 2H), 2.65 (t, J=7.9 Hz, 2H), 1.75-1.65 (m, 2H) and 0.98 (t, J=7.5 Hz, 3H).

Physical properties of comparative compound (S-1) were as described below.

Transition temperature: C 80.3 I.

Maximum temperature (T$_{NI}$)=35.0° C.; optical anisotropy (Δn)=0.144; dielectric anisotropy (Δ∈)=19.6; dielectric constant in a minor axis direction (∈⊥)=5.2; viscosity (η)=19.6 mPa·s.

TABLE 1

Comparison of ∈⊥

| Liquid crystal compounds | Dielectric constant in a minor axis direction (∈⊥) |
|---|---|
| Compound (1-2-2) | 9.2 |
| Compound (1-2-51) | 12.5 |
| Compound (1-2-81) | 13.2 |
| Comparative compound (S-1) | 5.2 |

All of compounds (No. 1-2-2), (No. 1-2-51) and (No. 1-2-81) shown in Example 1 to Example 3 have a larger dielectric constant in the minor axis direction in comparison with comparative compound (S-1). Therefore, the compound of the invention is found to be a superior compound that can improve a transmittance of the liquid crystal composition to be used in the FFS mode liquid crystal display device.

Comparative Example 2

As a comparative compound, compound (S-2) was prepared. The reason is that the compound is described in JP 2002-80452 A and similar to the compound of the invention.

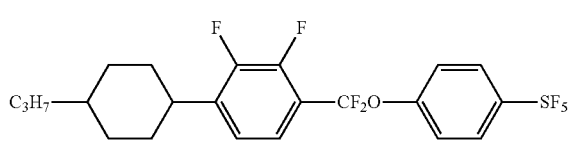

(S-2)

Chemical shifts δ (ppm; CDCl$_3$): 7.81-7.75 (m, 2H), 7.42-7.33 (m, 3H), 7.11-7.04 (m, 1H), 2.89 (tt, J=12.4 Hz, J=2.9 Hz, 1H), 1.93-1.84 (m, 4H), 1.55-1.43 (m, 2H), 1.41-1.27 (m, 3H), 1.27-1.19 (m, 2H), 1.16-1.03 (m, 2H) and 0.91 (t, J=7.4 Hz, 3H).

Physical properties of comparative compound (S-2) were as described below.

Transition temperature: C 53.8 I.

Maximum temperature (T$_{NI}$)=3.7° C.; optical anisotropy (Δn)=0.0703; dielectric anisotropy (Δ∈)=16.4; dielectric constant in a minor axis direction (∈⊥)=7.2; viscosity (η)=71.8 mPa·s.

TABLE 2

Comparison of ∈⊥ and viscosity

| Liquid crystal compounds | Dielectric constant in a minor axis direction (∈⊥) | Viscosity/ mPa · s |
|---|---|---|
| Compound (1-2-2) | 9.2 | 57.2 |
| Compound (1-2-51) | 12.5 | 57.2 |
| Compound (1-2-81) | 13.2 | 59.4 |
| Comparative compound (S-2) | 7.2 | 71.8 |

All of compounds (No. 1-2-2), (No. 1-2-51) and (No. 1-2-81) shown in Example 1 to Example 3 have a larger dielectric constant in the minor axis direction and a smaller viscosity in comparison with comparative compound (S-2). Therefore, the compound of the invention is found to be superior compound that can improve a transmittance of the liquid crystal composition to be used in the FFS mode liquid crystal display device and simultaneously can shorten a response time of the device.

1-2. Examples of Composition

The liquid crystal composition of the invention will be described in detail by way of Examples. However, the invention is not limited by the Examples. The invention contains a mixture of a composition in Example 1 and a composition in Example 2. The invention also contains a mixture in which at least two of the compositions in Example are mixed. Compounds in Examples were expressed using symbols according to definitions described in Table 3 below. In Table 3, a configuration of 1,4-cyclohexylene is trans. A parenthesized number next to a symbolized compound in Examples corresponds to the number of a compound. A symbol (–) means any other liquid crystal compound. A ratio (percentage) of the liquid crystal compound is expressed in terms of weight percent (% by weight) based on the weight of the liquid crystal composition. Values of physical properties of the composition were summarized in a last part. The physical properties were measured in accordance with the methods described above, and measured values were directly described (without extrapolation).

TABLE 3

Method for Description of Compounds using Symbols
R—(A$_1$)—Z$_1$— - - - —Z$_n$—(A$_n$)—R'

| 1) Left-terminal Group R— | Symbol |
|---|---|
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |

TABLE 3-continued

| 2) Right-terminal Group —R' | Symbol |
|---|---|
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |

| 3) Bonding Group —Zn— | Symbol |
|---|---|
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| —C$_n$H$_{2n}$—CF$_2$O— | nX |
| —OCH$_2$—CF$_2$O— | O1X |

| 4) Ring Structure —An— | Symbol |
|---|---|
|  | H |
|  | B |
| 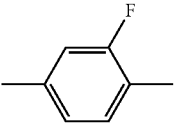 | B(F) |
| 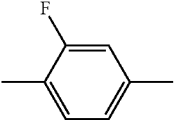 | B(2F) |
| 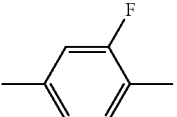 | B(F,F) |
| 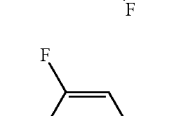 | B(2F,5F) |
| 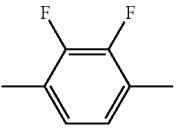 | B(2F,3F) |
| 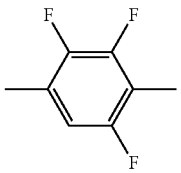 | B(2F,3F,5F) |
| 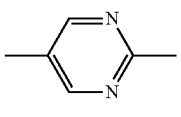 | Py |
| 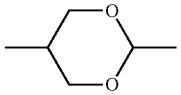 | G |
| 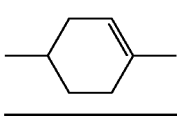 | ch |

5) Examples of Description

Example 1 3-BB(2F,3F)2B(F,F)-F

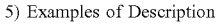

Example 2 3-BB(2F,3F)O1B(F,F)-F

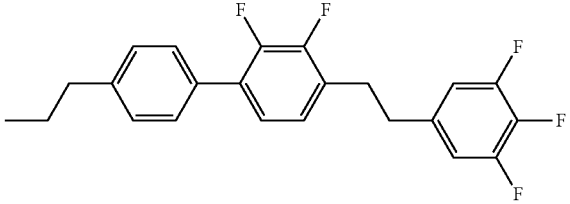 [SMILES: CCCc1ccc(-c2ccc(OCc3cc(F)c(F)c(F)c3)c(F)c2F)cc1]

Example 7

| 3-BB(2F,3F)2B(F,F)-F | (1-2-2) | 5% |
|---|---|---|
| 3-HB-O2 | (13-5) | 8% |
| 5-HB-CL | (2-2) | 10% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |
| 5-HBB(F)B-2 | (15-5) | 10% |
| 5-HBB(F)B-3 | (15-5) | 10% |

NI = 98.9° C.; η = 42.9 mPa · s; Δn = 0.193; Δε = 8.5.

Example 8

| | | |
|---|---|---|
| 3-BB(2F,3F)O1B(F,F)-F | (1-2-51) | 4% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 19% |
| 5-HBB(F,F)-F | (3-24) | 20% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 3% |
| 1O1-HBBH-5 | (15-1) | 3% |

NI = 91.9° C.; η = 35.3 mPa · s; Δn = 0.116; Δε = 9.3.

A pitch when 0.25 weight part of compound (Op-05) was added to 100 weight parts of the composition described above was 65.3 micrometers.

Example 9

| | | |
|---|---|---|
| 3-BB(2F,3F)O1XB(F,F)-F | (1-2-81) | 5% |
| 7-HB(F,F)-F | (2-4) | 3% |
| 3-HB-O2 | (13-5) | 7% |
| 2-HHB(F)-F | (3-2) | 8% |
| 3-HHB(F)-F | (3-2) | 9% |
| 5-HHB(F)-F | (3-2) | 10% |
| 2-HBB(F)-F | (3-23) | 9% |
| 3-HBB(F)-F | (3-23) | 9% |
| 5-HBB(F)-F | (3-23) | 16% |
| 2-HBB-F | (3-22) | 4% |
| 3-HBB-F | (3-22) | 4% |
| 5-HBB-F | (3-22) | 3% |
| 3-HBB(F,F)-F | (3-24) | 4% |
| 5-HBB(F,F)-F | (3-24) | 9% |

NI = 80.4° C.; η = 26.2 mPa · s; Δn = 0.115; Δε = 6.0.

Example 10

| | | |
|---|---|---|
| 3-BB(2F,3F)2B(F)-F | (1-2-9) | 4% |
| 2-HB-C | (5-1) | 5% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 12% |
| 3-HHEB-F | (3-10) | 4% |
| 5-HHEB-F | (3-10) | 4% |
| 2-HHB(F)-F | (3-2) | 6% |
| 3-HHB(F)-F | (3-2) | 6% |
| 5-HHB(F)-F | (3-2) | 7% |
| 3-HHB(F,F)-F | (3-3) | 5% |

Example 11

| | | |
|---|---|---|
| 3-BB(2F,3F)2B(F)-OCF3 | (1-2-10) | 5% |
| 5-HB-F | (2-2) | 11% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 4% |
| 3-HH2B-OCF3 | (3-4) | 4% |
| 5-HH2B-OCF3 | (3-4) | 3% |
| 3-HHB(F,F)-OCF2H | (3-3) | 4% |
| 3-HHB(F,F)-OCF3 | (3-3) | 4% |
| 3-HH2B(F)-F | (3-5) | 3% |
| 3-HBB(F)-F | (3-23) | 10% |
| 5-HBB(F)-F | (3-23) | 9% |
| 5-HBBH-3 | (15-1) | 3% |
| 3-HB(F)BH-3 | (15-2) | 3% |

Example 12

| | | |
|---|---|---|
| 2O-BB(2F,3F)2B(F,F)-F | (1-2-25) | 5% |
| 3-HB-CL | (2-2) | 5% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 13% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 9% |
| 5-H2HB(F,F)-F | (3-15) | 5% |
| 5-H4HB(F,F)-CF3 | (3-21) | 7% |
| 2-H2BB(F)-F | (3-26) | 5% |
| 3-H2BB(F)-F | (3-26) | 9% |
| 3-HBEB(F,F)-F | (3-39) | 5% |

Example 13

| | | |
|---|---|---|
| 1V2-BB(2F,3F)2B(F,F)-CF3 | (1-2-24) | 3% |
| 5-HB-CL | (2-2) | 3% |
| 7-HB(F)-F | (2-3) | 7% |
| 3-HB-O2 | (13-5) | 8% |
| 3-HH-EMe | (13-2) | 23% |
| 3-HHEB-F | (3-10) | 8% |
| 5-HHEB-F | (3-10) | 7% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 4% |
| 5-GHB(F,F)-F | (3-109) | 7% |

Example 14

| | | |
|---|---|---|
| 3-B(2F,3F)B2B(F,F)-F | (1-3-1) | 4% |
| 3-B(2F,3F)2B(F,F)-F | (1-1-1) | 3% |
| 3-HB-O2 | (13-5) | 10% |
| 5-HB-CL | (2-2) | 11% |
| 3-HBB(F,F)-F | (3-24) | 7% |
| 3-PyB(F)-F | (2-15) | 10% |
| 5-PyB(F)-F | (2-15) | 8% |
| 3-PyBB-F | (3-80) | 10% |
| 4-PyBB-F | (3-80) | 8% |
| 5-PyBB-F | (3-80) | 10% |
| 5-HBB(F)B-2 | (15-5) | 9% |
| 5-HBB(F)B-3 | (15-5) | 10% |

Example 15

| | | |
|---|---|---|
| 3-HBB(2F,3F)2B(F,F)-F | (1-4-12) | 5% |
| 7-HB(F,F)-F | (2-4) | 3% |
| 3-HB-O2 | (13-5) | 7% |
| 2-HHB(F)-F | (3-2) | 9% |
| 3-HHB(F)-F | (3-2) | 10% |
| 5-HHB(F)-F | (3-2) | 9% |
| 2-HBB(F)-F | (3-23) | 8% |
| 3-HBB(F)-F | (3-23) | 9% |
| 5-HBB(F)-F | (3-23) | 13% |
| 2-HBB-F | (3-22) | 4% |
| 3-HBB-F | (3-22) | 4% |
| 5-HBB-F | (3-22) | 4% |
| 3-HBB(F,F)-F | (3-24) | 5% |
| 5-HBB(F,F)-F | (3-24) | 10% |

Example 16

| | | |
|---|---|---|
| 3-GBB(2F,3F)2B(F,F)-F | (1-4-42) | 5% |
| 5-HB-F | (2-2) | 12% |
| 6-HB-F | (2-2) | 9% |
| 7-HB-F | (2-2) | 7% |
| 2-HHB-OCF3 | (3-1) | 6% |
| 3-HHB-OCF3 | (3-1) | 6% |
| 4-HHB-OCF3 | (3-1) | 6% |
| 5-HHB-OCF3 | (3-1) | 5% |
| 3-HH2B-OCF3 | (3-4) | 3% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 9% |
| 5-HBB(F)-F | (3-23) | 10% |
| 5-HBBH-3 | (15-1) | 3% |
| 3-HB(F)BH-3 | (15-2) | 3% |

Example 17

| | | |
|---|---|---|
| 3-BB(2F,3F)EB(F,F)-F | (1-2-62) | 4% |
| 5-HB-CL | (2-2) | 3% |
| 7-HB(F)-F | (2-3) | 7% |
| 3-HB-O2 | (13-5) | 9% |
| 3-HH-EMe | (13-2) | 22% |
| 3-HHEB-F | (3-10) | 8% |
| 5-HHEB-F | (3-10) | 7% |
| 3-HHEB(F,F)-F | (3-12) | 9% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 6% |

Example 18

| | | |
|---|---|---|
| 3-BB(2F,3F)2XB(F,F)-F | (1-2-69) | 3% |
| 3-HBB(2F,3F)O1XB(F,F)-F | (1-4-82) | 3% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 11% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 8% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 10% |
| 3-HBEB(F,F)-F | (3-39) | 5% |

Example 19

| | | |
|---|---|---|
| 3-HB(2F,3F)O1B(F,F)-F | (1-2-57) | 5% |
| 3-HB-O2 | (13-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 8% |
| 4-PyBB-F | (3-80) | 7% |
| 5-PyBB-F | (3-80) | 10% |
| 5-HBB(F)B-2 | (15-5) | 10% |
| 5-HBB(F)B-3 | (15-5) | 10% |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention satisfies at least one of physical properties such as a high stability to heat, light and so forth, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds. A liquid crystal composition of the invention contains the compound, and satisfies at least one of physical properties such as a high maximum temperature, a low minimum temperature, a small viscosity, a suitable optical anisotropy, a large dielectric anisotropy, a large dielectric constant in a minor axis direction and a suitable elastic constant. The composition has a suitable balance regarding at least two of physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a liquid crystal display to be used for a personal computer, a television and so forth.

What is claimed is:
1. A compound represented by formula (1):

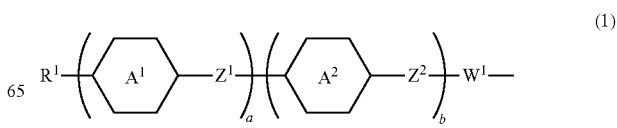

-continued

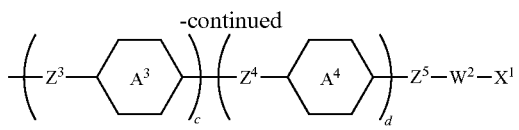

wherein, in formula (1),
R$^1$ is alkyl having 1 to 15 carbons, and in the alkyl, at least one of —CH$_2$— may be replaced by —O— or —S—, at least one of —(CH$_2$)$_2$— may be replaced by —CH═CH—, and in the groups, at least one of hydrogen may be replaced by halogen;
ring A$^1$, ring A$^2$, ring A$^3$ and ring A$^4$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl or 1,2,3,4-tetrahydronaphthalene-2,6-diyl, and at least one of hydrogen directly bonded to the rings thereof may be replaced by halogen;
W$^1$ is a group represented by formula (1a) or formula (1b);

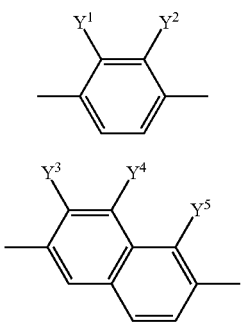

wherein, in formula (1a),
Y$^1$ and Y$^2$ are independently fluorine or chlorine;
in formula (1b),
Y$^3$, Y$^4$ and Y$^5$ are independently hydrogen, fluorine or chlorine, and at least two of Y$^3$, Y$^4$ and Y$^5$ are fluorine or chlorine; and
in formula (1),
W$^2$ is a group represented by formula (1c) or formula (1d);

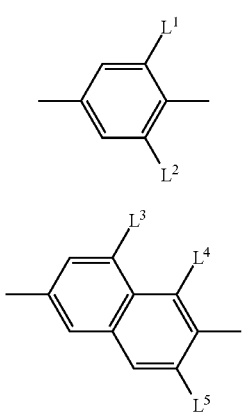

wherein, in formula (1c) and (1d),
L$^1$, L$^2$, L$^3$, L$^4$ and L$^5$ are independently hydrogen, fluorine or chlorine; and
in formula (1),
X$^1$ is fluorine, —C≡N, —N═C═S, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;
a, b, c and d are independently 0 or 1, and a sum of a, b, c and d is 0, 1, 2 or 3;
Z$^1$, Z$^2$, Z$^3$, Z$^4$ and Z$^5$ are independently a single bond, —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—;
at least one of Z$^1$ when a is 1, Z$^2$ when b is 1, Z$^3$ when c is 1, Z$^4$ when d is 1 and Z$^5$ is —(CH$_2$)$_2$—, —CH$_2$O—, —OCH$_2$—, —COO—, —OCO—, —(CH$_2$)$_4$—, —(CH$_2$)$_2$CF$_2$O—, —OCH$_2$CF$_2$O—, —(CH$_2$)$_3$O—, —O(CH$_2$)$_3$— or —(CH$_2$)$_2$COO—;
when Z$^5$ is —COO—, ring W$^1$ is a group represented by formula (1a) and ring W$^2$ is a group represented by formula (1c), X$^1$ is fluorine, or alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;
when Z$^5$ is —COO—, ring W$^1$ is a group represented by formula (1a), ring W$^2$ is a group represented by formula (1c), a sum of a and b is 1, a sum of c and d is 0, ring A$^1$ when a is 1 or ring A$^2$ when b is 1 is 1,4-phenylene, Z$^1$ when a is 1 or Z$^2$ when b is 1 is a single bond, both Y$^1$ and Y$^2$ are fluorine and X$^1$ is fluorine, both L$^1$ and L$^2$ are hydrogen or fluorine; and
when Z$^5$ is —COO—, ring W$^1$ is a group represented by formula (1a), ring W$^2$ is a group represented by formula (1c), a sum of a, b, c and d is 0, both Y$^1$ and Y$^2$ are fluorine and X$^1$ is —CF$_3$, at least one of L$^1$ and L$^2$ is fluorine.

2. The compound according to claim 1, wherein, in formula (1), R$^1$ is alkyl having 1 to 15 carbons, alkenyl having 2 to 15 carbons, alkoxy having 1 to 14 carbons or alkenyloxy having 2 to 14 carbons, and in the groups, at least one of hydrogen may be replaced by fluorine; and X$^1$ is fluorine, —C≡N, —N═C═S, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH═CHF, —CH═CF$_2$, —CF═CHF, —CF═CF$_2$, —CH═CHCH$_2$F, —CH═CHCF$_3$, —CF═CHCF$_3$, —CF═CFCF$_3$, —(CH$_2$)$_2$—CH═CF$_2$, —(CH$_2$)$_2$—CF═CF$_2$, —(CH$_2$)$_2$—CH═CHCF$_3$, —(CH$_2$)$_2$—CF═CHCF$_3$ or —(CH$_2$)$_2$—CF═CFCF$_3$.

3. The compound according to claim 1, wherein, in formula (1), R$^1$ is alkyl having 1 to 10 carbons, alkenyl having 2 to 10 carbons, alkoxy having 1 to 9 carbons or alkenyloxy having 2 to 9 carbons, and in the groups, at least one of hydrogen may be replaced by fluorine; and $X^1$ is fluorine, —C≡N, —$CF_3$, —$CHF_2$, —$OCF_3$, —$OCHF_2$, —CH=$CHCF_3$, —CF=$CHCF_3$ or —CF=$CFCF_3$.

4. The compound according to claim 1, represented by any one of formulas (1-1) to (1-8):

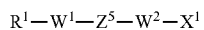
(1-1)

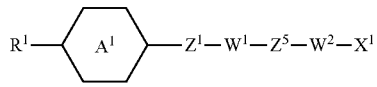
(1-2)

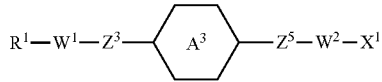
(1-3)

(1-4)

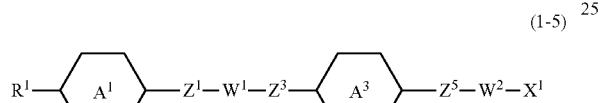
(1-5)

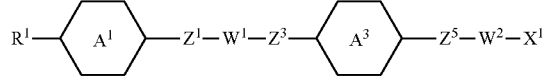
(1-6)

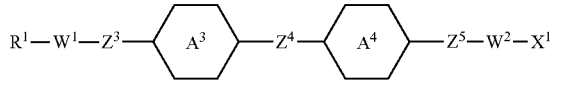
(1-7)

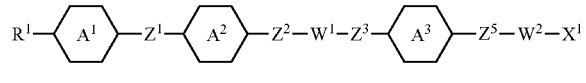
(1-8)

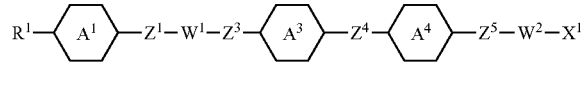

wherein, in formulas (1-1) to (1-8), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine; and $W^1$ is a group represented by formula (1a) or formula (1b);

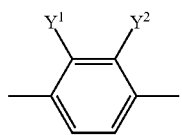
(1a)

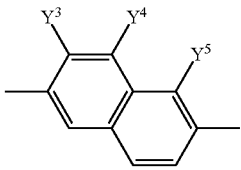
(1b)

wherein, in formula (1a), $Y^1$ and $Y^2$ are fluorine;

in formula (1b), $Y^3$, $Y^4$ and $Y^5$ are independently hydrogen or fluorine, and at least two of $Y^3$, $Y^4$ and $Y^5$ are fluorine; and in formulas (1-1) to (1-8), $W^2$ is a group represented by formula (1c) or formula (1d);

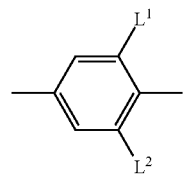
(1c)

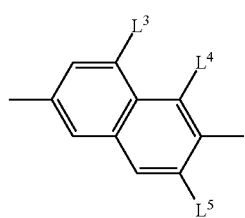
(1d)

wherein, in formula (1c) and (1d), $L^1$, $L^2$, $L^3$, $L^4$ and $L^5$ are independently hydrogen or fluorine; and in formulas (1-1) to (1-8), $Z^1$, $Z^2$, $Z^3$, $Z^4$ and $Z^5$ are independently a single bond, —$(CH_2)_2$—, —$CH_2O$—, —$OCH_2$—, —$(CH_2)_4$—, —$(CH_2)_2CF_2O$— or —$OCH_2CF_2O$—, and at least one of $Z^1$, $Z^2$, $Z^3$, $Z^4$ and $Z^5$ is —$(CH_2)_2$—, —$CH_2O$—, —$OCH_2$—, —$(CH_2)_4$—, —$(CH_2)_2CF_2O$— or —$OCH_2CF_2O$—; and $X^1$ is fluorine, —$CF_3$, —$CHF_2$, —$OCF_3$ or —$OCHF_2$.

5. The compound according to claim 1, represented by any one of formulas (1-9) to (1-22):

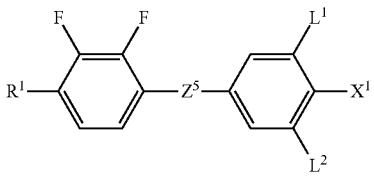
(1-9)

-continued

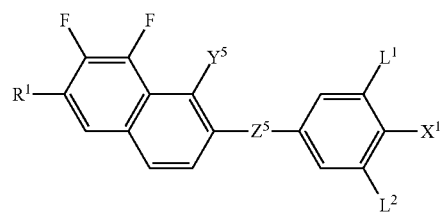
(1-10)

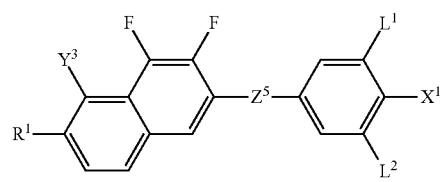
(1-11)

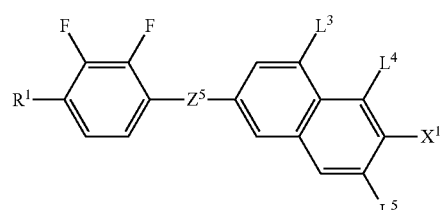
(1-12)

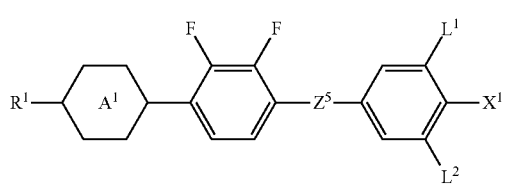
(1-13)

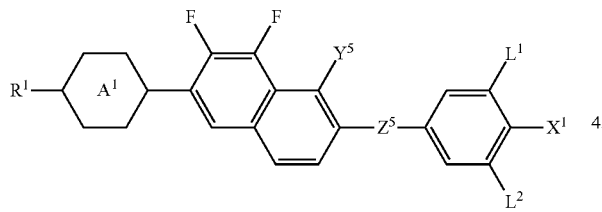
(1-14)

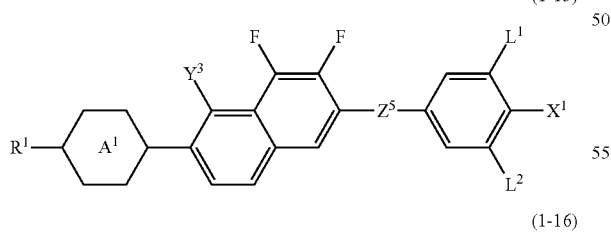
(1-15)

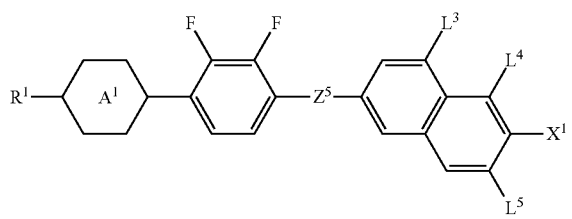
(1-16)

-continued

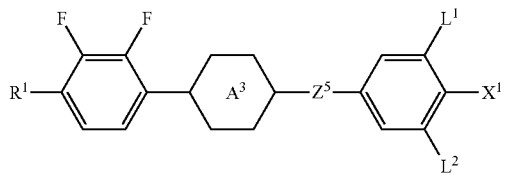
(1-17)

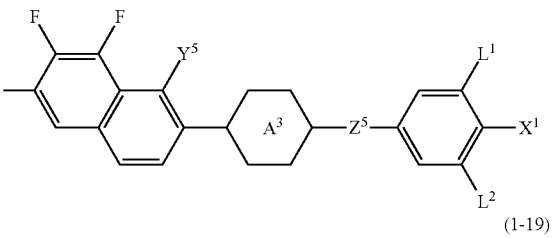
(1-18)

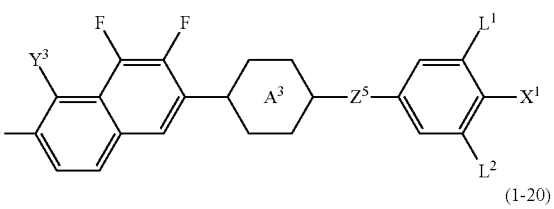
(1-19)

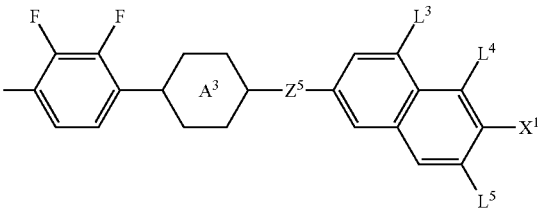
(1-20)

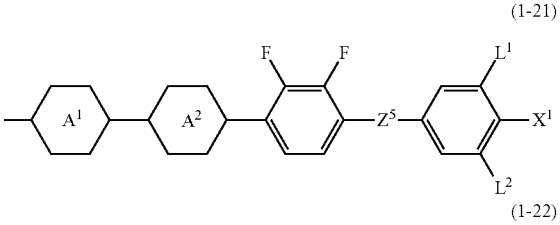
(1-21)

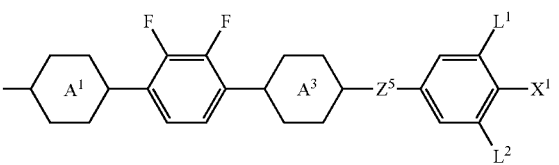
(1-22)

wherein, in formulas (1-9) to (1-22),
  $R^1$ is alkyl having 1 to 10 carbons or alkenyl having 2 to 10 carbons;
  ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl, 1,3-dioxane-2,5-diyl, naphthalene-2,6-diyl, or naphthalene-2,6-diyl in which at least one of hydrogen is replaced by fluorine;
  $Z^5$ is —$(CH_2)_2$—, —$CH_2O$—, —$OCH_2$—, —$(CH_2)_4$—, —$(CH_2)_2CF_2O$—, —$OCH_2CF_2O$—,
  $X^1$ is fluorine, —$CF_3$ or —$OCF_3$; and
  $L^1$, $L^2$, $L^3$, $L^4$, $L^5$, $Y^3$ and $Y^5$ are independently hydrogen or fluorine.

6. The compound according to claim 1, represented by any one of formulas (1-23) to (1-36):

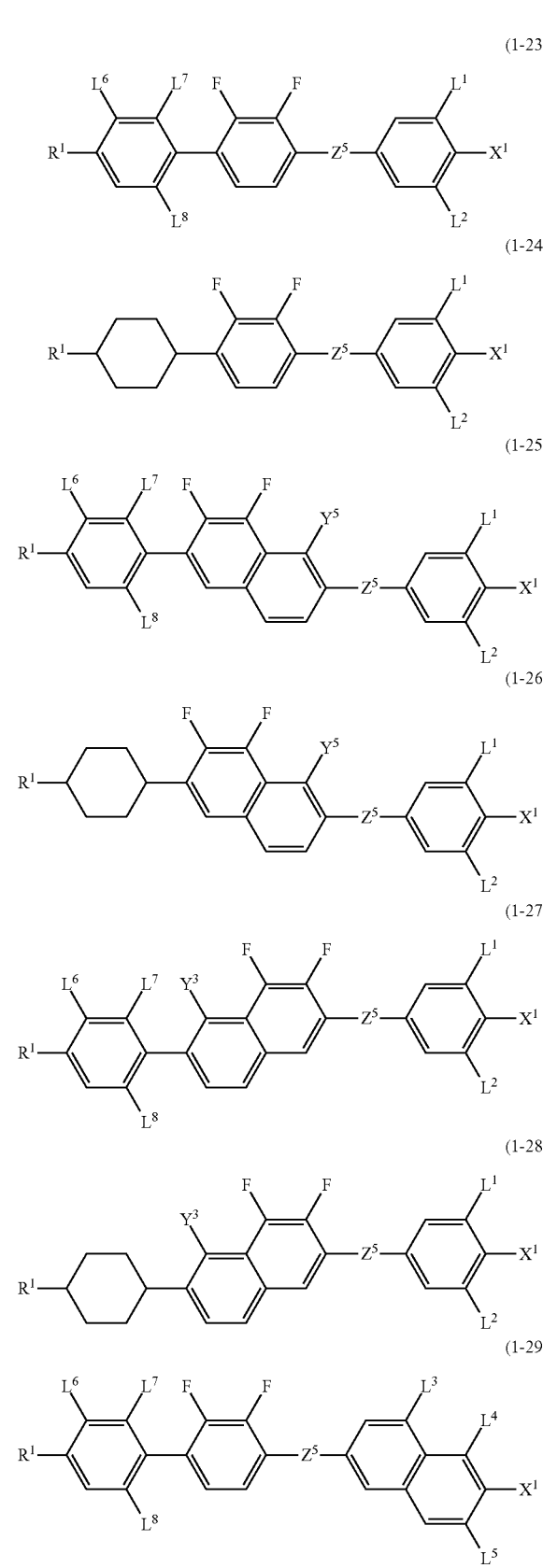

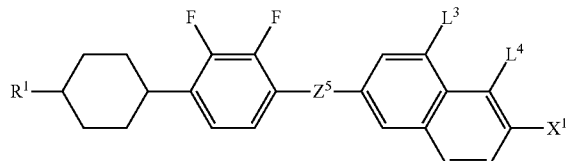

wherein, in formulas (1-23) to (1-36), $R^1$ is alkyl having 1 to 10 carbons or alkenyl having 2 to 10 carbons; $Z^5$ is —$(CH_2)_2$—, —$OCH_2$—, —$(CH_2)_2CF_2O$— or —$OCH_2CF_2O$—; $X^1$ is fluorine, —$CF_3$ or —$OCF_3$; and $L^1$, $L^2$, $L^3$, $L^4$, $L^5$, $L^6$, $L^7$, $L^8$, $Y^3$ and $Y^5$ are independently hydrogen or fluorine.

7. The compound according to claim 1, represented by any one of formulas (1-37) to (1-48):

(1-37) 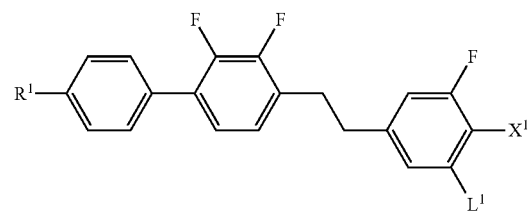

(1-38) 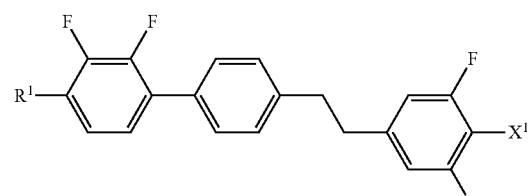

(1-39) 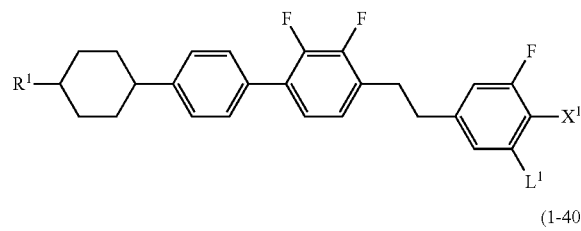

(1-40) 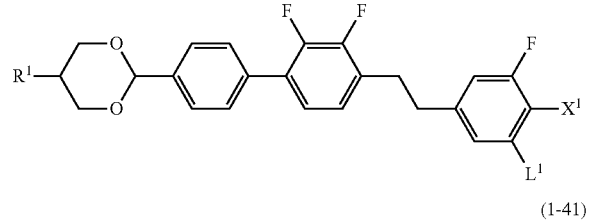

(1-41) 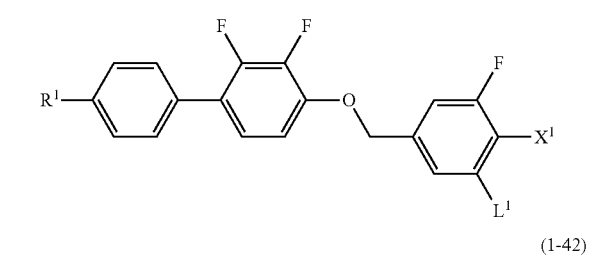

(1-42) 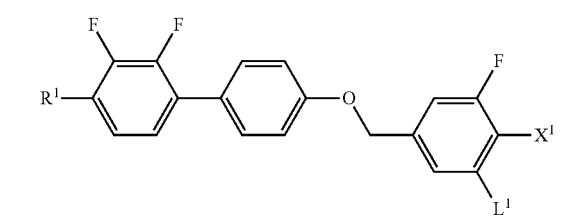

(1-43) 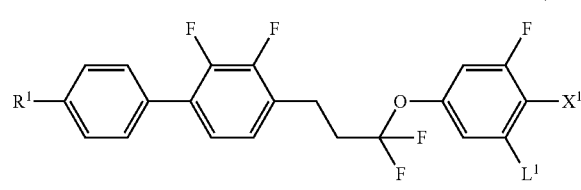

(1-44) 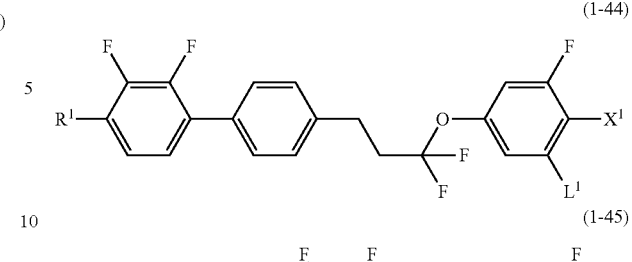

(1-45) 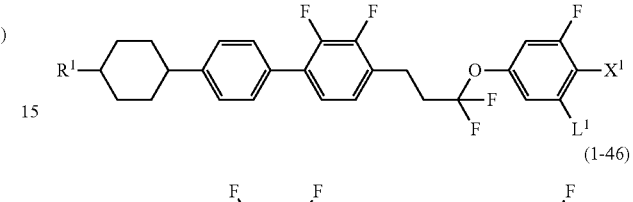

(1-46) 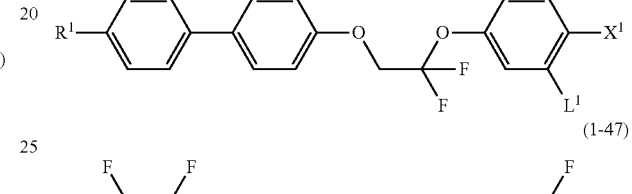

(1-47) 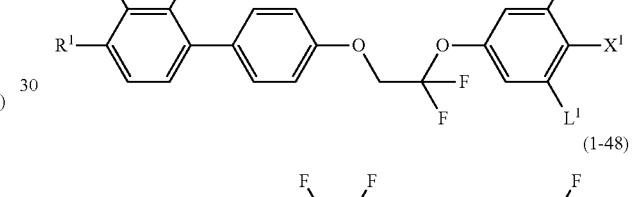

(1-48) 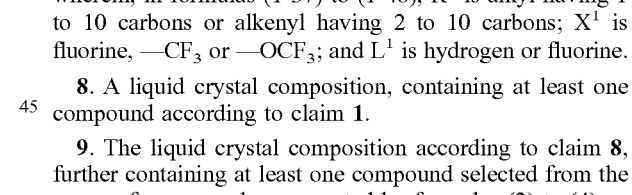

wherein, in formulas (1-37) to (1-48), $R^1$ is alkyl having 1 to 10 carbons or alkenyl having 2 to 10 carbons; $X^1$ is fluorine, —$CF_3$ or —$OCF_3$; and $L^1$ is hydrogen or fluorine.

8. A liquid crystal composition, containing at least one compound according to claim 1.

9. The liquid crystal composition according to claim 8, further containing at least one compound selected from the group of compounds represented by formulas (2) to (4):

(2) 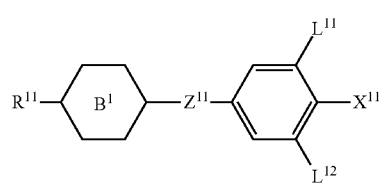

(3) 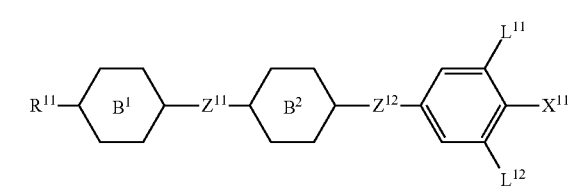

(4)

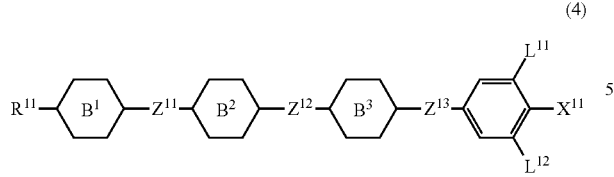

(5)

wherein, in formulas (2) to (4),
R$^{11}$ is alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring B$^1$, ring B$^2$ and ring B$^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;
Z$^{11}$, Z$^{12}$ and Z$^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and
L$^{11}$ and L$^{12}$ are independently hydrogen or fluorine.

10. The liquid crystal composition according to claim 8, further containing at least one compound selected from the group of compounds represented by formula (5):

wherein, in formula (5),
R$^{12}$ is alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;
X$^{12}$ is —C≡N or —C≡C—C≡N;
ring C$^1$ is 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;
Z$^{14}$ is a single bond, —CH$_2$CH$_2$—, —COO—, —CF$_2$O—, —OCF$_2$— or —CH$_2$O—;
L$^{13}$ and L$^{14}$ are independently hydrogen or fluorine; and
i is 1, 2, 3 or 4.

11. The liquid crystal composition according to claim 8, further containing at least one compound selected from the group of compounds represented by formulas (6) to (12):

(6)

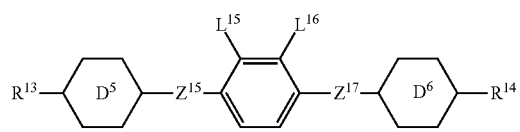

(7)

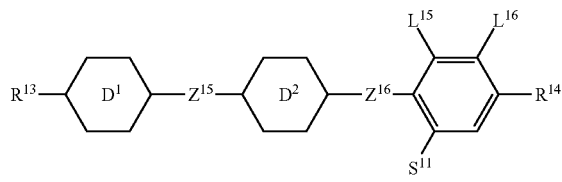

(8)

(9)

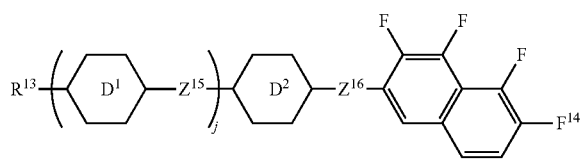

(10)

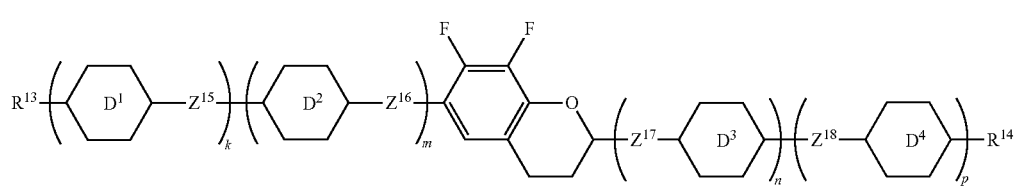

(11)

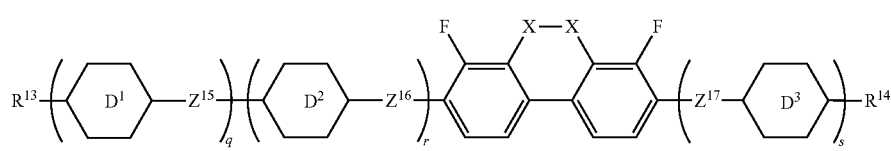

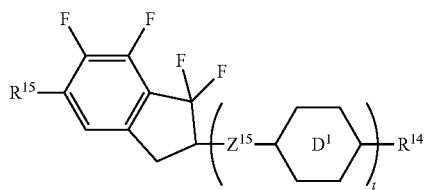

(12)

wherein, in formulas (6) to (12),
$R^{13}$ and $R^{14}$ are independently alkyl having 1 to 10 carbons or alkenyl having 2 to 10 carbons, and in the alkyl and the alkenyl, at least one of —$CH_2$— may be replaced by —O—;
$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$S^{11}$ is hydrogen or methyl;
X is —$CF_2$—, —O— or —CHF—;
ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;
$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;
$L^{15}$ and $L^{16}$ are independently fluorine or chlorine; and
j, k, m, n, p, q, r and s are independently 0 or 1, and a sum of k, m, n and p is 1 or 2, a sum of q, r and s is 0, 1, 2 or 3, and t is 1, 2 or 3.

12. The liquid crystal composition according to claim 8, further containing at least one compound selected from the group of compounds represented by formulas (13) to (15):

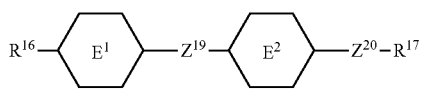
(13)

(14)

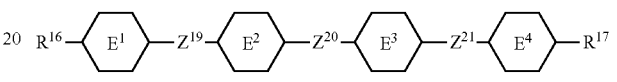
(15)

wherein, in formulas (13) to (15),
$R^{16}$ and $R^{17}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine;
ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and
$Z^{19}$, $Z^{20}$ and $Z^{21}$ are independently a single bond, —$CH_2CH_2$—, —CH=CH—, —C≡C— or —COO—.

13. The liquid crystal composition according to claim 8, further containing at least one of a polymerizable compound, an optically active compound, an antioxidant, an ultraviolet light absorber, a light stabilizer, a heat stabilizer and an antifoaming agent.

14. A liquid crystal display device, including the liquid crystal composition according to claim 8.

* * * * *